(12) United States Patent
Mahr et al.

(10) Patent No.: US 10,618,948 B2
(45) Date of Patent: Apr. 14, 2020

(54) PEPTIDES AND COMBINATION OF PEPTIDES FOR USE IN IMMUNOTHERAPY AND METHODS FOR GENERATING SCAFFOLDS FOR THE USE AGAINST PANCREATIC CANCER AND OTHER CANCERS

(71) Applicant: Immatics Biotechnologies GmbH, Tübingen (DE)

(72) Inventors: Andrea Mahr, Tübingen (DE); Toni Weinschenk, Aichwald (DE); Oliver Schoor, Tübingen (DE); Jens Fritsche, Dusslingen (DE); Harpreet Singh, Houston, TX (US)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 15/984,681

(22) Filed: May 21, 2018

(65) Prior Publication Data

US 2018/0251519 A1 Sep. 6, 2018

Related U.S. Application Data

(63) Continuation of application No. 15/185,990, filed on Jun. 17, 2016, now Pat. No. 10,385,109.

(60) Provisional application No. 62/182,026, filed on Jun. 19, 2015.

(51) Int. Cl.

| C07K 14/74 | (2006.01) |
| C07K 14/47 | (2006.01) |
| A61K 39/00 | (2006.01) |
| A61K 51/10 | (2006.01) |
| C07K 14/705 | (2006.01) |
| C07K 16/28 | (2006.01) |
| C07K 16/30 | (2006.01) |
| C12N 5/0783 | (2010.01) |
| C12N 15/115 | (2010.01) |
| C12P 21/02 | (2006.01) |
| C12Q 1/6881 | (2018.01) |
| G01N 33/569 | (2006.01) |

(52) U.S. Cl.
CPC .... C07K 14/70539 (2013.01); A61K 39/0011 (2013.01); A61K 51/1027 (2013.01); A61K 51/1057 (2013.01); C07K 14/4748 (2013.01); C07K 14/70503 (2013.01); C07K 16/2833 (2013.01); C07K 16/303 (2013.01); C12N 5/0636 (2013.01); C12N 15/115 (2013.01); C12P 21/02 (2013.01); C12Q 1/6881 (2013.01); G01N 33/56977 (2013.01); A61K 2039/5158 (2013.01); A61K 2039/572 (2013.01); C07K 2317/72 (2013.01); C07K 2317/73 (2013.01); C07K 2319/00 (2013.01); C07K 2319/30 (2013.01); C07K 2319/55 (2013.01); C12N 2310/16 (2013.01); C12Q 2600/156 (2013.01); C12Q 2600/158 (2013.01); G01N 2333/70539 (2013.01)

(58) Field of Classification Search
CPC .............. C07K 7/08; A61K 2039/5158; C12N 5/0636; C12N 5/0638
See application file for complete search history.

(56) References Cited

U.S. PATENT DOCUMENTS

| 2003/0228284 A1 | 12/2003 | McCown |
| 2013/0009601 A1 | 4/2013 | Weinschenk |
| 2013/0259923 A1 | 10/2013 | Bancel |

FOREIGN PATENT DOCUMENTS

| EP | 1760089 A1 | 3/2007 |
| WO | 2003010327 A2 | 2/2003 |
| WO | 2003093295 A2 | 11/2003 |
| WO | 2009015842 A2 | 2/2009 |
| WO | 2011113819 A2 | 9/2011 |
| WO | 2011/151403 A | 12/2011 |

OTHER PUBLICATIONS

Montagna et al (Cytotherapy, 2012, vol. 14, pp. 80-90) (Year: 2012).*
Yee et al (Journal of Immunology, 1999, vol. 162, pp. 2227-2234) (Year: 1999).*
Great Britain Search Report dated Apr. 6, 2016, Issued in Application No. GB1510771.7.
Walter et al., "Multipeptide immune response to cancer vaccine IMA901 after single-dose cyclophosphamide associates with longer patient survival," Nature Medicine, vol. 18, 2012, pp. 1254-1265.
International Search Report for PCT/EP2016/063976, dated Jan. 12, 2017.
Weinschenk, et al., "Integrated functional genomics approach for the design of patient-individual antitumor vaccines." 2 Cancer Research, American Association for Cancer Research, US. vol. 62, No. 20, Oct. 15, 2002 {Oct. 15, 2002), pp. 5818-5827.

* cited by examiner

*Primary Examiner* — Karen A. Canella
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

11 Claims, 37 Drawing Sheets

Specification includes a Sequence Listing.

Peptide: ILIGETIKI (A*02), SEQ ID No. 3

Peptide: AQYKFVVQV (A*02) SEQ ID No. 12

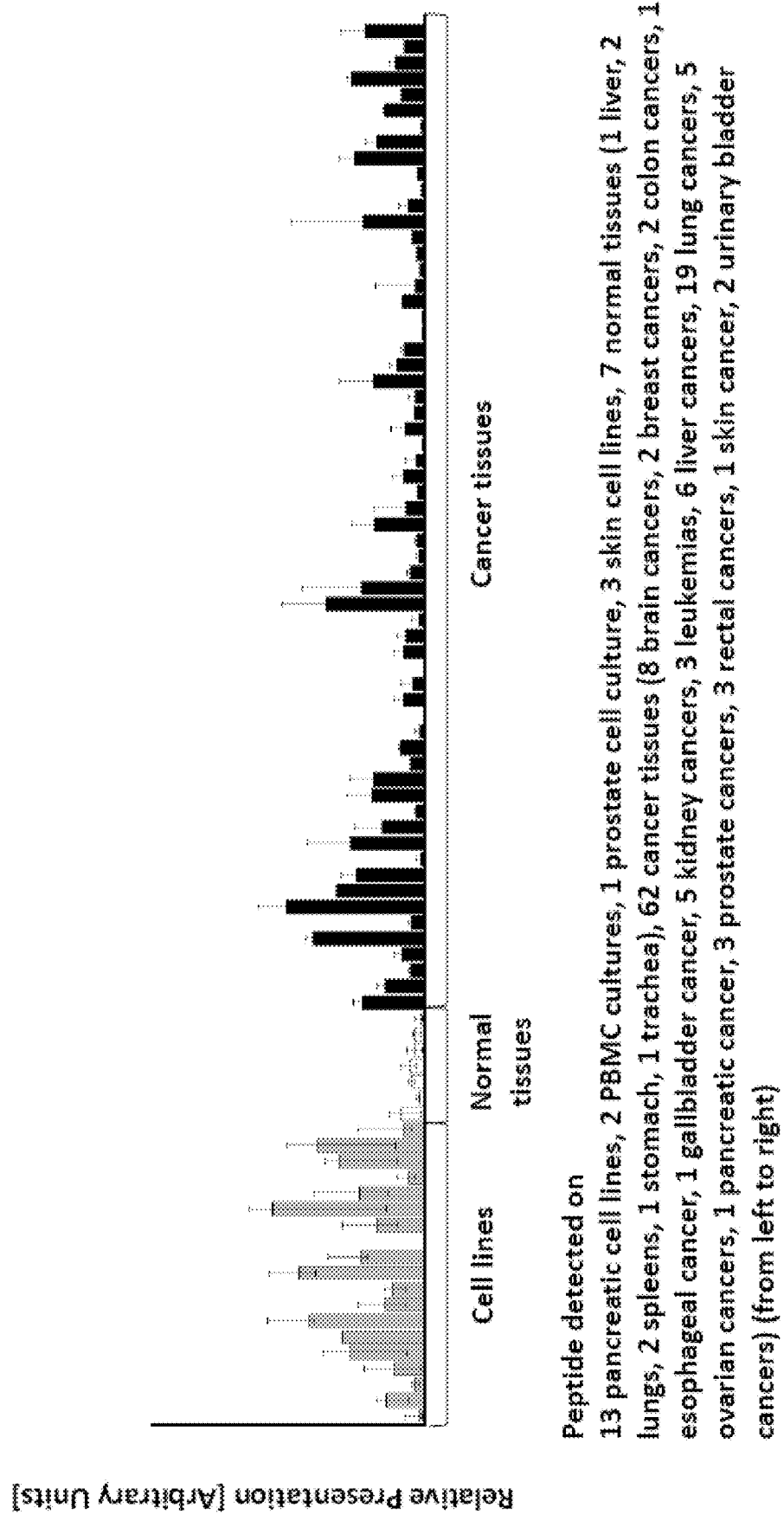

Figure 1D

Peptide: SLMDPNKFLLL (A*02) SEQ ID No. 115

Peptide detected on
13 pancreatic cell lines, 2 PBMC cultures, 1 prostate cell culture, 3 skin cell lines, 7 normal tissues (1 liver, 2 lungs, 2 spleens, 1 stomach, 1 trachea), 62 cancer tissues (8 brain cancers, 2 breast cancers, 2 colon cancers, 1 esophageal cancer, 1 gallbladder cancer, 5 kidney cancers, 3 leukemias, 6 liver cancers, 19 lung cancers, 5 ovarian cancers, 1 pancreatic cancer, 3 prostate cancers, 3 rectal cancers, 1 skin cancer, 2 urinary bladder cancers) (from left to right)

Peptide: ALLTGIISKA (A*02)
Seq ID NO: 5

Figure 1F

Peptide: ALWHDAENQTVV (A*02)

Seq ID NO: 19

Relative Presentation [Arbitrary Units]

20 cIPC samples 383 normal tissues 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases Peptide: ILSTEIFGV (A*02)
Seq ID NO: 22

Peptide: FLNPDEVHAI (A*02)
Seq ID NO: 37

Peptide: TMVEHNYYV (A*02)
Seq ID NO: 46

Peptide: RLSELGITQA (A*02)
Seq ID NO : 57

Figure 1K

Peptide: VLFSGSLRL (A*02)
Seq ID NO: 69

Relative Presentation [Arbitrary Units]

383 normal tissues
6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases 20 clPC samples Peptide: KISTITPQI (A*02)
Seq ID NO: 123

Peptide: ALYDVRTILL (A*02)
Seq ID NO: 128

Peptide: VLISGVVHEI (A*02)
Seq ID NO: 146

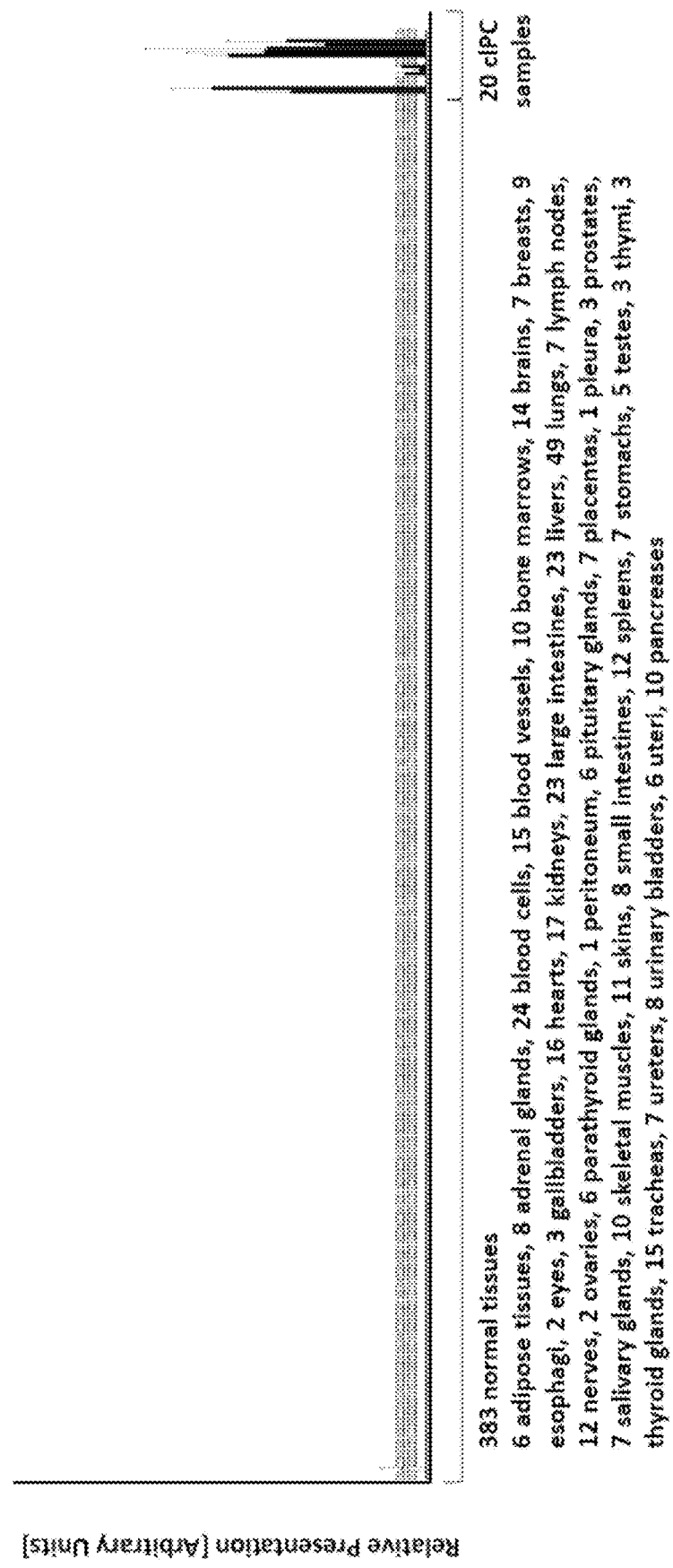

Figure 1P

Peptide: ALVEENGIFEL (A*02)
Seq ID NO: 101

Relative Presentation [Arbitrary Units]

383 normal tissues
6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases 20 cIPC samples Peptide: LMMSEDRISL (A*02)
Seq ID NO: 113

Peptide: ALSDLALHFL (A*02)
Seq ID NO: 127

Peptide: ALLTGIISKA (A*02)
SEQ ID NO: 5

Peptide detected on
12 cancer cell lines, 1 normal tissue (1 spleen), 22 cancer tissues (2 brain cancers, 1 breast cancer, 1 colon cancer, 1 esophageal cancer, 1 head and neck cancer, 1 liver cancer, 8 lung cancers, 1 lymph node cancer, 1 ovarian cancer, 1 rectum cancer, 1 skin cancer, 2 urinary bladder cancers, 1 uterus cancer) (from left to right)

Peptide: ALWHDAENQTVV (A*02)
SEQ ID NO: 19

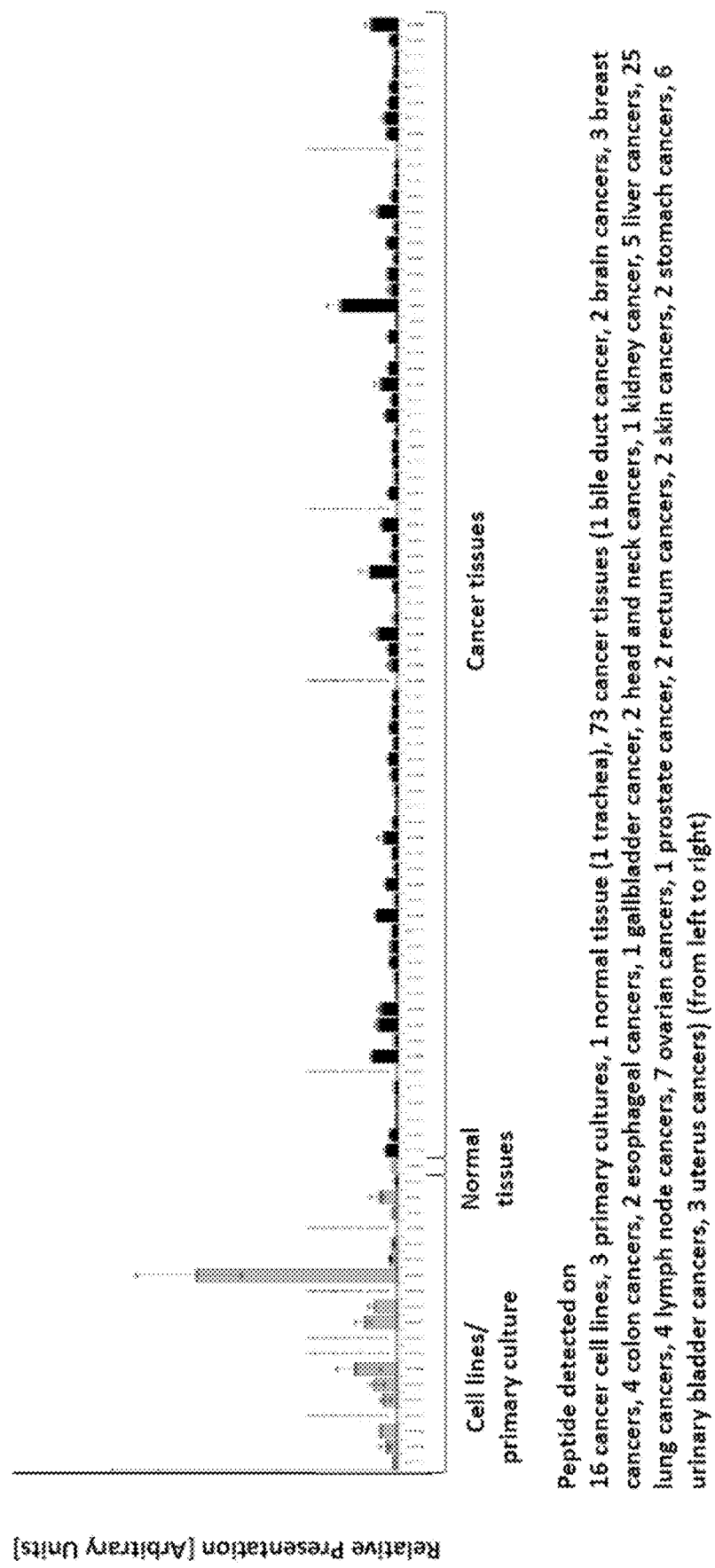

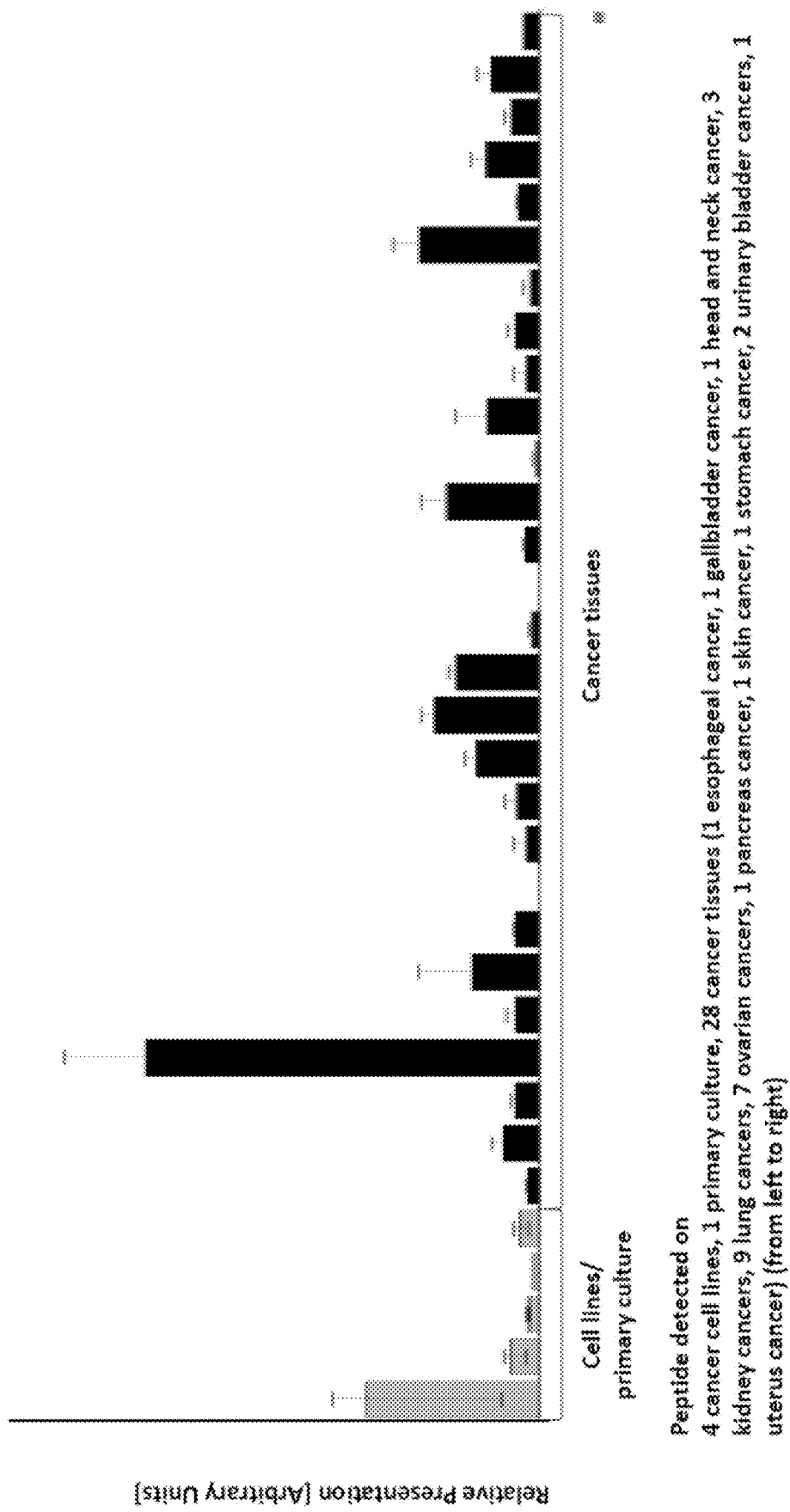

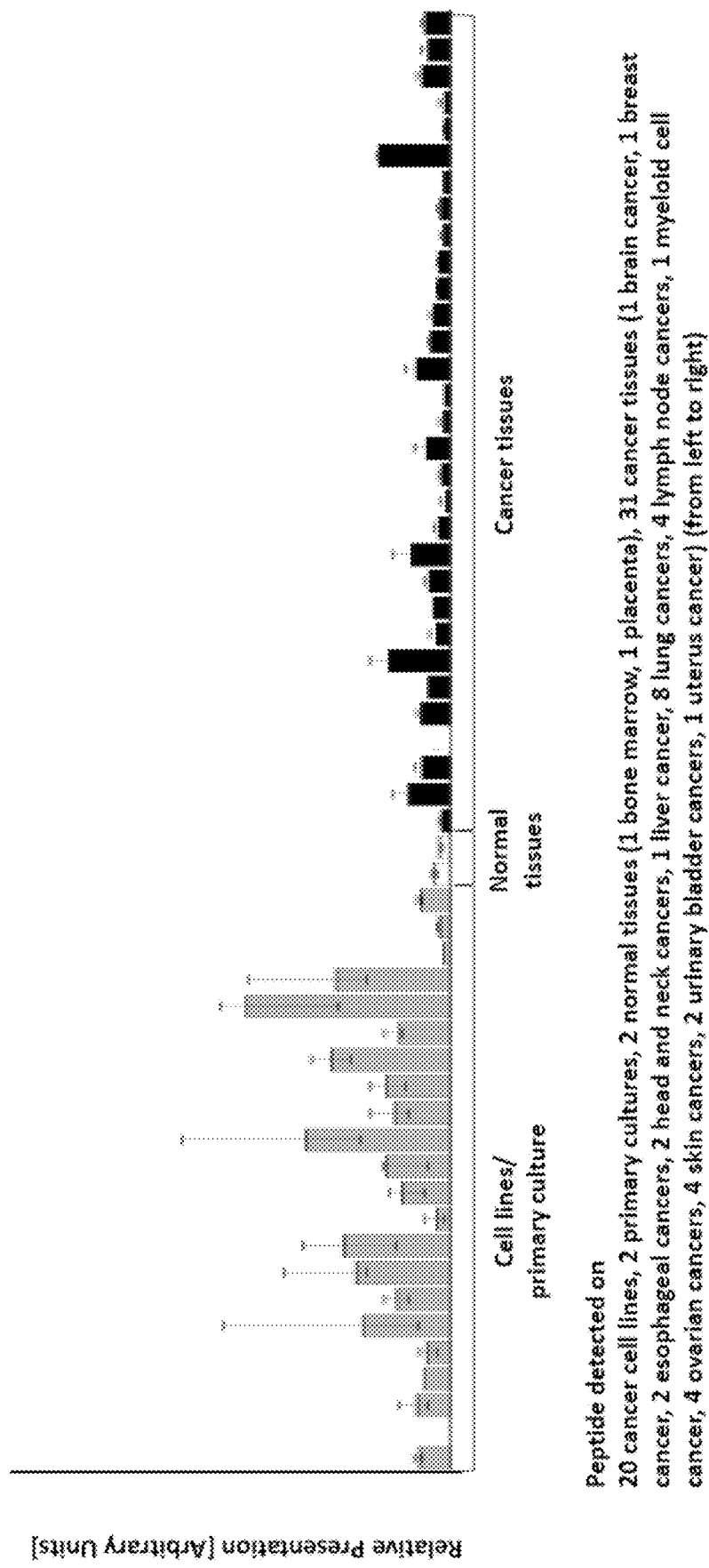

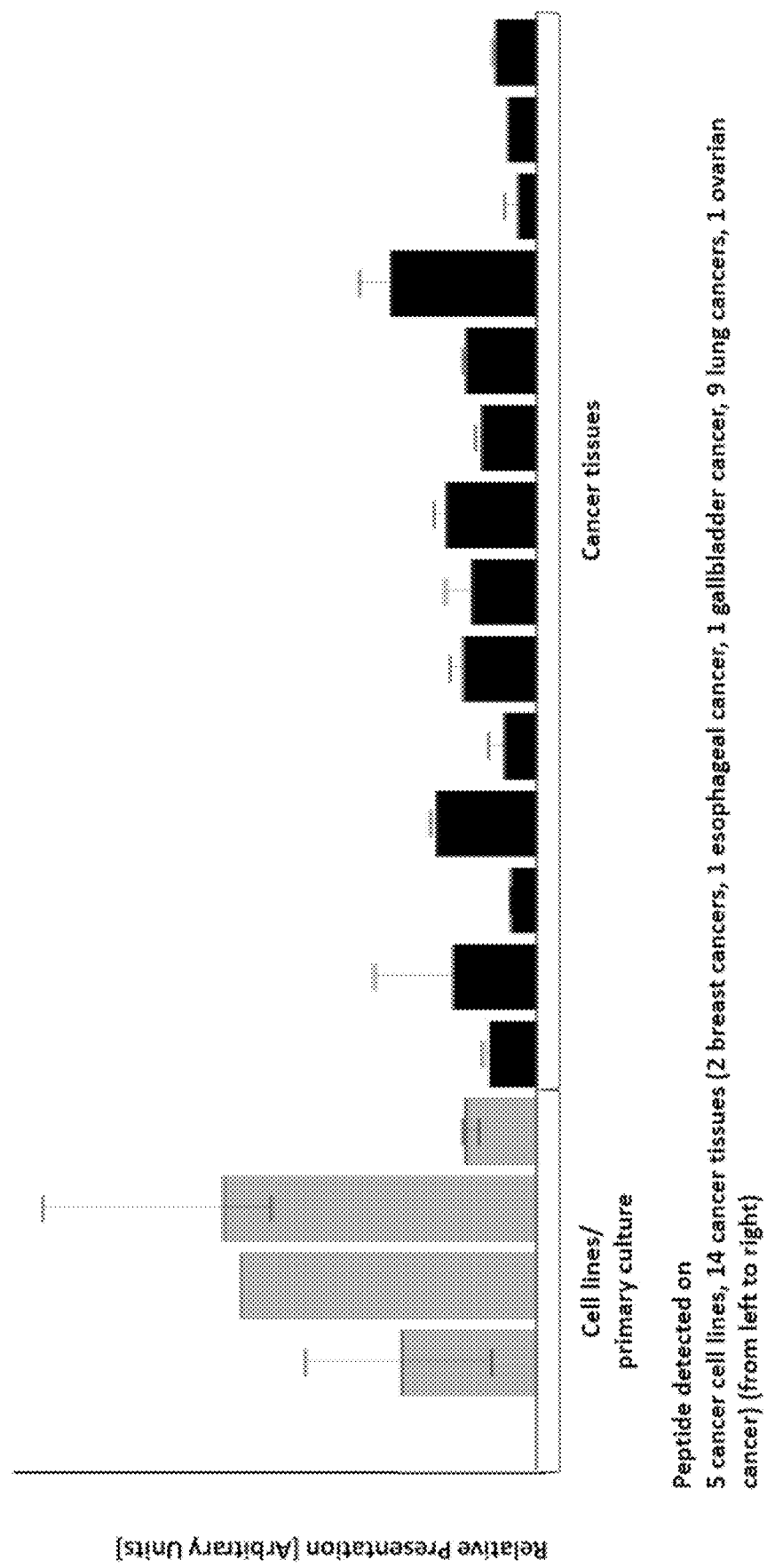

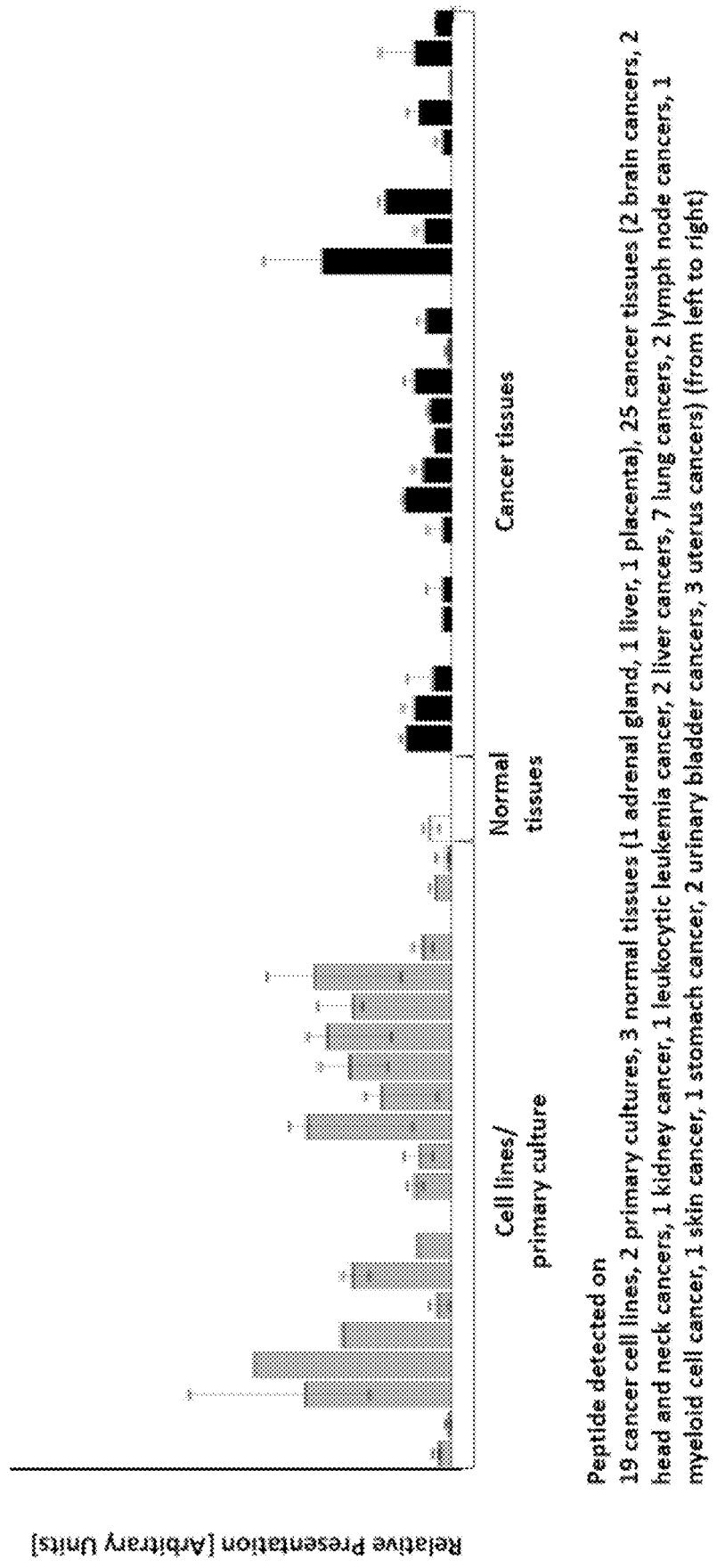

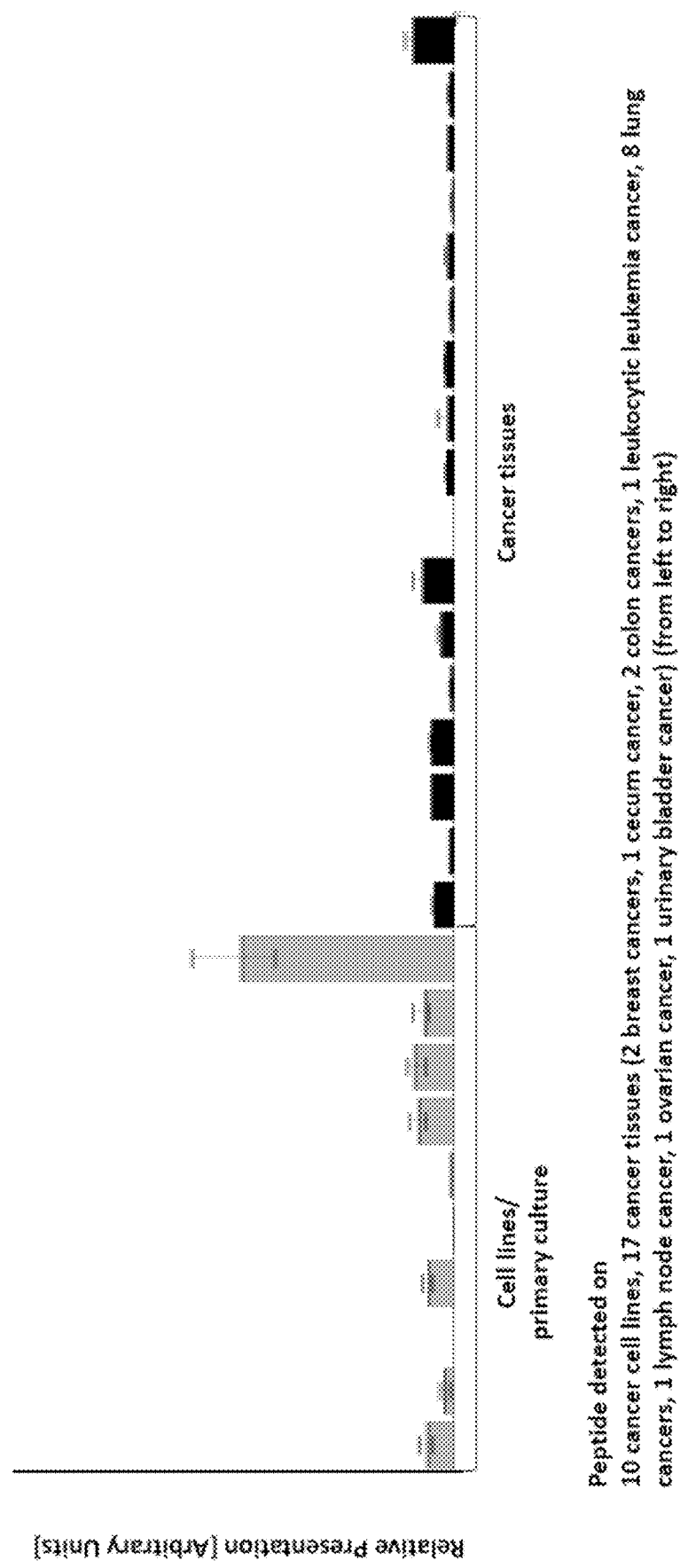

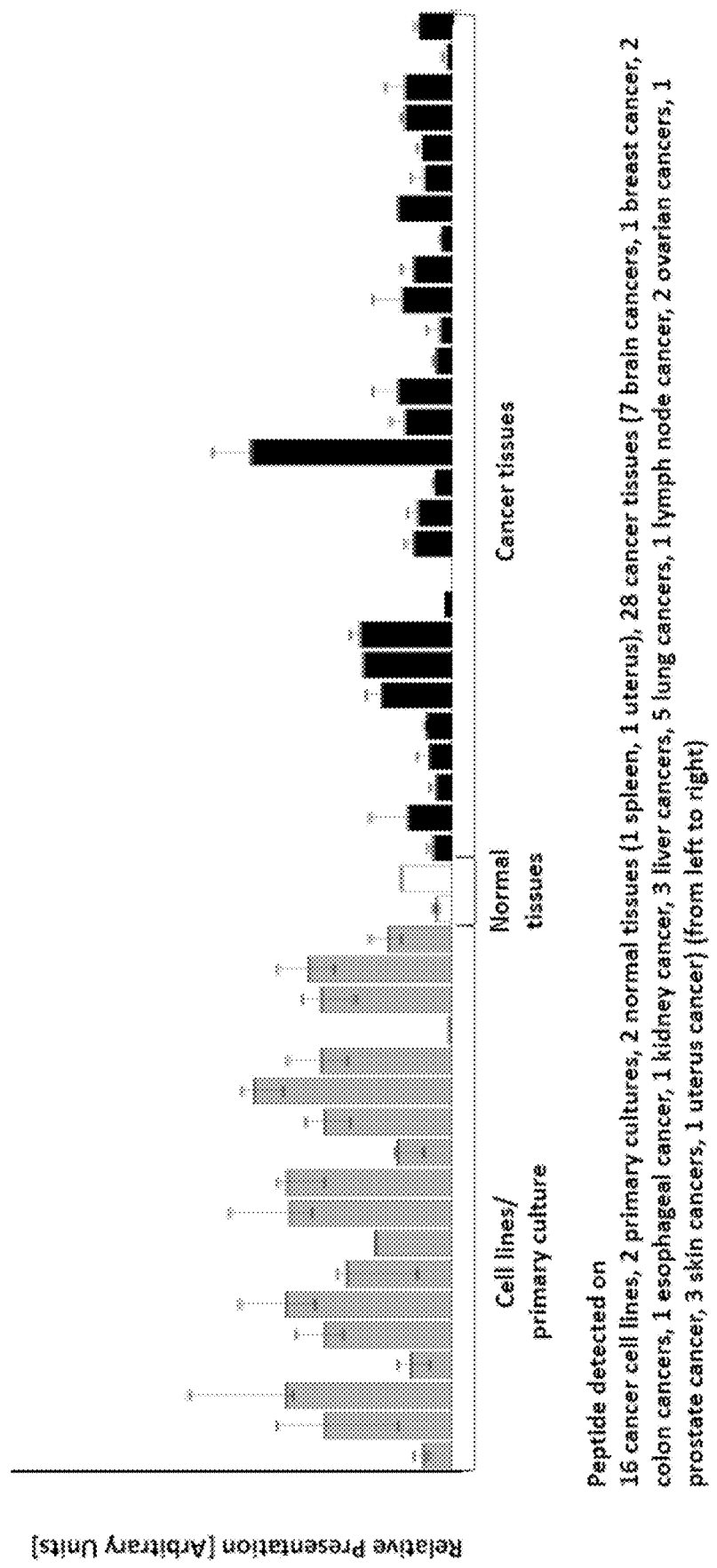

Peptide: KLADIQIEQL (A*02)
SEQ ID NO: 89

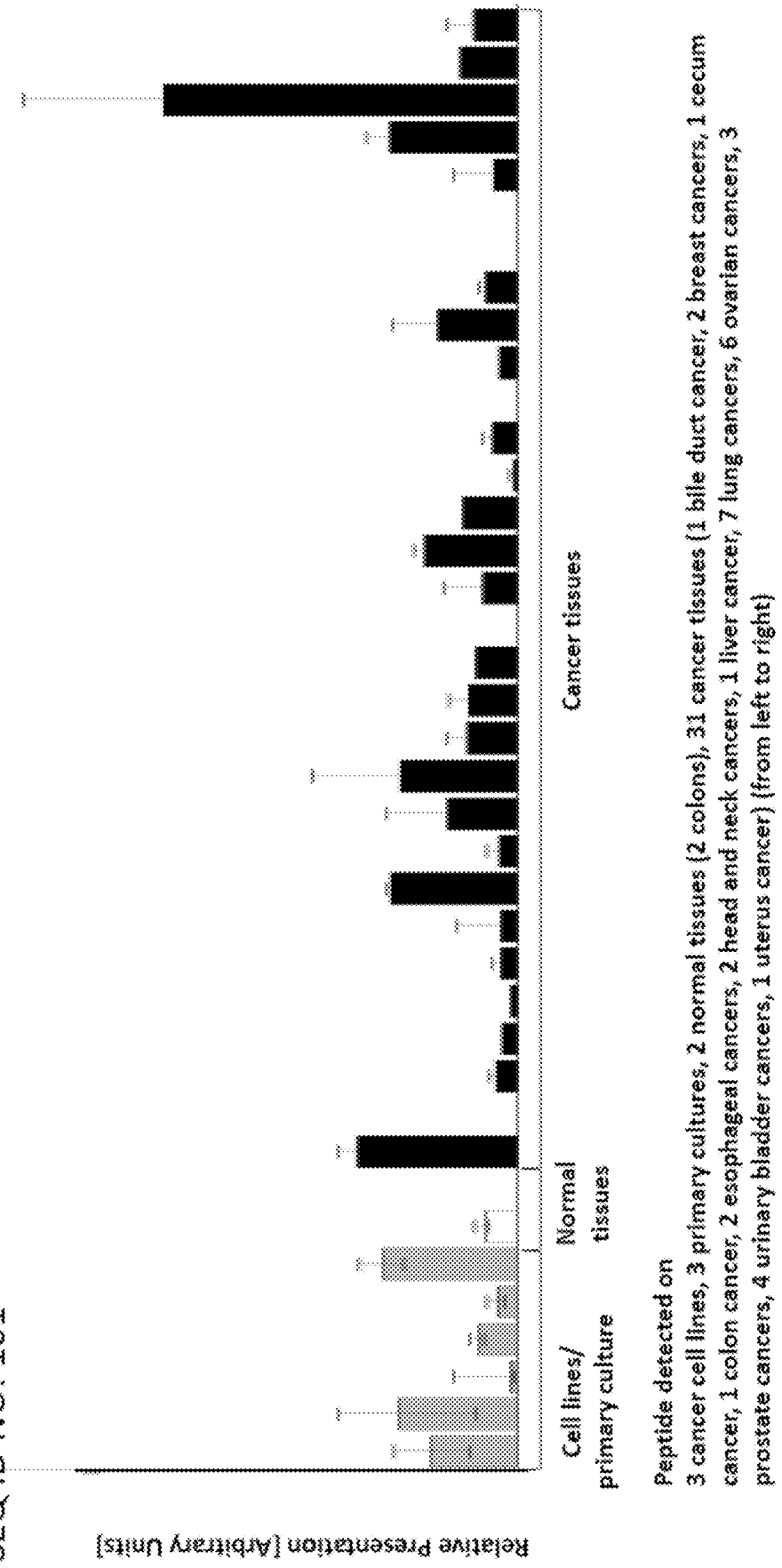

Peptide: LMMSEDRISL (A*02)
SEQ ID NO: 113

Peptide: ALSDLALHFL (A*02)
SEQ ID NO: 127

Gene: FN1

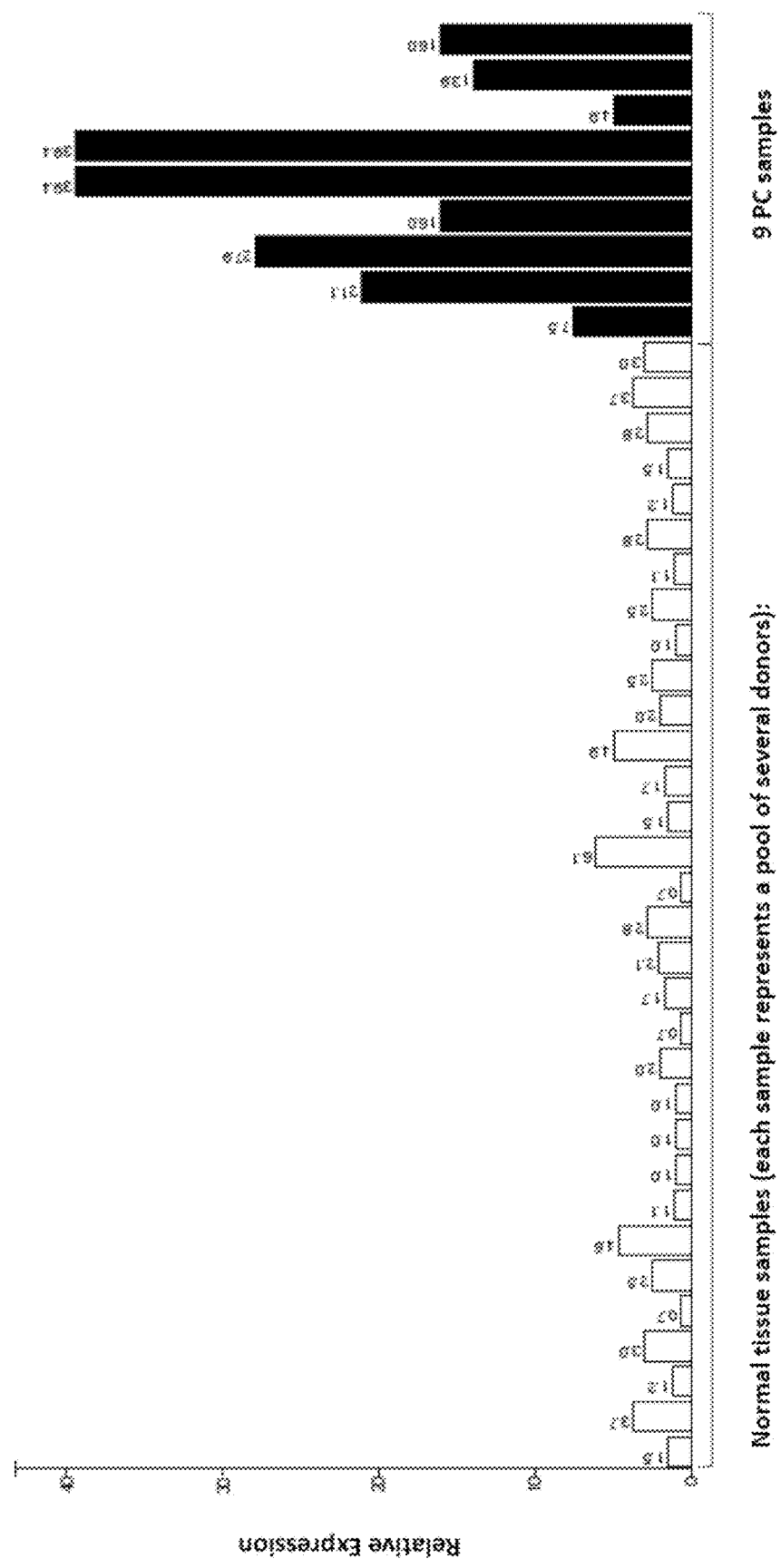

Figure 3C
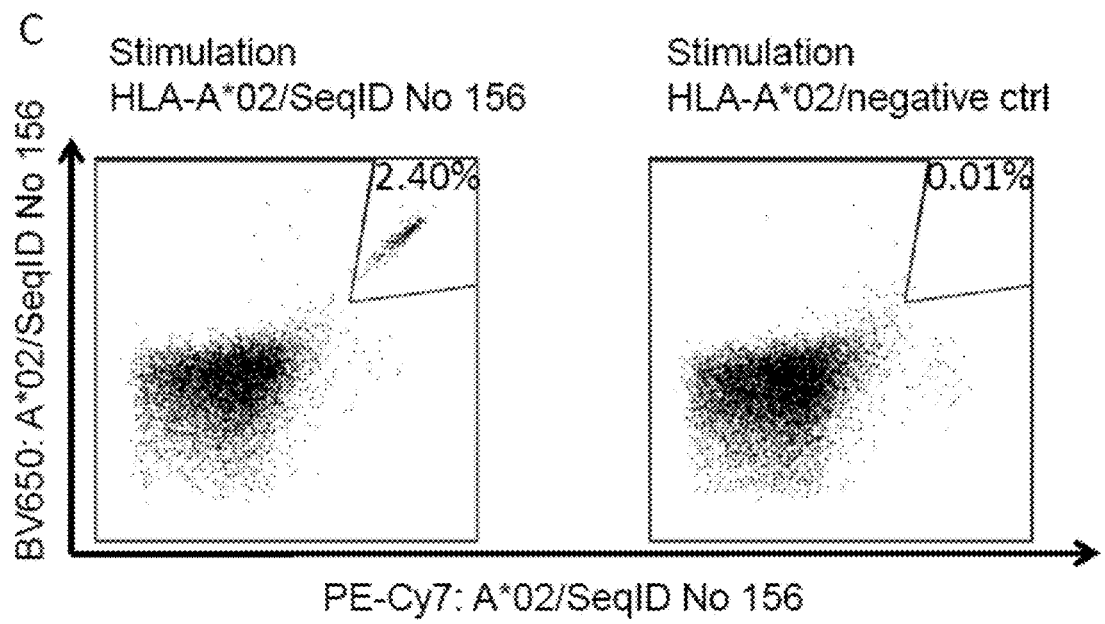
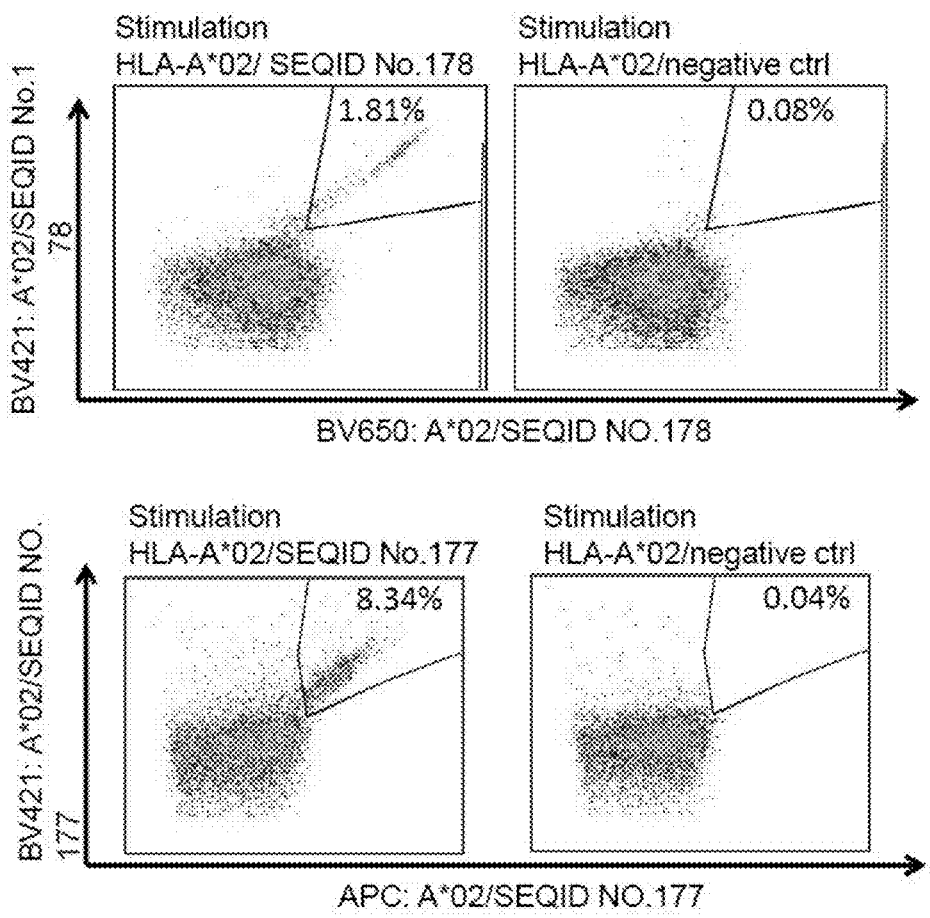
Figure 3D

SEQUENCE LISTING

```
<160> NUMBER OF SEQ ID NOS: 180

<210> SEQ ID NO 1
<211> LENGTH: 8
<212> TYPE: PRT
<213> ORGANISM: Homo sapiens

<400> SEQUENCE: 1

Phe Val Asp Thr Arg Thr Leu Leu
1               5

<210> SEQ ID NO 2
<211> LENGTH: 10
<212> TYPE: PRT
<213> ORGANISM: Homo sapiens

<400> SEQUENCE: 2

Phe Gly Tyr Asp Gly Asp Phe Tyr Arg Ala
1               5                   10

<210> SEQ ID NO 3
<211> LENGTH: 9
<212> TYPE: PRT
<213> ORGANISM: Homo sapiens

<400> SEQUENCE: 3

Ile Leu Ile Gly Glu Thr Ile Lys Ile
1               5

<210> SEQ ID NO 4
<211> LENGTH: 11
<212> TYPE: PRT
<213> ORGANISM: Homo sapiens

<400> SEQUENCE: 4

Ala Leu Asp Pro Ala Ala Gln Ala Phe Leu Leu
1               5                   10

<210> SEQ ID NO 5
<211> LENGTH: 10
<212> TYPE: PRT
<213> ORGANISM: Homo sapiens

<400> SEQUENCE: 5

Ala Leu Leu Thr Gly Ile Ile Ser Lys Ala
1               5                   10

<210> SEQ ID NO 6
<211> LENGTH: 10
<212> TYPE: PRT
<213> ORGANISM: Homo sapiens
```

```
<400> SEQUENCE: 6

Ala Leu Thr Gly Ile Pro Leu Pro Leu Ile
1               5                   10

<210> SEQ ID NO 7
<211> LENGTH: 9
<212> TYPE: PRT
<213> ORGANISM: Homo sapiens

<400> SEQUENCE: 7

Ala Leu Val Asp Ile Val Arg Ser Leu
1               5

<210> SEQ ID NO 8
<211> LENGTH: 11
<212> TYPE: PRT
<213> ORGANISM: Homo sapiens

<400> SEQUENCE: 8

Ala Leu Tyr Thr Gly Ser Ala Leu Asp Phe Val
1               5                   10

<210> SEQ ID NO 9
<211> LENGTH: 9
<212> TYPE: PRT
<213> ORGANISM: Homo sapiens

<400> SEQUENCE: 9

Gln Ile Ile Asp Ala Ile Asn Lys Val
1               5

<210> SEQ ID NO 10
<211> LENGTH: 9
<212> TYPE: PRT
<213> ORGANISM: Homo sapiens

<400> SEQUENCE: 10

Val Leu Leu Asp Lys Ile Lys Asn Leu
1               5

<210> SEQ ID NO 11
<211> LENGTH: 9
<212> TYPE: PRT
<213> ORGANISM: Homo sapiens

<400> SEQUENCE: 11

Ala Leu Tyr Tyr Asn Pro His Leu Leu
1               5

<210> SEQ ID NO 12
<211> LENGTH: 9
<212> TYPE: PRT
<213> ORGANISM: Homo sapiens

<400> SEQUENCE: 12

Ala Gln Tyr Lys Phe Val Tyr Gln Val
1               5

<210> SEQ ID NO 13
<211> LENGTH: 9
<212> TYPE: PRT
<213> ORGANISM: Homo sapiens

<400> SEQUENCE: 13
```

```
Phe Ile Asp Ser Ser Asn Pro Gly Leu
1               5
```

<210> SEQ ID NO 14
<211> LENGTH: 11
<212> TYPE: PRT
<213> ORGANISM: Homo sapiens

<400> SEQUENCE: 14

```
Phe Ile Ile Asp Asn Pro Gln Asp Leu Lys Val
1               5                   10
```

<210> SEQ ID NO 15
<211> LENGTH: 9
<212> TYPE: PRT
<213> ORGANISM: Homo sapiens

<400> SEQUENCE: 15

```
Phe Ile Leu Ala Asn Glu His Asn Val
1               5
```

<210> SEQ ID NO 16
<211> LENGTH: 9
<212> TYPE: PRT
<213> ORGANISM: Homo sapiens

<400> SEQUENCE: 16

```
Gly Leu Ile Asp Tyr Asp Thr Gly Ile
1               5
```

<210> SEQ ID NO 17
<211> LENGTH: 11
<212> TYPE: PRT
<213> ORGANISM: Homo sapiens

<400> SEQUENCE: 17

```
Gly Leu Ile Asp Tyr Asp Thr Gly Ile Arg Leu
1               5                   10
```

<210> SEQ ID NO 18
<211> LENGTH: 9
<212> TYPE: PRT
<213> ORGANISM: Homo sapiens

<400> SEQUENCE: 18

```
Ala Leu Phe Val Arg Leu Leu Ala Leu
1               5
```

<210> SEQ ID NO 19
<211> LENGTH: 12
<212> TYPE: PRT
<213> ORGANISM: Homo sapiens

<400> SEQUENCE: 19

```
Ala Leu Trp His Asp Ala Glu Asn Gln Thr Val Val
1               5                   10
```

<210> SEQ ID NO 20
<211> LENGTH: 11
<212> TYPE: PRT
<213> ORGANISM: Homo sapiens

<400> SEQUENCE: 20

Gly Leu Ile Asp Ile Glu Asn Pro Asn Arg Val

<210> SEQ ID NO 21
<211> LENGTH: 11
<212> TYPE: PRT
<213> ORGANISM: Homo sapiens

<400> SEQUENCE: 21

Gly Leu Val Asp Gly Arg Asp Leu Val Ile Val
1               5                   10

<210> SEQ ID NO 22
<211> LENGTH: 9
<212> TYPE: PRT
<213> ORGANISM: Homo sapiens

<400> SEQUENCE: 22

Ile Leu Ser Thr Glu Ile Phe Gly Val
1               5

<210> SEQ ID NO 23
<211> LENGTH: 11
<212> TYPE: PRT
<213> ORGANISM: Homo sapiens

<400> SEQUENCE: 23

Lys Leu Asp Ser Ser Gly Gly Ala Val Gln Leu
1               5                   10

<210> SEQ ID NO 24
<211> LENGTH: 11
<212> TYPE: PRT
<213> ORGANISM: Homo sapiens

<400> SEQUENCE: 24

Lys Leu Ser Glu Asn Ala Gly Ile Gln Ser Leu
1               5                   10

<210> SEQ ID NO 25
<211> LENGTH: 9
<212> TYPE: PRT
<213> ORGANISM: Homo sapiens

<400> SEQUENCE: 25

Leu Ile Asn Pro Asn Ile Ala Thr Val
1               5

<210> SEQ ID NO 26
<211> LENGTH: 9
<212> TYPE: PRT
<213> ORGANISM: Homo sapiens

<400> SEQUENCE: 26

Ser Leu Tyr Thr Ala Leu Thr Glu Ala
1               5

<210> SEQ ID NO 27
<211> LENGTH: 9
<212> TYPE: PRT
<213> ORGANISM: Homo sapiens

<400> SEQUENCE: 27

Thr Leu Leu Ala His Pro Val Thr Leu
1               5

```
<210> SEQ ID NO 28
<211> LENGTH: 9
<212> TYPE: PRT
<213> ORGANISM: Homo sapiens

<400> SEQUENCE: 28

Val Leu Asp Glu Phe Tyr Ser Ser Leu
1               5

<210> SEQ ID NO 29
<211> LENGTH: 9
<212> TYPE: PRT
<213> ORGANISM: Homo sapiens

<400> SEQUENCE: 29

Tyr Ile Leu Pro Phe Ser Glu Val Leu
1               5

<210> SEQ ID NO 30
<211> LENGTH: 9
<212> TYPE: PRT
<213> ORGANISM: Homo sapiens

<400> SEQUENCE: 30

Tyr Ile Tyr Lys Asp Thr Ile Gln Val
1               5

<210> SEQ ID NO 31
<211> LENGTH: 9
<212> TYPE: PRT
<213> ORGANISM: Homo sapiens

<400> SEQUENCE: 31

Tyr Leu Asp Ser Met Tyr Ile Met Leu
1               5

<210> SEQ ID NO 32
<211> LENGTH: 9
<212> TYPE: PRT
<213> ORGANISM: Homo sapiens

<400> SEQUENCE: 32

Tyr Val Asp Asp Gly Leu Ile Ser Leu
1               5

<210> SEQ ID NO 33
<211> LENGTH: 11
<212> TYPE: PRT
<213> ORGANISM: Homo sapiens

<400> SEQUENCE: 33

Phe Leu Ala Asp Pro Asp Thr Val Asn His Leu
1               5                   10

<210> SEQ ID NO 34
<211> LENGTH: 10
<212> TYPE: PRT
<213> ORGANISM: Homo sapiens

<400> SEQUENCE: 34

Phe Leu Glu Asp Asp Asp Ile Ala Ala Val
1               5                   10

<210> SEQ ID NO 35
```

```
<211> LENGTH: 10
<212> TYPE: PRT
<213> ORGANISM: Homo sapiens

<400> SEQUENCE: 35

Phe Leu Phe Pro Ser Gln Tyr Val Asp Val
1               5                   10

<210> SEQ ID NO 36
<211> LENGTH: 9
<212> TYPE: PRT
<213> ORGANISM: Homo sapiens

<400> SEQUENCE: 36

Phe Leu Gly Asp Leu Ser His Leu Leu
1               5

<210> SEQ ID NO 37
<211> LENGTH: 10
<212> TYPE: PRT
<213> ORGANISM: Homo sapiens

<400> SEQUENCE: 37

Phe Leu Asn Pro Asp Glu Val His Ala Ile
1               5                   10

<210> SEQ ID NO 38
<211> LENGTH: 10
<212> TYPE: PRT
<213> ORGANISM: Homo sapiens

<400> SEQUENCE: 38

Phe Leu Thr Glu Ala Ala Leu Gly Asp Ala
1               5                   10

<210> SEQ ID NO 39
<211> LENGTH: 9
<212> TYPE: PRT
<213> ORGANISM: Homo sapiens

<400> SEQUENCE: 39

Phe Leu Thr Pro Ser Ile Phe Ile Ile
1               5

<210> SEQ ID NO 40
<211> LENGTH: 9
<212> TYPE: PRT
<213> ORGANISM: Homo sapiens

<400> SEQUENCE: 40

Gly Leu Ala Pro Gln Ile His Asp Leu
1               5

<210> SEQ ID NO 41
<211> LENGTH: 11
<212> TYPE: PRT
<213> ORGANISM: Homo sapiens

<400> SEQUENCE: 41

Gly Leu Leu Ala Gly Asn Glu Lys Leu Thr Met
1               5                   10

<210> SEQ ID NO 42
<211> LENGTH: 11
<212> TYPE: PRT
```

```
<213> ORGANISM: Homo sapiens

<400> SEQUENCE: 42

Ile Leu Ser Asp Met Arg Ser Gln Tyr Glu Val
1               5                   10

<210> SEQ ID NO 43
<211> LENGTH: 9
<212> TYPE: PRT
<213> ORGANISM: Homo sapiens

<400> SEQUENCE: 43

His Leu Gly Val Lys Val Phe Ser Val
1               5

<210> SEQ ID NO 44
<211> LENGTH: 9
<212> TYPE: PRT
<213> ORGANISM: Homo sapiens

<400> SEQUENCE: 44

Ile Leu Ala Gln Val Gly Phe Ser Val
1               5

<210> SEQ ID NO 45
<211> LENGTH: 12
<212> TYPE: PRT
<213> ORGANISM: Homo sapiens

<400> SEQUENCE: 45

Ile Leu Tyr Ser Asp Asp Gly Gln Lys Trp Thr Val
1               5                   10

<210> SEQ ID NO 46
<211> LENGTH: 9
<212> TYPE: PRT
<213> ORGANISM: Homo sapiens

<400> SEQUENCE: 46

Thr Met Val Glu His Asn Tyr Tyr Val
1               5

<210> SEQ ID NO 47
<211> LENGTH: 9
<212> TYPE: PRT
<213> ORGANISM: Homo sapiens

<400> SEQUENCE: 47

Leu Ile Tyr Lys Asp Leu Val Ser Val
1               5

<210> SEQ ID NO 48
<211> LENGTH: 10
<212> TYPE: PRT
<213> ORGANISM: Homo sapiens

<400> SEQUENCE: 48

Leu Leu Asp Glu Asn Gly Val Leu Lys Leu
1               5                   10

<210> SEQ ID NO 49
<211> LENGTH: 9
<212> TYPE: PRT
<213> ORGANISM: Homo sapiens
```

<400> SEQUENCE: 49

Leu Leu Asp Gly Phe Pro Arg Thr Val
1               5

<210> SEQ ID NO 50
<211> LENGTH: 10
<212> TYPE: PRT
<213> ORGANISM: Homo sapiens

<400> SEQUENCE: 50

Leu Leu Phe Gly Ser Asp Gly Tyr Tyr Val
1               5                   10

<210> SEQ ID NO 51
<211> LENGTH: 9
<212> TYPE: PRT
<213> ORGANISM: Homo sapiens

<400> SEQUENCE: 51

Leu Leu Gly Pro Ala Gly Ala Arg Ala
1               5

<210> SEQ ID NO 52
<211> LENGTH: 9
<212> TYPE: PRT
<213> ORGANISM: Homo sapiens

<400> SEQUENCE: 52

Leu Leu Ser Asp Pro Ile Pro Glu Val
1               5

<210> SEQ ID NO 53
<211> LENGTH: 11
<212> TYPE: PRT
<213> ORGANISM: Homo sapiens

<400> SEQUENCE: 53

Leu Leu Trp Asp Pro Ser Thr Gly Lys Gln Val
1               5                   10

<210> SEQ ID NO 54
<211> LENGTH: 10
<212> TYPE: PRT
<213> ORGANISM: Homo sapiens

<400> SEQUENCE: 54

Leu Thr Gln Pro Gly Pro Ile Ala Ser Ala
1               5                   10

<210> SEQ ID NO 55
<211> LENGTH: 9
<212> TYPE: PRT
<213> ORGANISM: Homo sapiens

<400> SEQUENCE: 55

Asn Leu Ala Pro Ala Pro Leu Asn Ala
1               5

<210> SEQ ID NO 56
<211> LENGTH: 9
<212> TYPE: PRT
<213> ORGANISM: Homo sapiens

<400> SEQUENCE: 56

```
Asn Leu Ile Gly Val Thr Ala Glu Leu
1               5
```

<210> SEQ ID NO 57
<211> LENGTH: 10
<212> TYPE: PRT
<213> ORGANISM: Homo sapiens

<400> SEQUENCE: 57

```
Arg Leu Ser Glu Leu Gly Ile Thr Gln Ala
1               5                   10
```

<210> SEQ ID NO 58
<211> LENGTH: 10
<212> TYPE: PRT
<213> ORGANISM: Homo sapiens

<400> SEQUENCE: 58

```
Arg Gln Tyr Pro Trp Gly Val Val Gln Val
1               5                   10
```

<210> SEQ ID NO 59
<211> LENGTH: 9
<212> TYPE: PRT
<213> ORGANISM: Homo sapiens

<400> SEQUENCE: 59

```
Ser Leu Ser Glu Ser Phe Phe Met Val
1               5
```

<210> SEQ ID NO 60
<211> LENGTH: 9
<212> TYPE: PRT
<213> ORGANISM: Homo sapiens

<400> SEQUENCE: 60

```
Ser Leu Trp Glu Asp Tyr Pro His Val
1               5
```

<210> SEQ ID NO 61
<211> LENGTH: 9
<212> TYPE: PRT
<213> ORGANISM: Homo sapiens

<400> SEQUENCE: 61

```
Ser Met Tyr Asp Gly Leu Leu Gln Ala
1               5
```

<210> SEQ ID NO 62
<211> LENGTH: 9
<212> TYPE: PRT
<213> ORGANISM: Homo sapiens

<400> SEQUENCE: 62

```
Ser Val Phe Pro Gly Ala Arg Leu Leu
1               5
```

<210> SEQ ID NO 63
<211> LENGTH: 9
<212> TYPE: PRT
<213> ORGANISM: Homo sapiens

<400> SEQUENCE: 63

```
Ser Val Thr Gly Ile Ile Val Gly Val
1               5
```

```
<210> SEQ ID NO 64
<211> LENGTH: 11
<212> TYPE: PRT
<213> ORGANISM: Homo sapiens

<400> SEQUENCE: 64

Thr Leu Phe Ser Glu Pro Lys Phe Ala Gln Val
1               5                   10

<210> SEQ ID NO 65
<211> LENGTH: 9
<212> TYPE: PRT
<213> ORGANISM: Homo sapiens

<400> SEQUENCE: 65

Thr Leu Asn Glu Lys Leu Thr Ala Leu
1               5

<210> SEQ ID NO 66
<211> LENGTH: 10
<212> TYPE: PRT
<213> ORGANISM: Homo sapiens

<400> SEQUENCE: 66

Thr Val Asp Asp Pro Tyr Ala Thr Phe Val
1               5                   10

<210> SEQ ID NO 67
<211> LENGTH: 9
<212> TYPE: PRT
<213> ORGANISM: Homo sapiens

<400> SEQUENCE: 67

Val Ile Trp Gly Thr Asp Val Asn Val
1               5

<210> SEQ ID NO 68
<211> LENGTH: 9
<212> TYPE: PRT
<213> ORGANISM: Homo sapiens

<400> SEQUENCE: 68

Val Leu Phe Asp Val Thr Gly Gln Val
1               5

<210> SEQ ID NO 69
<211> LENGTH: 9
<212> TYPE: PRT
<213> ORGANISM: Homo sapiens

<400> SEQUENCE: 69

Val Leu Phe Ser Gly Ser Leu Arg Leu
1               5

<210> SEQ ID NO 70
<211> LENGTH: 8
<212> TYPE: PRT
<213> ORGANISM: Homo sapiens

<400> SEQUENCE: 70

Val Leu Gly Val Ile Trp Gly Val
1               5
```

```
<210> SEQ ID NO 71
<211> LENGTH: 11
<212> TYPE: PRT
<213> ORGANISM: Homo sapiens

<400> SEQUENCE: 71

Val Leu Leu Pro Glu Gly Gly Ile Thr Ala Ile
1               5                   10

<210> SEQ ID NO 72
<211> LENGTH: 11
<212> TYPE: PRT
<213> ORGANISM: Homo sapiens

<400> SEQUENCE: 72

Val Met Ala Ser Pro Gly Gly Leu Ser Ala Val
1               5                   10

<210> SEQ ID NO 73
<211> LENGTH: 10
<212> TYPE: PRT
<213> ORGANISM: Homo sapiens

<400> SEQUENCE: 73

Val Met Val Asp Gly Lys Pro Val Asn Leu
1               5                   10

<210> SEQ ID NO 74
<211> LENGTH: 9
<212> TYPE: PRT
<213> ORGANISM: Homo sapiens

<400> SEQUENCE: 74

Tyr Ile Asp Lys Asp Leu Glu Tyr Val
1               5

<210> SEQ ID NO 75
<211> LENGTH: 9
<212> TYPE: PRT
<213> ORGANISM: Homo sapiens

<400> SEQUENCE: 75

Phe Ser Phe Val Asp Leu Arg Leu Leu
1               5

<210> SEQ ID NO 76
<211> LENGTH: 11
<212> TYPE: PRT
<213> ORGANISM: Homo sapiens

<400> SEQUENCE: 76

Leu Val Ser Glu Ser Ser Asp Val Leu Pro Lys
1               5                   10

<210> SEQ ID NO 77
<211> LENGTH: 9
<212> TYPE: PRT
<213> ORGANISM: Homo sapiens

<400> SEQUENCE: 77

Arg Leu Phe Pro Gly Ser Ser Phe Leu
1               5

<210> SEQ ID NO 78
<211> LENGTH: 11
```

```
<212> TYPE: PRT
<213> ORGANISM: Homo sapiens

<400> SEQUENCE: 78

Ser Leu Gln Asp Thr Glu Glu Lys Ser Arg Ser
1               5                   10

<210> SEQ ID NO 79
<211> LENGTH: 10
<212> TYPE: PRT
<213> ORGANISM: Homo sapiens

<400> SEQUENCE: 79

Val Val Tyr Glu Gly Gln Leu Ile Ser Ile
1               5                   10

<210> SEQ ID NO 80
<211> LENGTH: 11
<212> TYPE: PRT
<213> ORGANISM: Homo sapiens

<400> SEQUENCE: 80

Leu Leu Pro Gly Thr Glu Tyr Val Val Ser Val
1               5                   10

<210> SEQ ID NO 81
<211> LENGTH: 12
<212> TYPE: PRT
<213> ORGANISM: Homo sapiens

<400> SEQUENCE: 81

Val Val Tyr Asp Asp Ser Thr Gly Leu Ile Arg Leu
1               5                   10

<210> SEQ ID NO 82
<211> LENGTH: 9
<212> TYPE: PRT
<213> ORGANISM: Homo sapiens

<400> SEQUENCE: 82

Ala Leu Ile Ala Glu Gly Ile Ala Leu
1               5

<210> SEQ ID NO 83
<211> LENGTH: 9
<212> TYPE: PRT
<213> ORGANISM: Homo sapiens

<400> SEQUENCE: 83

Ala Leu Ser Lys Glu Ile Tyr Val Ile
1               5

<210> SEQ ID NO 84
<211> LENGTH: 9
<212> TYPE: PRT
<213> ORGANISM: Homo sapiens

<400> SEQUENCE: 84

Phe Ile Leu Pro Ile Gly Ala Thr Val
1               5

<210> SEQ ID NO 85
<211> LENGTH: 10
<212> TYPE: PRT
<213> ORGANISM: Homo sapiens
```

```
<400> SEQUENCE: 85

Phe Leu Ser Asp Gly Thr Ile Ile Ser Val
1               5                   10

<210> SEQ ID NO 86
<211> LENGTH: 10
<212> TYPE: PRT
<213> ORGANISM: Homo sapiens

<400> SEQUENCE: 86

Gly Leu Gly Asp Phe Ile Phe Tyr Ser Val
1               5                   10

<210> SEQ ID NO 87
<211> LENGTH: 9
<212> TYPE: PRT
<213> ORGANISM: Homo sapiens

<400> SEQUENCE: 87

Gly Leu Leu Pro Ala Leu Val Ala Leu
1               5

<210> SEQ ID NO 88
<211> LENGTH: 9
<212> TYPE: PRT
<213> ORGANISM: Homo sapiens

<400> SEQUENCE: 88

Ile Ile Asp Asp Thr Ile Phe Asn Leu
1               5

<210> SEQ ID NO 89
<211> LENGTH: 10
<212> TYPE: PRT
<213> ORGANISM: Homo sapiens

<400> SEQUENCE: 89

Lys Leu Ala Asp Ile Gln Ile Glu Gln Leu
1               5                   10

<210> SEQ ID NO 90
<211> LENGTH: 9
<212> TYPE: PRT
<213> ORGANISM: Homo sapiens

<400> SEQUENCE: 90

Lys Leu Leu Thr Pro Ile Thr Thr Leu
1               5

<210> SEQ ID NO 91
<211> LENGTH: 9
<212> TYPE: PRT
<213> ORGANISM: Homo sapiens

<400> SEQUENCE: 91

Leu Leu Phe Asn Asp Val Gln Thr Leu
1               5

<210> SEQ ID NO 92
<211> LENGTH: 10
<212> TYPE: PRT
<213> ORGANISM: Homo sapiens

<400> SEQUENCE: 92
```

Tyr Leu Thr Asn Glu Gly Ile Ala His Leu
1               5                   10

<210> SEQ ID NO 93
<211> LENGTH: 9
<212> TYPE: PRT
<213> ORGANISM: Homo sapiens

<400> SEQUENCE: 93

Ser Ile Asp Ser Glu Pro Ala Leu Val
1               5

<210> SEQ ID NO 94
<211> LENGTH: 9
<212> TYPE: PRT
<213> ORGANISM: Homo sapiens

<400> SEQUENCE: 94

Val Met Met Glu Glu Phe Val Gln Leu
1               5

<210> SEQ ID NO 95
<211> LENGTH: 10
<212> TYPE: PRT
<213> ORGANISM: Homo sapiens

<400> SEQUENCE: 95

Ala Leu Ala Asp Asp Phe Leu Thr Val
1               5                   10

<210> SEQ ID NO 96
<211> LENGTH: 13
<212> TYPE: PRT
<213> ORGANISM: Homo sapiens

<400> SEQUENCE: 96

Ala Leu Ala Pro Ala Thr Gly Gly Gly Ser Leu Leu Leu
1               5                   10

<210> SEQ ID NO 97
<211> LENGTH: 9
<212> TYPE: PRT
<213> ORGANISM: Homo sapiens

<400> SEQUENCE: 97

Ala Leu Asp Asp Met Ile Ser Thr Leu
1               5

<210> SEQ ID NO 98
<211> LENGTH: 9
<212> TYPE: PRT
<213> ORGANISM: Homo sapiens

<400> SEQUENCE: 98

Ala Leu Asp Gln Lys Val Arg Ser Val
1               5

<210> SEQ ID NO 99
<211> LENGTH: 9
<212> TYPE: PRT
<213> ORGANISM: Homo sapiens

<400> SEQUENCE: 99

Ala Leu Glu Ser Phe Leu Lys Gln Val

<210> SEQ ID NO 100
<211> LENGTH: 10
<212> TYPE: PRT
<213> ORGANISM: Homo sapiens

<400> SEQUENCE: 100

Ala Leu Phe Gly Ala Gly Pro Ala Ser Ile
1               5                   10

<210> SEQ ID NO 101
<211> LENGTH: 11
<212> TYPE: PRT
<213> ORGANISM: Homo sapiens

<400> SEQUENCE: 101

Ala Leu Val Glu Glu Asn Gly Ile Phe Glu Leu
1               5                   10

<210> SEQ ID NO 102
<211> LENGTH: 10
<212> TYPE: PRT
<213> ORGANISM: Homo sapiens

<400> SEQUENCE: 102

Ala Leu Tyr Pro Gly Thr Asp Tyr Thr Val
1               5                   10

<210> SEQ ID NO 103
<211> LENGTH: 9
<212> TYPE: PRT
<213> ORGANISM: Homo sapiens

<400> SEQUENCE: 103

Ala Val Ala Ala Val Leu Thr Gln Val
1               5

<210> SEQ ID NO 104
<211> LENGTH: 9
<212> TYPE: PRT
<213> ORGANISM: Homo sapiens

<400> SEQUENCE: 104

Phe Leu Gln Pro Asp Leu Asp Ser Leu
1               5

<210> SEQ ID NO 105
<211> LENGTH: 9
<212> TYPE: PRT
<213> ORGANISM: Homo sapiens

<400> SEQUENCE: 105

Phe Leu Ser Glu Val Phe His Gln Ala
1               5

<210> SEQ ID NO 106
<211> LENGTH: 9
<212> TYPE: PRT
<213> ORGANISM: Homo sapiens

<400> SEQUENCE: 106

Phe Val Trp Ser Gly Thr Ala Glu Ala
1               5

<210> SEQ ID NO 107
<211> LENGTH: 10
<212> TYPE: PRT
<213> ORGANISM: Homo sapiens

<400> SEQUENCE: 107

Phe Val Tyr Gly Gly Pro Gln Val Gln Leu
1               5                   10

<210> SEQ ID NO 108
<211> LENGTH: 9
<212> TYPE: PRT
<213> ORGANISM: Homo sapiens

<400> SEQUENCE: 108

Ile Ala Asp Gly Gly Phe Thr Glu Leu
1               5

<210> SEQ ID NO 109
<211> LENGTH: 9
<212> TYPE: PRT
<213> ORGANISM: Homo sapiens

<400> SEQUENCE: 109

Ile Leu Ala Ser Val Ile Leu Asn Val
1               5

<210> SEQ ID NO 110
<211> LENGTH: 9
<212> TYPE: PRT
<213> ORGANISM: Homo sapiens

<400> SEQUENCE: 110

Ile Leu Leu Thr Gly Thr Pro Ala Leu
1               5

<210> SEQ ID NO 111
<211> LENGTH: 11
<212> TYPE: PRT
<213> ORGANISM: Homo sapiens

<400> SEQUENCE: 111

Leu Leu Leu Ala Ala Ala Arg Leu Ala Ala Ala
1               5                   10

<210> SEQ ID NO 112
<211> LENGTH: 9
<212> TYPE: PRT
<213> ORGANISM: Homo sapiens

<400> SEQUENCE: 112

Leu Leu Ser Asp Val Arg Phe Val Leu
1               5

<210> SEQ ID NO 113
<211> LENGTH: 10
<212> TYPE: PRT
<213> ORGANISM: Homo sapiens

<400> SEQUENCE: 113

Leu Met Met Ser Glu Asp Arg Ile Ser Leu
1               5                   10

<210> SEQ ID NO 114

```
<211> LENGTH: 10
<212> TYPE: PRT
<213> ORGANISM: Homo sapiens

<400> SEQUENCE: 114

Ser Leu Phe Pro His Asn Pro Gln Phe Ile
1               5                   10

<210> SEQ ID NO 115
<211> LENGTH: 11
<212> TYPE: PRT
<213> ORGANISM: Homo sapiens

<400> SEQUENCE: 115

Ser Leu Met Asp Pro Asn Lys Phe Leu Leu Leu
1               5                   10

<210> SEQ ID NO 116
<211> LENGTH: 9
<212> TYPE: PRT
<213> ORGANISM: Homo sapiens

<400> SEQUENCE: 116

Ser Met Met Asp Pro Asn His Phe Leu
1               5

<210> SEQ ID NO 117
<211> LENGTH: 9
<212> TYPE: PRT
<213> ORGANISM: Homo sapiens

<400> SEQUENCE: 117

Ser Val Asp Gly Val Ile Lys Glu Val
1               5

<210> SEQ ID NO 118
<211> LENGTH: 9
<212> TYPE: PRT
<213> ORGANISM: Homo sapiens

<400> SEQUENCE: 118

Thr Leu Trp Tyr Arg Pro Pro Glu Leu
1               5

<210> SEQ ID NO 119
<211> LENGTH: 11
<212> TYPE: PRT
<213> ORGANISM: Homo sapiens

<400> SEQUENCE: 119

Val Leu Gly Asp Asp Pro Gln Leu Met Lys Val
1               5                   10

<210> SEQ ID NO 120
<211> LENGTH: 9
<212> TYPE: PRT
<213> ORGANISM: Homo sapiens

<400> SEQUENCE: 120

Val Leu Val Asn Asp Phe Phe Leu Val
1               5

<210> SEQ ID NO 121
<211> LENGTH: 10
<212> TYPE: PRT
```

<213> ORGANISM: Homo sapiens

<400> SEQUENCE: 121

Tyr Leu Asp Glu Asp Thr Ile Tyr His Leu
1               5                   10

<210> SEQ ID NO 122
<211> LENGTH: 11
<212> TYPE: PRT
<213> ORGANISM: Homo sapiens

<400> SEQUENCE: 122

Met Gln Ala Pro Arg Ala Ala Leu Val Phe Ala
1               5                   10

<210> SEQ ID NO 123
<211> LENGTH: 9
<212> TYPE: PRT
<213> ORGANISM: Homo sapiens

<400> SEQUENCE: 123

Lys Ile Ser Thr Ile Thr Pro Gln Ile
1               5

<210> SEQ ID NO 124
<211> LENGTH: 11
<212> TYPE: PRT
<213> ORGANISM: Homo sapiens

<400> SEQUENCE: 124

Ala Leu Phe Glu Glu Ser Gly Leu Ile Arg Ile
1               5                   10

<210> SEQ ID NO 125
<211> LENGTH: 11
<212> TYPE: PRT
<213> ORGANISM: Homo sapiens

<400> SEQUENCE: 125

Ala Leu Leu Gly Lys Leu Asp Ala Ile Asn Val
1               5                   10

<210> SEQ ID NO 126
<211> LENGTH: 10
<212> TYPE: PRT
<213> ORGANISM: Homo sapiens

<400> SEQUENCE: 126

Ala Leu Leu Ser Leu Asp Pro Ala Ala Val
1               5                   10

<210> SEQ ID NO 127
<211> LENGTH: 10
<212> TYPE: PRT
<213> ORGANISM: Homo sapiens

<400> SEQUENCE: 127

Ala Leu Ser Asp Leu Ala Leu His Phe Leu
1               5                   10

<210> SEQ ID NO 128
<211> LENGTH: 10
<212> TYPE: PRT
<213> ORGANISM: Homo sapiens

<400> SEQUENCE: 128

Ala Leu Tyr Asp Val Arg Thr Ile Leu Leu
1               5                   10

<210> SEQ ID NO 129
<211> LENGTH: 10
<212> TYPE: PRT
<213> ORGANISM: Homo sapiens

<400> SEQUENCE: 129

Ala Leu Tyr Glu Lys Asp Asn Thr Tyr Leu
1               5                   10

<210> SEQ ID NO 130
<211> LENGTH: 10
<212> TYPE: PRT
<213> ORGANISM: Homo sapiens

<400> SEQUENCE: 130

Phe Leu Phe Gly Glu Glu Pro Ser Lys Leu
1               5                   10

<210> SEQ ID NO 131
<211> LENGTH: 10
<212> TYPE: PRT
<213> ORGANISM: Homo sapiens

<400> SEQUENCE: 131

Phe Leu Ile Glu Glu Gln Lys Ile Val Val
1               5                   10

<210> SEQ ID NO 132
<211> LENGTH: 12
<212> TYPE: PRT
<213> ORGANISM: Homo sapiens

<400> SEQUENCE: 132

Phe Leu Trp Ala Gly Gly Arg Ala Ser Tyr Gly Val
1               5                   10

<210> SEQ ID NO 133
<211> LENGTH: 10
<212> TYPE: PRT
<213> ORGANISM: Homo sapiens

<400> SEQUENCE: 133

Ile Leu Asp Asp Val Ser Leu Thr His Leu
1               5                   10

<210> SEQ ID NO 134
<211> LENGTH: 11
<212> TYPE: PRT
<213> ORGANISM: Homo sapiens

<400> SEQUENCE: 134

Ile Leu Leu Ala Glu Gly Arg Leu Val Asn Leu
1               5                   10

<210> SEQ ID NO 135
<211> LENGTH: 9
<212> TYPE: PRT
<213> ORGANISM: Homo sapiens

<400> SEQUENCE: 135

```
Lys Leu Asp Asp Thr Tyr Ile Lys Ala
1               5
```

<210> SEQ ID NO 136
<211> LENGTH: 11
<212> TYPE: PRT
<213> ORGANISM: Homo sapiens

<400> SEQUENCE: 136

```
Lys Leu Phe Pro Gly Phe Glu Ile Glu Thr Val
1               5                   10
```

<210> SEQ ID NO 137
<211> LENGTH: 9
<212> TYPE: PRT
<213> ORGANISM: Homo sapiens

<400> SEQUENCE: 137

```
Lys Leu Gly Pro Glu Gly Glu Leu Leu
1               5
```

<210> SEQ ID NO 138
<211> LENGTH: 11
<212> TYPE: PRT
<213> ORGANISM: Homo sapiens

<400> SEQUENCE: 138

```
Asn Ile Phe Pro Asn Pro Glu Ala Thr Phe Val
1               5                   10
```

<210> SEQ ID NO 139
<211> LENGTH: 9
<212> TYPE: PRT
<213> ORGANISM: Homo sapiens

<400> SEQUENCE: 139

```
Ser Ile Asp Arg Asn Pro Pro Gln Leu
1               5
```

<210> SEQ ID NO 140
<211> LENGTH: 11
<212> TYPE: PRT
<213> ORGANISM: Homo sapiens

<400> SEQUENCE: 140

```
Ser Leu Leu Asn Pro Pro Glu Thr Leu Asn Leu
1               5                   10
```

<210> SEQ ID NO 141
<211> LENGTH: 9
<212> TYPE: PRT
<213> ORGANISM: Homo sapiens

<400> SEQUENCE: 141

```
Ser Leu Thr Glu Gln Val His Ser Leu
1               5
```

<210> SEQ ID NO 142
<211> LENGTH: 9
<212> TYPE: PRT
<213> ORGANISM: Homo sapiens

<400> SEQUENCE: 142

```
Ser Leu Tyr Gly Tyr Leu Arg Gly Ala
1               5
```

```
<210> SEQ ID NO 143
<211> LENGTH: 9
<212> TYPE: PRT
<213> ORGANISM: Homo sapiens

<400> SEQUENCE: 143

Thr Ala Asp Pro Leu Asp Tyr Arg Leu
1               5

<210> SEQ ID NO 144
<211> LENGTH: 9
<212> TYPE: PRT
<213> ORGANISM: Homo sapiens

<400> SEQUENCE: 144

Thr Ala Val Ala Leu Leu Arg Leu Leu
1               5

<210> SEQ ID NO 145
<211> LENGTH: 9
<212> TYPE: PRT
<213> ORGANISM: Homo sapiens

<400> SEQUENCE: 145

Thr Thr Phe Pro Arg Pro Val Thr Val
1               5

<210> SEQ ID NO 146
<211> LENGTH: 10
<212> TYPE: PRT
<213> ORGANISM: Homo sapiens

<400> SEQUENCE: 146

Val Leu Ile Ser Gly Val Val His Glu Ile
1               5                   10

<210> SEQ ID NO 147
<211> LENGTH: 9
<212> TYPE: PRT
<213> ORGANISM: Homo sapiens

<400> SEQUENCE: 147

Tyr Ala Phe Pro Lys Ala Val Ser Val
1               5

<210> SEQ ID NO 148
<211> LENGTH: 9
<212> TYPE: PRT
<213> ORGANISM: Homo sapiens

<400> SEQUENCE: 148

Tyr Leu His Asn Gln Gly Ile Gly Val
1               5

<210> SEQ ID NO 149
<211> LENGTH: 11
<212> TYPE: PRT
<213> ORGANISM: Homo sapiens

<400> SEQUENCE: 149

Ile Leu Gly Thr Glu Asp Leu Ile Val Glu Val
1               5                   10
```

-continued

```
<210> SEQ ID NO 150
<211> LENGTH: 10
<212> TYPE: PRT
<213> ORGANISM: Homo sapiens

<400> SEQUENCE: 150

Ala Leu Phe Gln Pro His Leu Ile Asn Val
1               5                   10

<210> SEQ ID NO 151
<211> LENGTH: 9
<212> TYPE: PRT
<213> ORGANISM: Homo sapiens

<400> SEQUENCE: 151

Ala Leu Leu Asp Ile Ile Arg Ser Leu
1               5

<210> SEQ ID NO 152
<211> LENGTH: 11
<212> TYPE: PRT
<213> ORGANISM: Homo sapiens

<400> SEQUENCE: 152

Ala Leu Leu Glu Pro Glu Phe Ile Leu Lys Ala
1               5                   10

<210> SEQ ID NO 153
<211> LENGTH: 10
<212> TYPE: PRT
<213> ORGANISM: Homo sapiens

<400> SEQUENCE: 153

Ala Leu Pro Lys Glu Asp Pro Thr Ala Val
1               5                   10

<210> SEQ ID NO 154
<211> LENGTH: 9
<212> TYPE: PRT
<213> ORGANISM: Homo sapiens

<400> SEQUENCE: 154

Lys Val Ala Asp Leu Val Leu Met Leu
1               5

<210> SEQ ID NO 155
<211> LENGTH: 12
<212> TYPE: PRT
<213> ORGANISM: Homo sapiens

<400> SEQUENCE: 155

Leu Leu Leu Asp Pro Asp Thr Ala Val Leu Lys Leu
1               5                   10

<210> SEQ ID NO 156
<211> LENGTH: 10
<212> TYPE: PRT
<213> ORGANISM: Homo sapiens

<400> SEQUENCE: 156

Leu Leu Leu Pro Pro Pro Cys Pro Ala
1               5                   10

<210> SEQ ID NO 157
<211> LENGTH: 10
```

```
<212> TYPE: PRT
<213> ORGANISM: Homo sapiens

<400> SEQUENCE: 157

Met Leu Leu Glu Ile Pro Tyr Met Ala Ala
1               5                   10

<210> SEQ ID NO 158
<211> LENGTH: 9
<212> TYPE: PRT
<213> ORGANISM: Homo sapiens

<400> SEQUENCE: 158

Ser Leu Ile Glu Lys Tyr Phe Ser Val
1               5

<210> SEQ ID NO 159
<211> LENGTH: 9
<212> TYPE: PRT
<213> ORGANISM: Homo sapiens

<400> SEQUENCE: 159

Ser Leu Leu Asp Leu His Thr Lys Val
1               5

<210> SEQ ID NO 160
<211> LENGTH: 11
<212> TYPE: PRT
<213> ORGANISM: Homo sapiens

<400> SEQUENCE: 160

Val Leu Leu Pro Asp Glu Arg Thr Ile Ser Leu
1               5                   10

<210> SEQ ID NO 161
<211> LENGTH: 11
<212> TYPE: PRT
<213> ORGANISM: Homo sapiens

<400> SEQUENCE: 161

Tyr Leu Pro Asp Ile Ile Lys Asp Gln Lys Ala
1               5                   10

<210> SEQ ID NO 162
<211> LENGTH: 9
<212> TYPE: PRT
<213> ORGANISM: Homo sapiens

<400> SEQUENCE: 162

Asn Ala Asp Pro Gln Ala Val Thr Met
1               5

<210> SEQ ID NO 163
<211> LENGTH: 9
<212> TYPE: PRT
<213> ORGANISM: Homo sapiens

<400> SEQUENCE: 163

Val Met Ala Pro Arg Thr Leu Val Leu
1               5

<210> SEQ ID NO 164
<211> LENGTH: 9
<212> TYPE: PRT
<213> ORGANISM: Homo sapiens
```

```
<400> SEQUENCE: 164

Tyr Leu Gly Arg Leu Ala His Glu Val
1               5

<210> SEQ ID NO 165
<211> LENGTH: 9
<212> TYPE: PRT
<213> ORGANISM: Homo sapiens

<400> SEQUENCE: 165

Tyr Leu Leu Ser Tyr Ile Gln Ser Ile
1               5

<210> SEQ ID NO 166
<211> LENGTH: 9
<212> TYPE: PRT
<213> ORGANISM: Homo sapiens

<400> SEQUENCE: 166

Ser Leu Phe Pro Gly Gln Val Val Ile
1               5

<210> SEQ ID NO 167
<211> LENGTH: 11
<212> TYPE: PRT
<213> ORGANISM: Homo sapiens

<400> SEQUENCE: 167

Met Leu Phe Gly His Pro Leu Leu Val Ser Val
1               5                   10

<210> SEQ ID NO 168
<211> LENGTH: 11
<212> TYPE: PRT
<213> ORGANISM: Homo sapiens

<400> SEQUENCE: 168

Ser Glu Trp Gly Ser Pro His Ala Ala Val Pro
1               5                   10

<210> SEQ ID NO 169
<211> LENGTH: 9
<212> TYPE: PRT
<213> ORGANISM: Homo sapiens

<400> SEQUENCE: 169

Phe Met Leu Pro Asp Pro Gln Asn Ile
1               5

<210> SEQ ID NO 170
<211> LENGTH: 11
<212> TYPE: PRT
<213> ORGANISM: Homo sapiens

<400> SEQUENCE: 170

Ile Leu Ala Pro Ala Gly Ser Leu Pro Lys Ile
1               5                   10

<210> SEQ ID NO 171
<211> LENGTH: 10
<212> TYPE: PRT
<213> ORGANISM: Homo sapiens

<400> SEQUENCE: 171
```

Leu Leu Leu Asp Val Thr Pro Leu Ser Leu
1               5                   10

<210> SEQ ID NO 172
<211> LENGTH: 9
<212> TYPE: PRT
<213> ORGANISM: Homo sapiens

<400> SEQUENCE: 172

Thr Met Met Ser Arg Pro Pro Val Leu
1               5

<210> SEQ ID NO 173
<211> LENGTH: 11
<212> TYPE: PRT
<213> ORGANISM: Homo sapiens

<400> SEQUENCE: 173

Ser Leu Ala Gly Asp Val Ala Leu Gln Gln Leu
1               5                   10

<210> SEQ ID NO 174
<211> LENGTH: 9
<212> TYPE: PRT
<213> ORGANISM: Homo sapiens

<400> SEQUENCE: 174

Thr Leu Asp Pro Arg Ser Phe Leu Leu
1               5

<210> SEQ ID NO 175
<211> LENGTH: 10
<212> TYPE: PRT
<213> ORGANISM: Homo sapiens

<400> SEQUENCE: 175

Ala Leu Leu Glu Ser Ser Leu Arg Gln Ala
1               5                   10

<210> SEQ ID NO 176
<211> LENGTH: 9
<212> TYPE: PRT
<213> ORGANISM: Homo sapiens

<400> SEQUENCE: 176

Tyr Leu Met Pro Gly Phe Ile His Leu
1               5

<210> SEQ ID NO 177
<211> LENGTH: 9
<212> TYPE: PRT
<213> ORGANISM: Homo sapiens

<400> SEQUENCE: 177

Ser Leu Tyr Lys Gly Leu Leu Ser Val
1               5

<210> SEQ ID NO 178
<211> LENGTH: 9
<212> TYPE: PRT
<213> ORGANISM: Homo sapiens

<400> SEQUENCE: 178

Lys Ile Gln Glu Ile Leu Thr Gln Val

```
<210> SEQ ID NO 179
<211> LENGTH: 10
<212> TYPE: PRT
<213> ORGANISM: Homo sapiens

<400> SEQUENCE: 179

Glu Leu Ala Gly Ile Gly Ile Leu Thr Val
1               5                   10

<210> SEQ ID NO 180
<211> LENGTH: 9
<212> TYPE: PRT
<213> ORGANISM: Homo sapiens

<400> SEQUENCE: 180

Tyr Leu Leu Pro Ala Ile Val His Ile
1               5
```

PEPTIDES AND COMBINATION OF PEPTIDES FOR USE IN IMMUNOTHERAPY AND METHODS FOR GENERATING SCAFFOLDS FOR THE USE AGAINST PANCREATIC CANCER AND OTHER CANCERS

CROSS REFERENCE TO RELATED APPLICATIONS

This application is a continuation of Ser. No. 15/185,990, filed Jun. 17, 2016, which claims the benefit of U.S. Provisional Application Ser. No. 62/182,026, filed Jun. 19, 2015, and claims priority from GB 1510771.7, filed Jun. 19, 2015, the content of each these applications is herein incorporated by reference in their entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-048002_SEQ_LIST.txt," created on May 21, 2018, and 28,596 bytes in size) is submitted concurrently with the instant application, and the entire contents of the Sequence Listing are incorporated herein by reference.

FIELD OF THE INVENTION

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Pancreatic cancer is one of the most aggressive and deadly cancers in the world. In 2012, it was the $12^{th}$ most common cancer in men with 178,000 cases and the $11^{th}$ most common cancer in women with 160,000 cases worldwide. In the same year, 330,000 deaths were reported, making pancreatic cancer the seventh most common cause of death from cancer (World Cancer Report, 2014).

Pancreatic cancer is not one single cancer entity, but several distinct subtypes have to be distinguished. Exocrine tumors account for approximately 95% of all pancreatic cancers and include ductal and acinary adenocarcinomas, intraductal papillary mucinous neoplasms (IPMN), solid pseudopapillary neoplasms, mucinous cystic adenomas and serous cystadenomas. The remaining 5% of all pancreatic cancers belong to the subgroup of pancreatic neuroendocrine tumors (World Cancer Report, 2014).

Infiltrating ductal adenocarcinoma represents the most aggressive form of pancreatic cancer and due to its high frequency (90% of all pancreatic cancers), epidemiologic data mainly reflect this specific subtype (World Cancer Report, 2014).

In 2012, 68% of all new cases occurred in developed countries, with highest incidence rates in central and Eastern Europe, North America, Argentina, Uruguay and Australia. In contrast, most countries in Africa and East Asia display low incidence rates. Globally, incidence rates appear to be rather stable over time in both genders (World Cancer Report, 2014).

Due to a lack of specific symptoms, pancreatic cancer is typically diagnosed at an advanced and often already metastatic stage. The prognosis upon diagnosis is very poor, with a 5 years survival rate of 5% and a mortality-to-incidence ratio of 0.98 (World Cancer Report, 2014).

Several factors have been reported to increase the risk to develop pancreatic cancer, including older age, as most patients are older than 65 years at diagnosis, and race, as in the USA the Black population has a 1.5-fold increased risk compared to the White population. Further risk factors are cigarette smoking, body fatness, diabetes, non-0 AB0 blood type, pancreatitis and a familial history of pancreatic cancer (World Cancer Report, 2014).

Up to 10% of all pancreatic cancer cases are thought to have a familial basis. Germline mutations in the following genes are associated with an increased risk to develop pancreatic cancer: p16/CDKN2A, BRCA2, PALB2, PRSS1, STK11, ATM and DNA mismatch repair genes. Additionally, the sporadic cases of pancreatic cancer are also characterized by mutations in different oncogenes and tumor suppressor genes. The most common mutations in ductal adenocarcinoma occur within the oncogenes KRAS (95%) and AIB1 (up to 60%) and the tumor suppressor genes TP53 (75%), p16/CDKN2A (95%) and SMAD4 (55%) (World Cancer Report, 2014).

Therapeutic options for pancreatic cancer patients are very limited. One major problem for effective treatment is the typically advanced tumor stage at diagnosis. Additionally, pancreatic cancer is rather resistant to chemotherapeutics, which might be caused by the dense and hypovascular desmoplastic tumor stroma.

According to the guidelines released by the German Cancer Society, the German Cancer Aid and the Association of the Scientific Medical Societies in Germany, resection of the tumor is the only available curative treatment option. Resection is recommended if the tumor is restricted to the pancreas or if metastases are limited to adjacent organs. Resection is not recommended if the tumor has spread to distant sites. Resection is followed by adjuvant chemotherapy with gemcitabine or 5-fluorouracil+/−leucovorin for six months (S3-Leitlinie Exokrines Pankreaskarzinom, 2013).

Patients with inoperable tumors in advanced stage can be treated with a combination of chemotherapy with radiation-chemotherapy (S3-Leitlinie Exokrines Pankreaskarzinom, 2013).

The standard regimen for palliative chemotherapy is gemcitabine, either as monotherapy or in combination with the EGF receptor tyrosine kinase inhibitor erlotinib. Alternative options are a combination of 5-fluorouracil, leucovorin, irinotecan and oxaliplatin, also known as FOLFIRINOX protocol or the combination of gemcitabine with nab-paclitaxel, which was shown to have superior effects compared to gemcitabine monotherapy in the MPACT study (Von Hoff et al., 2013; S3-Leitlinie Exokrines Pankreaskarzinom, 2013).

The high mortality-to-incidence ratio reflects the urgent need to implement more effective therapeutic strategies in pancreatic cancer.

Targeted therapies, which have already been shown to be efficient in several other cancer entities, represent an interesting option. Therefore, several studies have been performed to evaluate the benefit of targeted therapies in advanced pancreatic cancers, unfortunately with very limited success (Walker and Ko, 2014). Nevertheless, the genetic diversity of pancreatic cancer might offer the possibility of personalized therapy, as invasive ductal adenocarcinoma with bi-allelic inactivation of BRCA2 or PALB2 was shown to be more sensitive to poly (ADP-ribose) polymerase inhibitors and mitomycin C treatment (World Cancer Report, 2014).

Targeting the tumor stroma constitutes an alternative approach to develop new treatments for pancreatic cancer. The typically dense and hypovascular stroma might function as barrier for chemotherapeutics and was shown to deliver signals that promote tumor proliferation, invasion and cancer stem cell maintenance. Thus, different preclinical and clinical studies were designed to analyze the effect of stromal depletion and inactivation (Rucki and Zheng, 2014).

Vaccination strategies are investigated as further innovative and promising alternative for the treatment of pancreatic cancer. Peptide-based vaccines targeting KRAS mutations, reactive telomerase, gastrin, survivin, CEA and MUC1 have already been evaluated in clinical trials, partially with promising results. Furthermore, clinical trials for dendritic cell-based vaccines, allogeneic GM-CSF-secreting vaccines and algenpantucel-L in pancreatic cancer patients also revealed beneficial effects of immunotherapy. Additional clinical trials further investigating the efficiency of different vaccination protocols are currently ongoing (Salman et al., 2013).

Considering the severe side-effects and expense associated with treating cancer, there is a need to identify factors that can be used in the treatment of cancer in general and pancreatic cancer in particular. There is also a need to identify factors representing biomarkers for cancer in general and pancreatic cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-Helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-Class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 161 or a variant sequence thereof which is at least 77%, preferably at least 88%, homologous (preferably at least 77% or at least 88% identical) to SEQ ID NO: 1 to SEQ ID NO: 161, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 161 or a variant thereof, which is at least 77%, preferably at least 88%, homologous (preferably at least 77% or at least 88% identical) to SEQ ID NO: 1 to SEQ ID NO: 161, wherein said peptide or variant thereof has an overall length of between 8 and 100, preferably between 8 and 30, and most preferred of between 8 and 14 amino acids.

BRIEF DESCRIPTION OF THE DRAWINGS

FIGS. 2A-2C depict embodiments as described herein.
FIGS. 3A-3D depict embodiments as described herein.

DETAILED DESCRIPTION OF A PREFERRED EMBODIMENT

Figure 1A:
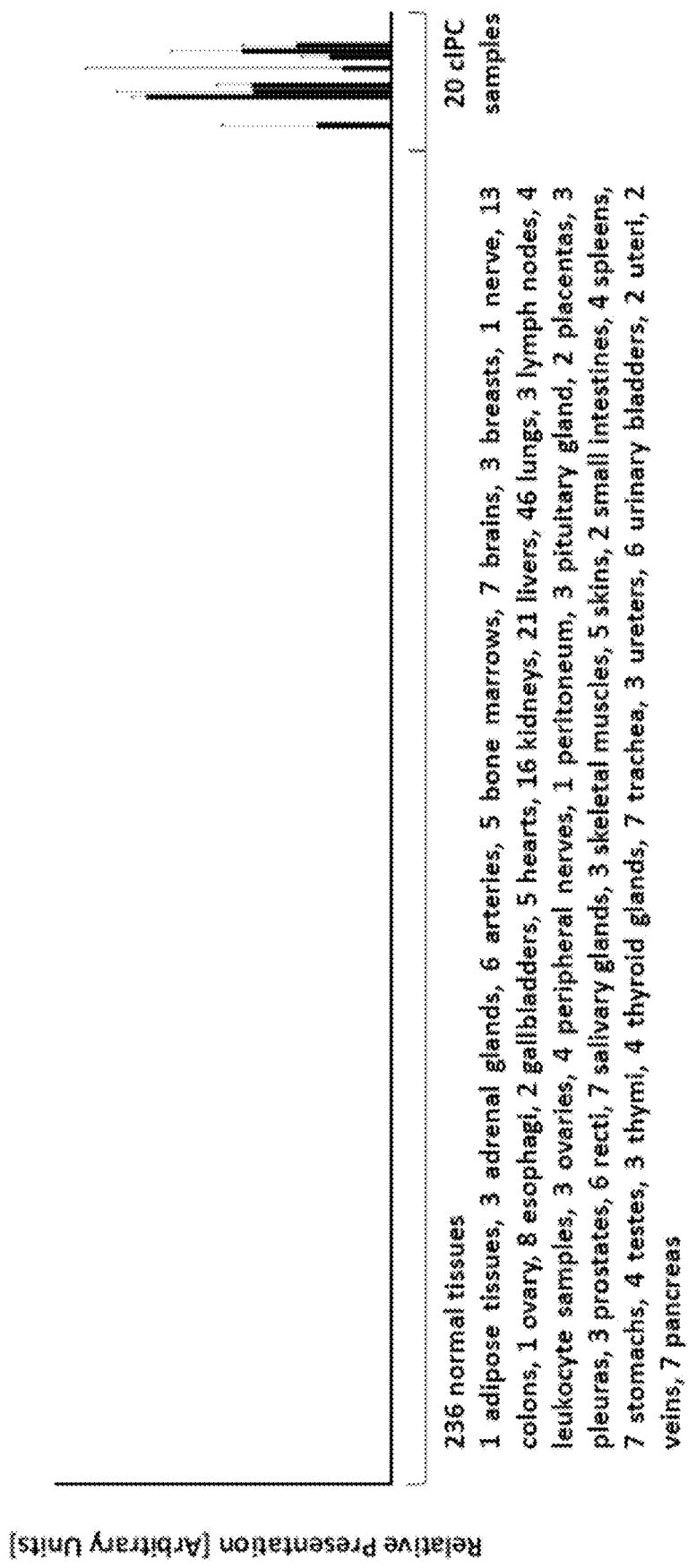
FIGS. 1A-1AF depict embodiments as described herein.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4 are furthermore useful in the diagnosis and/or treatment of various other malignancies that involve an over-expression or over-presentation of the respective underlying polypeptide.

TABLE 1

Peptides according to the present invention

| SEQ ID NO. | Sequence | Gene ID(s) | Official gene symbol(s) |
| --- | --- | --- | --- |
| 1 | FVDTRTLL | 1278 | COL1A2 |
| 2 | FGYDGDFYRA | 1278 | COL1A2 |
| 3 | ILIGETIKI | 5742, 5743 | PTGS1, PTGS2 |
| 4 | ALDPAAQAFLL | 84919 | PPP1R15B |
| 5 | ALLTGIISKA | 23165 | NUP205 |
| 6 | ALTGIPLPLI | 1017 | CDK2 |
| 7 | ALVDIVRSL | 3995 | FADS3 |
| 8 | ALYTGSALDFV | 1293 | COL6A3 |
| 9 | QIIDAINKV | 1293 | COL6A3 |
| 10 | VLLDKIKNL | 1293 | COL6A3 |
| 11 | ALYYNPHLL | 10527 | IPO7 |
| 12 | AQYKFVYQV | 5784 | PTPN14 |
| 13 | FIDSSNPGL | 92126 | DSEL |
| 14 | FIIDNPQDLKV | 5362 | PLXNA2 |
| 15 | FILANEHNV | 3843 | IPO5 |
| 16 | GLIDYDTGI | 667 | DST |
| 17 | GLIDYDTGIRL | 667 | DST |
| 18 | ALFVRLLAL | 7045 | TGFBI |
| 19 | ALWHDAENQTVV | 23279 | NUP160 |
| 20 | GLIDIENPNRV | 11333 | PDAP1 |
| 21 | GLVDGRDLVIV | 9943 | OXSR1 |
| 22 | ILSTEIFGV | 79703 | C11orf80 |

TABLE 1-continued

Peptides according to the present invention

| SEQ ID NO. | Sequence | Gene ID(s) | Official gene symbol(s) |
|---|---|---|---|
| 23 | KLDSSGGAVQL | 23677 | SH3BP4 |
| 24 | KLSENAGIQSL | 26064 | RAI14 |
| 25 | LINPNIATV | 790 | CAD |
| 26 | SLYTALTEA | 4124 | MAN2A1 |
| 27 | TLLAHPVTL | 27063 | ANKRD1 |
| 28 | VLDEFYSSL | 11321 | GPN1 |
| 29 | YILPFSEVL | 2132 | EXT2 |
| 30 | YIYKDTIQV | 346389 | MACC1 |
| 31 | YLDSMYIML | 8754 | ADAM9 |
| 32 | YVDDGLISL | 5315 | PKM |
| 33 | FLADPDTVNHL | 57231 | SNX14 |
| 34 | FLEDDDIAAV | 9945 | GFPT2 |
| 35 | FLFPSQYVDV | 9871 | SEC24D |
| 36 | FLGDLSHLL | 10945 | KDELR1 |
| 37 | FLNPDEVHAI | 81610 | FAM83D |
| 38 | FLTEAALGDA | 7980 | TFPI2 |
| 39 | FLTPSIFII | 79971 | WLS |
| 40 | GLAPQIHDL | 128239 | IQGAP3 |
| 41 | GLLAGNEKLTM | 3880 | KRT19 |
| 42 | ILSDMRSQYEV | 3880 | KRT19 |
| 43 | HLGVKVFSV | 1291 | COL6A1 |
| 44 | ILAQVGFSV | 55117 | SLC6A15 |
| 45 | ILYSDDGQKWTV | 131566 | DCBLD2 |
| 46 | TMVEHNYYV | 131566 | DCBLD2 |
| 47 | LIYKDLVSV | 85016 | C11orf70 |
| 48 | LLDENGVLKL | 1022 | CDK7 |
| 49 | LLDGFPRTV | 204 | AK2 |
| 50 | LLFGSDGYYV | 10897 | YIF1A |
| 51 | LLGPAGARA | 255738 | PCSK9 |
| 52 | LLSDPIPEV | 57521 | RPTOR |
| 53 | LLWDPSTGKQV | 54475 | NLE1 |
| 54 | LTQPGPIASA | 6374 | CXCL5 |
| 55 | NLAPAPLNA | 7035 | TFPI |
| 56 | NLIGVTAEL | 80210 | ARMC9 |
| 57 | RLSELGITQA | 79801 | SHCBP1 |
| 58 | RQYPWGVVQV | 151011, 23176, 55752 | SEPT10, SEP18, SEPT11 |
| 59 | SLSESFFMV | 54434 | SSH1 |
| 60 | SLWEDYPHV | 9697 | TRAM2 |

TABLE 1-continued

Peptides according to the present invention

| SEQ ID NO. | Sequence | Gene ID(s) | Official gene symbol(s) |
|---|---|---|---|
| 61 | SMYDGLLQA | 51393 | TRPV2 |
| 62 | SVFPGARLL | 10498 | CARM1 |
| 63 | SVTGIIVGV | 57722 | IGDCC4 |
| 64 | TLFSEPKFAQV | 84886 | C1orf198 |
| 65 | TLNEKLTAL | 55845 | BRK1 |
| 66 | TVDDPYATFV | 1072 | CFL1 |
| 67 | VIWGTDVNV | 4173 | MCM4 |
| 68 | VLFDVTGQV | 9961 | MVP |
| 69 | VLFSGSLRL | 115908 | CTHRC1 |
| 70 | VLGVIWGV | 100527943, 55969 | TGIF2-C20orf24, C20orf24 |
| 71 | VLLPEGGITAI | 9904 | RBM19 |
| 72 | VMASPGGLSAV | 54443 | ANLN |
| 73 | VMVDGKPVNL | 5879, 5881 | RAC1, RAC3 |
| 74 | YIDKDLEYV | 29102 | DROSHA |
| 75 | FSFVDLRLL | 1277 | COL1A1 |
| 76 | LVSESSDVLPK | 100129958, 3856 | KRT8P44, KRT8 |
| 77 | RLFPGSSFL | 90993 | CREB3L1 |
| 78 | SLQDTEEKSRS | 2641 | GCG |
| 79 | VVYEGQLISI | 2335 | FN1 |
| 80 | LLPGTEYVVSV | 2335 | FN1 |
| 81 | VVYDDSTGLIRL | 2898, 2899 | GRIK2, GRIK3 |
| 82 | ALIAEGIAL | 1778 | DYNC1H1 |
| 83 | ALSKEIYVI | 515 | ATP5F1 |
| 84 | FILPIGATV | 6509, 6510 | SLC1A4, SLC1A5 |
| 85 | FLSDGTIISV | 84916 | CIRH1A |
| 86 | GLGDFIFYSV | 5663, 5664 | PSEN1, PSEN2 |
| 87 | GLLPALVAL | 113278 | SLC52A3 |
| 88 | IIDDTIFNL | 257641, 4864 | NPC1 |
| 89 | KLADIQIEQL | 5201 | PFDN1 |
| 90 | KLLTPITTL | 1293 | COL6A3 |
| 91 | LLFNDVQTL | 5339 | PLEC |
| 92 | YLTNEGIAHL | 5339 | PLEC |
| 93 | SIDSEPALV | 23420, 283820, 408050 | NOMO1, NOMO2, NOMO3 |
| 94 | VMMEEFVQL | 9875 | URB1 |
| 95 | ALADDDFLTV | 4173 | MCM4 |
| 96 | ALAPATGGGSLLL | 80830 | APOL6 |
| 97 | ALDDMISTL | 7203 | CCT3 |

TABLE 1-continued

Peptides according to the present invention

| SEQ ID NO. | Sequence | Gene ID(s) | Official gene symbol(s) |
|---|---|---|---|
| 98 | ALDQKVRSV | 4130 | MAP1A |
| 99 | ALESFLKQV | 5591 | PRKDC |
| 100 | ALFGAGPASI | 1806 | DPYD |
| 101 | ALVEENGIFEL | 11187 | PKP3 |
| 102 | ALYPGTDYTV | 64420 | SUSD1 |
| 103 | AVAAVLTQV | 10280 | SIGMAR1 |
| 104 | FLQPDLDSL | 10514 | MYBBP1A |
| 105 | FLSEVFHQA | 5055 | SERPINB2 |
| 106 | FVWSGTAEA | 23326 | USP22 |
| 107 | FVYGGPQVQL | 91039 | DPP9 |
| 108 | IADGGFTEL | 1107, 1108, 26038 | CHD3, CHD4, CHD5 |
| 109 | ILASVILNV | 644538 | SMIM10 |
| 110 | ILLTGTPAL | 84083 | ZRANB3 |
| 111 | LLLAAARLAAA | 2923 | PDIA3 |
| 112 | LLSDVRFVL | 53339 | BTBD1 |
| 113 | LMMSEDRISL | 9945 | GFPT2 |
| 114 | SLFPHNPQFI | 80135 | RPF1 |
| 115 | SLMDPNKFLLL | 197131 | UBR1 |
| 116 | SMMDPNHFL | 23304 | UBR2 |
| 117 | SVDGVIKEV | 10577 | NPC2 |
| 118 | TLWYRPPEL | 100422910, 1025, 51755, 8621 | MIR2861, CDK9, CDK12, CDK13 |
| 119 | VLGDDPQLMKV | 10629 | TAF6L |
| 120 | VLVNDFFLV | 3646 | EIF3E |
| 121 | YLDEDTIYHL | 4144 | MAT2A |

TABLE 2

Additional peptides according to the present invention with no prior known cancer association

| SEQ ID No. | Sequence | Gene ID(s) | Official Gene Symbol(s) |
|---|---|---|---|
| 122 | MQAPRAALVFA | 201799 | TMEM154 |
| 123 | KISTITPQI | 996 | CDC27 |
| 124 | ALFEESGLIRI | 1951, 65010 | CELSR3, SLC26A6 |
| 125 | ALLGKLDAINV | 5876 | RABGGTB |
| 126 | ALLSLDPAAV | 5591 | PRKDC |
| 127 | ALSDLALHFL | 10575 | CCT4 |
| 128 | ALYDVRTILL | 11065 | UBE2C |
| 129 | ALYEKDNTYL | 80279 | CDK5RAP3 |
| 130 | FLFGEEPSKL | 23141 | ANKLE2 |
| 131 | FLIEEQKIVV | 6164 | RPL34 |
| 132 | FLWAGGRASYGV | 3192 | HNRNPU |
| 133 | ILDDVSLTHL | 5245 | PHB |

TABLE 2-continued

Additional peptides according to the present invention with no prior known cancer association

| SEQ ID No. | Sequence | Gene ID(s) | Official Gene Symbol(s) |
|---|---|---|---|
| 134 | ILLAEGRLVNL | 191 | AHCY |
| 135 | KLDDTYIKA | 7266 | DNAJC7 |
| 136 | KLFPGFEIETV | 440 | ASNS |
| 137 | KLGPEGELL | 6510 | SLC1A5 |
| 138 | NIFPNPEATFV | 11198 | SUPT16H |
| 139 | SIDRNPPQL | 6773 | STAT2 |
| 140 | SLLNPPETLNL | 890 | CCNA2 |
| 141 | SLTEQVHSL | 79598 | CEP97 |
| 142 | SLYGYLRGA | 9790 | BMS1 |
| 143 | TADPLDYRL | 4928 | NUP98 |
| 144 | TAVALLRLL | 9761 | MLEC |
| 145 | TTFPRPVTV | 4841 | NONO |
| 146 | VLISGVVHEI | 51360 | MBTPS2 |
| 147 | YAFPKAVSV | 9123 | SLC16A3 |
| 148 | YLHNQGIGV | 701 | BUB1B |
| 149 | ILGTEDLIVEV | 79719 | AAGAB |
| 150 | ALFQPHLINV | 10097 | ACTR2 |
| 151 | ALLDIIRSL | 9415 | FADS2 |
| 152 | ALLEPEFILKA | 7011 | TEP1 |
| 153 | ALPKEDPTAV | 22820 | COPG1 |
| 154 | KVADLVLML | 399761, 642517, 9790 | BMS1P5, AGAP9, BMS1 |
| 155 | LLLDPDTAVLKL | 2932 | GSK3B |
| 156 | LLLPPPPCPA | 2519 | FUCA2 |
| 157 | MLLEIPYMAA | 728689, 8663 | EIF3CL, EIF3C |
| 158 | SLIEKYFSV | 3838, 645680 | KPNA2 |
| 159 | SLLDLHTKV | 27340 | UTP20 |
| 160 | VLLPDERTISL | 1477 | CSTF1 |
| 161 | YLPDIIKDQKA | 5496 | PPM1G |

TABLE 3

Peptides useful for e.g. personalized cancer therapies

| SEQ ID No. | Sequence | Gene ID(s) | Official Gene Symbol(s) |
|---|---|---|---|
| 162 | NADPQAVTM | 10916 | MAGED2 |
| 163 | VMAPRTLVL | 100507703, 3105 | HLA-A |
| 164 | YLGRLAHEV | 23521, 387841, 728658 | RPL13A, RPL13AP20, RPL13AP5 |
| 165 | YLLSYIQSI | 64151 | NCAPG |
| 166 | SLFPGQVVI | 23649 | POLA2 |
| 167 | MLFGHPLLVSV | 8237 | USP11 |
| 168 | SEWGSPHAAVP | 5539 | PPY |
| 169 | FMLPDPQNI | 116461 | TSEN15 |
| 170 | ILAPAGSLPKI | 29914 | UBIAD1 |
| 171 | LLLDVTPLSL | 100287551, 3306, 3312, 3313 | HSPA8P8, HSPA2, HSPA8, HSPA9 |
| 172 | TMMSRPPVL | 57708, 79971 | MIER1, WLS |
| 173 | SLAGDVALQQL | 9918 | NCAPD2 |
| 174 | TLDPRSFLL | 2149 | F2R |
| 175 | ALLESSLRQA | 595 | CCND1 |
| 176 | YLMPGFIHL | 168400, 55510 | DDX53, DDX43 |
| 177 | SLYKGLLSV | 25788 | RAD54B |
| 178 | KIQEILTQV | 10643 | IGF2BP3 |

The present invention furthermore generally relates to the peptides according to the present invention for use in the treatment of proliferative diseases, such as, for example, lung cancer, kidney cancer, brain cancer, stomach cancer, colon or rectal cancer, liver cancer, prostate cancer, leukemia, breast cancer, Merkel cell carcinoma (MCC), melanoma, ovarian cancer, esophageal cancer, urinary bladder cancer, endometrial cancer, gall bladder cancer, and bile duct cancer.

Particularly preferred are the peptides—alone or in combination—according to the present invention selected from the group consisting of SEQ ID NO: 1 to SEQ ID NO: 161. More preferred are the peptides—alone or in combination—selected from the group consisting of SEQ ID NO: 1 to SEQ ID NO: 79 (see Table 1), and their uses in the immunotherapy of pancreatic cancer, lung cancer, kidney cancer, brain cancer, stomach cancer, colon or rectal cancer, liver cancer, prostate cancer, leukemia, breast cancer, Merkel cell carcinoma (MCC), melanoma, ovarian cancer, esophageal cancer, urinary bladder cancer, endometrial cancer, gall bladder cancer, bile duct cancer, and preferably pancreatic cancer.

As shown in the following Table 4, many of the peptides according to the present invention are also found on other tumor types and can, thus, also be used in the immunotherapy of other indications. Also refer to FIGS. 1A-1AF and Example 1.

TABLE 4

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs (cancer)/diseases |
|---|---|---|
| 1 | FVDTRTLL | Esophagus |
| 2 | FGYDGDFYRA | Pancreas, Breast, Esophagus |
| 3 | ILIGETIKI | Urinary bladder |
| 4 | ALDPAAQAFLL | NSCLC, Liver, Breast, Ovary, Esophagus, Urinary bladder |
| 5 | ALLTGIISKA | NSCLC, Colon, Rectum, Liver, Esophagus |
| 7 | ALVDIVRSL | Leukocytes |
| 8 | ALYTGSALDFV | NSCLC, Pancreas, Breast, Esophagus, Gallbladder, Bile duct |
| 9 | QIIDAINKV | Breast, Esophagus |
| 10 | VLLDKIKNL | Pancreas, Gallbladder, Bile duct |
| 11 | ALYYNPHLL | Esophagus |
| 12 | AQYKFVYQV | Esophagus |
| 13 | FIDSSNPGL | Kidney |
| 14 | FIIDNPQDLKV | NSCLC, SCLC, Kidney, Liver, Melanoma, Ovary, Esophagus |
| 16 | GLIDYDTGI | Brain, Breast |
| 17 | GLIDYDTGIRL | Brain, Melanoma |
| 19 | ALWHDAENQTVV | NSCLC, SCLC, Liver, Melanoma, Esophagus, Gallbladder, Bile duct |
| 20 | GLIDIENPNRV | Urinary bladder |
| 22 | ILSTEIFGV | NSCLC, Pancreas, Leukocytes, Breast |
| 26 | SLYTALTEA | Breast |
| 28 | VLDEFYSSL | Colon, Rectum |
| 29 | YILPFSEVL | NSCLC, Kidney, Brain, Colon, Rectum, Esophagus, Urinary bladder |
| 30 | YIYKDTIQV | NSCLC, Colon, Rectum |
| 31 | YLDSMYIML | NSCLC, Stomach, Colon, Rectum, Liver, Pancreas, Breast, Gallbladder, Bile duct |
| 32 | YVDDGLISL | Stomach |
| 34 | FLEDDDIAAV | Brain, Melanoma |
| 35 | FLFPSQYVDV | NSCLC, SCLC, Liver, Breast, Ovary, Esophagus |
| 37 | FLNPDEVHAI | NSCLC, Colon, Rectum, Liver, Breast, Melanoma, Ovary, Esophagus, Urinary bladder |
| 39 | FLTPSIFII | Brain, Pancreas |

TABLE 4-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs (cancer)/diseases |
|---|---|---|
| 40 | GLAPQIHDL | Colon, Rectum, Esophagus |
| 41 | GLLAGNEKLTM | Colon, Rectum, Breast, Urinary bladder, Endometrium |
| 42 | ILSDMRSQYEV | Urinary bladder |
| 45 | ILYSDDGQKWTV | Melanoma |
| 46 | TMVEHNYYV | NSCLC, SCLC, Kidney, Pancreas, Melanoma, Ovary, Esophagus |
| 48 | LLDENGVLKL | Leukocytes |
| 50 | LLFGSDGYYV | Liver, Esophagus |
| 51 | LLGPAGARA | Liver, Esophagus |
| 52 | LLSDPIPEV | SCLC, Melanoma, Ovary, Esophagus |
| 57 | RLSELGITQA | Esophagus |
| 58 | RQYPWGVVQV | Esophagus |
| 59 | SLSESFFMV | SCLC, Breast, Urinary bladder |
| 60 | SLWEDYPHV | NSCLC, SCLC, Colon, Rectum, Liver, Ovary, Urinary bladder |
| 62 | SVFPGARLL | SCLC, Leukocytes, Esophagus |
| 63 | SVTGIIVGV | Brain, Esophagus |
| 64 | TLFSEPKFAQV | SCLC, Liver, Urinary bladder |
| 67 | VIWGTDVNV | Brain, Esophagus |
| 68 | VLFDVTGQV | Stomach |
| 69 | VLFSGSLRL | NSCLC |
| 70 | VLGVIWGV | NSCLC, Liver, Ovary, Esophagus |
| 71 | VLLPEGGITAI | Leukocytes |
| 73 | VMVDGKPVNL | Liver, Gallbladder, Bile duct |
| 75 | FSFVDLRLL | SCLC, Esophagus, Gallbladder, Bile duct |
| 77 | RLFPGSSFL | Breast, Esophagus |
| 79 | VVYEGQLISI | NSCLC, SCLC, Pancreas, Breast, Esophagus |
| 80 | LLPGTEYVVSV | SCLC, Liver |
| 81 | VVYDDSTGLIRL | SCLC, Brain, Leukocytes, MCC, Ovary |
| 82 | ALIAEGIAL | Urinary bladder |
| 83 | ALSKEIYVI | Leukocytes |
| 84 | FILPIGATV | Kidney, Stomach, Breast |

TABLE 4-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs (cancer)/diseases |
|---|---|---|
| 85 | FLSDGTIISV | NSCLC, Colon, Rectum, Liver, Melanoma, Ovary, Esophagus, Endometrium |
| 86 | GLGDFIFYSV | Liver, Pancreas |
| 88 | IIDDTIFNL | Stomach, Urinary bladder |
| 90 | KLLTPITTL | NSCLC, SCLC, Colon, Rectum, Breast |
| 91 | LLFNDVQTL | Esophagus, Urinary bladder |
| 92 | YLTNEGIAHL | NSCLC, Colon, Rectum, Melanoma, Ovary, Esophagus |
| 93 | SIDSEPALV | Brain, Colon, Rectum, Breast, Urinary bladder |
| 94 | VMMEEFVQL | Brain, Colon, Rectum, Leukocytes, Ovary, Esophagus, Endometrium, Gallbladder, Bile duct |
| 95 | ALADDDFLTV | NSCLC, SCLC, Stomach, Leukocytes, Melanoma, Ovary, Esophagus, Urinary bladder |
| 96 | ALAPATGGGSLLL | Liver, Melanoma |
| 97 | ALDDMISTL | Stomach, Urinary bladder |
| 98 | ALDQKVRSV | Brain, Prostate |
| 99 | ALESFLKQV | Colon, Rectum, Liver, Breast, Urinary bladder |
| 100 | ALFGAGPASI | Liver |
| 101 | ALVEENGIFEL | NSCLC, Liver, MCC, Ovary, Urinary bladder |
| 102 | ALYPGTDYTV | NSCLC, SCLC, Brain, Liver, Prostate, Gallbladder, Bile duct |
| 103 | AVAAVLTQV | Liver |
| 104 | FLQPDLDSL | Brain, Liver, Pancreas, Leukocytes, Urinary bladder |
| 106 | FVWSGTAEA | Brain, Esophagus, Urinary bladder |
| 107 | FVYGGPQVQL | Melanoma |
| 109 | ILASVILNV | Prostate |
| 110 | ILLTGTPAL | SCLC, Leukocytes, Breast |
| 111 | LLLAAARLAAA | Liver, Pancreas |
| 113 | LMMSEDRISL | Brain, Melanoma |
| 114 | SLFPHNPQFI | SCLC, Brain, Colon, Rectum, Liver, Melanoma, Esophagus, Urinary bladder |

TABLE 4-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs (cancer)/diseases |
|---|---|---|
| 115 | SLMDPNKFLLL | Kidney, Brain, Colon, Rectum, Liver, Prostate, Melanoma, Urinary bladder, Gallbladder, Bile duct |
| 116 | SMMDPNHFL | Brain, Liver, MCC, Endometrium, Gallbladder, Bile duct |
| 117 | SVDGVIKEV | Stomach |
| 118 | TLWYRPPEL | NSCLC, Melanoma, Esophagus |
| 120 | VLVNDFFLV | Stomach, Colon, Rectum, Liver, Ovary, Esophagus, Urinary bladder, Endometrium |
| 121 | YLDEDTIYHL | Stomach |
| 122 | MQAPRAALVFA | Brain, Leukocytes, Urinary bladder, Gallbladder, Bile duct |
| 123 | KISTITPQI | NSCLC, Liver, Pancreas |
| 124 | ALFEESGLIRI | NSCLC, SCLC, Colon, Rectum, Liver, MCC, Melanoma, Ovary, Esophagus |
| 125 | ALLGKLDAINV | NSCLC, SCLC, Colon, Rectum, Liver, Ovary, Gallbladder, Bile duct |
| 128 | ALYDVRTILL | NSCLC, SCLC, Colon, Rectum |
| 129 | ALYEKDNTYL | SCLC, Brain, Liver, Ovary, Esophagus |
| 130 | FLFGEEPSKL | Pancreas, Endometrium |
| 131 | FLIEEQKIVV | NSCLC, SCLC, Colon, Rectum, Liver, Melanoma, Ovary, Esophagus, Urinary bladder, Gallbladder, Bile duct |
| 132 | FLWAGGRASYGV | Liver, Ovary, Esophagus |
| 134 | ILLAEGRLVNL | Ovary |
| 135 | KLDDTYIKA | Liver, Esophagus, Urinary bladder |
| 136 | KLFPGFEIETV | NSCLC, SCLC, Liver, Ovary, Esophagus |
| 137 | KLGPEGELL | Colon, Rectum, Liver, Breast, Esophagus, Urinary bladder |
| 138 | NIFPNPEATFV | NSCLC, SCLC, Brain, Melanoma |
| 142 | SLYGYLRGA | NSCLC, Colon, Rectum, Liver, Pancreas, Prostate, Breast, Ovary, Esophagus, Urinary bladder |
| 143 | TADPLDYRL | SCLC, Endometrium |
| 144 | TAVALLRLL | SCLC, Leukocytes |
| 145 | TTFPRPVTV | SCLC, Colon, Rectum, Leukocytes |
| 146 | VLISGVVHEI | Brain, Liver, Melanoma, Ovary |
| 147 | YAFPKAVSV | NSCLC, SCLC, Kidney, Stomach, Leukocytes, Ovary, Esophagus |

TABLE 4-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No. | Sequence | Other relevant organs (cancer)/diseases |
|---|---|---|
| 148 | YLHNQGIGV | SCLC, Colon, Rectum, Liver, Esophagus |
| 149 | ILGTEDLIVEV | NSCLC, SCLC, Liver, Leukocytes, Melanoma, Ovary, Esophagus, Gallbladder, Bile duct |
| 150 | ALFQPHLINV | NSCLC, SCLC, Liver, Leukocytes, Breast, Melanoma, Ovary, Urinary bladder |
| 151 | ALLDIIRSL | NSCLC, Brain, Colon, Rectum, Prostate, Urinary bladder |
| 152 | ALLEPEFILKA | Colon, Rectum, Leukocytes, Urinary bladder |
| 154 | KVADLVLML | NSCLC, Colon, Rectum, Leukocytes, Ovary, Esophagus, Urinary bladder |
| 155 | LLLDPDTAVLKL | Liver, Melanoma |
| 156 | LLLPPPPCPA | Pancreas, Urinary bladder |
| 157 | MLLEIPYMAA | Colon, Rectum, Melanoma, Ovary, Urinary bladder |
| 158 | SLIEKYFSV | NSCLC, SCLC, Colon, Rectum, Liver, Melanoma, Ovary, Esophagus |
| 159 | SLLDLHTKV | Brain, Colon, Rectum, Liver, Leukocytes |
| 160 | VLLPDERTISL | NSCLC, SCLC, Liver, Leukocytes, Ovary, Urinary bladder |
| 161 | YLPDIIKDQKA | Brain, Liver, Leukocytes, Melanoma |
| 162 | NADPQAVTM | SCLC, Kidney, Ovary, Endometrium |
| 163 | VMAPRTLVL | SCLC |
| 165 | YLLSYIQSI | SCLC, Colon, Rectum, Liver, Melanoma, Ovary, Esophagus, Endometrium |
| 166 | SLFPGQVVI | Brain, Urinary bladder, Endometrium |
| 167 | MLFGHPLLVSV | NSCLC, SCLC, Brain, Liver, Pancreas, Prostate, Ovary |
| 169 | FMLPDPQNI | NSCLC, SCLC, Brain, Liver, Breast, Melanoma, Esophagus, Urinary bladder |
| 170 | ILAPAGSLPKI | Urinary bladder |
| 171 | LLLDVTPLSL | Leukocytes, Urinary bladder |
| 172 | TMMSRPPVL | Brain |
| 174 | TLDPRSFLL | Stomach, Liver |
| 175 | ALLESSLRQA | Kidney, Breast, Urinary bladder |
| 176 | YLMPGFIHL | Liver, Leukocytes |

TABLE 4B

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 1 | FVDTRTLL | Melanoma, Urinary Bladder Cancer |
| 3 | ILIGETIKI | OC, AML |
| 4 | ALDPAAQAFLL | SCLC, GC, CRC, CLL, Uterine Cancer, Gallbladder Cancer, Bile Duct Cancer, AML, NHL |
| 5 | ALLTGIISKA | Melanoma, Urinary Bladder Cancer, Uterine Cancer |
| 6 | ALTGIPLPLI | NSCLC, SCLC, CLL, Melanoma, Urinary Bladder Cancer, Uterine Cancer, NHL |
| 9 | QIIDAINKV | Melanoma, NHL, GC, NSCLC |
| 11 | ALYYNPHLL | Brain Cancer |
| 12 | AQYKFVYQV | RCC, Melanoma, Urinary Bladder Cancer, Uterine Cancer |
| 14 | FIIDNPQDLKV | Brain Cancer, Urinary Bladder Cancer, Uterine Cancer |
| 15 | FILANEHNV | Urinary Bladder Cancer, Uterine Cancer |
| 16 | GLIDYDTGI | Melanoma |
| 18 | ALFVRLLAL | Melanoma |
| 19 | ALWHDAENQTVV | Brain Cancer, Urinary Bladder Cancer, Uterine Cancer |
| 20 | GLIDIENPNRV | Esophageal Cancer |
| 21 | GLVDGRDLVIV | NSCLC, Melanoma, Gallbladder Cancer, Bile Duct Cancer, AML, NHL |
| 22 | ILSTEIFGV | Melanoma, Gallbladder Cancer, Bile Duct Cancer |
| 23 | KLDSSGGAVQL | SCLC, Melanoma |
| 25 | LINPNIATV | Melanoma |
| 28 | VLDEFYSSL | Melanoma |
| 29 | YILPFSEVL | BRCA, Melanoma, Uterine Cancer, AML, NHL |
| 30 | YIYKDTIQV | RCC, Urinary Bladder Cancer, Gallbladder Cancer, Bile Duct Cancer, AML |
| 31 | YLDSMYIML | Melanoma, Esophageal Cancer, Urinary Bladder Cancer |
| 32 | YVDDGLISL | Melanoma, AML |
| 34 | FLEDDDIAAV | CRC |

TABLE 4B-continued

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 37 | FLNPDEVHAI | SCLC, Uterine Cancer, NHL |
| 38 | FLTEAALGDA | RCC, Urinary Bladder Cancer, Uterine Cancer |
| 39 | FLTPSIFII | Uterine Cancer |
| 41 | GLLAGNEKLTM | GC, Esophageal Cancer |
| 42 | ILSDMRSQYEV | BRCA, Uterine Cancer, Gallbladder Cancer, Bile Duct Cancer |
| 44 | ILAQVGFSV | Melanoma |
| 46 | TMVEHNYYV | Urinary Bladder Cancer, Uterine Cancer, Gallbladder Cancer, Bile Duct Cancer |
| 47 | LIYKDLVSV | OC |
| 50 | LLFGSDGYYV | Uterine Cancer, Gallbladder Cancer, Bile Duct Cancer |
| 52 | LLSDPIPEV | Urinary Bladder Cancer, AML, NHL |
| 55 | NLAPAPLNA | Melanoma |
| 56 | NLIGVTAEL | Melanoma, Uterine Cancer |
| 57 | RLSELGITQA | Melanoma, Urinary Bladder Cancer, Uterine Cancer, AML, NHL, OC |
| 58 | RQYPWGVVQV | Melanoma |
| 59 | SLSESFFMV | NHL |
| 60 | SLWEDYPHV | BRCA, Melanoma, Esophageal Cancer, Uterine Cancer |
| 61 | SMYDGLLQA | Melanoma |
| 65 | TLNEKLTAL | Melanoma, Urinary Bladder Cancer, AML |
| 66 | TVDDPYATFV | Melanoma |
| 67 | VIWGTDVNV | Melanoma, Urinary Bladder Cancer, AML |
| 68 | VLFDVTGQV | Melanoma |
| 69 | VLFSGSLRL | BRCA, Esophageal Cancer, Gallbladder Cancer, Bile Duct Cancer |
| 70 | VLGVIWGV | Brain Cancer, BRCA, Urinary Bladder Cancer, Uterine Cancer |
| 71 | VLLPEGGITAI | Brain Cancer, Urinary Bladder Cancer |
| 74 | YIDKDLEYV | Urinary Bladder Cancer, Uterine Cancer |

TABLE 4B-continued

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 75 | FSFVDLRLL | RCC, BRCA, Melanoma, NHL |
| 77 | RLFPGSSFL | GC |
| 79 | VVYEGQLISI | Gallbladder Cancer, Bile Duct Cancer, NHL |
| 80 | LLPGTEYVVSV | BRCA, Gallbladder Cancer, Bile Duct Cancer |
| 82 | ALIAEGIAL | BRCA, Uterine Cancer |
| 83 | ALSKEIYVI | Brain Cancer |
| 84 | FILPIGATV | AML, CLL, CRC, HCC, Melanoma, NHL, OC, Esophageal Cancer, NSCLC, Urinary Bladder Cancer, Uterine Cancer |
| 86 | GLGDFIFYSV | NSCLC, BRCA, Esophageal Cancer, Urinary Bladder Cancer |
| 87 | GLLPALVAL | Brain Cancer, Melanoma |
| 88 | IIDDTIFNL | Melanoma |
| 89 | KLADIQIEQL | Urinary Bladder Cancer, OC |
| 90 | KLLTPITTL | Melanoma, Gallbladder Cancer, Bile Duct Cancer |
| 91 | LLFNDVQTL | CLL, Uterine Cancer, NHL |
| 92 | YLTNEGIAHL | Urinary Bladder Cancer |
| 93 | SIDSEPALV | Melanoma, AML |
| 94 | VMMEEFVQL | NSCLC, SCLC, Melanoma, Urinary Bladder Cancer |
| 95 | ALADDDFLTV | RCC, BRCA, Uterine Cancer, Gallbladder Cancer, Bile Duct Cancer |
| 96 | ALAPATGGGSLLL | NSCLC, Gallbladder Cancer, Bile Duct Cancer, NHL |
| 97 | ALDDMISTL | Melanoma |
| 99 | ALESFLKQV | NSCLC, RCC, Brain Cancer, CLL, Melanoma, OC, Esophageal Cancer, AML, NHL |
| 100 | ALFGAGPASI | Urinary Bladder Cancer |
| 101 | ALVEENGIFEL | Uterine Cancer |
| 102 | ALYPGTDYTV | AML |
| 103 | AVAAVLTQV | Esophageal Cancer, Urinary Bladder Cancer, Uterine Cancer, Gallbladder Cancer, Bile Duct Cancer, AML |

TABLE 4B-continued

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thyroid gland, trachea, ureter, urinary bladder.

| SEQ ID NO. | Sequence | Additional Entities |
|---|---|---|
| 104 | FLQPDLDSL | SCLC, Uterine Cancer |
| 106 | FVWSGTAEA | Melanoma, Uterine Cancer, AML, NHL |
| 107 | FVYGGPQVQL | CLL, Urinary Bladder Cancer, NHL |
| 108 | IADGGFTEL | AML |
| 109 | ILASVILNV | Urinary Bladder Cancer |
| 110 | ILLTGTPAL | Uterine Cancer |
| 111 | LLLAAARLAAA | AML, PrC, BRCA, CRC, Gallbladder Cancer, Bile Duct Cancer, Melanoma, NHL, OC, Brain Cancer, NSCLC, RCC, SCLC, Urinary Bladder Cancer, Uterine Cancer |
| 113 | LMMSEDRISL | NSCLC, Urinary Bladder Cancer |
| 114 | SLFPHNPQFI | NSCLC, CLL, AML, NHL |
| 116 | SMMDPNHFL | NSCLC, Melanoma |
| 117 | SVDGVIKEV | Melanoma, AML |
| 118 | TLWYRPPEL | CLL, Urinary Bladder Cancer, Uterine Cancer |
| 120 | VLVNDFFLV | BRCA, Melanoma, Gallbladder Cancer, Bile Duct Cancer, AML |
| 121 | YLDEDTIYHL | Melanoma |
| 123 | KISTITPQI | Brain Cancer, Melanoma, Urinary Bladder Cancer, Uterine Cancer, AML, NHL |
| 124 | ALFEESGLIRI | BRCA, NHL |
| 125 | ALLGKLDAINV | NHL |
| 126 | ALLSLDPAAV | Brain Cancer, Urinary Bladder Cancer, AML |
| 127 | ALSDLALHFL | CLL, BRCA, Melanoma, Urinary Bladder Cancer, AML, NHL |
| 128 | ALYDVRTILL | BRCA, Urinary Bladder Cancer, AML |
| 129 | ALYEKDNTYL | NSCLC, BRCA, Urinary Bladder Cancer, Uterine Cancer, Gallbladder Cancer, Bile Duct Cancer, NHL |
| 130 | FLFGEEPSKL | RCC, CLL, Melanoma, Esophageal Cancer, Urinary Bladder Cancer, AML |
| 131 | FLIEEQKIVV | AML, NHL |
| 132 | FLWAGGRASYGV | Brain Cancer, Melanoma, Uterine Cancer, AML |

TABLE 4B-continued

Peptides according to the present invention and their specific uses in other proliferative diseases, especially in other cancerous diseases (amendment of Table 4). The table shows, like Table 4, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pleura, pituitary, salivary gland, skeletal muscle, skin, small intestine, spleen, stomach, thyroid gland, trachea, ureter, urinary bladder.

| SEQ ID NO. | Sequence | Additional Entities |
|---|---|---|
| 133 | ILDDVSLTHL | Melanoma |
| 134 | ILLAEGRLVNL | NSCLC, Melanoma |
| 135 | KLDDTYIKA | Melanoma, Uterine Cancer |
| 137 | KLGPEGELL | Melanoma, AML |
| 138 | NIFPNPEATFV | BRCA, Urinary Bladder Cancer, AML, NHL, OC |
| 139 | SIDRNPPQL | Melanoma, AML |
| 140 | SLLNPPETLNL | AML |
| 142 | SLYGYLRGA | CLL, Melanoma, Gallbladder Cancer, Bile Duct Cancer, AML |
| 143 | TADPLDYRL | Melanoma, AML |
| 144 | TAVALLRLL | BRCA, Gallbladder Cancer, Bile Duct Cancer |
| 145 | TTFPRPVTV | HCC, Gallbladder Cancer, Bile Duct Cancer |
| 146 | VLISGVVHEI | CRC, Uterine Cancer |
| 147 | YAFPKAVSV | Gallbladder Cancer, Bile Duct Cancer |
| 148 | YLHNQGIGV | Urinary Bladder Cancer, Uterine Cancer, AML, NHL, OC |
| 149 | ILGTEDLIVEV | PrC, BRCA, CRC, MCC, GC, Urinary Bladder Cancer, Uterine Cancer |
| 151 | ALLDIIRSL | BRCA, Uterine Cancer, AML |
| 152 | ALLEPEFILKA | NSCLC, Brain Cancer, Gallbladder Cancer, Bile Duct Cancer |
| 154 | KVADLVLML | Gallbladder Cancer, Bile Duct Cancer |
| 155 | LLLDPDTAVLKL | SCLC, CLL, BRCA |
| 156 | LLLPPPPCPA | Melanoma, Uterine Cancer, Gallbladder Cancer, Bile Duct Cancer |
| 157 | MLLEIPYMAA | Uterine Cancer |
| 158 | SLIEKYFSV | CLL, BRCA, Urinary Bladder Cancer, Uterine Cancer, AML, NHL |
| 159 | SLLDLHTKV | NSCLC, Melanoma, Urinary Bladder Cancer, Uterine Cancer |

TABLE 4B-continued

Peptides according to the present invention and their
specific uses in other proliferative diseases, especially
in other cancerous diseases (amendment of Table 4).
The table shows, like Table 4, for selected peptides on
which additional tumor types they were found showing
over-presentation (including specific presentation) on
more than 5% of the measured tumor samples, or
presentation on more than 5% of the measured tumor
samples with a ratio of geometric means tumor vs
normal tissues being larger than 3. Over-presentation
is defined as higher presentation on the tumor sample
as compared to the normal sample with highest
presentation. Normal tissues against which over-
presentation was tested were: adipose tissue, adrenal
gland, blood cells, blood vessel, bone marrow, brain,
esophagus, eye, gallbladder, heart, kidney, large
intestine, liver, lung, lymph node, nerve, pancreas,
parathyroid gland, peritoneum, pituitary, pleura,
salivary gland, skeletal muscle, skin, small intestine,
spleen, stomach, thyroid gland, trachea, ureter,
urinary bladder.

| SEQ ID NO. | Sequence | Additional Entities |
|---|---|---|
| 160 | VLLPDERTISL | BRCA, CRC, Gallbladder Cancer, Bile Duct Cancer, Melanoma, Brain Cancer, GC, RCC, Uterine Cancer |
| 161 | YLPDIIKDQKA | Uterine Cancer |

NSCLC = non-small cell lung cancer,
SCLC = small cell lung cancer,
RCC = kidney cancer,
CRC = colon or rectum cancer,
GC = stomach cancer,
HCC = liver cancer,
PrC = prostate cancer,
BRCA = breast cancer,
MCC = Merkel cell carcinoma,
OC = ovarian cancer,
NHL = non-Hodgkin lymphoma,
AML = acute myeloid leukemia,
CLL = chronic lymphocytic leukemia.

Thus, another aspect of the present invention relates to the use of at least one peptide according to the present invention according to any one of SEQ ID No. 4, 5, 8, 14, 19, 22, 29, 30, 31, 35, 37, 46, 60, 69, 70, 79, 85, 90, 92, 95, 101, 102, 118, 123, 124, 125, 128, 131, 136, 138, 142, 147, 149, 150, 151, 154, 158, 160, 167, 6, 9, 21, 84, 85, 94, 96, 99, 111, 113, 114, 116, 129, 134, 152, 159, and 169 for the—in one preferred embodiment combined—treatment of non-small cell lung cancer (NSCLC).

Thus, another aspect of the present invention relates to the use of at least one peptide according to the present invention according to any one of SEQ ID No. 14, 19, 35, 46, 52, 59, 60, 62, 64, 75, 79, 80, 81, 90, 95, 102, 110, 114, 124, 125, 128, 129, 131, 136, 138, 143, 144, 145, 147, 148, 149, 150, 158, 160, 162, 163, 165, 167, 169, 4, 6, 23, 37, 94, 104, and 155 for the—in one preferred embodiment combined—treatment of small cell lung cancer (SCLC).

Thus, another aspect of the present invention relates to the use of at least one peptide according to the present invention according to any one of SEQ ID No. 13, 14, 29, 46, 84, 115, 147, 162, 175, 12, 30, 38, 75, 95, 99, 111, 130, and 160 for the—in one preferred embodiment combined—treatment of kidney cancer.

Thus, another aspect of the present invention relates to the use of at least one peptide according to the present invention according to any one of SEQ ID No. 16, 17, 29, 34, 39, 63, 67, 81, 93, 94, 98, 102, 104, 106, 113, 114, 115, 116, 122, 129, 138, 146, 151, 159, 161, 166, 167, 169, 172, 11, 14, 19, 70, 71, 83, 87, 99, 112, 123, 126, 132, 152, and 160 for the—in one preferred embodiment combined—treatment of brain cancer.

Thus, another aspect of the present invention relates to the use of at least one peptide according to the present invention according to any one of SEQ ID No. 31, 32, 68, 84, 88, 95, 97, 117, 120, 121, 147, 174, 4, 9, 41, 77, 149, and 160 for the—in one preferred embodiment combined—treatment of stomach cancer.

Thus, another aspect of the present invention relates to the use of at least one peptide according to the present invention according to any one of SEQ ID No. 5, 28, 29, 30, 31, 37, 40, 41, 60, 85, 90, 92, 93, 94, 99, 114, 115, 120, 124, 125, 128, 131, 137, 142, 145, 148, 151, 152, 154, 157, 158, 159, 165, 4, 34, 84, 111, 146, 149, and 160 for the—in one preferred embodiment combined—treatment of colon and rectal cancer.

Thus, another aspect of the present invention relates to the use of at least one peptide according to the present invention according to any one of SEQ ID No. 4, 5, 14, 19, 31, 35, 37, 48, 50, 51, 60, 64, 70, 73, 80, 85, 86, 96, 99, 100, 101, 102, 103, 104, 111, 114, 115, 116, 120, 123, 124, 125, 129, 131, 132, 135, 136, 137, 142, 145, 146, 148, 149, 150, 155, 158, 159, 160, 161, 165, 167, 169, 174, and 176 for the—in one preferred embodiment combined—treatment of liver cancer.

Thus, another aspect of the present invention relates to the use of at least one peptide according to the present invention according to any one of SEQ ID No. 2, 8, 10, 22, 31, 39, 46, 79, 86, 104, 111, 123, 130, 142, 156, and 167 for the—in one preferred embodiment combined—treatment of pancreatic cancer.

Thus, another aspect of the present invention relates to the use of at least one peptide according to the present invention according to any one of SEQ ID No. 98, 102, 109, 111, 115, 142, 148, 151, and 167 for the—in one preferred embodiment combined—treatment of prostate cancer.

Thus, another aspect of the present invention relates to the use of at least one peptide according to the present invention according to any one of SEQ ID No. 7, 22, 48, 62, 71, 81, 83, 94, 95, 104, 110, 122, 144, 145, 147, 149, 150, 152, 154, 159, 160, 161, 171, and 176 for the—in one preferred embodiment combined—treatment of leukemia.

Thus, another aspect of the present invention relates to the use of at least one peptide according to the present invention according to any one of SEQ ID No. 3, 4, 21, 29, 30, 32, 52, 57, 65, 67, 84, 93, 99, 102, 103, 106, 108, 111, 114, 117, 120, 123, 126, 127, 128, 139, 140, 142, 143, 148, 151, and 158 for the—in one preferred embodiment combined—treatment of AML.

Thus, another aspect of the present invention relates to the use of at least one peptide according to the present invention according to any one of SEQ ID No. 4, 6, 84, 91, 99, 107, 114, 118, 127, 130, 142, 155, and 158 for the—in one preferred embodiment combined—treatment of CLL.

Thus, another aspect of the present invention relates to the use of at least one peptide according to the present invention according to any one of SEQ ID No. 2, 4, 8, 9, 16, 22, 26, 31, 35, 37, 41, 59, 77, 79, 84, 90, 93, 99, 110, 137, 142, 150, 169, 175, 29, 42, 60, 69, 70, 75, 80, 82, 86, 95, 111, 120, 124, 127, 128, 129, 138, 144, 149, 151, 155, 158, and 160 for the—in one preferred embodiment combined—treatment of breast cancer.

Thus, another aspect of the present invention relates to the use of at least one peptide according to the present invention according to any one of SEQ ID No. 149, 81, 101, 116, and 124 for the—in one preferred embodiment combined—treatment of Merkel cell carcinoma (MCC).

Thus, another aspect of the present invention relates to the use of at least one peptide according to the present invention according to any one of SEQ ID No. 14, 17, 19, 34, 37, 45, 46, 52, 85, 92, 95, 96, 107, 113, 114, 115, 118, 124, 131, 138, 146, 149, 150, 155, 157, 158, 161, 165, 169, 1, 5, 6, 9, 12, 16, 18, 21, 22, 23, 25, 28, 29, 31, 32, 44, 55, 56, 57, 58, 60, 61, 65, 66, 67, 68, 75, 84, 87, 88, 90, 93, 94, 97, 99, 106, 111, 116, 117, 120, 121, 123, 127, 128, 129, 130, 132, 133, 134, 135, 137, 139, 142, 143, 156, 159, and 160 for the—in one preferred embodiment combined—treatment of melanoma.

Thus, another aspect of the present invention relates to the use of at least one peptide according to the present invention according to any one of SEQ ID No. 4, 14, 35, 37, 46, 52, 60, 70, 81, 85, 92, 94, 95, 101, 120, 124, 125, 129, 131, 132, 134, 136, 142, 146, 147, 149, 150, 154, 157, 158, 160, 162, 165, 167, 3, 47, 57, 84, 89, 99, 111, 138, and 148 for the—in one preferred embodiment combined—treatment of ovarian cancer.

Thus, another aspect of the present invention relates to the use of at least one peptide according to the present invention according to any one of SEQ ID No. 1, 2, 4, 5, 8, 9, 11, 12, 14, 19, 29, 35, 37, 40, 46, 50, 51, 52, 57, 58, 62, 63, 67, 70, 75, 77, 79, 85, 91, 92, 94, 95, 106, 114, 118, 120, 124, 129, 131, 132, 135, 136, 137, 142, 147, 148, 149, 154, 158, 165, 169, 1, 2, 4, 5, 8, 9, 11, 12, 14, 19, 29, 35, 37, 40, 46, 50, 51, 52, 57, 58, 62, 63, 67, 70, 75, 77, 79, 85, 91, 92, 94, 95, 106, 114, 118, 120, 124, 129, 131, 132, 135, 136, 137, 142, 147, 148, 149, 154, 158, 165, and 169 for the—in one preferred embodiment combined—treatment of esophageal cancer.

Thus, another aspect of the present invention relates to the use of at least one peptide according to the present invention according to any one of SEQ ID No. 3, 4, 20, 29, 37, 41, 42, 59, 60, 64, 82, 88, 91, 93, 95, 97, 99, 101, 104, 106, 114, 115, 120, 122, 131, 135, 137, 142, 150, 151, 152, 154, 156, 157, 160, 166, 169, 170, 171, 175, 1, 5, 6, 12, 14, 15, 19, 30, 31, 38, 46, 52, 57, 65, 67, 70, 71, 74, 84, 86, 89, 92, 94, 100, 103, 107, 109, 111, 113, 118, 123, 126, 127, 128, 129, 130, 138, 148, 149, 158, and 159 for the—in one preferred embodiment combined—treatment of urinary bladder cancer.

Thus, another aspect of the present invention relates to the use of at least one peptide according to the present invention according to any one of SEQ ID No. 41, 85, 94, 116, 120, 130, 143, 162, 165, and 166 for the—in one preferred embodiment combined—treatment of endometrial cancer.

Thus, another aspect of the present invention relates to the use of at least one peptide according to the present invention according to any one of SEQ ID No. 8, 10, 19, 31, 73, 75, 94, 102, 115, 116, 122, 125, 131, 149, 4, 21, 22, 30, 46, 50, 69, 70, 80, 90, 95, 96, 103, 111, 120, 129, 142, 144, 145, 147, 152, 154, 156, and 160 for the—in one preferred embodiment combined—treatment of gall bladder and bile duct cancer.

Thus, another aspect of the present invention relates to the use of at least one peptide according to the present invention according to any one of SEQ ID No. 4, 5, 6, 12, 14, 15, 19, 29, 37, 38, 39, 42, 46, 50, 56, 57, 60, 70, 74, 82, 84, 91, 95, 101, 103, 104, 106, 110, 111, 118, 123, 129, 132, 135, 146, 148, 149, 151, 156, 157, 158, 159, 160, and 161 for the—in one preferred embodiment combined—treatment of uterine cancer.

Thus, another aspect of the present invention relates to the use of the peptides according to the present invention for the—preferably combined—treatment of a proliferative disease selected from the group of pancreatic cancer, lung cancer, kidney cancer, brain cancer, stomach cancer, colon or rectal cancer, liver cancer, prostate cancer, leukemia, breast cancer, Merkel cell carcinoma (MCC), melanoma, ovarian cancer, esophageal cancer, urinary bladder cancer, endometrial cancer, gall bladder cancer, and bile duct cancer.

The present invention furthermore relates to peptides according to the present invention that have the ability to bind to a molecule of the human major histocompatibility complex (MHC) Class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 161.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 161, preferably containing SEQ ID No. 1 to SEQ ID No. 79, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are pancreatic cancer, lung cancer, kidney cancer, brain cancer, stomach cancer, colon or rectal cancer, liver cancer, prostate cancer, leukemia, breast cancer, Merkel cell carcinoma (MCC), melanoma, ovarian cancer, esophageal cancer, urinary bladder cancer, endometrial cancer, gall bladder cancer, bile duct cancer, and preferably pancreatic cancer cells.

The present invention further relates to biomarkers based on the peptides according to the present invention, herein called "targets" that can be used in the diagnosis of cancer, preferably pancreatic cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally, the antibody carries a further effector function such as an immune stimulating domain or toxin.

The present invention also relates to the use of these novel targets in the context of cancer treatment.

AAGAB encodes a protein that interacts with the gamma-adaptin and alpha-adaptin subunits of complexes involved in clathrin-coated vesicle trafficking. Mutations in this gene are associated with type I punctate palmoplantar keratoderma (RefSeq, 2002). AAGAB is a target of miR-205, which is over-expressed in cervical cancer (Xie et al., 2012). Knockdown of AAGAB leads to increased cell division and proliferation (Pohler et al., 2012).

ACTR2 encodes ARP2 actin-related protein 2 homolog, a major constituent of the ARP2/3 complex. This complex is essential for cell shape and motility through lamellipodial actin assembly and protrusion (RefSeq, 2002). ARP2/3 in complex with other proteins was shown to play a critical role in cancer cell invasion and migration (Nurnberg et al., 2011; Feldner and Brandt, 2002; Frugtniet et al., 2015; Kurisu and Takenawa, 2010; Kirkbride et al., 2011). The ARP2/3 complex with WASP/WAVE protein family members contributes to cell invasion and migration in breast cancer (Frugtniet et al., 2015). The ARP2/3 complex with ArgBP2 is endowed with an anti-tumoral function, when the adhesion and migration of pancreatic cancer cells is regulated (Roignot and Soubeyran, 2009).

ADAM9 encodes one member of the ADAM (a disintegrin and metalloprotease domain) family (member 9). Members of this family take part in the cell-cell and cell-matrix interactions (RefSeq, 2002). ADAM9 gene silencing reduces esophageal squamous cell carcinoma (ESCC) cancer proliferation (Liu et al., 2015b). ADAM9 plays an important role in melanoma proliferation and invasion (Ebrahimi et al., 2014). ADAM9 was shown to be up-regulated in osteosarcoma cells, muscle invasive (MI) bladder cancer cells, non-small cell lung cancer, pancreatic cancer, colon cancer, oral squamous cell carcinoma, cervical cancer, prostate cancer, renal cancer, gastric cancer, lymph node cancer, and breast cancer (Shaker et al., 2011; Vincent-Chong et al., 2013; Li et al., 2013; Ebrahimi et al., 2014; Zhang et al., 2014a; Jia et al., 2014; O'Shea et al., 2003; Jiang et al., 2014a; Zubel et al., 2009). ADAM9 has been implicated in lung cancer metastasis to the brain (Sher et al., 2014; Lin et al., 2014a; Shintani et al., 2004).

AGAP9 encodes ArfGAP with GTPase domain, Ankyrin repeat and PH domain 9 and is located on chromosome 10q11.22 (RefSeq, 2002).

AHCY encodes adenosylhomocysteinase. It regulates the intracellular S-adenosylhomocysteine (SAH) concentration thought to be important for transmethylation reactions (RefSeq, 2002). AHCY down-regulation contributes to tumorigenesis (Leal et al., 2008). AHCY can promote apoptosis. It inhibits migration and adhesion of esophageal squamous cell carcinoma cells suggesting a role in carcinogenesis of the esophagus (Li et al., 2014b). AHCY protein expression is up-regulated in colon cancer (Kim et al., 2009; Watanabe et al., 2008; Fan et al., 2011). AHCY may be a potential biomarker in ovarian cancer (Peters et al., 2005).

AK2 encodes adenylate kinase 2. AK2 is localized in the mitochondrial intermembrane space and may play a role in apoptosis (RefSeq, 2002). AK2 mediates a novel intrinsic apoptotic pathway that may be involved in tumorigenesis (Lee et al., 2007).

ANKLE2 encodes Ankyrin repeat and LEM domain containing 2. ANKLE2 is a member of the LEM family of inner nuclear membrane proteins. The encoded protein functions as a mitotic regulator through post-mitotic formation of the nuclear envelope (RefSeq, 2002).

ANKRD1 encodes Ankyrin repeat domain-1. It is localized to the nucleus of endothelial cells and is induced by IL-1 and TNF-alpha stimulation. Interactions between this protein and the sarcometric proteins myopalladin and titin suggest that it may also be involved in the myofibrillar stretch-sensor system (RefSeq, 2002). The ectopic expression of ANKRD1 leads to reduced colony formation and to enhanced apoptotic cell death in hepatoma cells (Park et al., 2005). High expression of ANKRD1 in ovarian carcinoma is associated with poor survival (Lei et al., 2015).

ANLN encodes an actin-binding protein that plays a role in cell growth and migration, and in cytokinesis. ANLN is thought to regulate actin cytoskeletal dynamics in podocytes, components of the glomerulus. Mutations in this gene are associated with focal segmental glomerulosclerosis 8 (RefSeq, 2002). ANLN was found to be highly expressed in breast cancer tissues as well as head and neck squamous cell carcinomas. Knock-down of ANLN remarkably inhibited the proliferation rate, colony formation ability and migration of breast cancer cells (Zhou et al., 2015b). ANLN is overexpressed in proliferative gastric tumors, pancreatic carcinoma and hormone-refractory prostate cancers (Pandi et al., 2014; Tamura et al., 2007; Shimizu et al., 2007; Olakowski et al., 2009). ANLN is a biomarker for hepatocellular carcinoma (Kim et al., 2013a). ANLN expression is a marker of favorable prognosis in patients with renal cell carcinoma (Ronkainen et al., 2011).

APOL6 encodes apolipoprotein L, 6. APOL6 is a member of the apolipoprotein L gene family. The encoded protein is found in the cytoplasm, where it may affect the movement of lipids or allow the binding of lipids to organelles (RefSeq, 2002). APOL6 induces mitochondria-mediated apoptosis in cancer cells (Liu et al., 2005).

ARMC9 (also called KU-MEL-1) encodes an armadillo repeat-containing protein that was a previously isolated melanoma antigen preferentially expressed in melanocytes. It is associated with Vogt-Koyanagi-Harada disease (Otani et al., 2006). ARMC9 is strongly expressed in melanoma cell lines and tissue samples. Antigens against ARMC9 were detected in the sera of patients treated against brain, colon and esophageal cancer (Kiniwa et al., 2001).

ASNS encodes asparagine synthetase. The ASNS gene complements a mutation in the temperature-sensitive hamster mutant ts11, which blocks progression through the G1 phase of the cell cycle at non-permissive temperature (RefSeq, 2002). ASNS expression is induced by glucose deprivation and protects pancreatic cancer cells from apoptosis (Cui et al., 2007). ASNS is associated with drug resistance in leukemia and uterine cancer (Lin et al., 2012; Zhang et al., 2013a). Knock-down of ASNS in A375 cells down-regulates the expression levels of CDK4, CDK6, and cyclin D1 and up-regulates the expression of p21 (Li et al., 2015a). Down-regulation of ASNS induces cell cycle arrest and inhibits cell proliferation of breast cancer (Yang et al., 2014a). ASNS is highly expressed in gliomas (Panosyan et al., 2014). ASNS is a potential biomarker in ovarian cancer (Lorenzi et al., 2006; Lorenzi et al., 2008; Lorenzi and Weinstein, 2009).

ATP5F1 encodes ATP synthase, H+ transporting, mitochondrial F0 complex, subunit B1, a subunit of mitochondrial ATP synthase (RefSeq, 2002). ATP5F1 is up-regulated in hepatitis B virus-associated hepatocellular carcinoma (Lee et al., 2008a).

BMS1 encodes BMS1 ribosome biogenesis factor and is located on chromosome 10811.21. A similar protein in yeast functions in 35S-rRNA processing, which includes a series of cleavage steps critical for formation of 40S ribosomes (RefSeq, 2002; Perez-Fernandez et al., 2011).

BMS1P5 encodes BMS1 ribosome biogenesis factor pseudogene 5 and is located on chromosome 10q11.22 (RefSeq, 2002).

BRK1 (also called C3orf10 or HSPC300) encodes the smallest subunit of the Wave complex and is an important regulator of the Wave/Scar pathway involved in actin cytoskeleton dynamics during embryonic development and cell transformation (Derivery et al., 2008; Escobar et al., 2010). BRK1 has oncogenic potential in different cancer types including lung cancer and renal cell carcinomas (Cascon et al., 2007; Cai et al., 2009; Escobar et al., 2010). BRK1 is regulated by the transcription factors Sp1 and NRF-1. It is involved in the Wave/Scar pathway following Arp2/3 regulation and required for cell proliferation and transformation (Li et al., 2014a; van't Veer et al., 2006; Escobar et al., 2010; Wang et al., 2013c).

BTBD1 encodes BTB (POZ) domain containing 1. The C-terminus of the protein binds topoisomerase I. The N-terminus contains proline rich region and a BTB/POZ domain, both of which are typically involved in protein-protein interactions (RefSeq, 2002).

BUB1B encodes a kinase involved in spindle checkpoint function. The protein is localized to the kinetochore and plays a role in the inhibition of the anaphase-promoting complex/cyclosome (APC/C), delaying the onset of anaphase and ensuring proper chromosome segregation. Impaired spindle checkpoint has been found in many forms of cancer (RefSeq, 2002). BUB1B is a tumor inhibitory protein. BUB1B regulates the spindle assembly checkpoint. BUB1B is inactivated or down-regulated in tumors. Mutations in BUB1B are also linked to tumor development (Ayton and Oren, 2011; Fagin, 2002; Malumbres and Barbacid, 2007; Rao et al., 2009). BUB1B is associated with gastric carcinogenesis through oncogenic activation (Resende et al., 2010). BUB1B mutation is one of the causes for colorectal cancer (Karess et al., 2013; Grady, 2004).

C11orf70 encodes a protein with uncharacterized function, but is linked to the binding of a mutated protein that causes amyotrophic lateral sclerosis (Wang et al., 2015i). C11orf70 is down-regulated in testicular germ cell tumors in comparison to normal testis tissue (Gonzalez-Exposito et al., 2015; Alagaratnam et al., 2009). The genetic region of C11orf70 displays DNA copy number aberrations in oral squamous cell carcinomas, which is associated with oral cancer-specific mortality (Chen et al., 2015a). C11orf80 encodes chromosome 11 open reading frame 80 and is located on chromosome 11q13.2 (RefSeq, 2002).

C1orf198 encodes chromosome 1 open reading frame 198 and is located on chromosome 1q42.2 (RefSeq, 2002).

C20orf24 encodes chromosome 20 open reading frame 24 and is located on chromosome 20q11.23 (RefSeq, 2002). C20orf24 plays an important role in chromosomal instability-related progression from adenoma to carcinoma. C20orf24 is significantly over-expressed in carcinomas compared with adenomas. C20orf24 may serve as a highly specific biomarker for colorectal cancer (Carvalho et al., 2009).

CAD encodes for trifunctional protein carbamoylphosphate synthetase 2, aspartate transcarbamylase, and dihydroorotase, which catalyzes the first three reactions of the pyrimidine biosynthesis pathway (RefSeq, 2002). CAD activity is increased in different cancer types, including hepatomas, sarcomas and kidney adenocarcinomas and is very frequently associated with the amplification of the CAD gene (Smith et al., 1990; Aoki and Weber, 1981; Smith et al., 1997). CAD is a target of different oncogenes and tumorigenesis regulating pathways like MAPK, mTORC1 and c-Myc (Mac and Farnham, 2000; Graves et al., 2000; Sharma et al., 2014). CAD promotes androgen receptor translocation into the nucleus and stimulates its transcriptional activity in prostate tumor cells. After radical prostatectomy a higher CAD mRNA level is associated with local tumor extension and cancer relapse (Morin et al., 2012).

CARM1 encodes coactivator-associated arginine methyltransferase 1. CARM1 belongs to the protein arginine methyltransferase (PRMT) family. The encoded enzyme catalyzes the methylation of guanidine nitrogens of arginyl residues of proteins. The enzyme is involved in gene expression (RefSeq, 2002). CARM1 has shown to be dysregulated in colorectal and prostate cancer, melanoma and breast cancer. CARM1 is over-expressed not only in prostate tumors, but also in prostatic intraepithelial neoplasia (PIN). CARM1 is significantly over-expressed in non-small cell lung carcinomas (NSCLC). CARM1 expression is elevated in adenomas and aberrant in carcinomas during hepatocellular carcinogenesis (Limm et al., 2013; Osada et al., 2013; Elakoum et al., 2014; Baldwin et al., 2014). CARM1 methylates chromatin remodeling factor BAF155 to enhance tumor progression and metastasis (Wang et al., 2014a; Stefansson and Esteller, 2014).

CCNA2 encodes cyclin A2, a member of the highly conserved cyclin family. CCNA2 binds and activates CDC2 or CDK2 kinases, and thus promotes both cell cycle G1/S and G2/M transitions (RefSeq, 2002). Over-expression of CCNA2 inhibits the proliferation of hepatocellular carcinoma cells. Over-expression of CCNA2 in endometrial adenocarcinoma cells decreases cell growth and increases apoptosis. CCNA2 expression in melanoma cells reduces tumor growth and metastasis and concomitantly increases apoptosis in tumors (Lau, 2011). CCNA2 can promote cancer cell proliferation, invasion, adhesion, differentiation, survival and metastasis. It plays an important role in angiogenesis and extracellular matrix production. CCNA2 promotes tumor growth and increases tumor vascularization when over-expressed in gastric adenocarcinoma cells. Silencing of CCNA2 expression decreases tumor growth in pancreatic cancer cells. CCNA2 can promote the proliferation of prostate cancer cells (Lau, 2011; Chen and Du, 2007). CCNA2 over-expression induces epithelial-mesenchymal transition, leading to laryngeal tumor invasion and metastasis (Liu et al., 2015e). CCNA2 is dysregulated in colorectal cancer (Chang et al., 2014). CCNA2 is over-expressed in prostate cancer, gliomas, pancreatic cancer, and breast cancer. CCNA2 is associated with increased aggressiveness, vascularization, and estrogen independence in breast cancer, suggesting a major role of CCNA2 in breast cancer progression (Zuo et al., 2010).

CCND1 encodes cyclin D1. It belongs to the highly conserved cyclin family, whose members are characterized by a dramatic periodicity in protein abundance throughout the cell cycle. Mutations, amplifications and over-expression of CCND1, which alters cell cycle progression, are observed frequently in a variety of tumors and may contribute to tumorigenesis (RefSeq, 2002). CCND1 is amplified and over-expressed in cases of lymph node metastasis in oral squamous cell carcinoma, gastrointestinal stromal tumor, non-small cell lung cancer, pituitary tumors and breast cancer (Noorlag et al., 2015; Dworakowska, 2005; Gautschi et al., 2007; Lambros et al., 2007; Yang et al., 2008; Yu and Melmed, 2001). CCND1 is over-expressed in mantle cell lymphoma, pancreatic neuroendocrine tumors, parathyroid adenoma, and Ewing sarcoma (Navarro et al., 2011; Sander, 2011; Capurso et al., 2012; Delas et al., 2013; Setoodeh et al., 2013; Sanchez et al., 2008; Westin et al., 2009). CCND1 can increase colorectal cancer risk (Yang et al., 2012b; Andersen et al., 2013). CCND1 genetic alterations can cause bladder cancer (Zhang et al., 2003; Baffa et al., 2006).

CCT3 encodes chaperonin containing TCP1, subunit 3 (gamma), a molecular chaperone (RefSeq, 2002). CCT3 is elevated in hepatocellular carcinoma (Midorikawa et al., 2002; Skawran et al., 2008). CCT3 is a potentially novel biomarker for ovarian cancer (Peters et al., 2005).

CCT4 encodes chaperonin containing TCP1, subunit 4. CCT4 assists the folding of newly translated polypeptide substrates through multiple rounds of ATP-driven release and rebinding of partially folded intermediate forms (RefSeq, 2002). CCT4 deregulation causes esophageal squamous cell carcinoma and lung adenocarcinoma (Wang et al., 2015j; Tano et al., 2010). CCT4 is upregulated in gastric cancers (Malta-Vacas et al., 2009).

CDC27 encodes cell division cycle 27. The protein encoded by this gene is a component of the anaphase-promoting complex (APC). The protein may be involved in controlling the timing of mitosis (RefSeq, 2002). CDC27 confers increased radio-resistance of triple negative breast cancer cells and squamous cell cervix carcinoma, when it is down-regulated (Rajkumar et al., 2005; Ren et al., 2015). CDC27 plays a crucial role in the progression of hepatocellular carcinoma, and also correlates with poor prognosis in esophageal squamous cell carcinoma and pancreatic cancer (Ahn et al., 2014; Wang et al., 2015h). CDC27 polymorphisms may contribute to the susceptibility of breast cancer through influencing the mitotic progression of cells (Guo et al., 2015). CDC27 mutation is involved in prostate cancer (Lindberg et al., 2013). CDC27 mutation and down-regulation is involved in several breast and colon carcinoma cell lines (Fan et al., 2004; Roy et al., 2010; Pawar et al., 2010).

CDK12 encodes cyclin dependent kinase 12 and is located on chromosome 17q12 (RefSeq, 2002). CDK12 mutations were identified in a variety of tumors, including ovarian, breast, prostate, and intestinal tumors (Vrabel et al., 2014).

CDK13 encodes cyclin dependent kinase 13, a member of the cyclin dependent serine/threonine protein kinase family. Members of this family are known for their essential roles as master switches in cell cycle control. They may play a role in mRNA processing and may be involved in regulation of hematopoiesis (RefSeq, 2002). CDK13 is associated with pancreatic cancer and skin cancer (Ansari et al., 2015; Nelson et al., 1999; Chandramouli et al., 2007). CDK13 is amplified in hepatocellular carcinoma (Kim et al., 2012b).

CDK2 encodes cyclin dependent kinase 2, a serine/threonine protein kinase that participates in cell cycle regulation. Activity of this protein is especially critical during the G1 to S phase transition (RefSeq, 2002). CDK2 over-expression indicates the abnormal regulation of cell cycle, which would be directly related to hyper-proliferation in cancer cells (Chohan et al., 2015). CDK2 is associated with leukemia, colorectal carcinoma, melanoma, human papillomavirus-associated cervical neoplasia, lung cancer, breast cancer and prostate cancer (Foster et al., 2001; Zajac-Kaye, 2001; Raso et al., 2013; He et al., 2013; Duensing and Munger, 2002; Hu and Zuckerman, 2014; Agarwal, 2000). CDK2 is highly-expressed in mantle cell lymphoma (Rummel et al., 2004).

CDK5RAP3 encodes CDK5 regulatory subunit associated protein 3. CDK5RAP3 plays a role in signaling pathways governing transcriptional regulation and cell cycle progression. It may have a function in tumorigenesis and metastasis (RefSeq, 2002). CDK5RAP3 is over-expressed in hepatocellular carcinoma and promotes metastasis (Mak et al., 2011; Mak et al., 2012).

CDK7 encodes cyclin dependent kinase 7, a member of the cyclin dependent protein kinase family. It is an essential component of the transcription factor TFIIH, which is involved in transcription initiation and DNA repair. This protein is thought to serve as a direct link between the regulation of transcription and the cell cycle (RefSeq, 2002). CDK7 genetic polymorphisms predispose individuals to breast cancer by gene-environment or gene-gene interactions (Yoo and Kang, 2003). CDK7 is associated with an increased risk for pancreatic cancer (Efthimiou et al., 2001). CDK7 has been associated with breast cancer (Cance and Liu, 1995).

CDK9 encodes cyclin dependent kinase 9, a member of the cyclin dependent protein kinase family. This protein forms a complex with and is regulated by its regulatory subunit cyclin T or cyclin K (RefSeq, 2002). CDK9 appears to be involved in the differentiation program of several cell types, such as muscle cells, monocytes and neurons. CDK9 seems to have an anti-apoptotic function in monocytes. Involvement of CDK9 in several physiological processes in the cell may lead to the onset of cancer (De and Giordano, 2002).

CELSR3 encodes cadherin, EGF LAG seven-pass G-type receptor 3. The encoded protein may be involved in the regulation of contact dependent neurite growth and may play a role in tumor formation (RefSeq, 2002). Microarray screening revealed that CELSR3 hyper-methylated in primary oral squamous cell carcinoma compared to normal oral mucosa (Khor et al., 2014). CELSR3 is associated with ovarian cancer and brain tumors (Asad et al., 2014; Katoh and Katoh, 2007). CELSR3 is up-regulated in pancreatic and hepatic tumor stellate cells (Erkan et al., 2010).

CEP97 encodes centrosomal protein 97 kDa and is located on chromosome 3q12.3 (RefSeq, 2002). CEP97 is associated with breast cancer (Rappa et al., 2014).

CFL1 encodes cofilin 1. It is involved in the translocation of the actin-cofilin complex from cytoplasm to nucleus (RefSeq, 2002). CFL1 mutation is associated with multiple endocrine neoplasia type 4 and glioblastoma multiforme (Solomon et al., 2008; Georgitsi, 2010). CFL1 is over-expressed in lymphoma, leukemia, neuroblastoma, ovarian, prostate, breast and lung cancers and mesothelioma (Rana et al., 2008). CFL1 is down-regulated in testicular germ cell tumors (von Eyben, 2004).

CHD3 encodes chromodomain helicase DNA binding protein 3. The protein is one of the components of a histone deactelylase complex referred to as the Mi-2/NuRD complex which participates in the remodeling of chromatin by deacetylating histones (RefSeq, 2002). CHD3 is up-regulated in pancreatic intraepithelial neoplasia and pancreatic carcinoma (Wang et al., 2011). CHD3 mutation is associated with gastric and colorectal cancer (Kim et al., 2011a). CHD3 is over-expressed in acute myeloid leukemia (Camos et al., 2006).

CHD4 encodes chromodomain helicase DNA binding protein 4. It represents the main component of the nucleosome remodeling and deacetylase complex and plays an important role in epigenetic transcriptional repression. Somatic mutations in this gene are associated with serous endometrial tumors (RefSeq, 2002). CHD4 is a novel therapeutic target for acute myeloid leukemia (Sperlazza et al., 2015). CHD4 epigenetically controls gene regulation and DNA damage responses in EpCAM+ liver cancer stem cells (Nio et al., 2015). CHD4 modulates therapeutic response in BRCA2 mutant cancer cells (Guillemette et al., 2015). CHD4 is associated with glioblastoma and colon cancer (Cai et al., 2014; Chudnovsky et al., 2014).

CHD5 encodes chromodomain helicase DNA binding protein 5. CHD5 is a potential tumor suppressor that may play a role in the development of neuroblastoma (RefSeq, 2002). CHD5 functions as a tumor suppressor gene in gliomas and a variety of other tumor types, including breast, colon, lung, ovary, and prostate cancer (Kolla et al., 2014).

CIRH1A (also called Cirhin) encodes cirrhosis autosomal recessive 1 A, a WD40-repeat-containing protein localized in the nucleolus. It causes North American Indian childhood cirrhosis (NAIC) (RefSeq, 2002). CIRH1A can up-regulate a canonical NF-kappaB element and might participate in the regulation of other genes containing NF-kappaB elements. This suggests that CIRH1A can influence the cancer-related NF-kappaB pathway (Yu et al., 2009).

COL1A1 encodes collagen, type 1, alpha 1. Type 1 is a fibril forming collagen found in most connective tissues and is abundant in bone, cornea, dermis, and tendon. Reciprocal translocations between chromosomes 17 and 22, where this gene and the gene for platelet derived growth factor beta are located, are associated with a particular type of skin tumor called dermatofibrosarcoma protuberans, resulting from unregulated expression of the growth factor (RefSeq, 2002). COL1A1 is differentially expressed in gastric cancer (Yasui et al., 2004). COL1A1 is associated with pigmented dermatofibrosarcoma protuberans (Zhang et al., 2013c).

COL1A2 encodes collagen, type 1, alpha 2. Type 1 is a fibril forming collagen found in most connective tissues and is abundant in bone, cornea, dermis and tendon (RefSeq, 2002). COL1A2 is associated with gastric cancer (Yasui et al., 2004; Yasui et al., 2005).

COL6A1 encodes collagen, type 6, alpha 1. Collagen VI is a major structural component of microfibrils. Mutations in the genes that code for the collagen VI subunits result in the autosomal dominant disorder Bethlem myopathy (RefSeq, 2002). COL6A1 is up-regulated in the reactive stroma of castration-resistant prostate cancer and promotes tumor growth (Zhu et al., 2015c). COL6A1 is over-expressed in CD166− pancreatic cancer cells that show stronger invasive and migratory activities than those of CD166+ cancer cells (Fujiwara et al., 2014). COL6A1 is highly expressed in bone metastasis (Blanco et al., 2012). COL6A1 was found to be up-regulated in cervical and ovarian cancer (Zhao et al., 2011; Parker et al., 2009). COL6A1 is differentially expressed in astrocytomas and glioblastomas (Fujita et al., 2008).

COL6A3 encodes collagen, type VI, alpha 3, one of the three alpha chains of type VI collagen, a beaded filament collagen found in most connective tissues, and important in organizing matrix components (RefSeq, 2002). COL6A3 encodes the alpha-3 chain of type VI collagen, a beaded filament collagen found in most connective tissues, playing an important role in the organization of matrix components (RefSeq, 2002). COL6A3 is alternatively spliced in colon, bladder and prostate cancer. The long isoform of COL6A3 is expressed almost exclusively in cancer samples and could potentially serve as a new cancer marker (Thorsen et al., 2008). COL6A3 is highly expressed in pancreatic ductal adenocarcinoma tissue and undergoes tumor-specific alternative splicing (Kang et al., 2014). COL6A3 has been demonstrated to correlate with high-grade ovarian cancer and contributes to cisplatin resistance. COL6A3 was observed to be frequently over-expressed in gastric cancer tissues (Xie et al., 2014). COL6A3 mutation(s) significantly predicted a better overall survival in patients with colorectal carcinoma independent of tumor differentiation and TNM staging (Yu et al., 2015b). COL6A3 expression was reported to be increased in pancreatic cancer, colon cancer, gastric cancer, mucoepidermoid carcinomas and ovarian cancer. Cancer associated transcript variants including exons 3, 4 and 6 were detected in colon cancer, bladder cancer, prostate cancer and pancreatic cancer (Arafat et al., 2011; Smith et al., 2009; Yang et al., 2007; Xie et al., 2014; Leivo et al., 2005; Sherman-Baust et al., 2003; Gardina et al., 2006; Thorsen et al., 2008). In ovarian cancer COL6A3 levels correlated with higher tumor grade and in pancreatic cancer COL6A3 was shown to represent a suitable diagnostic serum biomarker (Sherman-Baust et al., 2003; Kang et al., 2014).

COPG1 (also called COPG) encodes for the gamma subunit of the coatomer protein complex (COPI) that mediates retrograde transport from the Golgi back to the ER and intra-Golgi transport. COPG1 binds to ARF-GAP (Waters et al., 1991; Watson et al., 2004). COPG1 correlates with the age of the patients as well as a higher grade of malignancy and the grade of gliosarcomas (Coppola et al., 2014). COPG1 was found abundantly expressed in lung cancer and lung cancer-related endothelial cells (Park et al., 2008).

CREB3L1 encodes cAMP responsive element binding protein 3-like 1. In response to ER stress, CREB3L1 is cleaved and the released cytoplasmic transcription factor domain translocates to the nucleus. There it activates the transcription of target genes by binding to box-B elements (RefSeq, 2002). CREB3L1 mutations are frequently found in sclerosing epithelioid fibrosarcoma (SEF) (Prieto-Granada et al., 2015). CREB3L1 is induced by ER stress in human glioma cell lines and contributes to the unfolded protein response, extracellular matrix production and cell migration (Vellanki et al., 2013). CREB3L1 is epigenetically silenced in bladder cancer, facilitating tumor cell spreading and migration (Rose et al., 2014). CREB3L1 plays an important role in suppressing tumorigenesis in breast cancer. Loss of expression is required for the development of a metastatic phenotype (Mellor et al., 2013).

CSTF1 encodes cleavage stimulation factor, 3' pre-RNA, subunit 1, 50 kDa. It is involved in the polyadenylation and 3' end cleavage of pre-mRNAs (RefSeq, 2002). CSTF1 variation was found to be associated with breast cancer risk in BRCA2 mutation carriers (Blanco et al., 2015).

CTHRC1 encodes collagen triple helix repeat containing 1. CTHRC1 may play a role in the cellular response to arterial injury through involvement in vascular remodeling. Mutations at this locus have been associated with Barrett esophagus and esophageal adenocarcinoma (RefSeq, 2002). CTHRC1 shows increased expression in gastric cancer and ductal carcinoma of the breast (Kim et al., 2013b; Yu et al., 2015a; Song et al., 2015). CTHRC1 is up-regulated in colorectal cancer (Yan et al., 2015a; Yan et al., 2015b). CTHRC1 expression is highly correlated with hepatocellular carcinoma progression in patients infected with hepatitis B virus. CTHRC1 enhances colony formation, migration and invasion of hepatoma cells (Tameda et al., 2014; Zhang et al., 2015b). CTHRC1 is over-expressed in non-small cell lung cancer. Over-expression is associated with tumor aggressiveness and poor prognosis (Ke et al., 2014b). CTHRC1 is up-regulated in esophageal squamous cell carcinoma and Barrett's adenocarcinoma (Timme et al., 2014). CTHRC1 promotes cell adhesion and survival in melanoma (Ip et al., 2011).

CXCL5 encodes chemokines C-X-C motif ligand 5. This protein is proposed to bind the G-protein coupled receptor chemokine C-X-C motif receptor 2 to recruit neutrophils, to promote angiogenesis and to remodel connective tissues. This protein is thought to play a role in cancer cell proliferation, migration, and invasion (RefSeq, 2002). CXCL5 plays a crucial role in survival, growth and metastasis of renal cell carcinoma (Parihar and Tunuguntla, 2014). CXCL5 is involved in the transition of chronic inflammation to esophageal and gastric cancer (Verbeke et al., 2012). CXCL5 is associated with acute myelogenous leukemia (Kittang et al., 2010).

DCBLD2 encodes discoidin, CUB and LCCL domain-containing protein 2 also referred to as endothelial and smooth muscle cell-derived neuropilin-like protein, a transmembrane co-receptor protein (RefSeq, 2002). DCBLD2 is up-regulated in glioblastomas and head and neck cancers (HNCs) and is required for EGFR-stimulated tumorigenesis (Feng et al., 2014). Furthermore, DCBLD2 is up-regulated in highly metastatic lung cancer sublines and tissue samples (Koshikawa et al., 2002). In contrast, the expression of DCBLD2 is silenced by hypermethylation of its promoter in gastric cancer (Kim et al., 2008).

DDX43 encodes DEAD (Asp-Glu-Ala-Asp) box polypeptide 43. DDX43 is an ATP dependent RNA helicase and displays tumor specific expression (RefSeq, 2002). DDX43 is over-expressed in uveal melanoma cells and in acute and chronic myeloid leukemia (Chen et al., 2011a; Lin et al., 2014b; Ambrosini et al., 2014). DDX43 is a biomarker for breast cancer prognosis (Wiese and Pajeva, 2014). DDX43 is expressed on glioma cell lines (Akiyama et al., 2014).

DDX53 encodes DEAD (Asp-Glu-Ala-Asp) box polypeptide 53. DDX53 contains several domains found in members of the DEAD box helicase protein family (RefSeq, 2002). Cancer/testis antigen DDX53 exerts negative regulation on p53 expression through HDAC2 and confers resistance to anti-cancer drugs (Kim et al., 2010b). miR-200b and cancer/testis antigen DDX53 form a feedback loop to regulate the invasion and tumorigenic and angiogenic responses of a cancer cell line to microtubule-targeting drugs (Kim et al., 2013c). miR-217 and DDX53 form a feedback loop to regulate the response to anti-cancer drugs through EGFR and HER2 (Kim et al., 2016). DDX53 is one of several genes with an abnormal DNA hypo-methylation status in uterine leiomyoma (Maekawa et al., 2011). In cell lines derived from 21 B-cell and 4 T-cell malignancies, a broad mRNA expression profile was observed for DDX53 (Liggins et al., 2010).

DNAJC7 encodes DnaJ (Hsp40) homolog, subfamily C, member 7, a member of the DNAJ heat shock protein (HSP) 40 family of proteins. This protein binds the chaperone proteins HSP70 and HSP90 in an ATP dependent manner and may function as a co-chaperone (RefSeq, 2002).

DNAJC7 enhances p53 stability and activity through blocking the complex formation between p53 and MDM2 (Kubo et al., 2013).

DPP9 encodes dipeptidyl peptidase 9. DPP9 appears to be involved in the regulation of the activity of its substrates and has been linked to a variety of diseases including type 2 diabetes, obesity and cancer (RefSeq, 2002). DPP9 plays a potential role in breast and ovarian cancer (Wilson and Abbott, 2012). DPP9 plays an important signaling role in the regulation of cell survival and proliferation pathways (Yao et al., 2011). DPP9 mRNA levels are elevated in testicular tumors (Yu et al., 2010). DPP9 is over-expressed in meningiomas (Stremenova et al., 2010).

DPYD (also known as DPD) encodes dihydropyrimidine dehydrogenase, a pyrimidine catabolic enzyme and the initial and rate-limiting factor in the pathway of uracil and thymidine catabolism. Mutations in this gene result in dihydropyrimidine dehydrogenase deficiency, an error in pyrimidine metabolism associated with thymine-uraciluria and an increased risk of toxicity in cancer patients receiving 5-fluorouracil chemotherapy (RefSeq, 2002). The DPYD expression level can be used as a predictive factor for the efficacy of chemotherapy in gastric cancer (Wan et al., 2016). Statistically significant associations were found between DPYD variants and increased incidence of grade 3 or greater fluorouracil-related adverse events in patients treated with adjuvant fluorouracil-based combination chemotherapy (Cavalcante et al., 2015; Lee et al., 2016; Boige et al., 2016). There is a correlation between DPYD polymorphism and KRAS wild type expression in colorectal cancer (Kleist et al., 2015). The up-regulation of DPYD gene expression leads to fluoropyrimidine toxicity in colorectal cancer (Chai et al., 2015; Falvella et al., 2015; van Staveren et al., 2015; Nakamura et al., 2015; Chen et al., 2015c; Hu et al., 2015b). Polymorphic expression of DPYD may be important in determining the treatment response in patients with head and neck cancer, pancreatic cancer, esophageal squamous cell carcinoma, digestive cancer, gastric cancer, hepatocellular carcinoma, and colorectal cancer (Kim et al., 2015; Toffoli et al., 2015; Ishizuka et al., 2015; Baba et al., 2015; Launay et al., 2016; Kikuchi et al., 2015; Li et al., 2016; Shimamoto et al., 2016; Bai et al., 2015; Dhawan et al., 2016).

DROSHA, one of the two critical enzymes in microRNA biosynthesis, is over-expressed in a number of cancers including gastrointestinal tumors, breast cancer and cervical cancer and appears to enhance proliferation, colony formation and migration of tumor cells (Avery-Kiejda et al., 2014; Havens et al., 2014; Zhou et al., 2013).

DSEL encodes dermatan sulfate epimerase-like and is located on chromosome 18q22.1 (RefSeq, 2002). DSE is an important paralog of DSEL. DSE is an immunogenic target for immunotherapy of hepatocellular carcinoma and colorectal carcinoma (Mizukoshi et al., 2011; Sasatomi et al., 2002).

DST (also known as bullous pemphigoid antigen I (BPAG1)) encodes dystonin, a member of the plakin protein family of adhesion junction plaque proteins. The full-length isoform is not defined, however, there are several isoforms expressed in neural and muscle tissue or in epithelial tissue, anchoring either neural intermediate filaments to the actin cytoskeleton or keratin-containing intermediate filaments to hemidesmosomes (RefSeq, 2002; Bouameur et al., 2014; Li et al., 2007). DST may be related to breast cancer metastasis (Sun et al., 2006). Autoantibodies against DST can be found in lymphocytic leukemia and follicular lymphomas (Aisa et al., 2005; Taintor et al., 2007). DST is up-regulated in 5-8F cells (high tumorigenic and metastatic ability) in comparison to 6-10B cells (tumorigenic, but lacking metastatic ability) in nasopharyngeal carcinoma (Fang et al., 2005). DST is highly expressed in head and neck squamous cell carcinoma (Lin et al., 2004). There are autoantibodies against DST in paraneoplastic pemphigus which is associated with neoplasms (Yong and Tey, 2013; Wang et al., 2005; Preisz and Karpati, 2007; Zhu and Zhang, 2007). DST expression in prostate cancer is strongly inverse correlated with progression (Vanaja et al., 2003). Anti-DST autoantibodies are a promising marker for the diagnosis of melanoma (Shimbo et al., 2010). DST can be found in the urine of cachectic cancer patients (Skipworth et al., 2010). DST is differentially expressed in adenocarcinomas and squamous cell carcinomas of the lung (McDoniels-Silvers et al., 2002). DST is distinctly up-regulated with the onset of invasive cell growth (Herold-Mende et al., 2001).

DYNC1H1 encodes the dynein heavy chain 1, a subunit of the main motor protein for retrograde transport along microtubules. A whole exome sequencing study uncovered somatic mutations within the DYNC1H1 gene in patients with intra-ductal papillary mucinous neoplasm of the pancreas (Furukawa et al., 2011).

EIF3C encodes eukaryotic translation initiation factor 3, subunit C and is located on chromosome 16p11.2 (RefSeq, 2002). EIF3C is over-expressed and promotes cell proliferation in human U-87 MG cells (Hao et al., 2015). EIF3C is highly expressed in colon cancer (Song et al., 2013). EIF3C mRNA is over-expressed in testicular seminomas (Rothe et al., 2000).

EIF3CL encodes eukaryotic translation initiation factor 3, subunit C-like. It is located on chromosome 16p11.2 (RefSeq, 2002).

EIF3E encodes eukaryotic translation initiation factor 3, subunit E and is located on chromosome 8q22-q23 (RefSeq, 2002). EIF3E might play a role in the carcinogenesis of oral squamous cell carcinoma (Yong et al., 2014). EIF3E is essential for proliferation and survival of glioblastoma cells (Sesen et al., 2014). EIF3E has an oncogenic role in breast cancer progression. Decreased EIF3E expression causes epithelial to mesenchymal transition in breast epithelial cells (Gillis and Lewis, 2013; Grzmil et al., 2010). EIF3E expression level is significantly increased in bladder cancer (Chen et al., 2011b). EIF3E is involved in non-small lung carcinoma (Marchetti et al., 2001).

EXT2 encodes exostosin glycosyltransferase 2, one of two glycosyltransferases involved in the chain elongation step of heparin sulfate biosynthesis. Mutations in his gene cause the type II form of multiple exostoses (RefSeq, 2002). EXT2 mutation plays a role in chondrosarcoma (Samuel et al., 2014). EXT2 mutation induces multiple osteochondroma syndrome (Jochmann et al., 2014). EXT2 mutation causes hereditary multiple exostoses, leading to heparan sulfate deficiency (Huegel et al., 2013).

F2R (also known as PAR1) encodes coagulation factor II thrombin receptor, a transmembrane receptor involved in the regulation of thrombotic response (RefSeq, 2002). F2R binds to the pleckstrin homology (PH) domain of Etk/Bmx. A F2R mutant, which is unable to bind the PH domain, reduces mammary tumors and extravillous trophoblast invasion (Kancharla et al., 2015). F2R is thought to promote cancer invasion and metastasis by facilitating tumor cell migration, angiogenesis, and interactions with host vascular cells (Wojtukiewicz et al., 2015). Down-regulation of F2R leads to cancer cell death (Burns and Thevenin, 2015). Polymorphisms in F2R are associated with acute injury in rectal cancer patients (Zhang et al., 2015a). F2R is correlated with poor prognosis specifically in ER-negative breast cancer patients (Lidfeldt et al., 2015). F2R-deficient mice show reduced colonic adenocarcinoma growth (Adams et al., 2015). Matrix metalloproteinase (MMP)-1 activates F2R to induce angiogenesis (Fan et al., 2015). F2R is involved in PTEN down-regulation in lung cancer (Xu et al., 2015). F2R activation induces the Hippo-YAP pathway which is correlated with epithelial mesenchymal transition (Jia et al., 2015; Owens et al., 2015; Yang et al., 2015a; Fujimoto et al., 2015). Inhibition of F2R activation reduces cancer cell migration and invasion in HER-2 negative breast cancer, hepatocellular carcinoma and gastric cancer (Mussbach et al., 2015; Wang et al., 2015g; Gonda et al., 2015).

FADS2 encodes fatty acid desaturase 2, a member of the fatty acid desaturase gene family. Desaturase enzymes regulate unsaturation of fatty acids through the introduction of double bonds between defined carbons of the fatty acyl chain (RefSeq, 2002). FADS2 is up-regulated in hepatocellular carcinoma (Muir et al., 2013). FADS2 activity is increased in breast cancer tissue (Pender-Cudlip et al., 2013). FADS2 expression is associated with aggressiveness of breast cancer (Lane et al., 2003). FADS2 inhibition impedes intestinal tumorigenesis (Hansen-Petrik et al., 2002).

FADS3 encodes fatty acid desaturase 3. Desaturase enzymes regulate unsaturation of fatty acids through the introduction of double bonds between defined carbons of the fatty acyl chain (RefSeq, 2002).

FAM83D encodes family with sequence similarity 83, member D and is located on chromosome 20q11.23 (RefSeq, 2002). Up-regulation of FAM83D affects the proliferation and invasion of hepatocellular carcinoma cells (Wang et al., 2015a; Liao et al., 2015). FAM83D is significantly elevated in breast cancer cell lines and in primary human breast cancers (Wang et al., 2013e).

FN1 encodes fibronectin 1, a glycoprotein present in a soluble dimeric form in plasma, and in a dimeric or a multimeric form at the cell surface and in extracellular matrix. It is involved in cell adhesion and migration processes including embryogenesis, wound healing, blood coagulation, host defense, and metastasis (RefSeq, 2002). FN1 is an important tumor-associated angiogenesis targeting agent (Sollini et al., 2015). FN1 is one of several biomarkers for pancreatic cancer (Ansari et al., 2014). FN1 is one of many factors responsible for endocrine resistance in breast cancer. FN1 is significantly deregulated and promotes tumor progression and metastatic spread in breast cancer (Oskarsson, 2013; Zheng et al., 2014). It is a biomarker of epithelial-mesenchymal transition in squamous cell carcinoma (Scanlon et al., 2013). FN1 plays an important role in multiple myeloma (Neri and Bahlis, 2012).

FUCA2, secreted human a-I-fucosidase 2, was identified to be the key enzyme responsible for the transfer of I-fucose. The hydrolytic enzyme was found to be essential for *H. pylori* adhesion to human gastric cancer cells and shows great potential as a diagnostic marker and a target for therapeutic treatment *H. pylori* associated gastric cancer (Liu et al., 2009).

GCG encodes glucagon. It is a pancreatic hormone that counteracts the glucose lowering action of insulin by stimulating glycogenolysis and gluconeogenesis. It is a ligand for a specific G-protein linked receptor whose signaling pathway controls cell proliferation (RefSeq, 2002). GCG receptor imaging seems to be a potential tool to evaluate pancreatic beta cell mass. It might also become a target for imaging other tumors such as gastrinoma, pheochromocytoma and medullary thyroid cancer (Hubalewska-Dydejczyk et al., 2015). GCG plays a key role in colon carcinogenesis (Kannen et al., 2013). GCG is an emerging tracer for neuroendocrine tumors (Reubi and Maecke, 2008).

GFPT2 encodes glutamine fructose 6 phosphate transaminase 2 and is located on chromosome 5q34-q35 (RefSeq, 2002). GFPT2 plays an important role in breast cancer and lymphocytic leukemia (Kuang et al., 2008; Simpson et al., 2012).

GPN1 encodes GPN loop GTPase 1 and is located on chromosome 2p23.3 (RefSeq, 2002). GPN1 is a cytoplasmic GTPase involved in nuclear localization of the DNA repair gene XPA, a critical factor controlling nucleotide excision repair signaling pathways (Nitta et al., 2000).

GRIK2 encodes glutamate receptor, ionotropic, kainite 2. Mutations in this gene have been associated with autosomal recessive mental retardation (RefSeq, 2002). TRMT11-GRIK2 is one of several fusion transcripts found in prostate cancer and is associated with tumor aggressiveness (Yu et al., 2014). GRIK2 SNPs are associated with increased risk or susceptibility to oral cancer (Bhatnagar et al., 2012). GRIK2 is a potential biomarker for lung cancer (Rauch et al., 2012). GRIK2 inactivation by chromosomal deletion may contribute to the onset of T-cell lymphomas. GRIK2 inactivation plays a role in gastric carcinogenesis (Resende et al., 2011; Lopez-Nieva et al., 2012).

GRIK3 encodes glutamate receptor, ionotropic, kainite 3. It belongs to a family of glutamate receptors, which are the predominant excitatory neurotransmitter receptors in the mammalian brain and are activated in a variety of normal neurophysiologic processes (RefSeq, 2002). GRIK3 is associated with lung adenocarcinoma (methylation, functional modifications), pediatric central nervous system tumors, lymphocytic leukemia, and neuroblastoma (Pradhan et al., 2013). GRIK3 is differentially expressed in several pediatric tumors of the central nervous system (Brocke et al., 2010).

GSK3B encodes glycogen synthase kinase 3 beta. It is involved in energy metabolism, neuronal cell development, and body pattern formation (RefSeq, 2002). Aberrant regulation of GSK3B has been shown to promote cell growth in some cancers, while suppressing it in others, and may play an important role in esophageal cancer (Gao et al., 2014b). GSK3B is dysregulated in glioblastoma multiforme (Atkins et al., 2013). Deregulated GSK3B promotes gastrointestinal, pancreatic, and liver cancers (Miyashita et al., 2009).

HLA-A encodes the major histocompatibility complex class 1 A that plays a central role in the immune system by presenting peptides derived from the endoplasmic reticulum lumen (RefSeq, 2002). The loss of HLA-A antigens is a common feature in human tumors. Decrease in the percentage of HLA-A, HLA-B, and HLA-C-positive cells, selective loss of particular antigens and total loss of class 1 molecule expression is documented in melanomas, carcinomas, lymphomas, neuroblastomas and acute leukemias (Garrido and Ruiz-Cabello, 1991; Salerno et al., 1990). HLA-A expression is predominantly regulated by the MAPK pathway in gastric and esophageal cancer and in part influenced by the Akt pathway with a strong inverse correlation between p-Erk expression and HLA class 1 expression in clinical tumor samples (Mimura et al., 2013).

HNRNPU (also called SAF-A) encodes the heterogeneous nuclear ribonucleoprotein U that belongs to the RNA binding subfamily of heterogeneous nuclear riboproteins (hnRNPs), which is associated with pre-mRNA processing and other aspects of mRNA metabolism and transport in the nucleus. HNRNPU is thought to be involved in the packaging of hnRNA into large ribonucleoprotein complexes (RefSeq, 2002). Up-regulation of the miR-193a-3p that inhibits the metastasis of lung cancer cells down-regulates the expression of HNRNPU (Deng et al., 2015b). The long non-coding RNA H19 can—via association with the HNRNPU/PCAF/RNAPol II protein complex—activate the miR-200 pathway, thus contributing to mesenchymal-to-epithelial cell transition and to the suppression of tumor metastasis in hepatocellular carcinoma (Zhang et al., 2013d). HNRNPU interacts with SOX2, a key gene for maintaining the stemness of embryonic and adult stem cells that appears to be re-activated in several human cancers (Fang et al., 2011).

HSPA2 encodes the testis specific heat-shock protein 70-2, essential for the growth of spermatocytes and cancer cells. Different studies suggest an important role of HSPA2 in disease progression of cervical cancer, renal cell carcinoma and bladder cancer. Polymorphisms within the gene are associated with the development of gastric cancer (Ferrer-Ferrer et al., 2013; Garg et al., 2010a; Garg et al., 2010b; Singh and Suri, 2014). HSPA8 was shown to be over-expressed in esophageal squamous cell carcinoma. High expression levels of HSPA8 in esophageal cancer cells counter-acted oxidative stress-induced apoptosis of these cells in vitro. Furthermore, HSPA8 is over-expressed in multiple myeloma and colonic carcinoma and BCR-ABL1-induced expression of HSPA8 promotes cell survival in chronic myeloid leukemia (Chatterjee et al., 2013; Dadkhah et al., 2013; Jose-Eneriz et al., 2008; Kubota et al., 2010; Wang et al., 2013a).

HSPA8P8 is a pseudogene (RefSeq, 2002).

HSPA9 encodes heat shock 70 kDa protein 9. This protein plays a role in cell proliferation, stress response and maintenance of the mitochondria (RefSeq, 2002). HSPA9 regulates cellular processes ranging from viral infection to neurodegeneration, which also includes carcinogenesis (Flachbartova and Kovacech, 2013). HSPA9 is up-regulated in hepatocellular carcinoma and colorectal cancer (Rozenberg et al., 2013; Chen et al., 2014a; Kuramitsu and Nakamura, 2005). HSPA9 plays a role in the development of gastric cancer (Ando et al., 2014). HSPA9 is a potential therapeutic target for improved treatment of drug-resistant ovarian cancer (Yang et al., 2013).

IGDCC4 encodes immunoglobulin superfamily, DCC subclass, member 4 and is located on chromosome 15q22.31 (RefSeq, 2002). GDCC4 is expressed in hepatocellular carcinoma (Joy and Burns, 1988; Marquardt et al., 2011). GDCC4 plays a role in acute lymphoblastic leukemia (Taylor et al., 2007).

IGF2BP3 encodes insulin-like growth factor II mRNA binding protein 3, an oncofetal protein, which represses translation of insulin-like growth factor II (RefSeq, 2002). Several studies have shown that IGF2BP3 acts in various important aspects of cell function, such as cell polarization, migration, morphology, metabolism, proliferation and differentiation. In vitro studies have shown that IGF2BP3 promotes tumor cell proliferation, adhesion, and invasion. Furthermore, IGF2BP3 has been shown to be associated with aggressive and advanced cancers (Bell et al., 2013; Gong et al., 2014). IGF2BP3 over-expression has been described in numerous tumor types and correlated with poor prognosis, advanced tumor stage and metastasis, as for example in neuroblastoma, colorectal carcinoma, intrahepatic cholangiocarcinoma, hepatocellular carcinoma, prostate cancer, and renal cell carcinoma (Bell et al., 2013; Findeis-Hosey and Xu, 2012; Hu et al., 2014a; Szarvas et al., 2014; Jeng et al., 2009; Chen et al., 2011c; Chen et al., 2013; Hoffmann et al., 2008; Lin et al., 2013b; Yuan et al., 2009).

IPO5 encodes importin 5, a member of the importin beta family. Importins are essential in the translocation of proteins through the nuclear pore complex (RefSeq, 2002).

IPO7 encodes importin 7. The importin alpha/beta complex and the GTPase Ran mediate nuclear import of proteins with a classical nuclear localization signal (RefSeq, 2002). IPO7 is frequently over-expressed in cancers (Golomb et al., 2012). IPO7 is dysregulated in glioblastoma, Hodgkin lymphoma and breast cancer (Jung et al., 2013; Ju et al., 2013; Nagel et al., 2014; Xue et al., 2015). IPO7 is a microRNA target that is down-regulated in prostate carcinoma (Szczyrba et al., 2013). Elevated levels of IPO7 mRNA in colorectal carcinoma are associated with increased proliferation (Li et al., 2000).

IQGAP3 encodes a member of the 10-motif-containing GAP family which acts at the interface between cellular signaling and the cytoskeleton. IQGAP3 regulates the Rac1/Cdc42-promoted neurite outgrowth and interacts directly with calmodulin and the myosin light chain (Wang et al., 2007; Atcheson et al., 2011). IQGAP3 is over-expressed in lung cancer and is associated with tumor cell growth, migration and invasion. Furthermore, it is up-regulated by chromosomal amplification in hepatocellular carcinoma and the expression of IQGAP3 is increased in p53-mutated colorectal cancer patients with poor survival (Katkoori et al., 2012; Yang et al., 2014b; Skawran et al., 2008). IQGAP3 is modulating the EGFR/Ras/ERK signaling cascade and interacts with Rac/Cdc42 (Yang et al., 2014b; Kunimoto et al., 2009).

KDELR1 encodes KDEL (Lys-Asp-Glu-Leu) endoplasmic reticulum protein retention receptor 1. KDELR1 is structurally and functionally similar to the yeast ERD2 gene product (RefSeq, 2002). KDELR1 has a role in tumorigenesis (Yi et al., 2009). Decreased KDELR1 levels are found in hepatoma cells (Hou et al., 2015). Down-regulation of KDELR1 is seen in acute myeloid leukemia (Caldarelli et al., 2013).

KPNA2 encodes karyopherin alpha 2. KPNA2 may be involved in the nuclear transport of proteins (RefSeq, 2002). KPNA2 expression is dysregulated in epithelial ovarian cancer (Lin et al., 2015). KPNA2 is down-regulated in large oral squamous cell carcinoma tumors in comparison to small tumors (Diniz et al., 2015). KPNA2 contributes to the aberrant localization of key proteins and to poor prognosis of breast cancer (Alshareeda et al., 2015). The expression of KPNA2 is significantly up-regulated in the upper tract urothelial carcinoma and in endometrial cancers (Ikenberg et al., 2014; Shi et al., 2015). KPNA2 promotes tumor growth in hepatocellular carcinoma (Hu et al., 2014b).

KRT19 encodes a member of the keratin family. Keratins are intermediate filament proteins responsible for the structural integrity of epithelial cells and are subdivided into cytokeratins and hair keratins. KRT19 is specifically expressed in the periderm, the transiently superficial layer that envelopes the developing epidermis (RefSeq, 2002). KRT19 expression in tumor cells is a prognostic marker for several tumor entities such as breast, lung, ovarian and hepatocellular cancer (Skondra et al., 2014; Gao et al., 2014a; Liu et al., 2013a; Lee et al., 2013). KRT19 has been shown to be an independent prognostic factor for pancreatic neuroendocrine tumors, especially the insulin-negative tumors. KRT19 positive tumors are associated with poor outcome irrespective of the established pathologic parameters such as size, mitoses, lymphovascular invasion, and necrosis (Jain et al., 2010).

KRT8 (also called CK8) encodes a member of type II keratin family that dimerizes with keratin 18 to form an intermediate filament in single-layered epithelial cells. KRT8 plays a role in maintaining cellular structural integrity and also has a function in signal transduction and cellular differentiation (RefSeq, 2002). KRT8 is up-regulated and secreted from different cancer cells including lung, prostate and breast cancer. High levels of KRT8 correlate with increased migration and invasion (Gonias et al., 2001; Kuchma et al., 2012; Fukunaga et al., 2002; Takei et al., 1995). The MEK/ERK pathway regulates sphingosylphosphorycholine-induced KRT8 phosphorylation at Ser431. This leads to keratin cytoskeleton re-organization and consequently enhances the migration of tumor cells (Busch et al., 2012). The tumor suppressor SMAR down-regulates KRT8 expression and this leads to a decreased migration and invasiveness of cells (Pavithra et al., 2009; Mukhopadhyay and Roth, 1996).

KRT8P44 encodes keratin 8 pseudogene 44, which is located on chromosome 6q26 (RefSeq, 2002).

MACC1 encodes a key regulator of the hepatocyte growth factor (HGF) receptor pathway which is involved in cellular growth, epithelial-mesenchymal transition, angiogenesis, cell motility, invasiveness and metastasis (RefSeq, 2002). MACC1 is over-expressed in many cancer entities including gastric, colorectal, lung and breast cancer and is associated with cancer progression, metastasis and poor survival of patients (Huang et al., 2013b; Ma et al., 2013; Stein, 2013; Wang et al., 2015b; Wang et al., 2015m; Ilm et al., 2015). MACC1 promotes carcinogenesis through targeting beta-catenin and PI3K/AKT signaling pathways, which leads to an increase of c-Met and beta-catenin and their downstream target genes including c-Myc, cyclin D1, caspase9, BAD and MMP9 (Zhen et al., 2014; Yao et al., 2015).

MAGED2 encodes melanoma antigen family D, 2, a member of a new defined MAGE-D cluster in Xp11.2, a hot spot for X-linked mental retardation. MAGED2 is expressed ubiquitously with high expression levels in specific brain regions and in the interstitium of testes. MAGED2 is a potential negative regulator of wildtype p53 activity (Langnaese et al., 2001; Papageorgio et al., 2007). MAGED2 over-expression is associated with melanoma, breast cancer and colon cancer (Li et al., 2004; Strekalova et al., 2015).

MAN2A1 encodes mannosidase alpha class 2A, member 1, which is localized in the Golgi and catalyzes the final hydrolytic step in the asparagine-linked oligosaccharide maturation pathway (RefSeq, 2002). Swainsonine inhibits MAN2A1, resulting in the inhibition of the production of beta 1,6-branched N-linked glycans, which are related to the malignant phenotype of tumor cells (Yagel et al., 1990; Gerber-Lemaire and Juillerat-Jeanneret, 2010; Santos et al., 2011; Przybylo et al., 2005; Dennis and Laferte, 1987; Baptista et al., 1994; Goss et al., 1994; Fujieda et al., 1994; Korczak and Dennis, 1993; Roberts et al., 1998; Goss et al., 1997; Goss et al., 1995; Seftor et al., 1991). A SNP in MAN2A1 is strongly associated with childhood acute lymphoblastic leukemia (Han et al., 2010).

MAP1A encodes microtubule associated protein 1A which is involved in microtubule assembly, an essential step in neurogenesis (RefSeq, 2002). MAP1A accumulates in retinoic acid-induced P19 embryonal carcinoma cells (Vaillant and Brown, 1995). MAP1A is down-regulated in the tumor-adjacent stroma of prostate cancer (Zhu et al., 2015b). MAP1A may play a role in cell proliferation (Matsuno et al., 2004). Danusertib significantly increases the expression level of membrane-bound MAP1A in breast cancer (Li et al., 2015c). Baicalein up-regulates MAP1A in the hepatocellular carcinoma cell line HepG2 (Wang et al., 2015l). MAP1A is inversely correlated to p62 in cutaneous squamous cell carcinoma (Yoshihara et al., 2014). Gamma-tocotrienol induces an increased conversion of MAP1A from its cytosolic to its lipidated isoform (Tiwari et al., 2014).

MAT2A encodes methionine adenosyltransferase 2A which catalyzes the production of S-adenosylmethionine from methionine and ATP (RefSeq, 2002). MAT2A is up-regulated in tamoxifen-resistant MCF-7 breast cancer cells (Phuong et al., 2015). There are higher levels of sumoylated and total MAT2A in colon cancer. Interaction between Ubc9, Bcl2, and MAT2A enhance growth and survival of cancer cells (Tomasi et al., 2015). MAT2A expression is down-regulated in renal cell carcinoma and in the S-adenosylmethionine-treated hepatocellular carcinoma cell line WCH17 (Kuang et al., 2014; Wang et al., 2014b). The MAT1A:MAT2A switch is associated with global DNA hypomethylation, decreased DNA repair, genomic instability, and signaling deregulation in hepatocellular carcinoma (Woodburn et al., 2013; Frau et al., 2013). MAT2A is up-regulated in hepatocellular cell carcinoma, gastric cancer, and colon cancer (Frau et al., 2012; Zhang et al., 2013e; Tomasi et al., 2013; Frau et al., 2013; Lo et al., 2013). MAT2A is correlated with tumor classification, lymph node metastasis, and poor tumor differentiation in gastric cancer patients (Liu et al., 2011b; Zhang et al., 2013e). MAT2A is a transcriptional co-repressor of the oncoprotein MafK (Katoh et al., 2011). MAT2A is linked to tumor growth and progression in liver cancer (Vazquez-Chantada et al., 2010; Liu et al., 2011a; Lu and Mato, 2008).

MBTPS2 is a membrane-embedded zinc metalloprotease that activates signaling of proteins involved in sterol control of transcription and plays a role in ER stress response (Oeffner et al., 2009).

MCM4 encodes the minichromosome maintenance complex component 4 which is essential for the initiation of eukaryotic genome replication (RefSeq, 2002). MCM4 expression is associated with up-regulated carbonic anhydrase IX, a transmembrane glycoprotein which is correlated with decreased survival and cancer progression in several entities including esophageal cancer (Huber et al., 2015). Has-miR-615-3p may be involved in nasopharyngeal carcinoma by regulating MCM4 (Chen et al., 2015b). MCM4 might play a role in the development of bladder cancer (Zekri et al., 2015). A gain-of-function mutant of p53 increases the expression of MCM4 in breast cancer (Polotskaia et al., 2015). There is a mutation of MCM4 in human skin cancer which shows reduced DNA helicase activity (Ishimi and Irie, 2015). MCM4 over-expression alone is only weakly associated with shorter survival in breast cancer. Over-expression of all six parts of the MCM complex is strongly associated with shorter survival (Kwok et al., 2015). MCM4 is differentially expressed in lung adenocarcinoma and laryngeal squamous cell carcinoma (Lian et al., 2013; Zhang et al., 2014c). MCM4 is significantly over-expressed in cervical cancer (Das et al., 2013; Das et al., 2015). MCM4 may be used as a biomarker for colorectal cancer (Fijneman et al., 2012).

MIER1 (also called MI-ER1) encodes a transcriptional regulator that was first identified in *Xenopus leavis* (RefSeq, 2002). MIER1 is up-regulated in chronic myeloid leukemia (CML) and breast cancer, where loss of the nuclear transcript variant alpha is associated with cancer progression and proliferation (McCarthy et al., 2008; Ding et al., 2003; Mascarenhas et al., 2014). The transcriptional repressor MIER1 functions due to interaction with HDAC1 (Ding et al., 2003).

MIR2861 is a short non-coding RNAs that is involved in post-transcriptional regulation of gene expression by affecting both the stability and translation of mRNAs (RefSeq, 2002). MIR2861 expression is up-regulated in papillary thyroid carcinoma (PTC) with lymph node metastasis in comparison to PTC without lymph node metastasis (Wang et al., 2013f).

MLEC encodes malectin, which is a type I membrane-anchored ER protein. MLEC has an affinity for Glc2Man9GlcNAc2 (G2M9) N-glycans and is involved in regulating glycosylation in the ER. MLEC has also been shown to interact with ribophorin I and may be involved in directing the degradation of misfolded proteins (RefSeq, 2002; Pierce and Taniguchi, 2009). MLEC is de-regulated in colorectal cancer and enhanced in glioblastoma (Sethi et al., 2015; Demeure et al., 2016). MLEC might be a biomarker for thyroid papillary carcinoma (Ban et al., 2012).

MVP encodes the major compartment of the vault complex, a protein which may play a role in multiple cellular processes by regulating MAPK, JAK/STAT and PI3K/Akt signaling pathways. It also plays a role in multidrug resistance, innate immunity, cell survival and differentiation, and expression of this gene may be a prognostic marker for several types of cancer (RefSeq, 2002; Tucci et al., 2009; Lara et al., 2011; Scagliotti et al., 1999; van den Heuvel-Eibrink M M et al., 2000; Perez-Tomas, 2006; Scheffer et al., 2000; Ramachandran, 2007; Sekine et al., 2007; Lu and Shervington, 2008). MVP is highly expressed in several central nervous system tumors (Yang et al., 2012a). MVP is highly expressed in cancer, and in several chemoresistant cancer cell lines (Szaflarski et al., 2011; Mossink et al., 2003). MVP expression level increases with age and facilitates apoptosis resistance (Ryu and Park, 2009).

MYBBP1A (also called p160) encodes a nucleolar transcriptional regulator that was first identified by its ability to bind to the Myb proto-oncogene protein. MYBBP1A might play a role in many cellular processes, including response to nucleolar stress, tumor suppression and synthesis of ribosomal DNA (RefSeq, 2002). MYBBP1A is de-regulated in different cancer entities, including lung, breast and head and neck cancer. It is associated with cell proliferation and metastasis (Bidkhori et al., 2013; George et al., 2015; Acuna Sanhueza et al., 2012; Akaogi et al., 2013). MYBBP1A promotes transcriptional activity via p53 activation as well as Myb binding and regulates cell cycle and mitosis leading to G2/M arrest or anomalous mitosis by affecting the control of chromosomal segregation (Tavner et al., 1998; Tsuchiya et al., 2011; Mori et al., 2012; Ono et al., 2013).

NCAPD2 (also called CNAP1) encodes non-SMC condensin I complex subunit D2 that is involved in chromosome condensation and associated with Alzheimer's disease (Ball, Jr. et al., 2002; Zhang et al., 2014b). NCAPD2 overexpression was found in the development of ovarian cancer together with its amplification and mutation during tumor progression (Emmanuel et al., 2011).

NCAPG encodes the non-SMC condensing I complex subunit G which is responsible for the condensation and stabilization of chromosomes during mitosis and meiosis (RefSeq, 2002). NCAPG is down-regulated in patients with multiple myeloma, acute myeloid leukemia, and leukemic cells from blood or myeloma cells (Cohen et al., 2014). NCAPG may be a multi-drug resistant gene in colorectal cancer (Li et al., 2012). NCAPG is highly up-regulated in the chromophobe subtype of human cell carcinoma but not in conventional human renal cell carcinoma (Kim et al., 2010a). Up-regulation of NCAPG is associated with melanoma progression (Ryu et al., 2007). NCAPG is associated with uveal melanoma (Van Ginkel et al., 1998). NCAPG shows variable expression in different tumor cells (Jager et al., 2000).

NLE1 encodes a notchless homolog and member of the WD40-repeat protein family that is involved in embryonic development through different signal pathways and seems to play a role in ribosome maturation (Beck-Cormier et al., 2014; Romes et al., 2016; Lossie et al., 2012).

NOMO1 (also called PM5) encodes Nodal modulator 1, a protein that might be part of a protein complex that participates in the Nodal signaling pathway during vertebrate development (RefSeq, 2002). NOMO1 is de-regulated in prostate cancer and in T-cell lymphoma cells (Stubbs et al., 1999; Lange et al., 2009).

NOMO2 encodes Nodal modulator 2, a protein that might be part of a protein complex that participates in the Nodal signaling pathway during vertebrate development (RefSeq, 2002). NOMO2 is up-regulated at the epithelium/stroma cell interface in the transition to cervical intraepithelial neoplasia (CIN) 3 and cervical cancer as part of a pro-invasive genomic signature that may be a response to epithelial tumor cell over-crowding (Gius et al., 2007).

NOMO3 encodes Nodal modulator 3, a protein that might be part of a protein complex that participates in the Nodal signaling pathway during vertebrate development (RefSeq, 2002). NOMO3 is de-regulated by DNA methylation in non-small cell lung cancer (Mullapudi et al., 2015). NOMO3 is an enriched membrane protein associated with glycosylation in ovarian cancer tissues (Allam et al., 2015).

NONO (also known as p54nrb) encodes non-POU domain containing, octamer-binding. NONO is an RNA-binding protein which plays various roles in the nucleus, including transcriptional regulation and RNA splicing. A rearrangement between this gene and the transcription factor E3 has been observed in papillary renal cell carcinoma (RefSeq, 2002; Macher-Goeppinger et al., 2012). NONO expression strongly correlates with vascular invasion and decreased survival (Barboro et al., 2008). Furospinosulin selectively inhibits the growth of hypoxia-adapted cancer cells, maybe through direct binding to NONO (Arai et al., 2016). NONO mediates MIA/CD-RAP action to promote chondrogenesis and progression of malignant melanoma (Schmid et al., 2013). NONO expression correlates with the expression of c-Myc, cyclin D1, and CDK4 (Nelson et al., 2012). Knock-out of NONO in YB-1 over-expressing colorectal cancers can sensitize them to oxaliplatin (Tsofack et al., 2011). Simvastatin strongly down-regulates NONO and reduces melanoma progression (Schiffner et al., 2011; Zanfardino et al., 2013). NONO is over-expressed in breast cancer and melanoma (Schiffner et al., 2011; Zhu et al., 2015d).

NPC1 encodes Niemann-Pick disease, type C1, a large protein that resides in the limiting membrane of endosomes and lysosomes and mediates intracellular cholesterol trafficking via binding of cholesterol to its N-terminal domain (RefSeq, 2002). The promotor of NPC1 is hypo-methylated and NPC1 expression is up-regulated in esophageal cancer (Singh et al., 2015). NPC1 is differentially expressed in isogenic metastatic cancer cell lines, human embryonic stem cells, and human embryonal carcinoma cells (Lund et al., 2015; Dormeyer et al., 2008). NPC1 degradation is regulated by Akt. Thus NPC1 is linked to cell proliferation and migration in cervical cancer (Du et al., 2015). Treatment with sildenafil reduces NPC1 expression and kills brain cancer stem cells (Booth et al., 2015). Inhibitors of cholesterol metabolism, including NPC1 for cholesterol uptake, are thought to be beneficial for cancer treatment (Ali- Rahmani et al., 2014). NPC1 is up-regulated in TNF-alpha-resistant MCF-7 breast adenocarcinoma cells (Vincent et al., 2010; Moussay et al., 2011).

NPC2 encodes a protein with a lipid recognition domain that may function in regulating the transport of cholesterol through the late endosomal/lysosomal system. Mutations in this gene are associated with Niemann-Pick disease and frontal lobe atrophy (RefSeq, 2002). NPC2 is de-regulated in different cancer entities, including breast, colon, lung, kidney and liver cancer (McDonald et al., 2004; Garcia-Lorenzo et al., 2012; Liao et al., 2013). NPC-related cholesterol perturbation induces abnormal signaling pathways leading to p38 MAPK activation, Mdm2-mediated p53 degradation, ROCK activation and increased RhoA synthesis (Qin et al., 2010).

NUP160 encodes a nucleoporin of 160 kDa that is part of the nuclear pore complex that mediates the nucleoplasmic transport (RefSeq, 2002). NUP160-SLC43A3 is a recurrent fusion oncogene in angiosarcoma and associated with tumor progression (Shimozono et al., 2015).

NUP205 encodes nucleoporin 205 kDa (RefSeq, 2002). NUP205 is stabilized by TMEM209. This interaction is a critical driver for lung cancer proliferation (Fujitomo et al., 2012).

NUP98 encodes nucleoporin 98 kDa which participates in many cellular processes, including nuclear import, nuclear export, mitotic progression, and regulation of gene expression. Translocations between this gene and many other partner genes have been observed in different leukemias. Rearrangements typically result in chimeras with the N-terminal GLGF domain of this gene to the C-terminus of the partner gene (RefSeq, 2002). NUP98 rearrangement induces leukemia in mice. It enhances proliferation and disrupts differentiation in primary human hematopoietic precursors (Takeda and Yaseen, 2014). Dys-regulation of homeobox genes, which cause NUP98 rearrangement, result in leukemic transformation (Gough et al., 2011; De et al., 2014; Slape and Aplan, 2004; Grier et al., 2005; Abramovich et al., 2005; Nakamura, 2005; Shimada et al., 2000; Argiropoulos and Humphries, 2007). NUP98 rearranges with several partners in hematopoietic malignancies, including acute myeloid leukemia, chronic myeloid leukemia in blast crisis, myelodysplastic syndrome, acute lymphoblastic leukemia, and bilineage/biphenotypic leukemia (Tosic et al., 2009; Haznedaroglu and Beyazit, 2010; Shi et al., 2011; Gough et al., 2011; Panagopoulos et al., 2003; Morerio et al., 2006; Moore et al., 2007; Ahuja et al., 2001; McCormack et al., 2008; Lam and Aplan, 2001). NUP98 is linked to tumorigenesis (Xu and Powers, 2009; Simon and Rout, 2014). NUP98 is a modulator of genomic stability and a suppressor of tumor development (Rao et al., 2009).

OXSR1 encodes a the Ser/Thr protein kinase that regulates down-stream kinases in response to oxidative stress and may play a role in regulating the actin cytoskeleton (RefSeq, 2002). OXSR1 is up-regulated in the tumor stroma from human breast cancer patients and associated with recurrence (Pavlides et al., 2010).

PCSK9 encodes a member of the subtilisin-like proprotein convertase family, which includes proteases that process protein and peptide precursors trafficking through regulated or constitutive branches of the secretory pathway. It plays a role in cholesterol and fatty acid metabolism (RefSeq, 2002). PCSK9 is de-regulated in different cancer entities including liver, lung and gastric cancer (Bhat et al., 2015; Marimuthu et al., 2013; Demidyuk et al., 2013). PCSK9 deficiency reduces liver metastasis by its ability to lower cholesterol levels and by enhancing TNFalpha-mediated apoptosis. Other studies show in contrast no effect of cholesterol levels on cancer risk (Folsom et al., 2007; Sun et al., 2012).

PDAP1 encodes a phosphoprotein that may up-regulate the PDGFA-stimulated growth of fibroblasts and also down-regulate the mitogenicity of PDGFB (RefSeq, 2002). PDAP1 is over-expressed in different cancer types, including gastric and rectal cancer, and could thereby play a role as a biomarker (Choi et al., 2011; Marimuthu et al., 2013).

PDIA3 (also known as ERp57) encodes the protein disulfide isomerase family A member 3, a protein of the endoplasmic reticulum that interacts with lectin chaperons, calreticulin, and calnexin to modulate folding of newly synthesized glycoproteins (RefSeq, 2002; Coe and Michalak, 2010). PDIA3 may be used as a biomarker and in the diagnosis of tumors (Shishkin et al., 2013). PDIA3 is differentially expressed in gliomas (Deighton et al., 2010). PDIA3 is implicated in human pathology including cancer and Alzheimer's disease (Coe and Michalak, 2010). PDIA3 is an auxiliary factor of TAP which loads viral and self-peptides on MHC class I (Coe and Michalak, 2010; Abele and Tampe, 2011).

PFDN1 encodes prefoldin subunit 1, one of six subunits of prefoldin, a molecular chaperone complex that binds and stabilizes newly synthesized polypeptides, thereby allowing them to fold correctly (RefSeq, 2002). PFDN1 is involved in colorectal cancer progression, and is positively correlated with tumor size and invasion (Wang et al., 2015e). PFDN1 is up-regulated in several cancers including colorectal cancer (Wang et al., 2015e). PFDN1 can be used as a reference gene in nasopharyngeal carcinoma (Guo et al., 2010).

PHB encodes prohibitin which is proposed to play a role in human cellular senescence and tumor suppression (RefSeq, 2002; Mishra et al., 2010; Theiss and Sitaraman, 2011; Zhou and Qin, 2013; Mishra et al., 2005; McClung et al., 1995; Rajalingam and Rudel, 2005). PHB activates the Raf/MEK/ERK pathway which is involved in cell growth and malignant transformation (Rajalingam and Rudel, 2005). PHB is a potential biomarker in nasopharyngeal carcinoma that predicts the treatment response to radiotherapy (Chen et al., 2015e). PHB was identified in the proteomic analysis of drug-resistant cancer cells, drug action, and disease state tissues (Guo et al., 2013). PHB is over-expressed in many cancer entities (Zhou and Qin, 2013). The core protein of hepatitis C virus, which is a major risk factor for hepatocellular carcinoma, induces over-production of oxidative stress by impairing prohibitin (Theiss and Sitaraman, 2011; Schrier and Falk, 2011; Koike, 2014). PHB is differentially expressed in gliomas (Deighton et al., 2010).

PKM2 encodes pyruvate kinase, muscle, a protein involved in glycolysis. PKM2 interacts with thyroid hormone and thus may mediate cellular metabolic effects induced by thyroid hormones. It is also thought to be involved in bacterial pathogenesis (RefSeq, 2002; Israelsen and Vander Heiden, 2015). PKM2 was shown to be crucial for cancer cell proliferation and tumor growth (Chen et al., 2014b; Li et al., 2014c; DeLaBarre et al., 2014). N-myc acts as a transcriptional regulator for PKM2 in medulloblastoma (Tech et al., 2015). PKM2 seems to play a role in hepatocarcinogenesis, epithelial mesenchymal transition, and angiogenesis (Nakao et al., 2014). PKM2 is one of the two key factors of the Warburg effect in oncology (Tamada et al., 2012; Warner et al., 2014; Ng et al., 2015). Expression of PKM2 is up-regulated in cancer cells (Chaneton and Gottlieb, 2012; Luo and Semenza, 2012; Wu and Le, 2013). In malignant cells PKM2 functions in glycolysis, as a transcriptional coactivator and as a protein kinase. In the latter function it translocates to the nucleus and phosphorylates histone 3 which finally causes the progress of the cell cycle in glioblastomas (Semenza, 2011; Luo and Semenza, 2012; Tamada et al., 2012; Venneti and Thompson, 2013; Yang and Lu, 2013; Gupta et al., 2014; Iqbal et al., 2014; Chen et al., 2014b; Warner et al., 2014). The low-activity-dimeric PKM2 might play a role in cancer instead of the active tetrameric form (Mazurek, 2011; Wong et al., 2015; Iqbal et al., 2014; Mazurek, 2007).

PKP3 encodes plakophilin, 3 a member of the arm-repeat and plakophilin family, which is localized to desmosomes and nuclei and participates in linking cadherins to intermediate filaments in the cytoskeleton. PKP3 may act in cellular desmosome-dependent adhesion and signaling pathways (RefSeq, 2002). Increased PKP3 mRNA in the blood of gastrointestinal cancer patients can be used as a biomarker and predictor for disease outcome (Valladares-Ayerbes et al., 2010). Over-expression of PKP3 was correlated with a poor outcome in breast, lung and prostate cancer, whereas down-regulation in bladder cancer is linked to invasive behavior (Furukawa et al., 2005; Breuninger et al., 2010; Demirag et al., 2012; Takahashi et al., 2012). Loss of PKP3 leads to increased protein levels of MMP7 and PRL3, which are required for cell migration and tumor formation (Khapare et al., 2012; Basu et al., 2015b).

PLEC encodes the plakin family member plectin, a protein involved in the cross-linking and organization of the cytoskeleton and adhesion complexes (Bouameur et al., 2014). PLEC is over-expressed in colorectal adenocarcinoma, head and neck squamous cell carcinoma and pancreatic cancer (Lee et al., 2004; Katada et al., 2012; Bausch et al., 2011).

PLXNA2 encodes plexin A2 which is a semaphorin co-receptor. PLXNA2 is thought to transduce signals from semaphorin 3A and 3C (RefSeq, 2002). KIAA1199 binds to PLXNA2, resulting in the inhibition of semaphorin 3A mediated cell death via EGFR stabilization and signaling (Shostak et al., 2014). PLXNA2 is up-regulated in TMPRSS2-ERG-positive prostate cancer and metastatic prostate cancer, resulting in enhanced cell migration and invasion (Tian et al., 2014). PLXNA2 has higher expression levels in more aggressive breast cancer and is associated with tumorigenesis (Gabrovska et al., 2011).

POLA2 encodes an accessory subunit of DNA polymerase alpha (also called 70/68 kDa or B subunit) that plays an important role in the initiation of DNA replication by tethering the catalytic subunit A and the primase complex (Collins et al., 1993; Pollok et al., 2003). POLA2 is de-regulated in different cancer types including gastrointestinal stromal tumors and non-small cell lung cancer (Mah et al., 2014; Kang et al., 2015). During S-phase, POLA2 is attached to telomeres. It is associated with telomerase activity and is important for proper telomeric overhang processing through fill-in synthesis (Diotti et al., 2015).

PPM1G encodes protein phosphatase, Mg2+/Mn2+ dependent, 1G. This protein is found to be responsible for the dephosphorylation of pre-mRNA splicing factors, which is important for the formation of functional spliceosomes (RefSeq, 2002). PPM1G regulates the E3 ligase WWP2 which differentially regulates cellular p73 and DeltaNp73 (Chaudhary and Maddika, 2014). PPM1G is able to bind apoptosis-stimulating proteins of p53 which are uniquely over-expressed in various entities (Skene-Arnold et al., 2013). PPM1G down-regulates USP7S by dephosphorylation, resulting in p53 accumulation (Khoronenkova et al., 2012).

PPP1R15B encodes a protein phosphatase-1 (PP1) interacting protein. PPP1R15B promotes de-phosphorylation of the transcription initiation factor EIF2-alpha through recruitment of PP1 catalytic subunits (RefSeq, 2002). Down-regulation of PPP1R15B results in impaired proliferation due to unsuccessful transition from G1 to S phase of the cell cycle, induction of apoptosis by increased activity of caspase 3/7, and regulation of ERalpha activity (Shahmoradgoli et al., 2013).

PPY encodes a protein that is synthesized as a 95 amino acid polypeptide precursor in the pancreatic islets of Langerhans. It is cleaved into two peptide products; the active hormone of 36 amino acids and an icosapeptide of unknown function. The hormone acts as a regulator of pancreatic and gastrointestinal functions and may be important in the regulation of food intake (RefSeq, 2002). Patients with diabetes melitus secondary to pancreatic cancer have a blunted PPY response to a mixed meal compared to patients with type 2 diabetes melitus. However, the blunted PPY response is only observed in those pancreas carcinoma patients with a tumor located in the head of the pancreas (Hart et al., 2015).

PRKDC encodes the catalytic subunit of the DNA-dependent protein kinase (DNA-PK) (RefSeq, 2002). PRKDC is a frequently mutated gene in endometriosis-associated ovarian cancer and breast cancer (Er et al., 2016; Wheler et al., 2015). PRKDC is up-regulated in cancerous tissues compared with normal tissues in colorectal carcinoma. Patients with high PRKDC expression show poorer overall survival (Sun et al., 2016b).

PSEN1 encodes presenilin 1 which is linked to Alzheimer's disease. It is part of the gamma-secretase complex which is required for Notch activation (RefSeq, 2002; Ponnurangam et al., 2015). Over-expression of PSEN1 by a small interfering RNA sensitizes chemoresistant bladder cancer cells to drug-triggered cell death (Deng et al., 2015a). PSEN1 plays a key role in epithelial-mesenchymal transition and chemoresistance by down-regulating E-cadherin (Sehrawat et al., 2014; Dinicola et al., 2016). TRAF6-mediated PSEN1 activation results in promotion of tumor invasiveness (Gudey et al., 2014; Sundar et al., 2015). Down-regulated expression of the gamma-secretase complex is thought to be a risk factor for breast cancer specific mortality (Peltonen et al., 2013). PSEN1 is differentially expressed in T-cell acute lymphoblastic leukemia caused by dys-regulated Notch1 (Paryan et al., 2013). PSEN1 is over-expressed in oral squamous cell carcinoma cell lines and primary oral keratinocytes isolated from oral squamous cell carcinoma tissue. PSEN1 over-expression results in reduced cell adhesion in oral squamous cell carcinoma by affecting P-cadherin (Bauer et al., 2013). The endocannabinoid anandamide increases the expression and recruitment of PSEN1 in cholangiocarcinoma (Frampton et al., 2010). p53 is able to regulate PSEN1 expression (Checler et al., 2010). PSEN1 is involved in tumor reversion (Telerman and Amson, 2009).

PSEN2 encodes presenilin 2 which is linked to Alzheimer's disease. It is part of the gamma-secretase complex which is required for Notch activation (RefSeq, 2002). Oxidative stress and p53 expression level is increased in PC12 cells carrying a mutated PSEN2 gene (Nguyen et al., 2007). PSEN2 is a useful prognostic factor in breast cancer. The novel PSEN2 alleles R62H and R71W affect PSEN2 function and may potentially confer a moderate risk of susceptibility to breast cancer (To et al., 2006; Xu et al., 2006). PSEN2 is part of a 10-gene signature set which is associated with recurrence-free survival time but not overall survival time in ovarian carcinoma (Chen and Liu, 2015).

Loss of PSEN2 may cause lung tumor development by up-regulating iPLA2 (Yun et al., 2014). Down-regulated expression of the gamma-secretase complex is thought to be a risk factor for breast cancer specific mortality (Peltonen et al., 2013). PSEN2 is differentially expressed in megakaryocytic leukemia and gastric cancer. PSEN2 expression correlates with tumor type, UICC tumor stage, tumor grade, and patient survival (Warneke et al., 2013; Hao et al., 2006). The promotor of PSEN2 is de-methylated in glioma tissues, causing PSEN2 over-expression (Liu et al., 2012). 2-arachidonylglycerol increases the expression and recruitment of PSEN2 in cholangiocarcinoma (Frampton et al., 2010). PSEN2 causes tumor cell proliferation in rat pancreatic cancer by cleaving EpC (Maetzel et al., 2009; Thuma and Zoller, 2013).

PTGS1 (also known as Cox1) encodes the prostaglandin-endoperoxide synthase 1 (prostaglandin G/H synthase and cyclooxygenase). PTGS1 is constitutively expressed and catalyzes the conversion of arachinodate to prostaglandin. The encoded protein regulates angiogenesis in endothelial cells, and is inhibited by non-steroidal anti-inflammatory drugs, such as aspirin. Based on its ability to function as both a cyclooxygenase and as a peroxidase, PTGS1 has been identified as a moonlighting protein. The protein may promote cell proliferation during tumor progression (RefSeq, 2002; Tietz et al., 2013). PTGS1 may be involved in tumorigenesis (Rouzer and Marnett, 2009). Enhanced tumor growth is supported by up-regulation of PTGS1 which plays a role in prostaglandin and VEGF production (Campione et al., 2015). PTGS1 is associated with decreased survival for recurrent minor salivary gland carcinoma (Haymerle et al., 2015). PTGS1 is associated with breast carcinogenesis (Basu et al., 2015a; Serra et al., 2016). PTGS1 is frequently de-regulated in the progression of cancer (Karnezis et al., 2012). Deletion of PTGS1 results in robust decrease of basal cell carcinoma (Arbiser, 2010). Aspirin inhibits PTGS1-induced platelet activation which is thought to be involved in the development of inflammation and cancer, including colorectal carcinoma, head and neck cancer, gastrointestinal cancer, and pancreatic cancer (Pereira et al., 2009; Perrone et al., 2010; Schror, 2011; Garcia Rodriguez et al., 2013; Bruno et al., 2012; Yue et al., 2014; Sostres et al., 2014; Schror and Rauch, 2013; Guillem-Llobat et al., 2014; Patrignani and Patrono, 2015; Patrono, 2015; Dovizio et al., 2015; Jimenez et al., 2007; Klass and Shin, 2007).

PTGS2 (also called COX-2) encodes prostaglandin-endoperoxide synthase 2 (cyclooxygenase), the key enzyme in prostaglandin biosynthesis that acts as a dioxygenase and as a peroxidase (RefSeq, 2002). Expression of PTGS2 and prostaglandins is associated with various cancer types including breast, lung, gastric, pancreatic, colorectal and prostate tumors. The expression level is also directly proportional to tumor aggressiveness including metastasis (Shao et al., 2012; Kunzmann et al., 2013; Misra and Sharma, 2014; Aziz and Qiu, 2014; Thill et al., 2014; Knab et al., 2014; Huang and Huang, 2014; Wang et al., 2014c). Anti-inflammatory agents with activity against PTGS2 have a strong potential for the chemoprevention of cancer (Harris, 2009; Ghosh et al., 2010).

PTPN14 encodes protein tyrosine phosphatase, non-receptor type 14, which appears to regulate lymphatic development in mammals. A loss-of-function mutation has been found in kindred with a lymphedema-choanal atresia (RefSeq, 2002). PTPN14 induces TGF-beta signaling, regulates endothelial-mesenchymal transition, and organogenesis (Wyatt and Khew-Goodall, 2008). PTPN14 is down-regulated in cholangiocarcinoma and is inversely correlated with clinical-pathological features and survival (Wang et al., 2015d; Wang et al., 2015c). PTPN14 inhibits trafficking of soluble and membrane-bound proteins, resulting in prevention of metastasis (Belle et al., 2015). PTPN14 negatively regulates the oncoprotein Yes-associated protein (YAP), a key protein in the Hippo pathway, which is responsible for organ size and tumorigenesis (Liu et al., 2013b; Huang et al., 2013a; Lin et al., 2013a). Loss-of-function mutations in PTPN14 are involved in neuroblastoma relapse, breast cancer, and colorectal cancer (Laczmanska and Sasiadek, 2011; Wang et al., 2004; Schramm et al., 2015; Wyatt and Khew-Goodall, 2008).

RABGGTB is the beta subunit of Rab geranylgeranyltransferase that catalyzes the posttranslational geranylgeranylation of Rab GTPases (Pylypenko et al., 2003). RABGGTB is over-expressed in chemotherapy-refractory diffuse large B-cell lymphoma (Linderoth et al., 2008).

RAC1 encodes the ras-related C3 botulinum toxin substrate 1 (rho family, small GTP binding protein Rac1), a GTPase which belongs to the RAS superfamily of small GTP-binding proteins. Members of this superfamily appear to regulate a diverse array of cellular events, including the control of cell growth, cytoskeletal reorganization, and the activation of protein kinases (RefSeq, 2002). RAC1 is important for neural crest development and can prevent melanoma formation (Shakhova, 2014). RAC1 can be activated by the hepatocyte growth factor and the Met tyrosine kinase receptor, resulting in proliferation and migration of endothelial cells (Barrow-McGee and Kermorgant, 2014; Gallo et al., 2015). RAC1 induces ROS in the viral oncogenesis of Kaposi's sarcoma (Mesri et al., 2013). RAC1 is involved in melanoma initiation and progression, in breast cancer, and in head and neck cancer (Alan and Lundquist, 2013; Imianitov, 2013; Meierjohann, 2014). Tiam1 is able to regulate RAC1, which in turn regulates signaling pathways involved in cytoskeletal activity, cell polarity, endocytosis and membrane trafficking, cell migration, adhesion and invasion, cell growth and survival, metastasis, angiogenesis, and carcinogenesis (Bid et al., 2013; Boissier and Huynh-Do, 2014). RAC1 is thought to be an oncogene (Kunz, 2013; Kunz, 2014). Mutations in RAC1 can cause a variety of disorders, including malignant transformation (Read, 2013; Chi et al., 2013). Activation of Rac1 results in formation of actin stress fibers, membrane ruffles, lamellipodia, and filopodia (Klopocka et al., 2013; van and van Buul, 2012; Lane et al., 2014). RAC1 is down-regulated in astrocytic tumors, but is over-expressed in medulloblastoma tumors (Khalil and El-Sibai, 2012).

RAS3 encodes ras-related C3 botulinum toxin substrate 3 (rho family, small GTP binding protein Rac3), a GTPase which belongs to the RAS superfamily of small GTP-binding proteins. Members of this superfamily appear to regulate a diverse array of cellular events, including the control of cell growth, cytoskeletal reorganization, and the activation of protein kinases (RefSeq, 2002). Over-expression of RAC3 is associated with poor prognosis in endometrial carcinoma (Balmer et al., 2006). RAC3 is a target of ARHGAP6 which acts as a tumor suppressor in cervical cancer (Li et al., 2015b). RAC3 is involved in the organization of the cytoskeleton, cell migration, and invasion (Liu et al., 2015c). RAC3 is differentially expressed in leukemia and non-small cell lung cancer, and is involved in tumor growth (Tan and Chen, 2014; Liu et al., 2015c; Koldehoff et al., 2008). RAC3 is involved in the TGF-beta-induced down-regulation of E-cadherin in esophageal cancer (Dong et al., 2014; Xu et al., 2007). Rac3 induces the Rac3/ERK-2/NF-kappaB signaling pathway that triggers breast cancer cell aggressiveness. Endogenous Rac activity correlates with high metastatic potential in breast cancer cells (Gest et al., 2013; Baugher et al., 2005). RAC3 is up-regulated in several cancers, including leukemia, prostate cancer, and breast cancer (Fernandez Larrosa et al., 2012; Liu et al., 2015c; Culig and Bartsch, 2006; Calaf and Roy, 2007; Engers et al., 2007; Colo et al., 2007a; Colo et al., 2007b). RAC3 is an NF-kappaB coactivator which regulates cyclin D1 expression (Rubio et al., 2012; Colo et al., 2007b). Over-expression of RAC3 in ERalpha-positive breast cancer results in enhanced cell migration (Walker et al., 2011; Rubio et al., 2006).

RAD54 encodes a protein belonging to the DEAD-like helicase superfamily. It shares similarity with *Saccharomyces cerevisiae* RAD54 and RDH54, both of which are involved in homologous recombination and repair of DNA. This protein binds to double-stranded DNA, and displays ATPase activity in the presence of DNA. This gene is highly expressed in testis and spleen, which suggests active roles in meiotic and mitotic recombination (RefSeq, 2002). Homozygous mutations of RAD54B were observed in primary lymphoma and colon cancer (Hiramoto et al., 1999). RAD54B counteracts genome-destabilizing effects of direct binding of RAD51 to dsDNA in human tumor cells (Mason et al., 2015).

RAI14 (also called NORPEG) encodes retinoic acid induced 14. The gene is detected in retinal pigment epithelial cells where it is inducible by all-trans-retinoic acid that is ubiquitously expressed in human tissues and may have a role in human testis development and spermatogenesis (Kutty et al., 2001; Yuan et al., 2005). RAI14 is de-regulated in gastric cancer and connected with cell proliferation. It is a prognostic marker for relapse-free survival for lung and breast cancer patients (Zhou et al., 2015a; Hsu et al., 2013).

RBM19 encodes a nucleolar protein that contains six RNA-binding motifs and may be involved in ribosome biogenesis (RefSeq, 2002). RBM19 is widely expressed in human colorectal carcinoma (Lorenzen et al., 2005). Mutational inactivation of RBM19 results in elevated p53 activity and increased apoptosis in mice (Zhang et al., 2008; Deisenroth and Zhang, 2010).

RPF1 (also called BXDC5) encodes a nucleolar RNA binding protein that contains a sigma(70)-like motif and is required for ribosome biogenesis (Wehner and Baserga, 2002).

RPL13A encodes a member of the L13P family of ribosomal proteins that is a component of the 60S ribosomal subunit. The encoded protein also plays a role in the repression of inflammatory genes as a component of the IFN-gamma-activated inhibitor of translation (GAIT) complex (RefSeq, 2002). RPL13A is de-regulated in different cancer types including prostate, liver and colorectal cancer (Kasai et al., 2003; Ohl et al., 2005; Yoon et al., 2006). Depletion of RPL13A causes significant reduction of methylation of ribosomal RNA and of cap-independent translation mediated by RES elements derived from p27, p53 and SNAT2 mRNAs (Chaudhuri et al., 2007).

RPL13AP20 encodes ribosomal protein L13a pseudogene that is located on chromosome 12p13.1 (Balasubramanian et al., 2009).

RPL13AP5 encodes a ribosomal protein L13a pseudogene that is located on chromosome 10q24.1 (Balasubramanian et al., 2009).

RPL34 encodes the ribosomal protein L34 which is a component of the 60S subunit. Over-expression of this gene has been observed in some cancer cells (RefSeq, 2002). Over-expression of RPL34 results in the promotion of malignant proliferation in non-small cell lung cancer (Yang et al., 2016). RPL34 plays a critical role in cell proliferation, cell cycle distribution and apoptosis of human malignant gastric cells (Liu et al., 2015a).

RPTOR (also known as RAPTOR) encodes the regulatory associated protein of mTOR, complex 1. The protein is a compartment of a signaling pathway that regulates cell growth in response to nutrient and insulin levels. The protein positively regulates the down-stream effector ribosomal protein S6 kinase, and negatively regulates the mTOR kinase (RefSeq, 2002). In the absence of either tuberous sclerosis complex 1 or 2, mTOR-RPTOR signaling gets constitutively activated, resulting in enhanced and de-regulated protein synthesis and cell growth (Avruch et al., 2005; Kwiatkowski and Manning, 2005). mTOR positively regulates cell growth and survival primarily through direct interaction with RPTOR (Sun, 2013). In complex with mTOR, RPTOR controls cap-dependent translation, and this function is essential for PI3K-initiated oncogenesis (Vogt et al., 2010). Rapalogs are agents that primarily inhibit the mTOR-RPTOR complex 1 (mTORC1, rapamycin-sensitive) and are used in breast cancer therapy (Wysocki, 2009; De et al., 2013; Vinayak and Carlson, 2013; Le et al., 2008).

SEC24D encodes SEC24 homolog D, COPII coat complex component. SEC24D has similarity to yeast Sec24p component of COPII. COPII is the coat protein complex responsible for vesicle budding from the ER. This gene product is implicated in the shaping of the vesicle, and also in cargo selection and concentration. Mutations in this gene have been associated with Cole-Carpenter syndrome, a disorder affecting bone formation, resulting in craniofacial malformations and bones that break easily (RefSeq, 2002). The induction ratio of SEC24D is enhanced in the human prostate cancer cell line LNCaP (DePrimo et al., 2002; Zhao et al., 2004). SEC24D can be phosphorylated by Akt (Sharpe et al., 2011).

SEPT10 encodes a member of the septin family of filament-forming cytoskeletal GTPases. It is localized to the cytoplasm and nucleus and displays GTP-binding and GTPase activity (RefSeq, 2002). SEPT10 is down-regulated in different cancer types including bladder, breast, liver, lung, pancreas and prostate cancer as well as melanoma and leukemia. It is associated with poor prognosis for survival (Kienle et al., 2010; Liu et al., 2010b).

SEPT11 encodes a member of the conserved septin family of filament-forming cytoskeletal GTPases that are involved in a variety of cellular functions including cytokinesis and vesicle trafficking (RefSeq, 2002). SEPT11 is over-expressed in different cancer entities including brain, cervix, pancreas and prostate cancer, melanoma and leukemia (Liu et al., 2010b). Loss of heterozygosity (LOH) of SEPT11 is associated with poor prognosis in hepatocellular carcinomas. A fusion transcript with MLL has been identified in myeloid neoplasia (Huang et al., 2010; Cerveira et al., 2011).

SEPT8 encodes a member of the septin family of nucleotide binding proteins which is highly conserved and plays a role in the regulation of cytoskeletal organization and cytokinesis (RefSeq, 2002). SEPT8 is up-regulated in different cancer types including bladder, liver, pancreas and lung cancer as well as leukemia (Liu et al., 2010b).

SERPINB2 (also known as PAI2) encodes serpin peptidase inhibitor, clade B (ovalbumin), member 2 and is located on chromosome 18q21.3. It is a non-conventional serine protease inhibitor (SERPIN) which influences gene expression, cell proliferation and differentiation, and apoptosis (RefSeq, 2002; Medcalf and Stasinopoulos, 2005). SERPINB2 encodes serpin peptidase inhibitor, clade B (ovalbumin), member 2, an inhibitor of extracellular protease urokinase plasminogen activator and tissue plasminogen activator (Schroder et al., 2014). SERPINB2 is expressed in a number of different tumors. SERPINB2 expression is associated with favorable prognosis in breast and pancreatic cancers, but poor prognosis in endometrial, ovarian, and colorectal cancers (Schroder et al., 2014). SERPINB2 is an invasion- and metastasis-related gene (Pucci et al., 2016). SERPINB2 regulates urokinase-type plasminogen activator (uPA) which triggers the conversion of plasminogen to plasmin. Plasmin is able to degrade the extracellular matrix (ECM), an important process of tumor progression (Gershtein and Kushlinskii, 1999; Ulisse et al., 2009; Berger, 2002; Baldini et al., 2012; Mekkawy et al., 2014; Andreasen et al., 2000). Degradation of the ECM results in tumor progression, tumor mass expansion, tumor growth factor release, cytokine activation, tumor cell proliferation, migration, and invasion (Hildenbrand et al., 2010; Magdolen et al., 2003; Halamkova et al., 2012; Duffy, 2004; Mekkawy et al., 2014; Dass et al., 2008). Many tumors show a correlation between uPA system components and tumor aggressiveness and survival (Mekkawy et al., 2014; Duffy and Duggan, 2004; Han et al., 2005). High levels of SERPINB2 decrease tumor growth and metastasis (Croucher et al., 2008).

SH3BP4 encodes the SH3-domain binding protein 4 which is involved in cargo-specific control of clathrin-mediated endocytosis, specifically controlling the internalization of a specific protein receptor (RefSeq, 2002). SH3BP4 expression is 7-fold increased in the retinoblastoma cell line Y79 (Khanobdee et al., 2004). Fibroblast growth factor receptor 10 stimulation in SH3BP4-depleted cells causes a decreased cell migration in breast cancer cells and the inhibition of epithelial branching in mouse lung explants (Francavilla et al., 2013).

SHCBP1 encodes a protein that associates with human centralspindlin and is one of the crucial factors involved in midbody organization and cytokinesis completion (Asano et al., 2014). SHCBP1 is up-regulated in human hepatocellular carcinoma. Targeting SHCBP1 inhibits cell proliferation in human hepatocellular carcinoma cell lines (Tao et al., 2013). Among 16 genes with concomitant genomic alterations, SHCBP1 may be involved in tumorigenesis and in the processes of invasion and progression from pre-invasive ductal carcinoma in situ to invasive ductal carcinoma (Colak et al., 2013).

SIGMAR1 (also called OPRS1 or SIG-1R) encodes a sigma non-opioid intracellular receptor that interacts with a variety of psychotomimetic drugs, including cocaine and amphetamines. Mutations in this gene are associated with a juvenile amyotrophic lateral sclerosis (RefSeq, 2002). SIGMAR1 is over-expressed in tumor cell lines and tumors of various cancer tissues, including lung, colon, skin, and breast cancer. SIGMAR1 over-expression is associated with cell proliferation (Vilner et al., 1995; Aydar et al., 2004; Aydar et al., 2006; Bem et al., 1991; Skrzycki and Czeczot, 2013). SIGMAR1 promotes hERG/bet1-integrin signaling, triggers the activation of the PI3K/Akt pathway, and induces the phosphorylation of translational regulator proteins like p70S6K, S6 and 4E-BP1. SIGMAR1 increases motility and VEGF secretion, thus enhancing the aggressiveness of tumor cells (Crottes et al., 2016; Kim et al., 2012a).

SLC16A3 encodes solute carrier family 16 member 3, a proton-linked monocarboxylate transporter (RefSeq, 2002). Most solid tumors are known to rely on glycolysis for energy production. High rates of glycolysis result in an increased production of lactate which has been associated with poor clinical outcome and direct contribution to tumor growth and progression. SLC16A3 is one of few monocarboxylate transporters which facilitate the lactate export in cancer cells (Dhup et al., 2012; Draoui and Feron, 2011). The SLC16A3 expression has been associated with poor prognosis in hepatocellular cancer patients and increased cell proliferation, migration and invasion in cell line experiments (Gao et al., 2015). The functional involvement of SLC16A3 in the tumorigenesis was shown in a subset of pancreatic cancer (Baek et al., 2014).

SLC1A4 (also known as ASCT1) encodes solute carrier family (glutamate/neutral amino acid transporter), member 4 which is located on chromosome 2p15-p13 (RefSeq, 2002). The hepatocellular carcinoma cell line C3A enhances SLC1A4 expression after cysteine deprivation (Lee et al., 2008b). SLC1A4 acts as a recruiter of amino acids in esophageal adenocarcinoma (Younes et al., 2000). Knock-down of ASCT2 enhances SLC1A4 mRNA levels in human hepatoma cells (Fuchs et al., 2004). Activation of the v-myc myelocytomatosis viral oncogene homologue gene leads to an up-regulation of SLC1A4 in the human glioma cell line Hs683 (Jiang et al., 2012). Glutamine deprivation does not lead to an up-regulation of SLC1A4 in neuroblastoma (Wasa et al., 2002).

SLC1A5 (also known as ASCT2) encodes solute carrier family (glutamate/neutral amino acid transporter), member 5, which is a sodium-dependent neutral amino acid transporter that can act as a receptor for RD114/type D retrovirus (RefSeq, 2002). c-Myc activation increases SLC1A5 expression (Perez-Escuredo et al., 2016). Over-expression of SLC1A5 is associated with poor prognosis in clear-cell renal cell carcinoma (Liu et al., 2015d). A high expression of CD147 is significantly associated with SLC1A5 in patients with pancreatic cancer (Kaira et al., 2015). SLC1A5 might be a biomarker for non-small cell lung cancer (Hassanein et al., 2015; Hassanein et al., 2016). The ubiquitin ligase RNF5 regulates SLC1A5 in breast cancer (Jeon et al., 2015). SLC1A5 is over-expressed in several cancer entities, including advanced laryngeal cancer, prostate cancer, and adenoid cystic carcinoma (Koo and Yoon, 2015; Wang et al., 2015f; Bhutia et al., 2015; Nikkuni et al., 2015; Ganapathy et al., 2009). Inhibition of SLC1A5 in breast cancer leads to reduced glutamine uptake and proliferation (Chen et al., 2015d; van et al., 2015). SLC1A5 may stimulate tumor growth by regulating mTOR (Nakanishi and Tamai, 2011; Fuchs and Bode, 2005; Corbet et al., 2016; McGivan and Bungard, 2007).

SLC26A6 encodes a member of the solute carrier family 26 which consists of anion transport proteins. SLC26A6 is involved in transporting chloride, oxalate, sulfate and bicarbonate ions (RefSeq, 2002). Mutations of SLC26A6 have been identified in different colorectal cancer cell lines (Donnard et al., 2014). SLC26A6 gene expression and promoter activity are inhibited by IFN-gamma (Saksena et al., 2010).

SLC52A3 (also called RFT2 or C20orf54) encodes a member of the solute carrier family 52. It is a riboflavin transporter protein that likely plays a role in intestinal absorption of riboflavin (RefSeq, 2002). SLC52A3 is de-regulated in different cancer entities including gastric cancer, esophageal squamous cell carcinoma and cervical cancer. Single nucleotide polymorphisms of SLC52A3 correlate with cancer risks in esophageal squamous cell carcinoma and gastric cardia adenocarcinomas (Jiang et al., 2014b; Duan et al., 2015; Matnuri et al., 2015; Eli et al., 2012; Aili et al., 2013). Knock-down of SLC52A3 increases p21 and p27 protein levels and decreases their down-stream targets cyclin E1 and Cdk2, leading to cell cycle arrest at G1-G1/S.

Knock-down of SLC52A3 also leads to the activation of caspase-3 and apoptosis (Jiang et al., 2014b).

SLC6A15 encodes a member of the solute carrier family 6 which transports neutral amino acids. SLC6A15 might play a role in neuronal amino acid transport and might be associated with major depression (RefSeq, 2002). SLC6A15 is hyper-methylated and thereby down-regulated in colorectal cancer and may be a candidate biomarker for a stool-based assay (Kim et al., 2011b; Mitchell et al., 2014).

SMIM10 (also called CXorf69 or LOC644538) encodes a small integral membrane protein located on chromosome Xq26.3 (RefSeq, 2002).

SNX14 encodes a member of the sorting nexin family and contains a regulator of G protein signaling (RGS) domain (RefSeq, 2002). SNX14 is down-regulated upon rasV12/E1A transformation of mouse embryonic fibroblasts and may be associated with tumor development (Vasseur et al., 2005).

SSH1 (also called SSH1L) encodes a member of the slingshot homolog (SSH) family of phosphatases. The SSH family appears to play a role in actin dynamics by reactivating cofilin proteins (RefSeq, 2002). SSH1 is over-expressed in pancreatic cancer and associated with tumor cell migration (Wang et al., 2015k). Inhibition of PKD1 by neuregulin leads to the localization of SSH1 to F-actin, increased cofilin activity and increased reorganization of the actin cytoskeleton and cell migration. The SSH1-dependent activation of cofilin is induced by the PI3K/Akt signaling pathway (Wang et al., 2010; Doppler et al., 2013).

STAT2 operates as a positive regulator in the transcriptional activation response elicited by IFNs (Steen and Gamero, 2012). STAT2 may regulate tumor cell response to interferons (Shodeinde et al., 2013). A link between STAT2 and tumorigenesis was observed in transgenic mice lacking STAT2 (Yue et al., 2015). or expressing constitutively IFN-alpha in the brain (Wang et al., 2003).

SUPT16H encodes a subunit of FACT (facilitates chromatin transcription), an accessory factor which is needed for the transcription of DNA packaged into chromatin (RefSeq, 2002). SUPT16H is de-regulated in endothelial and stromal components of juvenile nasopharyngeal angiofibroma (JNA) and could thereby play a role as a potential molecular marker (Silveira et al., 2012). SUPT16H is involved in DNA double-strand break repair by remodeling of chromatin. SUPT16H activates p53 by forming a complex with CK2 (Keller et al., 2001; Kari et al., 2011).

SUSD1 encodes a sushi domain containing protein and is associated with an increased risk of venous thromboembolism (Tang et al., 2013). The heterozygous SUSD1-ROD1/PTBP3 fusion transcript is expressed in a human breast cancer cell line (Newman et al., 2013).

TAF6L encodes a protein with structurally similarity to the histone like TATA-box binding protein associated factor 6 (TAF6). It is a component of the PCAF histone acetylase complex which is required for myogenic transcription and differentiation (RefSeq, 2002). The expression of miR-145 and miR-196a negatively correlates with the expression of TAF6L (Havelange et al., 2011). TAF6L is inactivated in the small cell lung cancer cell line H187 by forming the fusion transcript TAF6L-GNG3 (Fernandez-Cuesta et al., 2015).

TEP1 encodes telomerase associated protein 1, a component of the ribonucleoprotein complex responsible for telomerase activity, which catalyzes the addition of new telomeres on the chromosome ends (RefSeq, 2002; Szaflarski et al., 2011). TEP1 is a main part of vaults to which also major vault protein (MVP) belongs (Lara et al., 2011; Mossink et al., 2003). TEP1 is expressed in thyroid carcinoma (Hoang-Vu et al., 2002).

TFPI encodes tissue factor pathway inhibitor, a protease inhibitor that regulates the tissue factor (TF)-dependent pathway of blood coagulation (RefSeq, 2002). TFPI is expressed in breast cancer, colorectal cancer, and pancreatic cancer cell lines (Kurer, 2007). TFPI induces HIF1alpha, c-Myc, c-SRC, and HDAC2 in breast cancer (Davies et al., 2014). TFPI expression level is decreased in sarcomas compared to non-malignant lesions (Savitskaya et al., 2012). TFPI inhibits the protease activity of the TF-VIIa complex which is involved in metastasis (Fischer et al., 1999; Sandset and Abildgaard, 1991; Lindahl et al., 1991).

TFPI2 encodes tissue factor pathway inhibitor 2 which can inhibit a variety of serine proteases including factor Vila/tissue factor, factor Xa, plasmin, trypsin, chymotrypsin, and plasma kallikrein. This gene has been identified as a tumor suppressor gene in several types of cancer (RefSeq, 2002; Sierko et al., 2007). TFPI2 may be used as a biomarker for relapse prediction in pancreatic carcinoma (Zhai et al., 2015c). DNA methylation of TFPI2 can be used as a biomarker for colorectal cancer in a fecal occult blood test (Koga et al., 2015). TFPI2 induces apoptosis and inhibits invasiveness, growth of neoplasms, metastasis, and angiogenesis (Ghilardi et al., 2015; Amirkhosravi et al., 2007; Sierko et al., 2007). TFPI2 is hyper-methylated and down-regulated in cancer, and expression is correlated with the degree of cancer, early tumor recurrence, and poor prognosis (Sun et al., 2016a; Sierko et al., 2007). TFPI2 is down-regulated in pancreatic cancer and cholangiocarcinoma (Chu et al., 2015; Zhai et al., 2015a; Zhai et al., 2015b). TFPI2 is methylated in gastric cancer, canine diffuse large B-cell lymphoma, acute myeloid leukemia, non-small cell lung cancer, cervical cancer, oral squamous cell carcinoma, inflammation-associated colon cancer, and hepatocellular carcinoma (Qu et al., 2013; Ferraresso et al., 2014; Liu et al., 2014b; Shao et al., 2014; Lai et al., 2014; Hamamoto et al., 2015; Li et al., 2015d; Gerecke et al., 2015; Dong et al., 2015; Sun et al., 2016a). TFPI2 is a well-validated DNA methylation biomarker in cancer (Fukushige and Horii, 2013; Huisman et al., 2015).

TGFBI encodes an RGD-containing protein that binds to type I, II and IV collagens, is induced by transforming growth factor-beta which plays a role in cell-collagen interactions and acts to inhibit cell adhesion (RefSeq, 2002). TGFBI expression was shown to be elevated in cholangiocarcinoma, hepatic carcinoma, gastric carcinoma, esophageal squamous cell carcinoma and clear cell renal cell carcinoma. Furthermore, TGFBI was shown to be associated with colorectal cancer (Lebdai et al., 2015; Ozawa et al., 2014; Zhu et al., 2015a; Han et al., 2015).

TGIF2-C20orf24 encodes a fusion protein that shares sequence identity with TGIF2 and C20orf24 (RefSeq, 2002).

TMEM154 encodes a transmembrane protein that is associated with an increased risk for type 2 diabetes and that seems to play a role in beta cell function (Harder et al., 2015). TRAM2 encodes translocation associated membrane protein 2. It is a component of the translocon, a gated macromolecular channel that controls the posttranslational processing of nascent secretory and membrane proteins at the endoplasmic reticulum (ER) membrane (RefSeq, 2002). Runx2 may regulate TRAM2 expression (Pregizer et al., 2007). SNPs in TRAM2 can increase the risk of bone fracture in ER-positive breast cancer patients (Liu et al., 2014a).

TRPV2 encodes an ion channel that is activated by temperatures above 52 degrees Celsius. It may be involved in transduction of high-temperature heat response s in sensory ganglia (RefSeq, 2002). TRPV2 is de-regulated in different cancer types including esophageal, prostate, liver and bladder cancer and leukemia. Loss or alterations of TRPV2 lead to uncontrolled proliferation and resistance to apoptotic stimuli (Liberati et al., 2014a; Zhou et al., 2014; Liberati et al., 2014b; Liu et al., 2010a; Morelli et al., 2013). Silencing of TRPV2 in glioma cells leads to down-regulation of Fas and pro-caspase 8 as well as up-regulation of Cyclin E1, CDK2 E2F1 and Bcl-2-associated X protein. TRPV2 over-expression in bladder cancer cells leads to an enhanced cell migration and invasion (Nabissi et al., 2010; Liu and Wang, 2013).

TSEN15 encodes tRNA splicing endonuclease subunit 15. This endonuclease catalyzes the removal of introns from tRNA precursors (RefSeq, 2002; Trotta et al., 2006). TSEN15 is a target of miRNA-449a, which functions as a tumor suppressor in neuroblastoma. TSEN15 plays an important role in mediating the differentiation-inducing function of miRNA-449a (Zhao et al., 2015). TSEN15 is associated with cell differentiation potential in human fetal femur-derived cells (Mirmalek-Sani et al., 2009).

UBE2C (also called UBCH10) encodes a member of the E2 ubiquitin-conjugating enzyme family. It is required for the destruction of mitotic cyclins and cell cycle progression (RefSeq, 2002). UBE2C is often up-regulated by gene amplification, as observed in patients with breast, lung and colorectal cancer. UBE2C up-regulation correlates with poor prognosis and tumor progression (Okamoto et al., 2003; Wagner et al., 2004; Fujita et al., 2009; Chen et al., 2010; Hao et al., 2012). UBE2C is up-regulated in U251 glioma cells and in tissues from colorectal carcinoma (CRC) patients. UBE2C knock-down induces apoptosis through the induction of Bax and p53, down-regulation of Bcl-2 and G2/M arrest of the cell cycle. UBE2C suppression de-regulates cyclin B and ERK1 in CRC (Cacciola et al., 2015; Jiang et al., 2010).

UBIAD1 (also called TERE1) encodes a protein containing an UbiA prenyltransferase domain that might be involved in cholesterol and phospholipid metabolism (RefSeq, 2002). The tumor suppressor UBIAD1 is down-regulated in different cancer entities, including bladder, prostate and renal cancer, and is associated with growth regulation (McGarvey et al., 2001; Fredericks et al., 2011; McGarvey et al., 2003; Fredericks et al., 2013). UBIAD1 regulates the phosphorylation of the growth factor-related p42/44 MAP kinase. The proper Golgi localization of UBIAD1 influences its tumor suppressor activities including apoptosis (McGarvey et al., 2005; Wang et al., 2013d).

UBR1 encodes ubiquitin protein ligase E3 component N-recognin 1. It binds to a destabilizing N-terminal residue of a substrate protein and participates in the formation of a substrate-linked multi-ubiquitin chain, addressing the protein for the proteolytic pathway of the ubiquitin system (RefSeq, 2002). Loss or reduction of UBR1 expression is associated with spontaneous B-cell lymphomas and T-cell acute lymphoblastic leukemia (Chen et al., 2006). UBR1 regulates the homeostasis of MGMT, a DNA repair enzyme that protects cells from carcinogenic effects of alkylating agents (Leng et al., 2015).

UBR2 encodes an E3 ubiquitin ligase of the N-end rule proteolytic pathway that targets proteins with destabilizing N-terminal residues for polyubiquitylation and proteasome-mediated degradation (RefSeq, 2002). Autoantibodies against UBR2 are detected in serum of patients with autoimmune pancreatitis and pancreatic cancer (Frulloni et al., 2009). UBR2 is up-regulated by tumor cell-induced cachectic stimuli via activation of p38beta/MAPK, C/EBPbeta phosphorylation and binding to the UBR2 promotor (Zhang et al., 2013b).

URB1 is required for ribosome biogenesis during early maturation of 60S ribosomal subunits (Rosado and de la Cruz, 2004).

USP11 encodes ubiquitin specific peptidase 11. Protein ubiquitination controls many intracellular processes, including cell cycle progression, transcriptional activation, and signal transduction (RefSeq, 2002). USP11 is a novel regulator of p53, which is required for p53 activation in response to DNA damage (Ke et al., 2014a). USP11 plays a major role in promyelocytic leukemia and pancreatic cancer (Burkhart et al., 2013; Wu et al., 2014).

USP22 encodes ubiquitin specific peptidase 22 and is located on chromosome 17p11.2 (RefSeq, 2002). High expression of USP22 was observed in hepatocellular carcinoma, colon carcinoma, gastric carcinoma, epithelial ovarian cancer, pancreatic cancer, glioma, salivary adenoid cystic carcinoma, and papillary thyroid carcinoma (Wang et al., 2013b; Dai et al., 2014; Liang et al., 2014a; Liang et al., 2014b; Ji et al., 2015; He et al., 2015; Wang et al., 2015n; Tang et al., 2015). USP22 promotes tumor progression and induces epithelial mesenchymal transition in lung adenocarcinoma (Hu et al., 2015a). USP22 acts as an oncogene by regulating the stability of cyclooxygenase 2 in non-small cell lung cancer (Xiao et al., 2015). USP22 plays a critical regulatory role in the pathologic processes of nasopharyngeal carcinoma, and it may be a potential treatment target (Zhuang et al., 2015). Over-expression of USP22 may contribute to the progression of breast cancer (Zhang et al., 2011).

UTP20 is a component of the U3 small nucleolar RNA protein complex and is involved in 18s rRNA processing (RefSeq, 2002). UTP20 expression is decreased in metastatic human breast tumor cell lines (Schwirzke et al., 1998; Goodison et al., 2003). UTP20 is expressed at high levels in gastric cancer tissues and premalignant lesions implicating the involvement of UTP20 in cell transformation (Xing et al., 2005).

WLS (also called EVI or GPR177) encodes Wntless Wnt ligand secretion mediator. WLS represents an ancient partner for Wnts dedicated to promoting their secretion into the extracellular milieu (Banziger et al., 2006). WLS is over-expressed in different cancer entities including breast, gastric, ovarian and colorectal cancer as well as leukemia and is associated with poor outcome (Chiou et al., 2014; Stewart et al., 2015; Lu et al., 2015; Voloshanenko et al., 2013). WLS is important for the secretion of all Wnt proteins. It regulates the expression of beta-catenin and cyclin-D1, thereby influencing cell proliferation (Yang et al., 2015b; Banziger et al., 2006).

YIF1A encodes Yip1 interacting factor homolog A and is located on chromosome 11q13 (RefSeq, 2002). Several mutations (amplifications and deletions) have been detected in the YIF1A gene in hepatocellular carcinoma (Nalesnik et al., 2012). YIF1A expression shows a significant difference between normal and squamous cell carcinoma samples (Sugimoto et al., 2009).

ZRANB3 encodes zinc finger, RAN-binding domain containing 3 and is located on chromosome 2q21.3 (RefSeq, 2002). ZRANB3 encodes a zinc finger protein that is a structure-specific ATP-dependent endonuclease. It is involved in replication stress response to maintain genomic integrity (Ciccia et al., 2012; Weston et al., 2012). Single nucleotide polymorphism rs4954256, located in ZRANB3 on chromosome 2q21.3, was associated with a 3.93-fold increase in pathologic complete response to concurrent chemoradiation therapy in the treatment of esophageal cancer (Chen et al., 2012). ZRANB3 is frequently mutated in endometrial cancer (Lawrence et al., 2014).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, or 13 amino acids or longer, and in case of MHC class II peptides (elongated variants of the peptides of the invention) they can be as long as 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |

TABLE 5-continued

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=$100[1-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

And R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity, then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 161 or a variant thereof which is 88% homologous to SEQ ID NO: 1 to SEQ ID NO: 161, or a variant thereof that will induce T cells cross-reacting with said peptide. The peptides of the invention have the ability to bind to a molecule of the human major histocompatibility complex (MHC) Class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 161. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 161, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) Class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) Class-I or -II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Preferred variants and motif of the peptides according to SEQ ID NO: 7, 32, 46, and 76.

| Position | 1 | 2 | 3 | 4 | 5 | 6 | 7 | 8 | 9 |
|---|---|---|---|---|---|---|---|---|---|
| SEQ ID NO. 7 | A | L | V | D | I | V | R | S | L |
| Variants | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |
| SEQ ID NO. 32 | Y | V | D | D | G | L | I | S | L |
| Variants | | I | | | | | | | V |
| | | I | | | | | | | I |
| | | I | | | | | | | |
| | | I | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | L | | | | | | | V |
| | | L | | | | | | | I |
| | | L | | | | | | | |
| | | L | | | | | | | A |

TABLE 6-continued

Preferred variants and motif of the peptides according to SEQ ID NO: 7, 32, 46, and 76.

|  | 1 | 2 | 3 | 4 | 5 | 6 | 7 | 8 | 9 | 10 | 11 |
|---|---|---|---|---|---|---|---|---|---|---|---|
|  |  | T |  |  |  |  |  |  |  |  | V |
|  |  | T |  |  |  |  |  |  |  |  | I |
|  |  | T |  |  |  |  |  |  |  |  |  |
|  |  | T |  |  |  |  |  |  |  |  | A |
|  |  | Q |  |  |  |  |  |  |  |  | V |
|  |  | Q |  |  |  |  |  |  |  |  | I |
|  |  | Q |  |  |  |  |  |  |  |  |  |
|  |  | Q |  |  |  |  |  |  |  |  | A |
| SEQ ID NO. 46 | T | M | V | E | H | N | Y | Y | V |  |  |
| Variants |  |  |  |  |  |  |  |  | L |  |  |
|  |  |  |  |  |  |  |  |  | I |  |  |
| Position | 1 | 2 | 3 | 4 | 5 | 6 | 7 | 8 | 9 | 10 | 11 |
| SEQ ID NO. 76 | I | V | S | E | S | S | D | V | A | P | K |
| Variants |  | A |  |  |  |  |  |  | L |  | V |
|  |  | L |  |  |  |  |  |  |  |  |  |
|  |  | A |  |  |  |  |  |  | I |  | I |
|  |  | L |  |  |  |  |  |  |  |  |  |
|  |  | A |  |  |  |  |  |  |  |  | L |
|  |  | L |  |  |  |  |  |  |  |  |  |
|  |  | A |  |  |  |  |  |  | A |  | A |
|  |  | L |  |  |  |  |  |  |  |  |  |
|  |  | L |  |  |  |  |  |  | L |  | V |
|  |  | M |  |  |  |  |  |  |  |  |  |
|  |  | L |  |  |  |  |  |  | I |  | I |
|  |  | M |  |  |  |  |  |  |  |  |  |
|  |  | L |  |  |  |  |  |  |  |  | L |
|  |  | M |  |  |  |  |  |  |  |  |  |
|  |  | L |  |  |  |  |  |  | A |  | A |
|  |  | M |  |  |  |  |  |  |  |  |  |
|  |  | V |  |  |  |  |  |  | L |  | V |
|  |  | A |  |  |  |  |  |  |  |  |  |
|  |  | V |  |  |  |  |  |  | I |  | I |
|  |  | A |  |  |  |  |  |  |  |  |  |
|  |  | V |  |  |  |  |  |  |  |  | L |
|  |  | A |  |  |  |  |  |  |  |  |  |
|  |  | V |  |  |  |  |  |  | A |  | A |
|  |  | A |  |  |  |  |  |  |  |  |  |
|  |  | T |  |  |  |  |  |  | L |  | V |
|  |  | T |  |  |  |  |  |  | I |  | I |
|  |  | T |  |  |  |  |  |  |  |  | L |
|  |  | T |  |  |  |  |  |  | A |  | A |
|  |  | Q |  |  |  |  |  |  | L |  | V |
|  |  | T |  |  |  |  |  |  |  |  |  |
|  |  | Q |  |  |  |  |  |  | I |  | I |
|  |  | T |  |  |  |  |  |  |  |  |  |
|  |  | Q |  |  |  |  |  |  |  |  | L |
|  |  | T |  |  |  |  |  |  |  |  |  |
|  |  | Q |  |  |  |  |  |  | A |  | A |
|  |  | T |  |  |  |  |  |  |  |  |  |
|  |  | Q |  |  |  |  |  |  |  |  | V |
|  |  | Q |  |  |  |  |  |  |  |  | I |
|  |  | Q |  |  |  |  |  |  |  |  | L |
|  |  | Q |  |  |  |  |  |  |  |  | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 161.

"Consisting essentially of" shall mean that a peptide according to the present invention, in addition to the sequence according to any of SEQ ID NO: 1 to SEQ ID NO 161 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethyl amino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other a-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of TUMAPs recorded from pancreatic cancer samples (N=20 A*02-positive samples) with the fragmentation patterns of corresponding synthetic reference peptides of identical sequences. Since the peptides were directly identified as ligands of HLA molecules of tumor cells, these results provide direct evidence for the processing and presentation of the identified peptides on pancreatic cancer.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from pancreatic cancer samples were purified and HLA-associated peptides were isolated and analyzed by LC-MS (see examples). All TUMAPs contained in the present application were identified with this approach on pancreatic cancer samples confirming their presentation on pancreatic cancer.

TUMAPs identified on multiple pancreatic cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention provides peptides that are useful in treating cancers/tumors, preferably pancreatic cancer, that over- or exclusively present the peptides of the invention. These peptides were shown by mass spectrometry to be naturally presented by HLA molecules on human pancreatic cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy pancreatic cells or other normal tissue cells, demonstrating a high degree of tumor association of the source genes (see Example 2). Moreover, the peptides themselves are strongly over-presented on tumor tissue—"tumor tissue" in relation to this invention shall mean a pancreatic cancer sample, but not on normal tissues (see Example 1).

HLA-bound peptides can be recognized by the immune system, specifically T lymphocytes. T cells can destroy the cells presenting the recognized HLA/peptide complex, e.g. pancreatic cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are HAVCR1-001 peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an HAVCR1-001 peptide-HLA molecule complex with a binding affinity (KD) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for an HAVCR1-001 peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a HAVCR1-001 peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to HAVCR1-001 can be enhanced by methods well known in the art.

The present description further relates to a method of identifying and isolating a TCR according to the present description, said method comprising incubating PBMCs from HLA-A*02-negative healthy donors with A2/HAVCR1-001 monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with HAVCR1-001, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3 (CD3 fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 161, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment, the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and Helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, Bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one Ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed, aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 161, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 161, or a variant thereof which is at least 88% homologous (preferably identical) to SEQ ID NO: 1 to SEQ ID NO: 161 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 161 or a variant thereof which is at least 88% homologous (preferably identical) to SEQ ID NO: 1 to SEQ ID NO: 161, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) Class-I or -II.

The present invention further relates to the peptides according to the invention wherein the peptide consists or consists essentially of an amino acid sequence according to SEQ ID NO: 1 to SEQ ID NO: 161.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of pancreatic cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 161 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are pancreatic cancer cells or other solid or hematological tumor cells such as lung cancer, kidney cancer, brain cancer, stomach cancer, colon or rectal cancer, liver cancer, prostate cancer, leukemia, breast cancer, Merkel cell carcinoma (MCC), melanoma, ovarian cancer, esophageal cancer, urinary bladder cancer, endometrial cancer, gall bladder cancer, and bile duct cancer.

The present invention further relates to particular marker proteins and biomarkers based on the peptides according to the present invention, herein called "targets" that can be used in the diagnosis and/or prognosis of pancreatic cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a pancreatic cancer marker (poly)peptide, delivery of a toxin to a pancreatic cancer cell expressing a cancer marker gene at an increased level, and/or inhibiting the activity of a pancreatic cancer marker polypeptide) according to the invention.

Whenever possible, the antibodies of the invention may be purchased from commercial sources. The antibodies of the invention may also be generated using well-known methods. The skilled artisan will understand that either full length pancreatic cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 161 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the pancreatic cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (µg/kg to up to 100 mg/kg of body weight or more per day, depending on the factors mentioned above. Following administration of an antibody, preferably for treating pancreatic cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occur in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 161, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore, such aAPCs-based systems often require the addition of appropriate soluble factors, e.g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, and vaccinia-infected target cells. In addition, plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 161.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed.

By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention is further directed at a kit comprising:

(a) A container containing a pharmaceutical composition as described above, in solution or in lyophilized form;

(b) Optionally a second container containing a diluent or reconstituting solution for the lyophilized formulation; and (c) Optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from pancreatic cancer, the medicament of the invention is preferably used to treat pancreatic cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of pancreatic cancer patients with various HLA-A HLA-B and HLA-C alleles. It may contain MHC class I and MHC class II peptides or elongated MHC class I peptides. In addition to the tumor associated peptides collected from several pancreatic cancer samples, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, pancreatic cancer samples and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (pancreatic cancer) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from pancreatic cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from pancreatic cancer samples and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for pancreatic cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

FIGURES

Figure 1B:
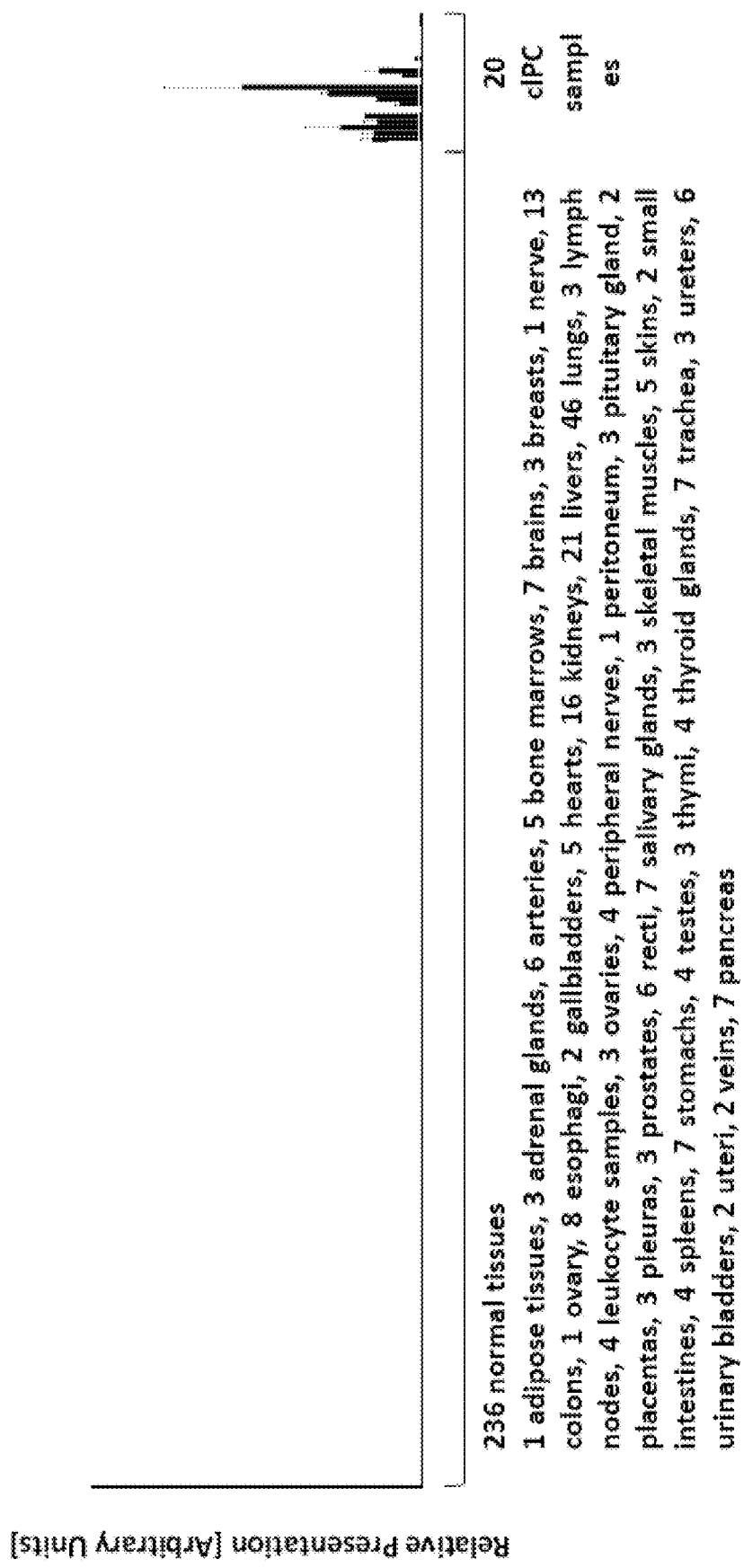
Figure 1C:
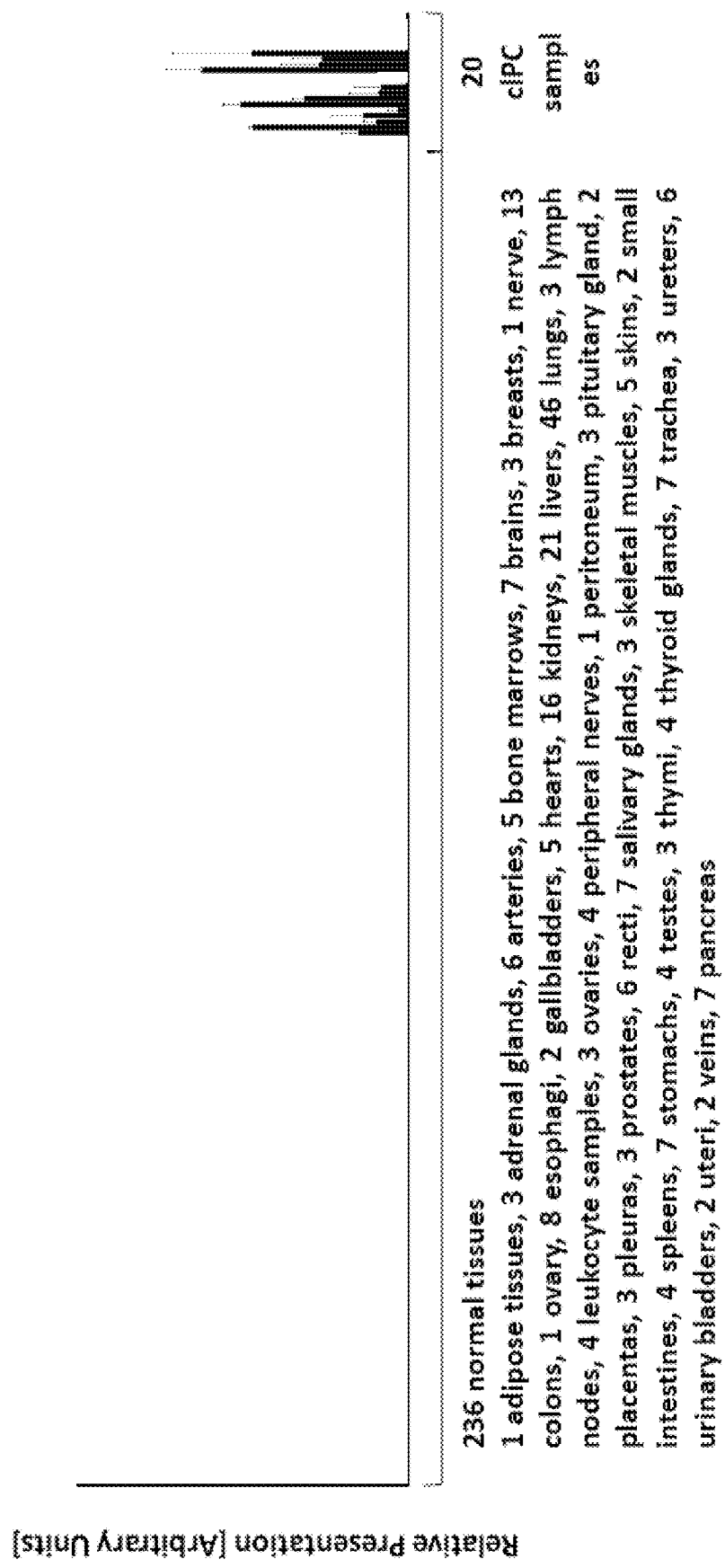
Figure 1E:
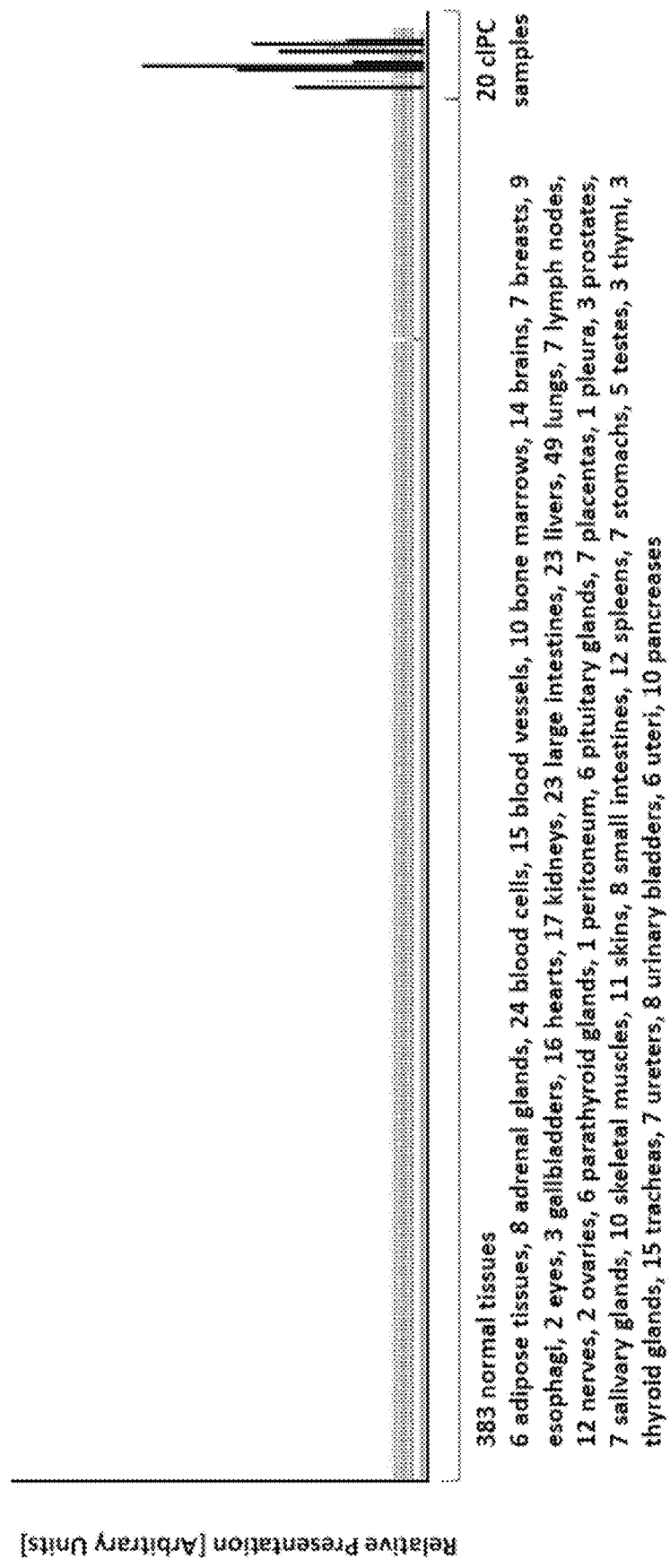
Figure 1G:
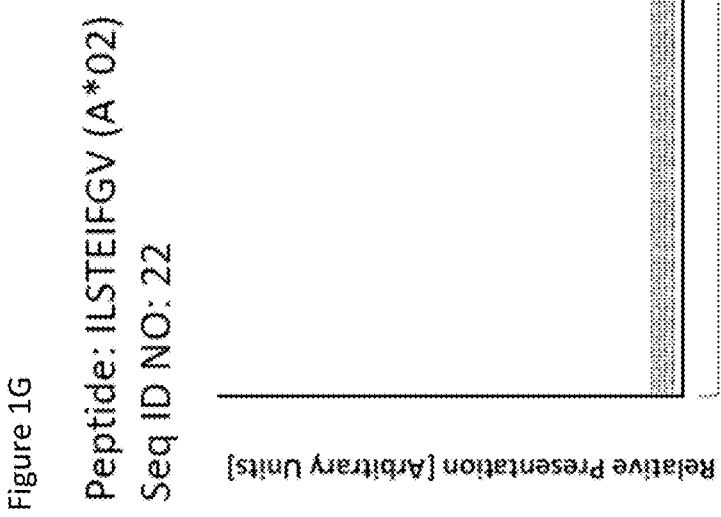
Figure 1H:
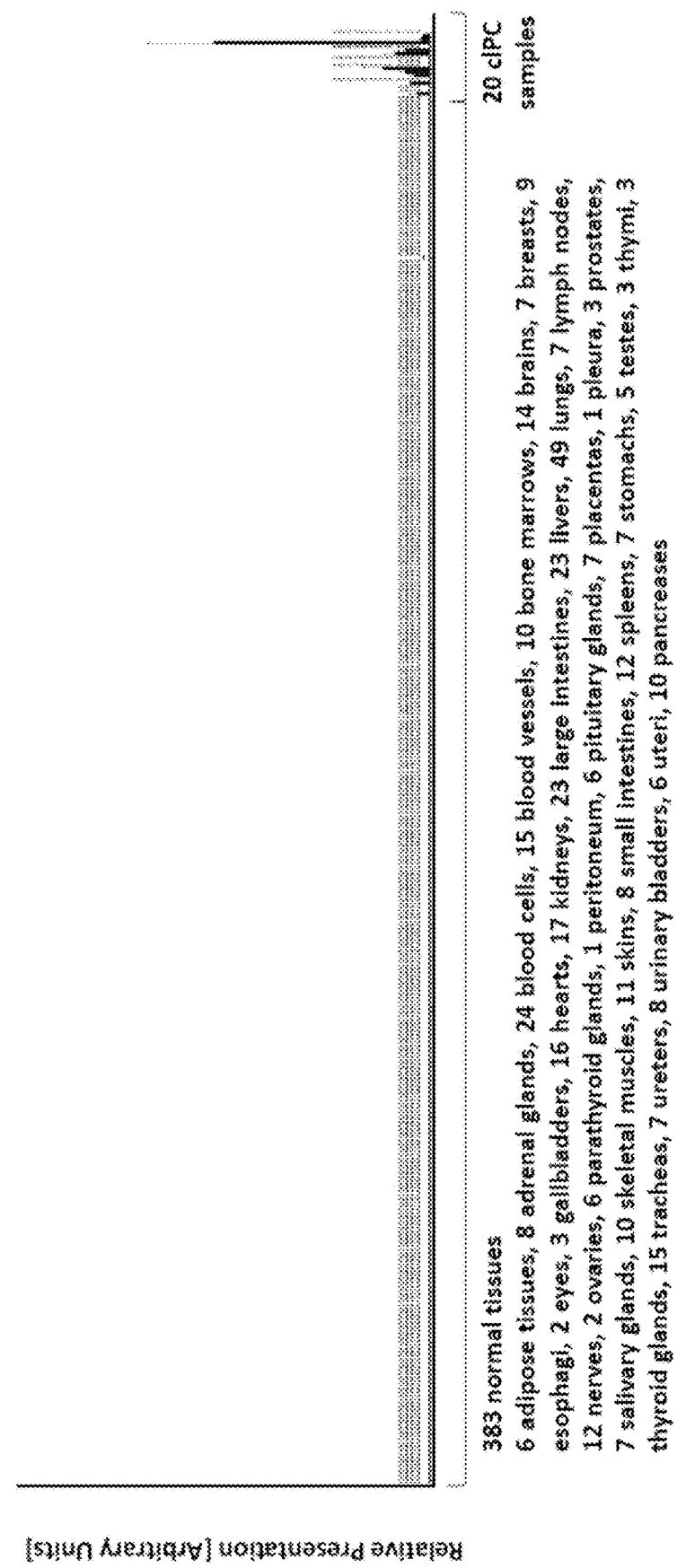
Figure 1I:
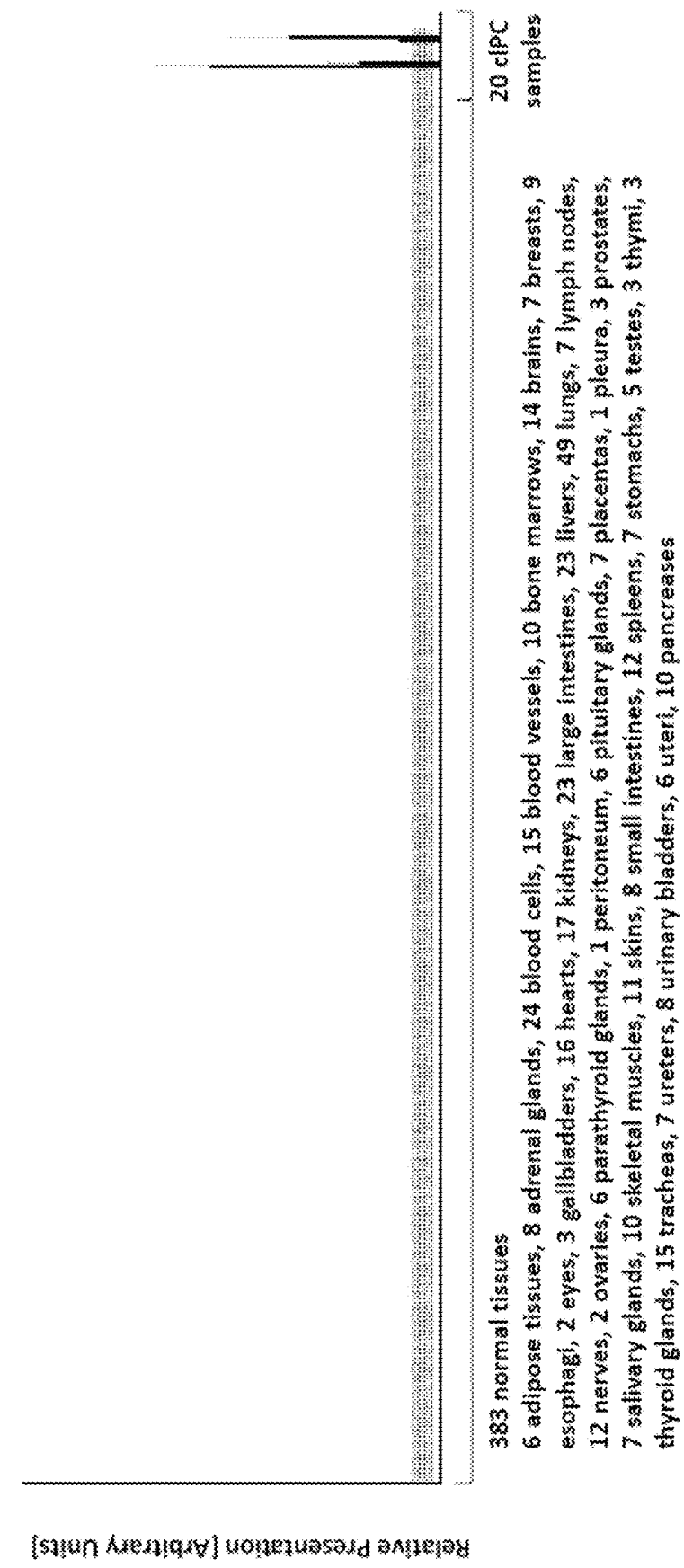
Figure 1J:
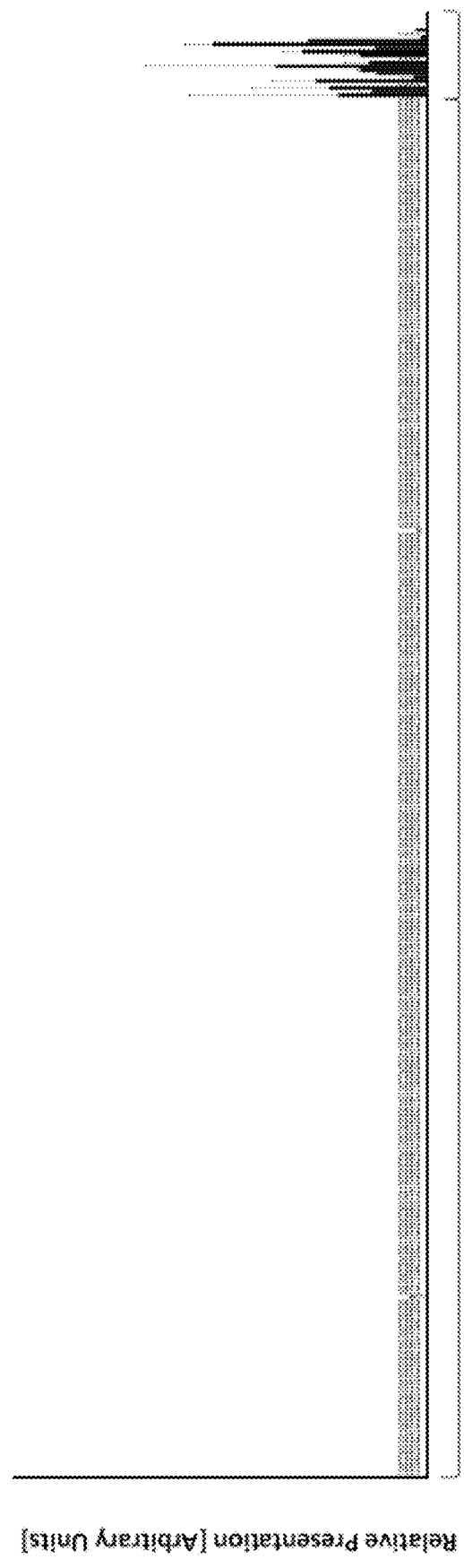
Figure 1L:
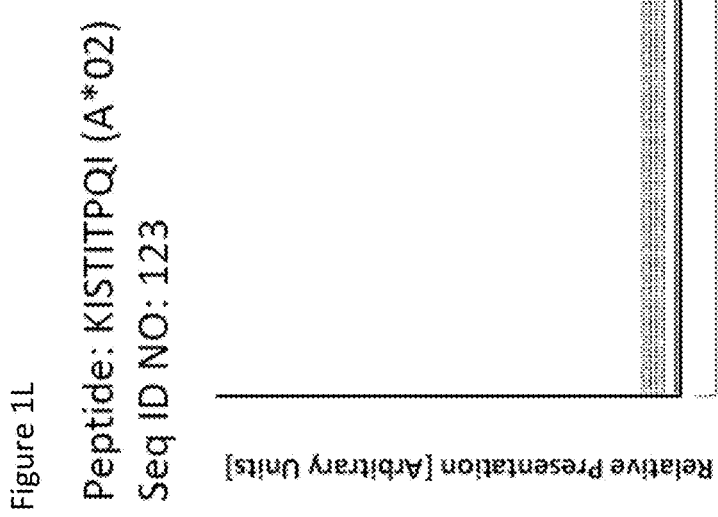
Figure 1M:
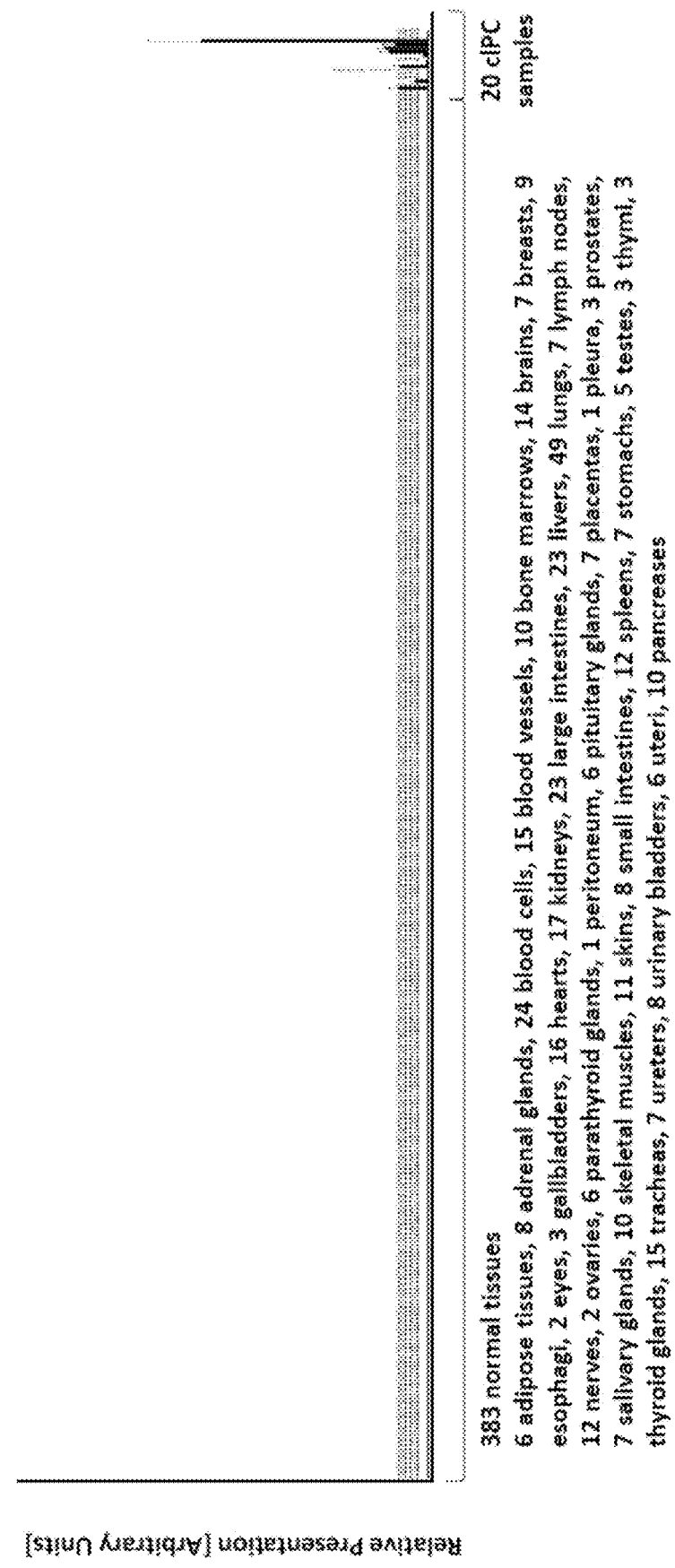
Figure 1N:
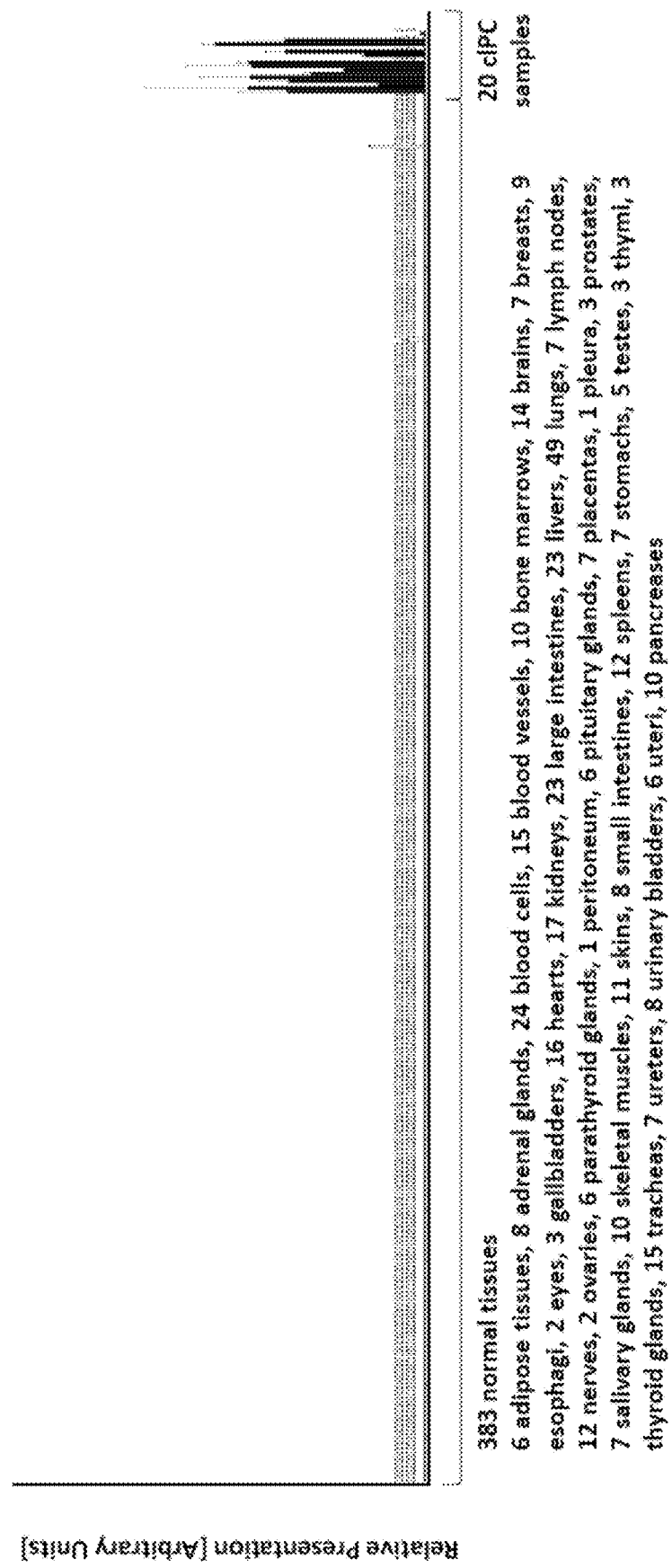
Figure 1Q:
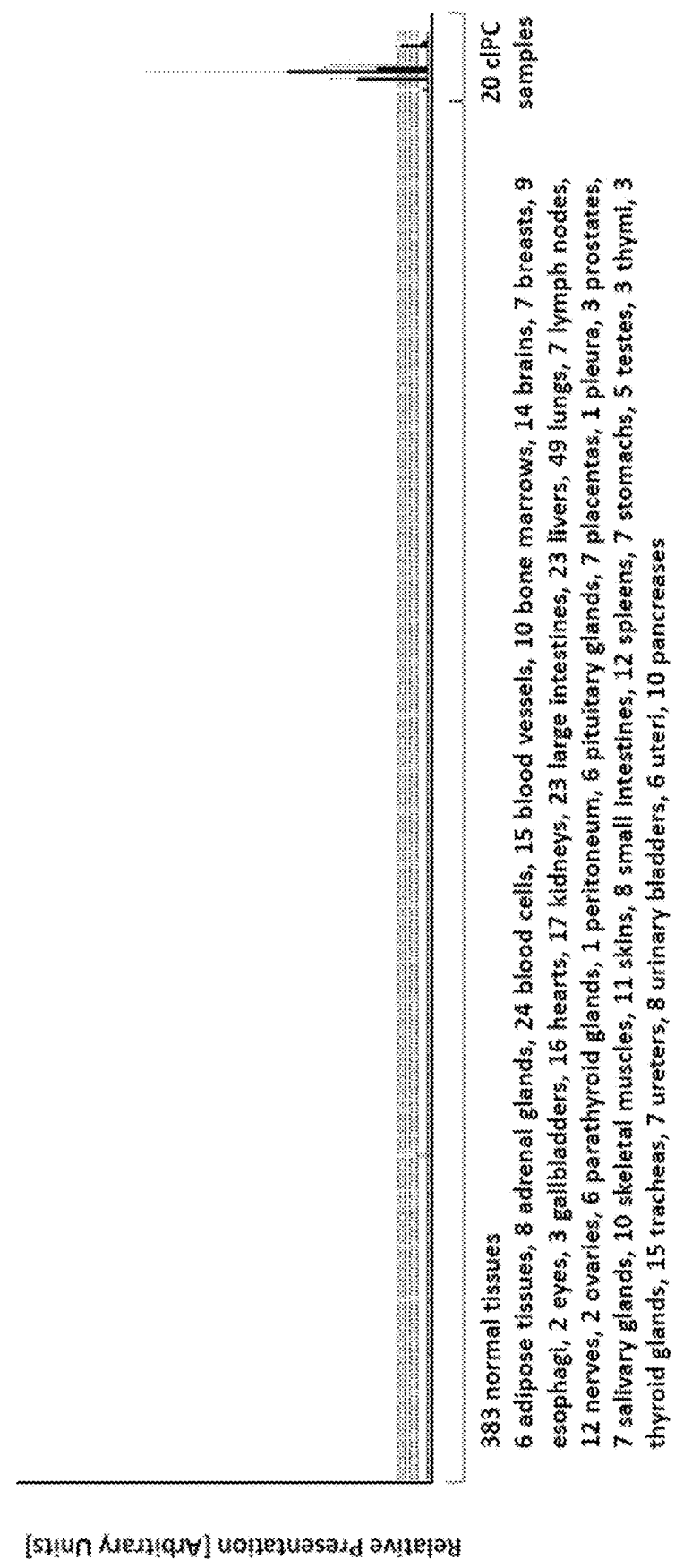
Figure 1R:
Figure 1S:
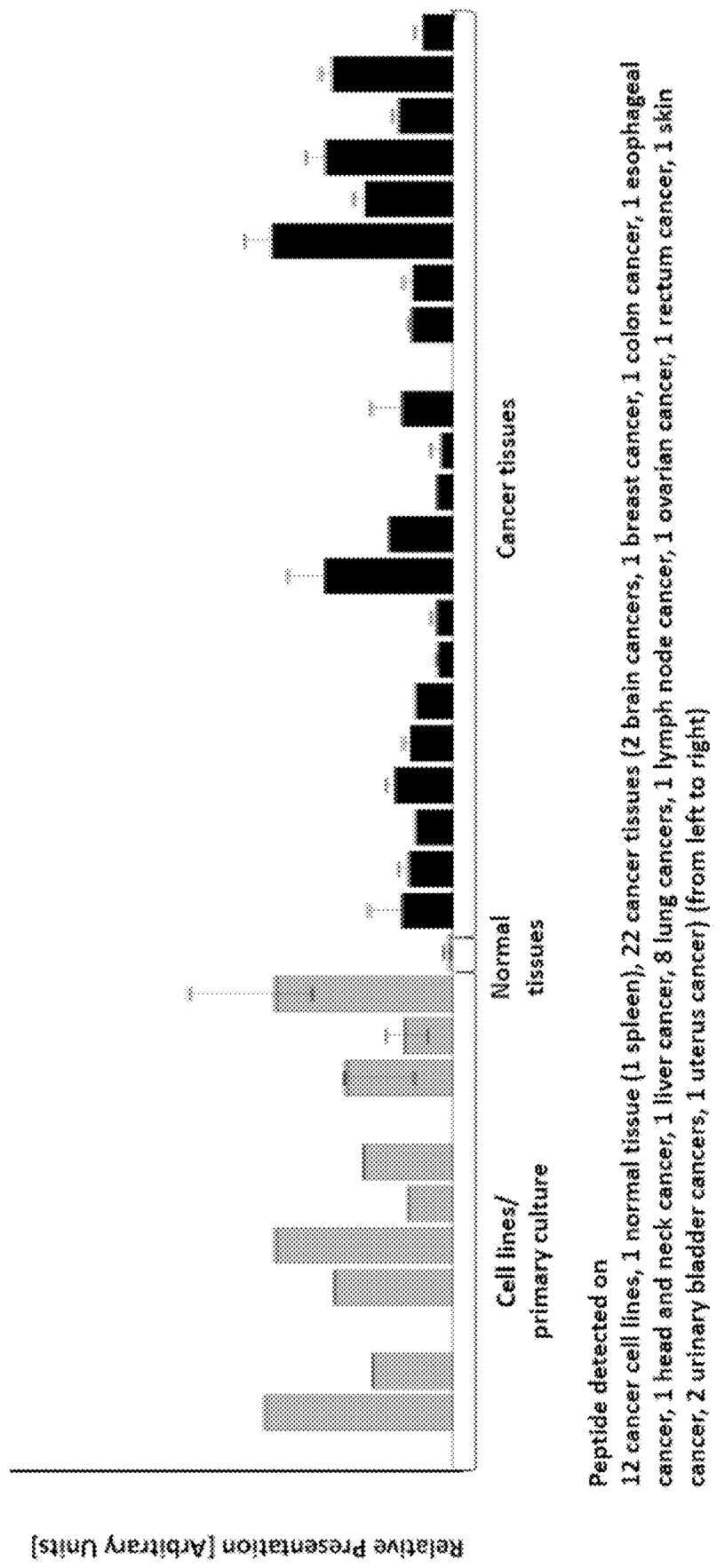
Figure 1T:
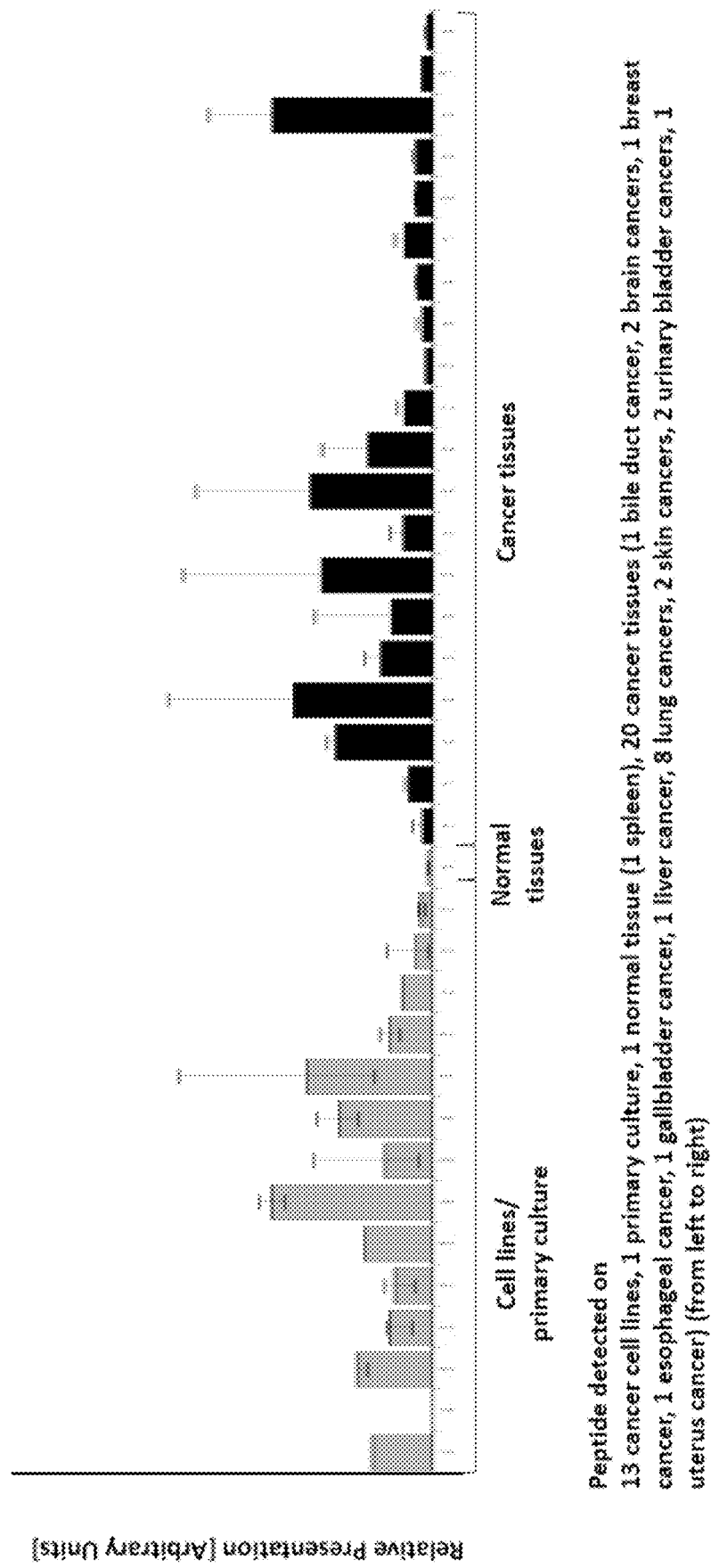
Figure 1U:
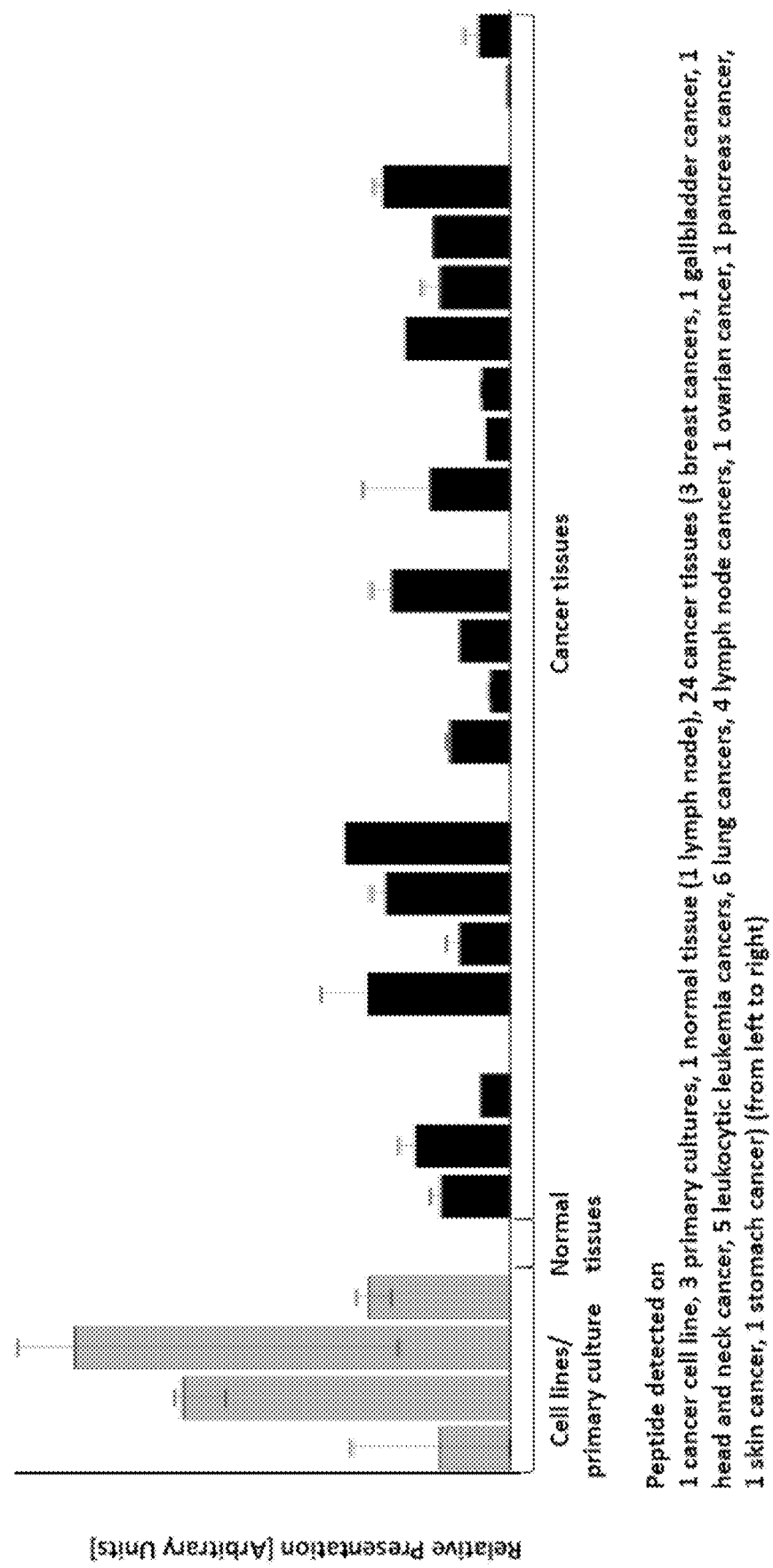
Figure 1A:
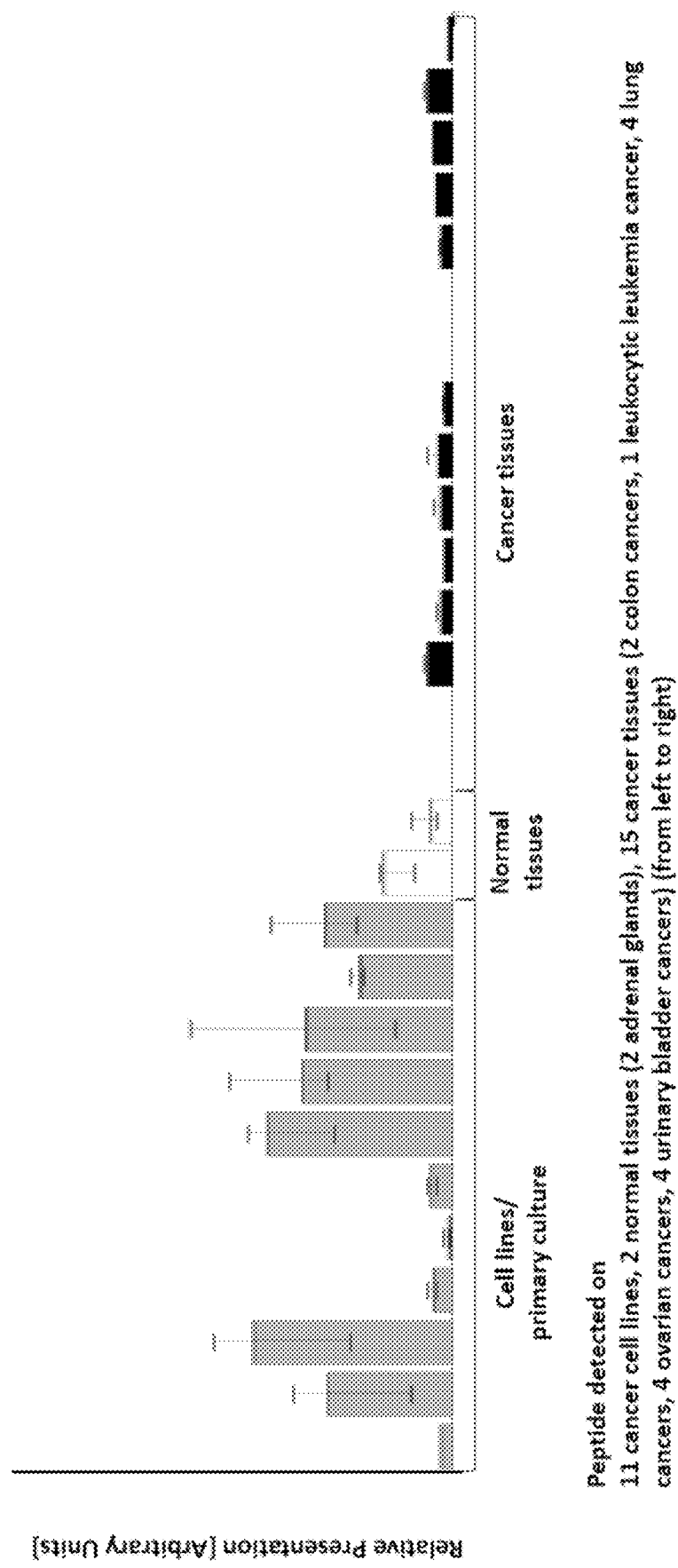
Figure 1A:
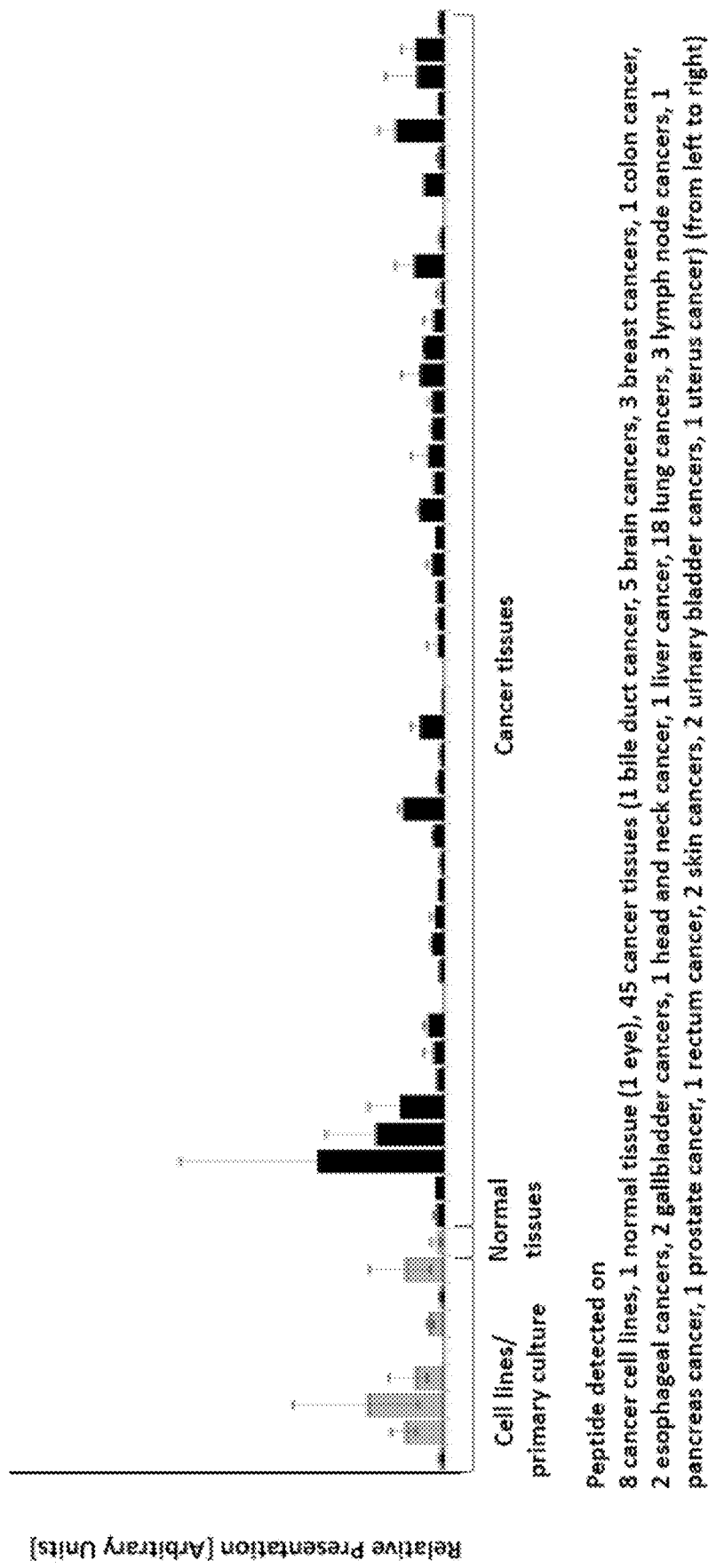
Figure 1A:
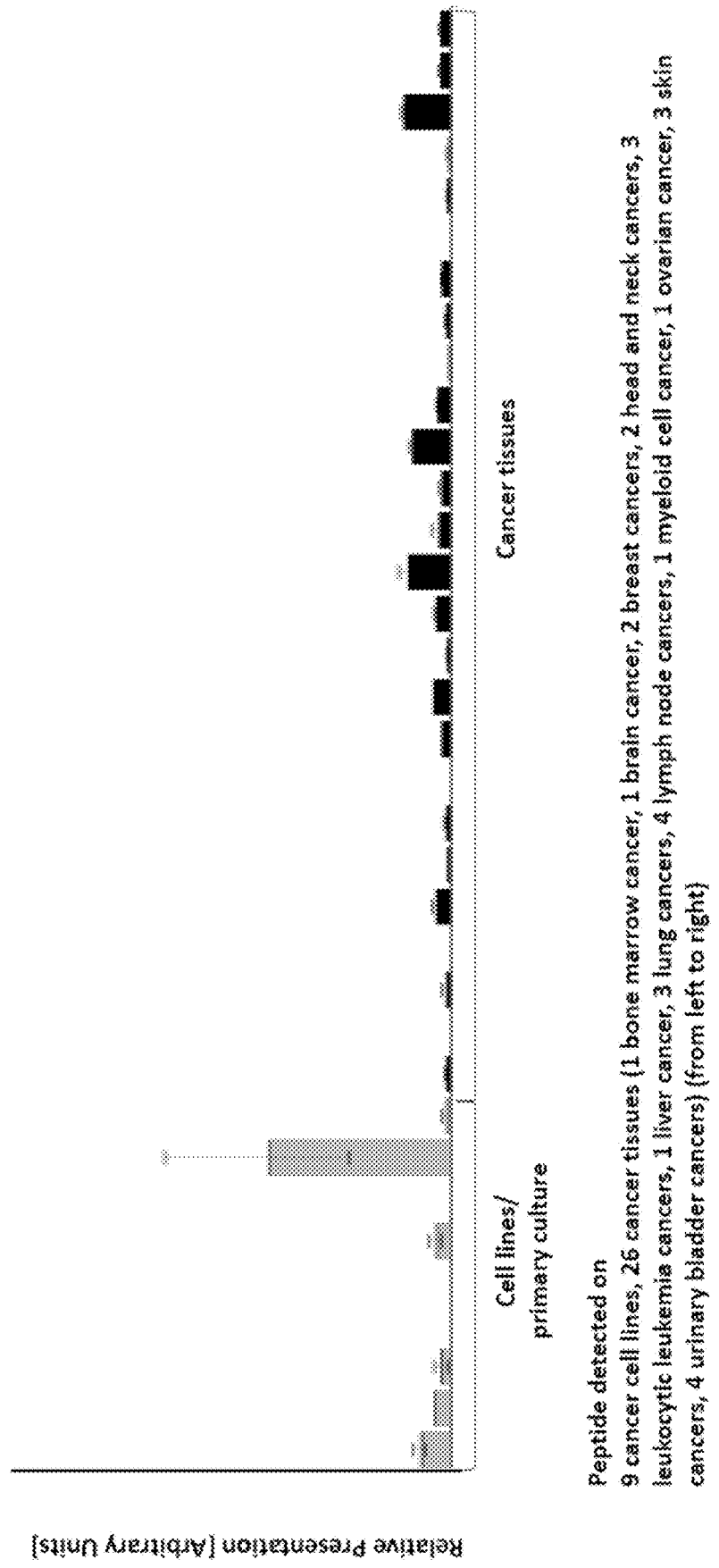

FIGS. 1A to 1AF show the over-presentation of various peptides in normal tissues (white bars) and pancreatic cancer (black bars). FIG. 1A) Gene symbol(s): PTGS1, PTGS2, Peptide: ILIGETIKI (SEQ ID NO.: 3), Tissues from left to right: 1 adipose tissue, 3 adrenal glands, 6 arteries, 5 bone marrows, 7 brains, 3 breasts, 1 nerve, 13 colons, 1 ovary, 8 esophagi, 2 gallbladders, 5 hearts, 16 kidneys, 21 livers, 46 lungs, 3 lymph nodes, 4 leukocyte samples, 3 ovaries, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testes, 3 thymi, 4 thyroid glands, 7 tracheas, 3 ureters, 6 urinary bladders, 2 uteri, 2 veins, 7 pancreas, 20 pancreatic cancer cell line and xenograft samples. The peptide has additionally been detected on 4/91 lung cancers, 1/20 ovarian cancers, 1/24 colorectal cancers, 1/18 kidney cancers, and 1/4 urinary bladder cancers (not shown). FIG. 1B) Gene symbol(s): COL1A2, Peptide: FVDTRTLL (SEQ ID NO.: 1), Tissues from left to right: 1 adipose tissue, 3 adrenal glands, 6 arteries, 5 bone marrows, 7 brains, 3 breasts, 1 nerve, 13 colons, 1 ovary, 8 esophagi, 2 gallbladders, 5 hearts, 16 kidneys, 21 livers, 46 lungs, 3 lymph nodes, 4 leukocyte samples, 3 ovaries, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testes, 3 thymi, 4 thyroid glands, 7 tracheas, 3 ureters, 6 urinary bladders, 2 uteri, 2 veins, 7 pancreas, 20 pancreatic cancer cell line and xenograft samples. The peptide has additionally been detected on 3/91 lung cancers and 1/17 esophageal cancers. FIG. 1C) Gene symbol(s): PTPN14, Peptide: AQYKFVYQV (SEQ ID NO.: 12), Tissues from left to right: 1 adipose tissue, 3 adrenal glands, 6 arteries, 5 bone marrows, 7 brains, 3 breasts, 1 nerve, 13 colons, 1 ovary, 8 esophagi, 2 gallbladders, 5 hearts, 16 kidneys, 21 livers, 46 lungs, 3 lymph nodes, 4 leukocyte samples, 3 ovaries, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testes, 3 thymi, 4 thyroid glands, 7 tracheas, 3 ureters, 6 urinary bladders, 2 uteri, 2 veins, 7 pancreas, 20 pancreatic cancer cell line and xenograft samples. The peptide has additionally been detected on 1/20 ovarian cancers, 2/17 esophageal cancers, 1/46 stomach cancers, 1/91 lung cancers, and 1/18 kidney cancers. FIG. 1D) Gene symbol(s): UBR1, Peptide: SLMDPNKFLLL (SEQ ID NO.: 115), Tissues from left to right: 13 pancreatic cell lines, 2 PBMC cultures, 1 prostate cell culture, 3 skin cell lines, 7 normal tissues (1 liver, 2 lungs, 2 spleens, 1 stomach, 1 trachea), 62 cancer tissues (8 brain cancers, 2 breast cancers, 2 colon cancers, 1 esophageal cancer, 1 gallbladder cancer, 5 kidney cancers, 3 leukemias, 6 liver cancers, 19 lung cancers, 5 ovarian cancers, 1 pancreatic cancer, 3 prostate cancers, 3 rectal cancers, 1 skin cancer, 2 urinary bladder cancers). The normal tissue panel (no disease) and the cancer cell lines and xenografts tested were the same as in FIG. 1A-1C, consisting of 1 adipose tissue, 3 adrenal glands, 6 arteries, 5 bone marrows, 7 brains, 3 breasts, 1 nerve, 13 colons, 1 ovary, 8 esophagi, 2 gallbladders, 5 hearts, 16 kidneys, 21 livers, 46 lungs, 3 lymph nodes, 4 leukocyte samples, 3 ovaries, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testes, 3 thymi, 4 thyroid glands, 7 tracheas, 3 ureters, 6 urinary bladders, 2 uteri, 2 veins, 7 pancreas, 20 pancreatic cancer cell line and xenograft samples. The peptide has additionally been detected on 1/6 breast cancers, 5/24 colorectal cancers, 1/2 gallbladder/bile duct cancers, 6/16 liver cancers, 1/2 melanomas, 5/20 ovarian cancers, 1/17 esophageal cancers, 3/12 leukemias, 7/29 brain cancers, 16/91 non-small cell lung carcinomas, 3/33 prostate cancers, 3/18 kidney cancers, 3/14 small cell lung carcinomas, and 1/4 urinary bladder cancers. Discrepancies regarding the list of tumor types between FIG. 1D and table 4 may be due to the more stringent selection criteria applied in table 4 (for details please refer to table 4). FIG. 1D shows all samples with detectable presentation of the peptide Y, regardless of over-presentation parameters and technical sample quality test. FIG. 1E) Gene symbol(s): NUP205, Peptide: ALLTGIISKA (SEQ ID NO.: 5), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/34 brain cancers, 1/18 breast cancers, 2/29 colon or rectum cancers, 1/18 esophageal cancers, 1/8 head and neck cancers, 1/21 liver cancers, 8/107 lung cancers, 1/20 lymph node cancers, 1/20 ovarian cancers, 1/18 skin cancers, 2/15 urinary bladder cancers, 1/16 uterus cancers. FIG. 1F) Gene symbol(s): NUP160, Peptide: ALWHDAENQTVV (SEQ ID NO.: 19), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/17 gallbladder or bile duct cancers, 2/34 brain cancers, 1/18 breast cancers, 1/18 esophageal cancers, 1/21 liver cancers, 8/107 lung cancers, 2/18 skin cancers, 2/15 urinary bladder cancers, 1/16 uterus cancers. FIG. 1G) Gene symbol(s): C11orf80, Peptide: ILSTEIFGV (SEQ ID NO.: 22), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 3/18 breast cancers, 1/17 gallbladder cancers, 1/8 head and neck cancers, 5/17 leukocytic leukemia cancers, 6/107 lung cancers, 4/20 lymph node cancers, 1/20 ovarian cancers, 1/19 pancreas cancers, 1/18 skin cancers, 1/21 stomach cancers. FIG. 1H) Gene symbol(s): FAM83D, Peptide: FLNPDEVHAI (SEQ ID NO.: 37), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/17 gallbladder or bile duct cancers, 2/34 brain cancers, 3/18 breast cancers, 6/29 colon or rectum cancers, 2/18 esophageal cancers, 2/8 head and neck cancers, 1/23 kidney cancers, 5/21 liver cancers, 25/107 lung cancers, 4/20 lymph node cancers, 7/20 ovarian cancers, 1/87 prostate cancers, 2/18 skin cancers, 2/45 stomach cancers, 6/15 urinary bladder cancers, 3/16 uterus cancers. FIG. 1I) Gene symbol(s): DCBLD2, Peptide: TMVEHNYYV (SEQ ID NO.: 46), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 1/18 esophageal cancer, 1/17 gallbladder cancers, 1/8 head and neck cancers, 3/23 kidney cancers, 9/107 lung cancers, 7/20 ovarian cancers, 1/19 pancreas cancers, 1/18 skin cancers, 1/45 stomach cancers, 2/15 urinary bladder cancers, 1/16 uterus cancers. FIG. 1J) Gene symbol(s): SHCBP1, Peptide: RLSELGITQA (SEQ ID NO.: 57), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 1/34 brain cancers, 1/18 breast cancers, 2/18 esophageal cancers, 2/8 head and neck cancers, 1/21 liver cancers, 8/107 lung cancers, 4/20 lymph node cancers, 1/18 myeloid cell cancers, 4/20 ovarian cancers, 4/18 skin cancers, 2/15 urinary bladder cancers, 1/16 uterus cancers. FIG. 1K) Gene symbol(s): CTHRC1, Peptide: VLFSGSLRL (SEQ ID NO.: 69), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/18 breast cancers, 1/18 esophageal cancers, 1/17 gallbladder cancers, 9/107 lung cancers, 1/20 ovarian cancers. FIG. 1L) Gene symbol(s): CDC27, Peptide: KISTITPQI (SEQ ID NO.: 123), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/34 brain cancers, 2/8 head and neck cancers, 1/23 kidney cancers, 1/17 leukocytic leukemia cancers, 2/21 liver cancers, 7/107 lung cancers, 2/20 lymph node cancers, 1/18 myeloid cell cancers, 1/18 skin cancers, 1/45 stomach cancers, 2/15 urinary bladder cancers, 3/16 uterus cancers. FIG. 1M) Gene symbol(s): UBE2C, Peptide: ALYDVRTILL (SEQ ID NO.: 128), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/18 breast cancers, 3/29 colon or rectum cancers, 1/17 leukocytic leukemia cancers, 8/107 lung cancers, 1/20 lymph node cancers, 1/20 ovarian cancers, 1/15 urinary bladder cancers. FIG. 1N) Gene symbol(s): MBTPS2, Peptide: VLISGVVHEI (SEQ ID NO.: 146), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 7/34 brain cancers, 1/18 breast cancers, 2/29 colon or rectum cancers, 1/18 esophageal cancers, 1/23 kidney cancers, 3/21 liver cancers, 5/107 lung cancers, 1/20 lymph node cancers, 2/20 ovarian cancers, 1/87 prostate cancers, 3/18 skin cancers, 1/16 uterus cancers. FIG. 1O) Gene symbol(s): PFDN1, Peptide: KLADIQIEQL (SEQ ID NO.: 89), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 2/29 colon or rectum cancers, 1/17 leukocytic leukemia cancers, 4/107 lung cancers, 4/20 ovarian cancers, 4/16 urinary bladder cancers. FIG. 1P) Gene symbol(s): PKP3, Peptide: ALVEENGIFEL (SEQ ID NO.: 101), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 1/17 bile duct cancers, 2/18 breast cancers, 2/29 colon or rectum cancers, 2/18 esophageal cancers, 2/8 head and neck cancers, 1/21 liver cancers, 7/107 lung cancers, 6/20 ovarian cancers, 3/87 prostate cancers, 4/15 urinary bladder cancers, 1/16 uterus cancers. FIG. 1Q) Gene symbol(s): GFPT2, Peptide: LMMSEDRISL (SEQ ID NO.: 113), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 3/17 gallbladder or bile duct cancers, 5/34 brain cancers, 3/18 breast cancers, 2/29 colon or rectum cancers, 2/18 esophageal cancers, 1/8 head and neck cancers, 1/21 liver cancers, 18/107 lung cancers, 3/20 lymph node cancers, 1/19 pancreas cancers, 1/87 prostate cancers, 2/18 skin cancers, 2/15 urinary bladder cancers, 1/16 uterus cancers. FIG. 1R) Gene symbol(s): CCT4, Peptide: ALSDLALHFL (SEQ ID NO.: 127), Tissues from left to right: 6 adipose tissues, 8 adrenal glands, 24 blood cells, 15 blood vessels, 10 bone marrows, 14 brains, 7 breasts, 9 esophagi, 2 eyes, 3 gallbladders, 16 hearts, 17 kidneys, 23 large intestines, 23 livers, 49 lungs, 7 lymph nodes, 12 nerves, 2 ovaries, 6 parathyroid glands, 1 peritoneum, 6 pituitary glands, 7 placentas, 1 pleura, 3 prostates, 7 salivary glands, 10 skeletal muscles, 11 skins, 8 small intestines, 12 spleens, 7 stomachs, 5 testes, 3 thymi, 3 thyroid glands, 15 tracheas, 7 ureters, 8 urinary bladders, 6 uteri, 10 pancreases, 20 pancreatic cancer cell line and xenograft samples. The peptide has additionally been found on 1/34 brain cancers, 2/18 breast cancers, 2/8 head and neck cancers, 3/17 leukocytic leukemia cancers, 1/21 liver cancers, 3/107 lung cancers, 4/20 lymph node cancers, 2/18 myeloid cell cancers, 1/20 ovarian cancers, 3/18 skin cancers, 4/15 urinary bladder cancers. FIG. 1S) Gene symbol(s): NUP205, Peptide: ALLTGIISKA (SEQ ID NO.: 5), Tissues from left to right: 12 cancer cell lines, 1 normal tissue (1 spleen), 22 cancer tissues (2 brain cancers, 1 breast cancer, 1 colon cancer, 1 esophageal cancer, 1 head and neck cancer, 1 liver cancer, 8 lung cancers, 1 lymph node cancer, 1 ovarian cancer, 1 rectum cancer, 1 skin cancer, 2 urinary bladder cancers, 1 uterus cancer). The normal tissue panel tested was the same as in FIG. 1E-1R. FIG. 1T) Gene symbol(s): NUP160, Peptide: ALWHDAENQTVV (SEQ ID NO.: 19), Tissues from left to right: 13 cancer cell lines, 1 primary culture, 1 normal tissue (1 spleen), 20 cancer tissues (1 bile duct cancer, 2 brain cancers, 1 breast cancer, 1 esophageal cancer, 1 gallbladder cancer, 1 liver cancer, 8 lung cancers, 2 skin cancers, 2 urinary bladder cancers, 1 uterus cancer). The normal tissue panel tested was the same as in FIG. 1E-1R. FIG. 1U) Gene symbol(s): C11orf80, Peptide: ILSTEIFGV (SEQ ID NO.: 22), Tissues from left to right: 1 cancer cell line, 3 primary cultures, 1 normal tissue (1 lymph node), 24 cancer tissues (3 breast cancers, 1 gallbladder cancer, 1 head and neck cancer, 5 leukocytic leukemia cancers, 6 lung cancers, 4 lymph node cancers, 1 ovarian cancer, 1 pancreas cancer, 1 skin cancer, 1 stomach cancer). The normal tissue panel tested was the same as in FIG. 1E-1R. FIG. 1V) Gene symbol(s): FAM83D, Peptide: FLNPDEVHAI (SEQ ID NO.: 37), Tissues from left to right: 16 cancer cell lines, 3 primary cultures, 1 normal tissue (1 trachea), 73 cancer tissues (1 bile duct cancer, 2 brain cancers, 3 breast cancers, 4 colon cancers, 2 esophageal cancers, 1 gallbladder cancer, 2 head and neck cancers, 1 kidney cancer, 5 liver cancers, 25 lung cancers, 4 lymph node cancers, 7 ovarian cancers, 1 prostate cancer, 2 rectum cancers, 2 skin cancers, 2 stomach cancers, 6 urinary bladder cancers, 3 uterus cancers). The normal tissue panel tested was the same as in FIG. 1E-1R. FIG. 1W) Gene symbol(s): DCBLD2, Peptide: TMVEHNYYV (SEQ ID NO.: 46), Tissues from left to right: 4 cancer cell lines, 1 primary culture, 28 cancer tissues (1 esophageal cancer, 1 gallbladder cancer, 1 head and neck cancer, 3 kidney cancers, 9 lung cancers, 7 ovarian cancers, 1 pancreas cancer, 1 skin cancer, 1 stomach cancer, 2 urinary bladder cancers, 1 uterus cancer). The normal tissue panel tested was the same as in FIG. 1E-1R. FIG. 1X) Gene symbol(s): SHCBP1, Peptide: RLSELGITQA (SEQ ID NO.: 57), Tissues from left to right: 20 cancer cell lines, 2 primary cultures, 2 normal tissues (1 bone marrow, 1 placenta), 31 cancer tissues (1 brain cancer, 1 breast cancer, 2 esophageal cancers, 2 head and neck cancers, 1 liver cancer, 8 lung cancers, 4 lymph node cancers, 1 myeloid cell cancer, 4 ovarian cancers, 4 skin cancers, 2 urinary bladder cancers, 1 uterus cancer). The normal tissue panel tested was the same as in FIG. 1E-1R. FIG. 1Y) Gene symbol(s): CTHRC1, Peptide: VLFSGSLRL (SEQ ID NO.: 69), Tissues from left to right: 5 cancer cell lines, 14 cancer tissues (2 breast cancers, 1 esophageal cancer, 1 gallbladder cancer, 9 lung cancers, 1 ovarian cancer). The normal tissue panel tested was the same as in FIG. 1E-1R. FIG. 1Z) Gene symbol(s): CDC27, Peptide: KISTITPQI (SEQ ID NO.: 123), Tissues from left to right: 19 cancer cell lines, 2 primary cultures, 3 normal tissues (1 adrenal gland, 1 liver, 1 placenta), 25 cancer tissues (2 brain cancers, 2 head and neck cancers, 1 kidney cancer, 1 leukocytic leukemia cancer, 2 liver cancers, 7 lung cancers, 2 lymph node cancers, 1 myeloid cell cancer, 1 skin cancer, 1 stomach cancer, 2 urinary bladder cancers, 3 uterus cancers). The normal tissue panel tested was the same as in FIG. 1E-1R. FIG. 1AA) Gene symbol(s): UBE2C, Peptide: ALYDVRTILL (SEQ ID NO.: 128), Tissues from left to right: 10 cancer cell lines, 17 cancer tissues (2 breast cancers, 1 cecum cancer, 2 colon cancers, 1 leukocytic leukemia cancer, 8 lung cancers, 1 lymph node cancer, 1 ovarian cancer, 1 urinary bladder cancer). The normal tissue panel tested was the same as in FIG. 1E-1R. FIG. 1AB) Gene symbol(s): MBTPS2, Peptide: VLISGVVHEI (SEQ ID NO.: 146), Tissues from left to right: 16 cancer cell lines, 2 primary cultures, 2 normal tissues (1 spleen, 1 uterus), 28 cancer tissues (7 brain cancers, 1 breast cancer, 2 colon cancers, 1 esophageal cancer, 1 kidney cancer, 3 liver cancers, 5 lung cancers, 1 lymph node cancer, 2 ovarian cancers, 1 prostate cancer, 3 skin cancers, 1 uterus cancer). The normal tissue panel tested was the same as in FIG. 1E-1R. FIG. 1AC) Gene symbol(s): PFDN1, Peptide: KLADIQIEQL (SEQ ID NO.: 89), Tissues from left to right: 11 cancer cell lines, 2 normal tissues (2 adrenal glands), 15 cancer tissues (2 colon cancers, 1 leukocytic leukemia cancer, 4 lung cancers, 4 ovarian cancers, 4 urinary bladder cancers). The normal tissue panel tested was the same as in FIG. 1E-1R. FIG. 1AD) Gene symbol(s): PKP3, Peptide: ALVEENGIFEL (SEQ ID NO.: 101), Tissues from left to right: 3 cancer cell lines, 3 primary cultures, 2 normal tissues (2 colons), 31 cancer tissues (1 bile duct cancer, 2 breast cancers, 1 cecum cancer, 1 colon cancer, 2 esophageal cancers, 2 head and neck cancers, 1 liver cancer, 7 lung cancers, 6 ovarian cancers, 3 prostate cancers, 4 urinary bladder cancers, 1 uterus cancer). The normal tissue panel tested was the same as in FIG. 1E-1R. FIG. 1AE) Gene symbol(s): GFPT2, Peptide: LMMSEDRISL (SEQ ID NO.: 113), Tissues from left to right: 8 cancer cell lines, 1 normal tissue (1 eye), 45 cancer tissues (1 bile duct cancer, 5 brain cancers, 3 breast cancers, 1 colon cancer, 2 esophageal cancers, 2 gallbladder cancers, 1 head and neck cancer, 1 liver cancer, 18 lung cancers, 3 lymph node cancers, 1 pancreas cancer, 1 prostate cancer, 1 rectum cancer, 2 skin cancers, 2 urinary bladder cancers, 1 uterus cancer). The normal tissue panel tested was the same as in FIG. 1E-1R. FIG. 1AF) Gene symbol(s): CCT4, Peptide: ALSDLALHFL (SEQ ID NO.: 127), Tissues from left to right: 9 cancer cell lines, 26 cancer tissues (1 bone marrow cancer, 1 brain cancer, 2 breast cancers, 2 head and neck cancers, 3 leukocytic leukemia cancers, 1 liver cancer, 3 lung cancers, 4 lymph node cancers, 1 myeloid cell cancer, 1 ovarian cancer, 3 skin cancers, 4 urinary bladder cancers). The normal tissue panel tested was the same as in FIG. 1E-1R.

Figure 2A:
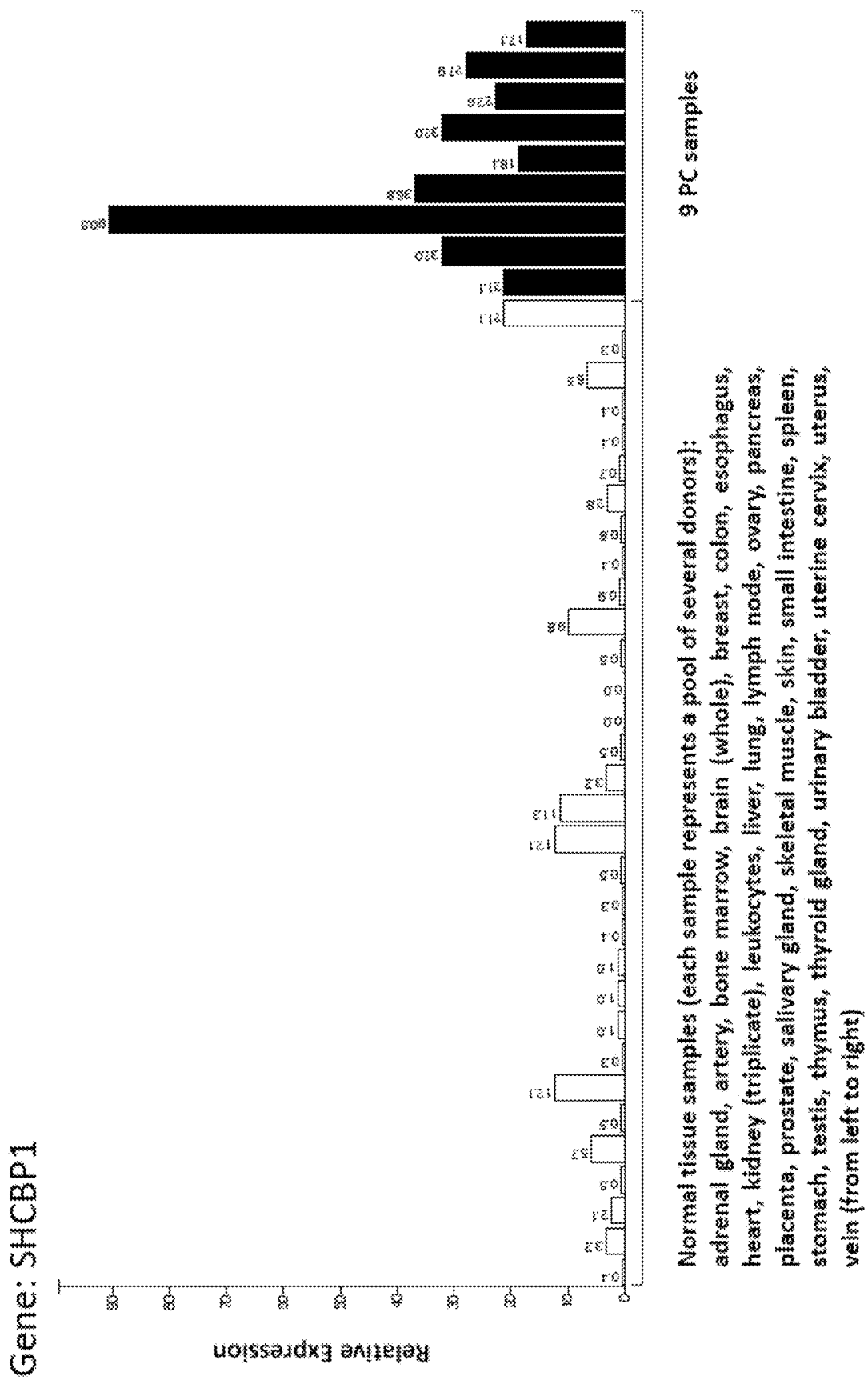
Figure 2B:
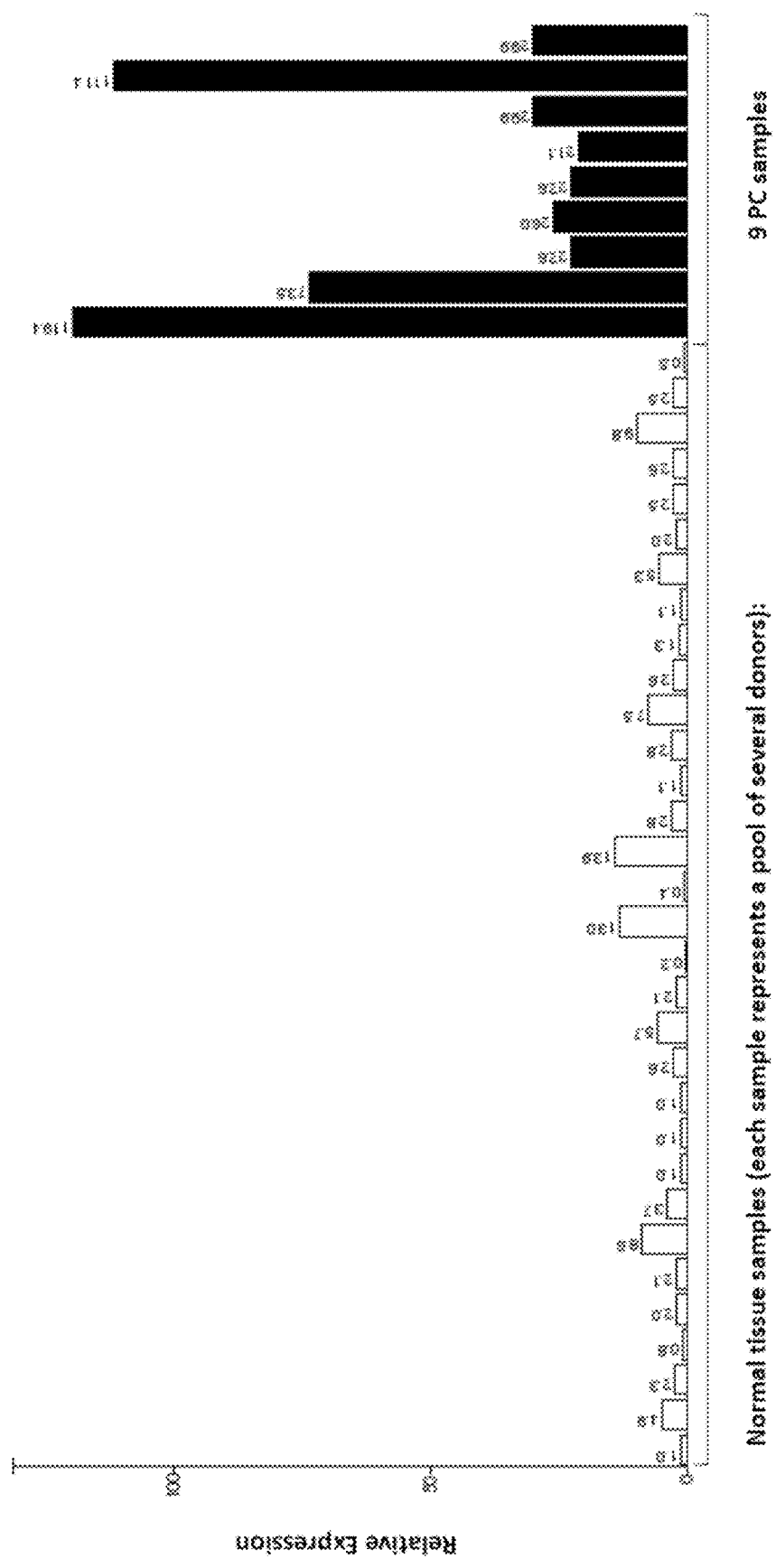

FIGS. 2A to 2C show exemplary expression profiles (relative expression compared to normal pancreas) of source genes of the present invention that are highly over-expressed or exclusively expressed in pancreatic cancer in a panel of normal tissues (white bars) and 9 pancreatic cancer samples (black bars). Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein, 9 pancreatic cancer samples. FIG. 2A) SHCBP1; FIG. 2B) FN1; and FIG. 2C) PLEC.

FIGS. 3A to 3D show exemplary immunogenicity data: flow cytometry results after peptide-specific multimer staining. CD8+ T cells were primed using artificial APCs coated with anti-CD28 mAb and HLA-A*02 in complex with SeqID No 125 peptide (FIG. 3A, left panel), SeqID No 148 peptide (FIG. 3B, left panel), SeqID No 156 peptide (FIG.

Figure 3A:
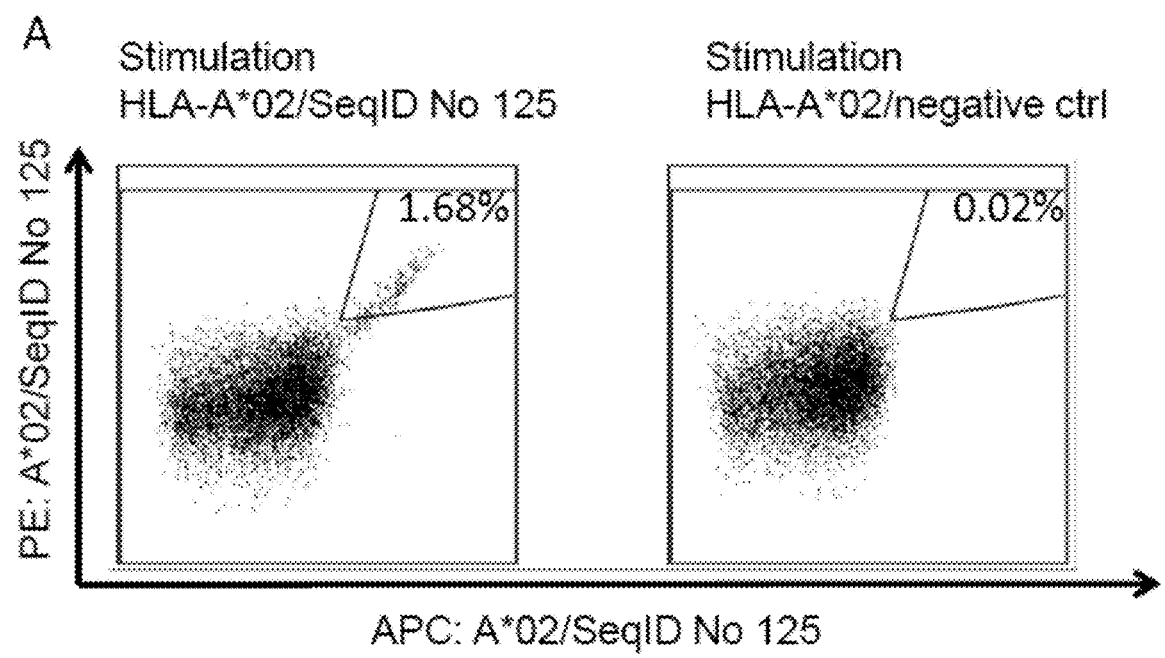
Figure 3B:
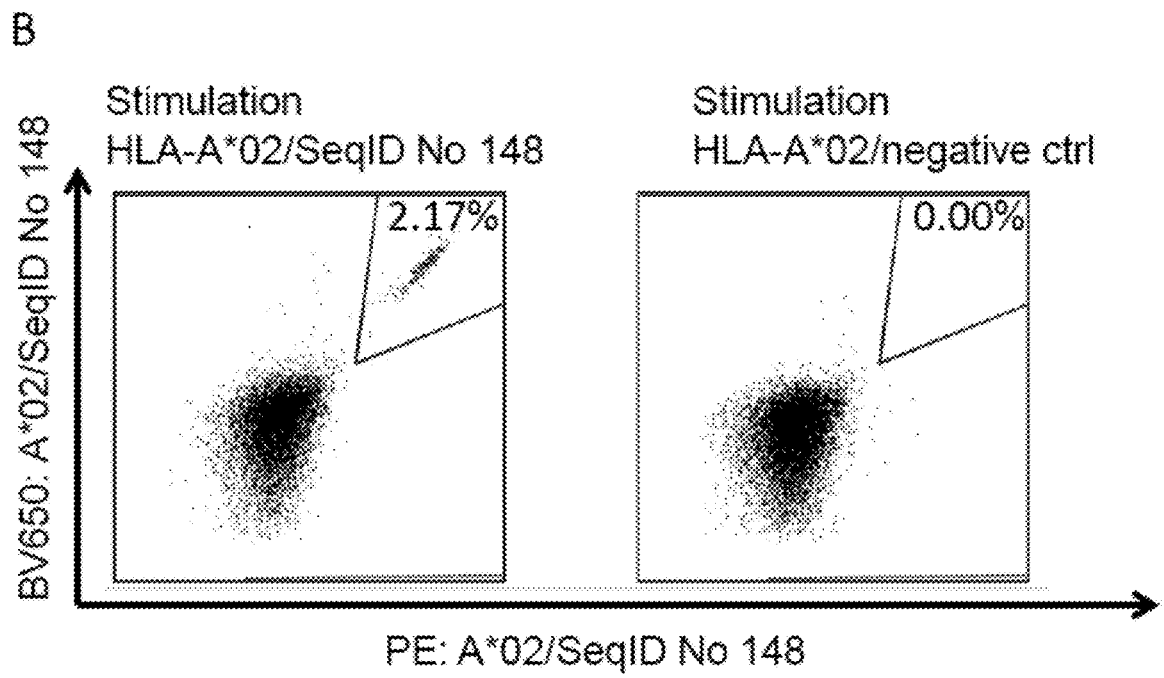

3C, left panel), SeqID No 178 peptide (FIG. 3D, left panel, top), and SeqID No 177 peptide (FIG. 3D, left panel, bottom), respectively. After three cycles of stimulation, the detection of peptide-reactive cells was performed by 2D multimer staining with A*02/SeqID No 125 (FIG. 3A), A*02/SeqID No 148 (FIG. 3B) or A*02/SeqID No 156 (FIG. 3C). Right panels (FIGS. 3A, 3B, 3C, and 3D) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1

Identification and Quantitation of Tumor Associated Peptides Presented on the Cell Surface Tissue Samples Patients' tumor tissues and cell lines were obtained from University Hospital of Tübingen, Germany, University Hospital of Heidelberg, Germany, NMI Reutlingen, Germany, Md. Anderson Cancer Center, Houston, Tex., USA. Normal tissues were obtained from Asterand, Detroit, USA and Royston, Herts, UK; Bio-Options Inc., CA, USA; BioServe, Beltsville, Md., USA; Capital BioScience Inc., Rockville, Md., USA; Geneticist Inc., Glendale, Calif., USA; Tissue Solutions Ltd, Glasgow, Scotland, UK; University Hospital of Geneva; University Hospital of Heidelberg; Kyoto Prefectural University of Medicine (KPUM); University Hospital Munich; ProteoGenex Inc., Culver City, Calif., USA; University Hospital of Tübingen, Germany. Written informed consents of all donors had been given before surgery or autopsy. Tissues were shock-frozen immediately after excision and stored until isolation of TUMAPs at −70° C. or below.

Isolation of HLA Peptides from Tissue Samples

HLA peptide pools from frozen tissue samples were obtained by immune precipitation according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features—a novel tool for high resolution LC-MS-based peptide/protein—a novel tool for high resolution LC-MS-based peptide/protein profiling (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose pancreatic cancer samples to a baseline of normal tissue samples. Presentation profiles of exemplary over-presented peptides are shown in FIGS. 1 A-1 AF. Presentation scores for exemplary peptides are shown in Table 8.

TABLE 8

Presentation scores.
The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | Peptide Presentation |
|---|---|---|
| 1 | FVDTRTLL | +++ |
| 3 | ILIGETIKI | +++ |
| 4 | ALDPAAQAFLL | +++ |
| 5 | ALLTGIISKA | +++ |
| 6 | ALTGIPLPLI | +++ |
| 7 | ALVDIVRSL | +++ |
| 8 | ALYTGSALDFV | +++ |
| 10 | VLLDKIKNL | + |
| 11 | ALYYNPHLL | +++ |
| 12 | AQYKFVYQV | +++ |
| 14 | FIIDNPQDLKV | +++ |
| 15 | FILANEHNV | +++ |
| 16 | GLIDYDTGI | +++ |

TABLE 8-continued

Presentation scores.
The table lists peptides that are very
highly over-presented on tumors compared
to a panel of normal tissues (+++),
highly over-presented on tumors compared
to a panel of normal tissues (++) or
over-presented on tumors compared to a
panel of normal tissues (+).

| SEQ ID No. | Sequence | Peptide Presentation |
|---|---|---|
| 17 | GLIDYDTGIRL | ++ |
| 18 | ALFVRLLAL | +++ |
| 19 | ALWHDAENQTVV | +++ |
| 21 | GLVDGRDLVIV | +++ |
| 22 | ILSTEIFGV | +++ |
| 23 | KLDSSGGAVQL | ++ |
| 24 | KLSENAGIQSL | +++ |
| 25 | LINPNIATV | +++ |
| 27 | TLLAHPVTL | + |
| 29 | YILPFSEVL | +++ |
| 30 | YIYKDTIQV | +++ |
| 31 | YLDSMYIML | ++ |
| 34 | FLEDDDIAAV | +++ |
| 35 | FLFPSQYVDV | +++ |
| 37 | FLNPDEVHAI | + |
| 39 | FLTPSIFII | +++ |
| 40 | GLAPQIHDL | +++ |
| 41 | GLLAGNEKLTM | ++ |
| 42 | ILSDMRSQYEV | +++ |
| 43 | HLGVKVFSV | +++ |
| 44 | ILAQVGFSV | +++ |
| 45 | ILYSDDGQKWTV | +++ |
| 46 | TMVEHNYYV | +++ |
| 47 | LIYKDLVSV | + |
| 48 | LLDENGVLKL | +++ |
| 49 | LLDGFPRTV | +++ |
| 50 | LLFGSDGYYV | +++ |
| 51 | LLGPAGARA | +++ |
| 52 | LLSDPIPEV | ++ |
| 53 | LLWDPSTGKQV | +++ |
| 54 | LTQPGPIASA | +++ |
| 55 | NLAPAPLNA | +++ |
| 56 | NLIGVTAEL | +++ |
| 57 | RLSELGITQA | ++ |

TABLE 8-continued

Presentation scores.
The table lists peptides that are very
highly over-presented on tumors compared
to a panel of normal tissues (+++),
highly over-presented on tumors compared
to a panel of normal tissues (++) or
over-presented on tumors compared to a
panel of normal tissues (+).

| SEQ ID No. | Sequence | Peptide Presentation |
|---|---|---|
| 58 | RQYPWGVVQV | +++ |
| 59 | SLSESFFMV | + |
| 60 | SLWEDYPHV | ++ |
| 61 | SMYDGLLQA | ++ |
| 62 | SVFPGARLL | +++ |
| 63 | SVTGIIVGV | +++ |
| 64 | TLFSEPKFAQV | ++ |
| 67 | VIWGTDVNV | ++ |
| 68 | VLFDVTGQV | +++ |
| 69 | VLFSGSLRL | +++ |
| 70 | VLGVIWGV | +++ |
| 71 | VLLPEGGITAI | +++ |
| 72 | VMASPGGLSAV | +++ |
| 73 | VMVDGKPVNL | + |
| 74 | YIDKDLEYV | +++ |
| 75 | FSFVDLRLL | +++ |
| 77 | RLFPGSSFL | +++ |
| 79 | VVYEGQLISI | + |
| 80 | LLPGTEYVVSV | + |
| 81 | VVYDDSTGLIRL | +++ |
| 82 | ALIAEGIAL | ++ |
| 83 | ALSKEIYVI | +++ |
| 85 | FLSDGTIISV | ++ |
| 86 | GLGDFIFYSV | + |
| 88 | IIDDTIFNL | ++ |
| 90 | KLLTPITTL | + |
| 91 | LLFNDVQTL | + |
| 92 | YLTNEGIAHL | + |
| 93 | SIDSEPALV | +++ |
| 94 | VMMEEFVQL | + |
| 95 | ALADDDFLTV | ++ |
| 96 | ALAPATGGGSLLL | + |
| 98 | ALDQKVRSV | + |
| 99 | ALESFLKQV | + |

TABLE 8-continued

Presentation scores.
The table lists peptides that are very
highly over-presented on tumors compared
to a panel of normal tissues (+++),
highly over-presented on tumors compared
to a panel of normal tissues (++) or
over-presented on tumors compared to a
panel of normal tissues (+).

| SEQ ID No. | Sequence | Peptide Presentation |
|---|---|---|
| 100 | ALFGAGPASI | +++ |
| 102 | ALYPGTDYTV | + |
| 104 | FLQPDLDSL | +++ |
| 105 | FLSEVFHQA | + |
| 106 | FVWSGTAEA | +++ |
| 107 | FVYGGPQVQL | + |
| 108 | IADGGFTEL | +++ |
| 109 | ILASVILNV | ++ |
| 111 | LLLAAARLAAA | + |
| 114 | SLFPHNPQFI | +++ |
| 115 | SLMDPNKFLLL | ++ |
| 116 | SMMDPNHFL | ++ |
| 118 | TLWYRPPEL | ++ |
| 119 | VLGDDPQLMKV | + |
| 120 | VLVNDFFLV | ++ |
| 122 | MQAPRAALVFA | + |
| 123 | KISTITPQI | +++ |
| 124 | ALFEESGLIRI | +++ |
| 125 | ALLGKLDAINV | +++ |
| 126 | ALLSLDPAAV | +++ |
| 128 | ALYDVRTILL | +++ |
| 130 | FLFGEEPSKL | + |
| 131 | FLIEEQKIVV | +++ |
| 132 | FLWAGGRASYGV | +++ |
| 133 | ILDDVSLTHL | +++ |
| 134 | ILLAEGRLVNL | +++ |
| 135 | KLDDTYIKA | +++ |
| 136 | KLFPGFEIETV | +++ |
| 137 | KLGPEGELL | +++ |
| 138 | NIFPNPEATFV | ++ |
| 140 | SLLNPPETLNL | +++ |
| 142 | SLYGYLRGA | +++ |
| 143 | TADPLDYRL | ++ |
| 144 | TAVALLRLL | +++ |

TABLE 8-continued

Presentation scores.
The table lists peptides that are very
highly over-presented on tumors compared
to a panel of normal tissues (+++),
highly over-presented on tumors compared
to a panel of normal tissues (++) or
over-presented on tumors compared to a
panel of normal tissues (+).

| SEQ ID No. | Sequence | Peptide Presentation |
|---|---|---|
| 145 | TTFPRPVTV | +++ |
| 146 | VLISGVVHEI | +++ |
| 147 | YAFPKAVSV | +++ |
| 148 | YLHNQGIGV | + |
| 149 | ILGTEDLIVEV | + |
| 150 | ALFQPHLINV | ++ |
| 151 | ALLDIIRSL | +++ |
| 153 | ALPKEDPTAV | + |
| 154 | KVADLVLML | + |
| 155 | LLLDPDTAVLKL | ++ |
| 156 | LLLPPPPCPA | + |
| 157 | MLLEIPYMAA | ++ |
| 158 | SLIEKYFSV | + |
| 159 | SLLDLHTKV | + |
| 160 | VLLPDERTISL | +++ |
| 162 | NADPQAVTM | +++ |
| 163 | VMAPRTLVL | ++ |
| 164 | YLGRLAHEV | ++ |
| 165 | YLLSYIQSI | ++ |
| 166 | SLFPGQVVI | +++ |
| 167 | MLFGHPLLVSV | +++ |
| 169 | FMLPDPQNI | +++ |
| 171 | LLLDVTPLSL | ++ |
| 172 | TMMSRPPVL | ++ |
| 173 | SLAGDVALQQL | +++ |
| 174 | TLDPRSFLL | ++ |
| 175 | ALLESSLRQA | ++ |
| 176 | YLMPGFIHL | +++ |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 μg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in pancreatic cancer are shown in FIGS. 2A-2C. Expression scores for further exemplary genes are shown in Table 9.

TABLE 9

Expression scores.
The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).

| SEQ ID No | Gene name | Sequence | Gene Expression |
|---|---|---|---|
| 1 | COL1A2 | FVDTRTLL | ++ |
| 2 | COL1A2 | FGYDGDFYRA | ++ |
| 3 | PTGS1, PTGS2 | ILIGETIKI | +++ |
| 6 | CDK2 | ALTGIPLPLI | + |
| 7 | FADS3 | ALVDIVRSL | ++ |
| 8 | COL6A3 | ALYTGSALDFV | + |
| 9 | COL6A3 | QIIDAINKV | + |
| 10 | COL6A3 | VLLDKIKNL | + |
| 11 | IPO7 | ALYYNPHLL | + |
| 12 | PTPN14 | AQYKFVYQV | + |
| 18 | TGFBI | ALFVRLLAL | +++ |
| 24 | RAI14 | KLSENAGIQSL | + |
| 26 | MAN2A1 | SLYTALTEA | + |
| 31 | ADAM9 | YLDSMYIML | + |
| 34 | GFPT2 | FLEDDDIAAV | ++ |
| 38 | TFPI2 | FLTEAALGDA | + |
| 43 | COL6A1 | HLGVKVFSV | +++ |
| 44 | SLC6A15 | ILAQVGFSV | ++ |
| 45 | DCBLD2 | ILYSDDGQKWTV | ++ |
| 46 | DCBLD2 | TMVEHNYYV | ++ |
| 53 | NLE1 | LLWDPSTGKQV | + |
| 54 | CXCL5 | LTQPGPIASA | + |
| 56 | ARMC9 | NLIGVTAEL | ++ |
| 57 | SHCBP1 | RLSELGITQA | +++ |
| 58 | SEPT10, SEPT8, SEPT11 | RQYPWGVVQV | ++ |
| 60 | TRAM2 | SLWEDYPHV | ++ |
| 61 | TRPV2 | SMYDGLLQA | ++ |
| 67 | MCM4 | VIWGTDVNV | +++ |
| 75 | COL1A1 | FSFVDLRLL | +++ |
| 77 | CREB3L1 | RLFPGSSFL | ++ |
| 79 | FN1 | VVYEGQLISI | +++ |
| 80 | FN1 | LLPGTEYVVSV | +++ |
| 84 | SLC1A4, SLC1A5 | FILPIGATV | + |
| 90 | COL6A3 | KLLTPITTL | + |

TABLE 9-continued

Expression scores.
The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).

| SEQ ID No | Gene name | Sequence | Gene Expression |
|---|---|---|---|
| 91 | PLEC | LLFNDVQTL | +++ |
| 92 | PLEC | YLTNEGIAHL | +++ |
| 95 | MCM4 | ALADDDFLTV | +++ |
| 99 | PRKDC | ALESFLKQV | + |
| 105 | SERPINB2 | FLSEVFHQA | + |
| 113 | GFPT2 | LMMSEDRISL | ++ |
| 119 | TAF6L | VLGDDPQLMKV | + |
| 123 | CDC27 | KISTITPQI | + |
| 124 | CELSR3, SLC26A6 | ALFEESGLIRI | + |
| 126 | PRKDC | ALLSLDPAAV | + |
| 128 | UBE2C | ALYDVRTILL | + |
| 132 | HNRNPU | FLWAGGRASYGV | + |
| 136 | ASNS | KLFPGFEIETV | +++ |
| 137 | SLC1A5 | KLGPEGELL | + |
| 139 | STAT2 | SIDRNPPQL | + |
| 140 | CCNA2 | SLLNPPETLNL | ++ |
| 145 | NONO | TTFPRPVTV | + |
| 146 | MBTPS2 | VLISGVVHEI | + |
| 151 | FADS2 | ALLDIIRSL | ++ |
| 153 | COPG1 | ALPKEDPTAV | + |
| 165 | NCAPG | YLLSYIQSI | +++ |
| 166 | POLA2 | SLFPGQVVI | + |
| 173 | NCAPD2 | SLAGDVALQQL | + |
| 175 | CCND1 | ALLESSLRQA | + |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 22 HLA-A*0201 restricted TUMAPs of the invention so far, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nûrnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 179) from modified Melan-A/MART-1) and A*0201/DDX5-001 (YLLPAIVHI from DDX5, SEQ ID NO. 180), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Pancreatic Cancer Peptides

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A-3D together with corresponding negative controls. Results for 4 peptides from the invention are summarized in Table 10.

TABLE 10

Table 10: In vitro immunogenicity of HLA class I peptides of the invention Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID No | Sequence | Wells positive [%] |
|---|---|---|
| 17 | GLIDYDTGIRL | "+" |
| 81 | VVYDDSTGLIRL | "+" |
| 122 | MQAPRAALVFA | "++" |
| 165 | YLLSYIQSI | "++" |
| 167 | MLFGHPLLVSV | "++" |
| 172 | TMMSRPPVL | "+" |
| 173 | SLAGDVALQQL | "+" |
| 174 | TLDPRSFLL | "++" |
| 119 | VLGDDPQLMKV | "+" |
| 125 | ALLGKLDAINV | "+" |
| 135 | KLDDTYIKA | "+++" |
| 137 | KLGPEGELL | "+" |
| 147 | YAFPKAVSV | "+" |
| 148 | YLHNQGIGV | "+++" |
| 149 | ILGTEDLIVEV | "++" |
| 156 | LLLPPPPCPA | "++" |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (βm) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1h at 37° C., washed again and detected with TMB solution that is stopped with NH2SO4. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

MHC class I binding scores. Binding of HLA-class I restricted peptides to HLA-A*02:01 was ranged by peptide exchange yield: ≥10%=+; ≥20%=++; ≥50=+++; ≥75%=++++

| SEQ ID No | Sequence | Peptide exchange |
|---|---|---|
| 1 | FVDTRTLL | "++" |
| 2 | FGYDGDFYRA | "+++" |
| 3 | ILIGETIKI | "+++" |
| 4 | ALDPAAQAFLL | "+++" |
| 5 | ALLTGIISKA | "+++" |
| 6 | ALTGIPLPLI | "+++" |
| 7 | ALVDIVRSL | "+++" |
| 8 | ALYTGSALDFV | "+++" |
| 9 | QIIDAINKV | "++" |
| 10 | VLLDKIKNL | "++" |
| 11 | ALYYNPHLL | "++" |
| 12 | AQYKFVYQV | "+++" |
| 13 | FIDSSNPGL | "++" |
| 14 | FIIDNPQDLKV | "+++" |
| 15 | FILANEHNV | "+++" |
| 16 | GLIDYDTGI | "+++" |
| 17 | GLIDYDTGIRL | "+++" |
| 18 | ALFVRLLAL | "++" |
| 19 | ALWHDAENQTVV | "+++" |

-continued

| SEQ ID No | Sequence | Peptide exchange |
|---|---|---|
| 20 | GLIDIENPNRV | "+++" |
| 21 | GLVDGRDLVIV | "+++" |
| 22 | ILSTEIFGV | "+++" |
| 23 | KLDSSGGAVQL | "++" |
| 24 | KLSENAGIQSL | "++" |
| 25 | LINPNIATV | "++" |
| 26 | SLYTALTEA | "+++" |
| 27 | TLLAHPVTL | "+++" |
| 28 | VLDEFYSSL | "+++" |
| 29 | YILPFSEVL | "++++" |
| 30 | YIYKDTIQV | "++" |
| 31 | YLDSMYIML | "+++" |
| 32 | YVDDGLISL | "++" |
| 34 | FLEDDDIAAV | "++" |
| 35 | FLFPSQYVDV | "+++" |
| 36 | FLGDLSHLL | "++" |
| 37 | FLNPDEVHAI | "++" |
| 38 | FLTEAALGDA | "+++" |
| 39 | FLTPSIFII | "++" |
| 40 | GLAPQIHDL | "++" |
| 41 | GLLAGNEKLTM | "++" |
| 42 | ILSDMRSQYEV | "+++" |
| 43 | HLGVKVFSV | "++" |
| 44 | ILAQVGFSV | "+++" |
| 45 | ILYSDDGQKWTV | "+++" |
| 46 | TMVEHNYYV | "+++" |
| 47 | LIYKDLVSV | "+++" |
| 48 | LLDENGVLKL | "+++" |
| 49 | LLDGFPRTV | "++" |
| 50 | LLFGSDGYYV | "+++" |
| 51 | LLGPAGARA | "++" |
| 52 | LLSDPIPEV | "+++" |
| 53 | LLWDPSTGKQV | "+++" |
| 54 | LTQPGPIASA | "+++" |
| 55 | NLAPAPLNA | "++" |
| 56 | NLIGVTAEL | "++" |
| 57 | RLSELGITQA | "+++" |
| 58 | RQYPWGVVQV | "++" |
| 59 | SLSESFFMV | "+++" |
| 60 | SLWEDYPHV | "++++" |
| 61 | SMYDGLLQA | "++" |
| 62 | SVFPGARLL | "+" |
| 63 | SVTGIIVGV | "++++" |
| 64 | TLFSEPKFAQV | "++++" |
| 65 | TLNEKLTAL | "+++" |
| 67 | VIWGTDVNV | "++++" |
| 68 | VLFDVTGQV | "+++" |
| 69 | VLFSGSLRL | "+++" |
| 70 | VLGVIWGV | "++++" |
| 71 | VLLPEGGITAI | "+++" |
| 72 | VMASPGGLSAV | "+++" |
| 73 | VMVDGKPVNL | "++++" |
| 74 | YIDKDLEYV | "+++" |
| 77 | RLFPGSSFL | "++++" |
| 78 | SLQDTEEKSRS | "+++" |
| 79 | VVYEGQLISI | "+++" |
| 80 | LLPGTEYVVSV | "+++" |
| 81 | VVYDDSTGLIRL | "+++" |
| 82 | ALIAEGIAL | "+++" |
| 83 | ALSKEIYVI | "+++" |
| 84 | FILPIGATV | "++++" |
| 85 | FLSDGTIISV | "++++" |
| 86 | GLGDFIFYSV | "++++" |
| 87 | GLLPALVAL | "+++" |
| 88 | IIDDTIFNL | "+++" |
| 89 | KLADIQIEQL | "+++" |
| 90 | KLLTPITTL | "+++" |
| 91 | LLFNDVQTL | "+++" |
| 92 | YLTNEGIAHL | "++++" |
| 93 | SIDSEPALV | "+++" |
| 94 | VMMEEFVQL | "+++" |
| 95 | ALADDDFLTV | "+++" |
| 96 | ALAPATGGGSLLL | "+++" |
| 97 | ALDDMISTL | "+++" |
| 98 | ALDQKVRSV | "++" |
| 99 | ALESFLKQV | "+++" |
| 100 | ALFGAGPASI | "+++" |

-continued

| SEQ ID No | Sequence | Peptide exchange |
|---|---|---|
| 101 | ALVEENGIFEL | "+++" |
| 102 | ALYPGTDYTV | "+++" |
| 103 | AVAAVLTQV | "+++" |
| 104 | FLQPDLDSL | "+++" |
| 105 | FLSEVFHQA | "+++" |
| 106 | FVWSGTAEA | "+++" |
| 107 | FVYGGPQVQL | "+++" |
| 109 | ILASVILNV | "++++" |
| 110 | ILLTGTPAL | "+++" |
| 111 | LLLAAARLAAA | "+++" |
| 112 | LLSDVRFVL | "+++" |
| 113 | LMMSEDRISL | "+++" |
| 114 | SLFPHNPQFI | "+++" |
| 115 | SLMDPNKFLLL | "+++" |
| 116 | SMMDPNHFL | "++++" |
| 117 | SVDGVIKEV | "+++" |
| 118 | TLWYRPPEL | "+++" |
| 119 | VLGDDPQLMKV | "+++" |
| 121 | YLDEDTIYHL | "++" |
| 122 | MQAPRAALVFA | "++++" |
| 123 | KISTITPQI | "++" |
| 124 | ALFEESGLIRI | "+++" |
| 125 | ALLGKLDAINV | "+++" |
| 126 | ALLSLDPAAV | "++++" |
| 127 | ALSDLALHFL | "++++" |
| 128 | ALYDVRTILL | "+++" |
| 129 | ALYEKDNTYL | "+++" |
| 130 | FLFGEEPSKL | "+++" |
| 131 | FLIEEQKIVV | "+++" |
| 132 | FLWAGGRASYGV | "+++" |
| 133 | ILDDVSLTHL | "++" |
| 134 | ILLAEGRLVNL | "+++" |
| 135 | KLDDTYIKA | "+++" |
| 136 | KLFPGFEIETV | "++++" |
| 137 | KLGPEGELL | "+++" |
| 138 | NIFPNPEATFV | "+++" |
| 139 | SIDRNPPQL | "+++" |
| 140 | SLLNPPETLNL | "+++" |
| 141 | SLTEQVHSL | "+++" |
| 142 | SLYGYLRGA | "+++" |
| 144 | TAVALLRLL | "++" |
| 145 | TTFPRPVTV | "+++" |
| 146 | VLISGVVHEI | "+++" |
| 147 | YAFPKAVSV | "++" |
| 148 | YLHNQGIGV | "++" |
| 149 | ILGTEDLIVEV | "+++" |
| 150 | ALFQPHLINV | "++++" |
| 151 | ALLDIIRSL | "++++" |
| 152 | ALLEPEFILKA | "++++" |
| 153 | ALPKEDPTAV | "+++" |
| 154 | KVADLVLML | "+++" |
| 155 | LLLDPDTAVLKL | "+++" |
| 156 | LLLPPPPCPA | "+++" |
| 157 | MLLEIPYMAA | "+++" |
| 158 | SLIEKYFSV | "++++" |
| 159 | SLLDLHTKV | "+++" |
| 160 | VLLPDERTISL | "++++" |
| 161 | YLPDIIKDQKA | "+++" |

REFERENCE LIST

Abele, R. et al., Essays Biochem. 50 (2011): 249-264
Abramovich, C. et al., Ann. N.Y. Acad. Sci. 1044 (2005): 109-116
Acuna Sanhueza, G. A. et al., BMC. Cancer 12 (2012): 72
Adams, G. N. et al., Cancer Res 75 (2015): 4235-4243
Agarwal, R., Biochem. Pharmacol. 60 (2000): 1051-1059
Ahn, J. W. et al., Genome Med. 6 (2014): 18
Aili, A. et al., PLoS. One. 8 (2013): e79937
Aisa, Y. et al., Int. J Hematol. 82 (2005): 266-269
Akaogi, K. et al., BMC. Cancer 13 (2013): 65
Akiyama, Y. et al., Oncol. Rep. 31 (2014): 1683-1690
Alagaratnam, S. et al., Mol. Cell Endocrinol. 306 (2009): 75-80
Alan, J. K. et al., Small GTPases. 4 (2013): 159-163
Ali-Rahmani, F. et al., PLoS. One. 9 (2014): e88724
Allam, H. et al., J Proteome. Res 14 (2015): 434-446
Allison, J. P. et al., Science 270 (1995): 932-933
Alshareeda, A. T. et al., Br. J Cancer 112 (2015): 1929-1937
Ambrosini, G. et al., Mol. Cancer Ther. 13 (2014): 2073-2080
Amirkhosravi, A. et al., Semin. Thromb. Hemost. 33 (2007): 643-652
Andersen, R. S. et al., Nat. Protoc. 7 (2012): 891-902
Andersen, V. et al., Aliment. Pharmacol. Ther. 37 (2013): 383-391
Ando, K. et al., Gastric. Cancer 17 (2014): 255-262
Ansari, D. et al., J Cancer Res Clin Oncol 141 (2015): 369-380

Ansari, D. et al., J Transl. Med. 12 (2014): 87
Aoki, T. et al., Science 212 (1981): 463-465
Appay, V. et al., Eur. J Immunol. 36 (2006): 1805-1814
Arai, M. et al., Chembiochem. 17 (2016): 181-189
Argiropoulos, B. et al., Oncogene 26 (2007): 6766-6776
Asad, M. et al., Cell Death. Dis. 5 (2014): e1346
Asano, E. et al., Cell Cycle 13 (2014): 2744-2751
Atcheson, E. et al., Biosci. Rep. 31 (2011): 371-379
Atkins, R. J. et al., J Clin Neurosci. 20 (2013): 1185-1192
Avery-Kiejda, K. A. et al., BMC. Cancer 14 (2014): 253
Avruch, J. et al., Curr. Opin. Clin Nutr. Metab Care 8 (2005): 67-72
Aydar, E. et al., Cancer Lett. 242 (2006): 245-257
Aydar, E. et al., Cancer Res 64 (2004): 5029-5035
Aylon, Y. et al., Mol. Oncol 5 (2011): 315-323
Aziz, F. et al., Curr. Drug Targets. 15 (2014): 469-476
Baek, G. et al., Cell Rep. 9 (2014): 2233-2249
Balasubramanian, S. et al., Genome Biol 10 (2009): R2
Baldwin, R. M. et al., World J Biol Chem 5 (2014): 115-129
Ball, A. R., Jr. et al., Mol. Cell Biol 22 (2002): 5769-5781
Balmer, N. N. et al., Mod. Pathol. 19 (2006): 1593-1605
Ban, Y. et al., J Thyroid Res 2012 (2012): 815079
Banchereau, J. et al., Cell 106 (2001): 271-274
Banziger, C. et al., Cell 125 (2006): 509-522
Baptista, J. A. et al., Clin Chem 40 (1994): 426-430
Barboro, P. et al., Cell Oncol 30 (2008): 13-26
Barrow-McGee, R. et al., Int. J Biochem. Cell Biol 49 (2014): 69-74
Basu, S. et al., PLoS. One. 10 (2015a): e0138443
Basu, S. et al., PLoS. One. 10 (2015b): e0123979
Bausch, D. et al., Clin Cancer Res 17 (2011): 302-309
Beatty, G. et al., J Immunol 166 (2001): 2276-2282
Beck-Cormier, S. et al., PLoS. One. 9 (2014): e98507
Beggs, J. D., Nature 275 (1978): 104-109
Bell, J. L. et al., Cell Mol Life Sci. 70 (2013): 2657-2675
Belle, L. et al., Sci. Signal. 8 (2015): ra18
Bern, W. T. et al., Cancer Res 51 (1991): 6558-6562
Benjamini, Y. et al., Journal of the Royal Statistical Society. Series B (Methodological), Vol. 57 (1995): 289-300
Bhat, M. et al., BMC. Gastroenterol. 15 (2015): 176
Bhatnagar, R. et al., Oral Oncol 48 (2012): 831-835
Bhutia, Y. D. et al., Cancer Res 75 (2015): 1782-1788
Bidkhori, G. et al., PLoS. One. 8 (2013): e67552
Blanco, I. et al., PLoS. One. 10 (2015): e0120020
Blanco, M. A. et al., Cell Res 22 (2012): 1339-1355
Boige, V. et al., JAMA Oncol (2016)
Booth, L. et al., J Cell Physiol 230 (2015): 1661-1676
Bouameur, J. E. et al., J Invest Dermatol. 134 (2014): 885-894
Boulter, J. M. et al., Protein Eng 16 (2003): 707-711
Braumuller, H. et al., Nature (2013)
Breuninger, S. et al., Am. J Pathol. 176 (2010): 2509-2519
Brocke, K. S. et al., Cancer Biol Ther. 9 (2010): 455-468
Brossart, P. et al., Blood 90 (1997): 1594-1599
Bruckdorfer, T. et al., Curr. Pharm. Biotechnol. 5 (2004): 29-43
Burkhart, R. A. et al., Mol. Cancer Res 11 (2013): 901-911
Burns, K. E. et al., Biochem. J 472 (2015): 287-295
Busch, T. et al., J Cell Sci. 125 (2012): 2148-2159
Cacciola, N. A. et al., Mol. Carcinog (2015)
Cai, X. et al., Lung Cancer 65 (2009): 299-305
Cai, Y. et al., Oncogene 33 (2014): 2157-2168
Caldarelli, A. et al., Leukemia 27 (2013): 2301-2310
Camos, M. et al., Cancer Res 66 (2006): 6947-6954
Campione, E. et al., Drug Des Devel. Ther. 9 (2015): 5843-5850
Cance, W. G. et al., Breast Cancer Res Treat. 35 (1995): 105-114
Capurso, G. et al., J Mol. Endocrinol. 49 (2012): R37-R50
Card, K. F. et al., Cancer Immunol Immunother. 53 (2004): 345-357
Carvalho, B. et al., Gut 58 (2009): 79-89
Cascon, A. et al., Hum. Mutat. 28 (2007): 613-621
Cavalcante, G. C. et al., Anticancer Res 35 (2015): 6971-6977
Cerveira, N. et al., Biol Chem 392 (2011): 713-724
Chandramouli, A. et al., Carcinogenesis 28 (2007): 2028-2035
Chaneton, B. et al., Trends Biochem. Sci. 37 (2012): 309-316
Chanock, S. J. et al., Hum. Immunol. 65 (2004): 1211-1223
Chatterjee, M. et al., Haematologica 98 (2013): 1132-1141
Chaudhary, N. et al., Mol. Cell Biol 34 (2014): 3754-3764
Chaudhuri, S. et al., RNA. 13 (2007): 2224-2237
Chen, C. et al., PLoS. One. 10 (2015a): e0135074
Chen, E. et al., Oncogene 25 (2006): 5752-5763
Chen, F. et al., Oncol Lett. 10 (2015): 1704-1708
Chen, J. et al., Int. J Oncol 44 (2014a): 247-255
Chen, J. et al., Int. J Clin Exp. Pathol. 8 (2015b): 2026-2032
Chen, L. et al., Int. J Mol. Sci. 15 (2014b): 11435-11445
Chen, P. C. et al., Int. J Radiat. Oncol Biol Phys. 82 (2012): 1996-2003
Chen, Q. et al., Zhongguo Shi Yan. Xue. Ye. Xue. Za Zhi. 19 (2011a): 1171-1175
Chen, R. et al., J Int. Med. Res 39 (2011b): 533-540
Chen, S. et al., J Cancer Res Clin Oncol 136 (2010): 419-426
Chen, S. T. et al., Cancer Sci. 102 (2011c): 2191-2198
Chen, Y. et al., J Cell Biochem. 100 (2007): 1337-1345
Chen, Y. L. et al., Int J Surg. 11 (2013): 85-91
Chen, Z. T. et al., Int. J Mol. Sci. 16 (2015c): 15497-15530
Chiou, S. S. et al., Carcinogenesis 35 (2014): 2357-2364
Chohan, T. A. et al., Curr. Med. Chem 22 (2015): 237-263
Choi, S. Y. et al., Clin Exp. Med. 11 (2011): 219-226
Chu, X. et al., Int. J Clin Exp. Pathol. 8 (2015): 328-336
Chudnovsky, Y. et al., Cell Rep. 6 (2014): 313-324
Ciccia, A. et al., Mol. Cell 47 (2012): 396-409
Coe, H. et al., Int. J Biochem. Cell Biol 42 (2010): 796-799
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A. 69 (1972): 2110-2114
Cohen, Y. et al., Hematology. 19 (2014): 286-292
Colak, D. et al., PLoS. One. 8 (2013): e63204
Coligan, J. E. et al., Current Protocols in Protein Science (1995)
Collins, K. L. et al., EMBO J 12 (1993): 4555-4566
Colombetti, S. et al., J Immunol. 176 (2006): 2730-2738
Coppola, D. et al., J Geriatr. Oncol 5 (2014): 389-399
Crottes, D. et al., Cancer Res 76 (2016): 607-618
Cui, H. et al., Cancer Res 67 (2007): 3345-3355
Dadkhah, E. et al., Arch. Iran Med. 16 (2013): 463-470
Dai, W. et al., PLoS. One. 9 (2014): e87148
Davies, G. F. et al., PLoS. One. 9 (2014): e84611
De, Braekeleer E. et al., Future. Oncol 10 (2014): 475-495
De, Falco G. et al., Cancer Biol Ther. 1 (2002): 342-347
De, P. et al., Cancer Treat. Rev 39 (2013): 403-412
Deighton, R. F. et al., Brain Pathol. 20 (2010): 691-703
Deisenroth, C. et al., Oncogene 29 (2010): 4253-4260
DeLaBarre, B. et al., Chem Biol 21 (2014): 1143-1161
Delas, A. et al., Pathol. Res Pract. 209 (2013): 115-119
Demeure, K. et al., Mol. Cell Proteomics. 15 (2016): 481-492

Demidyuk, I. V. et al., PLoS. One. 8 (2013): e55752
Demirag, G. G. et al., Med. Oncol 29 (2012): 1518-1522
Deng, H. et al., Biochim. Biophys. Acta 1852 (2015a): 520-528
Deng, W. et al., Cell Physiol Biochem. 35 (2015b): 1677-1688
Dengjel, J. et al., Clin Cancer Res 12 (2006): 4163-4170
Denkberg, G. et al., J Immunol 171 (2003): 2197-2207
Dennis, J. W. et al., Cancer Metastasis Rev 5 (1987): 185-204
DePrimo, S. E. et al., Genome Biol 3 (2002): RESEARCH0032
Derivery, E. et al., PLoS. One. 3 (2008): e2462
Dhup, S. et al., Curr. Pharm. Des 18 (2012): 1319-1330
Ding, Z. et al., Mol. Cell Biol 23 (2003): 250-258
Dinicola, S. et al., Life Sci. 145 (2016): 174-183
Diniz, M. G. et al., Tumour. Biol (2015)
Diotti, R. et al., Mol. Cancer Res 13 (2015): 402-410
Dong, S. et al., Mol. Cancer 13 (2014): 76
Donnard, E. et al., Oncotarget. 5 (2014): 9199-9213
Doppler, H. et al., J Biol Chem 288 (2013): 455-465
Dormeyer, W. et al., J Proteome. Res 7 (2008): 2936-2951
Draoui, N. et al., Dis. Model. Mech. 4 (2011): 727-732
Du, X. et al., Biochem. J 471 (2015): 243-253
Duan, F. et al., Sci. Rep. 5 (2015): 11961
Duensing, S. et al., Oncogene 21 (2002): 6241-6248
Dworakowska, D., Pneumonol. Alergol. Pol. 73 (2005): 297-300
Ebrahimi, F. et al., Exp. Mol. Pathol. 96 (2014): 98-107
Efthimiou, E. et al., Pancreatology. 1 (2001): 571-575
Elakoum, R. et al., Biochimie 97 (2014): 210-218
Eli, M. et al., World J Gastroenterol. 18 (2012): 3112-3118
Emmanuel, C. et al., PLoS. One. 6 (2011): e17617
Er, T. K. et al., J Mol. Med. (Berl) (2016)
Erkan, M. et al., Mol. Cancer 9 (2010): 88
Escobar, B. et al., Cancer Res 70 (2010): 9349-9359
Fagin, J. A., Mol. Endocrinol. 16 (2002): 903-911
Falk, K. et al., Nature 351 (1991): 290-296
Fan, C. W. et al., Scand. J Gastroenterol. 39 (2004): 464-469
Fan, H. X. et al., Onco. Targets. Ther. 8 (2015): 1619-1626
Fan, J. et al., Clin Cancer Res 17 (2011): 2908-2918
Fang, W. Y. et al., Acta Biochim. Biophys. Sin. (Shanghai) 37 (2005): 541-546
Fang, X. et al., Proteomics. 11 (2011): 921-934
Feldner, J. C. et al., Exp. Cell Res 272 (2002): 93-108
Feng, H. et al., J Clin Invest 124 (2014): 3741-3756
Fernandez-Cuesta, L. et al., Genome Biol 16 (2015): 7
Ferrer-Ferrer, M. et al., Arch. Med. Res 44 (2013): 467-474
Findeis-Hosey, J. J. et al., Biotech. Histochem. 87 (2012): 24-29
Fischer, E. G. et al., J Clin Invest 104 (1999): 1213-1221
Flachbartova, Z. et al., Acta Virol. 57 (2013): 3-15
Folsom, A. R. et al., Cancer Epidemiol. Biomarkers Prev. 16 (2007): 2455-2458
Fong, L. et al., Proc. Natl. Acad. Sci. U.S.A. 98 (2001): 8809-8814
Foster, J. S. et al., Trends Endocrinol. Metab 12 (2001): 320-327
Francavilla, C. et al., Mol. Cell 51 (2013): 707-722
Frau, M. et al., J Hepatol. 59 (2013): 830-841
Frau, M. et al., Hepatology 56 (2012): 165-175
Fredericks, W. J. et al., DNA Cell Biol 30 (2011): 851-864
Fredericks, W. J. et al., Int. J Oncol 43 (2013): 638-652
Frugtniet, B. et al., Breast Cancer (Dove. Med. Press) 7 (2015): 99-109
Frulloni, L. et al., N. Engl. J Med. 361 (2009): 2135-2142
Fuchs, B. C. et al., Am. J Physiol Gastrointest. Liver Physiol 286 (2004): G467-G478
Fujieda, S. et al., Arch. Otolaryngol. Head Neck Surg. 120 (1994): 389-394
Fujita, A. et al., Genet. Mol. Res 7 (2008): 371-378
Fujita, T. et al., Cancer Sci. 100 (2009): 238-248
Fujitomo, T. et al., Cancer Res 72 (2012): 4110-4118
Fujiwara, K. et al., PLoS. One. 9 (2014): e107247
Fukunaga, Y. et al., Lung Cancer 38 (2002): 31-38
Furukawa, C. et al., Cancer Res 65 (2005): 7102-7110
Gabrilovich, D. I. et al., Nat Med. 2 (1996): 1096-1103
Gabrovska, P. N. et al., Gene 489 (2011): 63-69
Gallo, S. et al., Clin Sci. (Lond) 129 (2015): 1173-1193
Ganapathy, V. et al., Pharmacol. Ther. 121 (2009): 29-40
Gao, H. J. et al., J Cancer Res. Clin Oncol 141 (2015): 1151-1162
Gao, J. et al., PLoS. One. 9 (2014a): e101979
Gao, S. et al., Arch. Immunol. Ther. Exp. (Warsz.) 62 (2014b): 131-144
Garcia-Lorenzo, A. et al., Int. J Mol. Sci. 13 (2012): 14401-14420
Garg, M. et al., Cancer 116 (2010a): 3785-3796
Garg, M. et al., Eur. J Cancer 46 (2010b): 207-215
Garrido, F. et al., Semin. Cancer Biol 2 (1991): 3-10
Gattinoni, L. et al., Nat Rev. Immunol 6 (2006): 383-393
Gautschi, O. et al., Lung Cancer 55 (2007): 1-14
George, B. et al., Cancer Lett. 358 (2015): 191-199
Georgitsi, M., Best. Pract. Res Clin Endocrinol. Metab 24 (2010): 425-437
Gerber-Lemaire, S. et al., Chimia (Aarau.) 64 (2010): 634-639
Ghilardi, C. et al., Oncotarget. 6 (2015): 28389-28400
Ghosh, N. et al., Pharmacol. Rep. 62 (2010): 233-244
Gillis, L. D. et al., Oncogene 32 (2013): 3598-3605
Gius, D. et al., Cancer Res 67 (2007): 7113-7123
Gnjatic, S. et al., Proc Natl. Acad. Sci. U.S.A. 100 (2003): 8862-8867
Godkin, A. et al., Int. Immunol 9 (1997): 905-911
Golomb, L. et al., Mol. Cell 45 (2012): 222-232
Gong, Y. et al., Adv. Anat. Pathol. 21 (2014): 191-200
Gonias, S. L. et al., Front Biosci. 6 (2001): D1403-D1411
Gonzalez-Exposito, R. et al., Clin Transl. Oncol (2015)
Goodison, S. et al., BMC. Genomics 4 (2003): 39
Goss, P. E. et al., Clin Cancer Res 1 (1995): 935-944
Goss, P. E. et al., Cancer Res 54 (1994): 1450-1457
Goss, P. E. et al., Clin Cancer Res 3 (1997): 1077-1086
Gough, S. M. et al., Blood 118 (2011): 6247-6257
Grady, W. M., Cancer Metastasis Rev 23 (2004): 11-27
Graves, L. M. et al., Nature 403 (2000): 328-332
Green, M. R. et al., Molecular Cloning, A Laboratory Manual 4th (2012)
Greenfield, E. A., Antibodies: A Laboratory Manual 2nd (2014)
Grier, D. G. et al., J Pathol. 205 (2005): 154-171
Grzmil, M. et al., Oncogene 29 (2010): 4080-4089
Gudey, S. K. et al., Sci. Signal. 7 (2014): ra2
Guillemette, S. et al., Genes Dev. 29 (2015): 489-494
Guo, H. et al., Tumour. Biol 36 (2015): 5299-5304
Guo, S. et al., Drug Des Devel. Ther. 7 (2013): 1259-1271
Guo, Y. et al., Acta Pharmacol. Sin. 31 (2010): 1487-1494
Han, B. et al., Mol. Cancer 14 (2015): 64
Han, S. et al., Leuk. Res 34 (2010): 1271-1274
Hansen-Petrik, M. B. et al., Cancer Lett. 175 (2002): 157-163
Hao, J. et al., Oncol Lett. 9 (2015): 2525-2533
Hao, Z. et al., Tumour. Biol 33 (2012): 723-730
Harder, M. N. et al., PLoS. One. 10 (2015): e0120890

Harris, R. E., Inflammopharmacology. 17 (2009): 55-67
Hart, P. A. et al., Pancreatology. 15 (2015): 162-166
Hassanein, M. et al., Mol. Imaging Biol 18 (2016): 18-23
Hassanein, M. et al., Int. J Cancer 137 (2015): 1587-1597
Havelange, V. et al., Cancer 117 (2011): 4696-4706
Havens, M. A. et al., PLoS. Genet. 10 (2014): e1004312
Haymerle, G. et al., Eur. Arch. Otorhinolaryngol. (2015)
He, L. et al., Toxicology 312 (2013): 36-47
He, Y. et al., Transl. Res 165 (2015): 407-416
Hiramoto, T. et al., Oncogene 18 (1999): 3422-3426
Hoang-Vu, C. et al., Int. J Oncol 21 (2002): 265-272
Hoffmann, N. E. et al., Cancer 112 (2008): 1471-1479
Hou, J. et al., Mol. Oncol 9 (2015): 1312-1323
Hsu, Y. C. et al., BMC. Med. 11 (2013): 106
Hu, J. et al., Lung Cancer 88 (2015): 239-245
Hu, S. et al., J Cancer Res Clin Oncol 140 (2014a): 883-893
Hu, X. T. et al., Cell Prolif. 47 (2014): 200-210
Hu, Z. Y. et al., J Exp. Clin Cancer Res 33 (2014b): 61
Huang, G. L. et al., World J Gastroenterol. 16 (2010): 2046-2054
Huang, J. M. et al., Oncogene 32 (2013a): 2220-2229
Huang, Q. C. et al., Cancer Lett. 354 (2014): 28-32
Huang, Y. et al., Cell Biosci. 3 (2013b): 16
Hubalewska-Dydejczyk, A. et al., Q. J Nucl. Med. Mol. Imaging 59 (2015): 152-160
Huber, A. R. et al., BMC. Gastroenterol. 15 (2015): 80
Huegel, J. et al., Dev. Dyn. 242 (2013): 1021-1032
Hwang, M. L. et al., J Immunol. 179 (2007): 5829-5838
Ikenberg, K. et al., J Pathol. 234 (2014): 239-252
Ilm, K. et al., Mol. Cancer 14 (2015): 38
Imianitov, E. N., Arkh. Patol. 75 (2013): 63-72
Ip, W. et al., J Cutan. Med. Surg. 15 (2011): 103-110
Ishimi, Y. et al., J Biochem. 157 (2015): 561-569
Israelsen, W. J. et al., Semin. Cell Dev. Biol 43 (2015): 43-51
Jager, D. et al., Cancer Res 60 (2000): 3584-3591
Jain, R. et al., Appl. Immunohistochem. Mol Morphol. 18 (2010): 9-15
Jeng, Y. M. et al., Br. J Surg. 96 (2009): 66-73
Jeon, Y. J. et al., Cancer Cell 27 (2015): 354-369
Ji, M. et al., Oncol Rep. 33 (2015): 133-140
Jia, A. Y. et al., Br. J Cancer 110 (2014): 2945-2954
Jiang, L. et al., J Cancer Res Clin Oncol 136 (2010): 211-217
Jiang, L. et al., Tumour. Biol 35 (2014a): 12645-12654
Jiang, X. R. et al., Cancer Lett. 353 (2014b): 78-86
Jiang, Y. X. et al., J Int. Med. Res 40 (2012): 887-898
Jochmann, K. et al., Matrix Biol 34 (2014): 55-63
Jose-Eneriz, E. S. et al., Br. J Haematol. 142 (2008): 571-582
Joy, R. M. et al., Neurotoxicology 9 (1988): 637-643
Ju, J. H. et al., Clin Cancer Res 19 (2013): 4335-4346
Jung, G. et al., Proc Natl Acad Sci USA 84 (1987): 4611-4615
Jung, J. H. et al., Evid. Based. Complement Alternat. Med. 2013 (2013): 879746
Kaira, K. et al., Am. J Transl. Res 7 (2015): 356-363
Kancharla, A. et al., Nat Commun. 6 (2015): 8853
Kang, C. Y. et al., J Gastrointest. Surg. 18 (2014): 7-15
Kang, G. et al., Oncotarget. (2015)
Kannen, V. et al., Pharmacol. Ther. 139 (2013): 87-94
Karess, R. E. et al., Int. Rev Cell Mol. Biol 306 (2013): 223-273
Kari, V. et al., Cell Cycle 10 (2011): 3495-3504
Kasai, H. et al., J Histochem. Cytochem. 51 (2003): 567-574
Katada, K. et al., J Proteomics. 75 (2012): 1803-1815
Katkoori, V. R. et al., PLoS. One. 7 (2012): e30020
Katoh, M. et al., Int. J Mol. Med. 20 (2007): 405-409
Ke, J. Y. et al., J Zhejiang. Univ Sci. B 15 (2014a): 1032-1038
Ke, Z. et al., Oncotarget. 5 (2014b): 9410-9424
Keller, D. M. et al., Mol. Cell 7 (2001): 283-292
Khanobdee, K. et al., Mol. Vis. 10 (2004): 933-942
Khapare, N. et al., PLoS. One. 7 (2012): e38561
Khor, G. H. et al., Asian Pac. J Cancer Prev. 15 (2014): 8957-8961
Khoronenkova, S. V. et al., Mol. Cell 45 (2012): 801-813
Kibbe, A. H., Handbook of Pharmaceutical Excipients rd (2000)
Kienle, D. et al., Haematologica 95 (2010): 102-109
Kim, D. S. et al., J Proteome. Res 9 (2010a): 3710-3719
Kim, F. J. et al., Biochem. Biophys. Res Commun. 426 (2012a): 177-182
Kim, H. et al., PLoS. One. 8 (2013a): e63468
Kim, H. E. et al., PLoS. One. 7 (2012b): e43223
Kim, H. J. et al., J Proteome. Res 8 (2009): 1368-1379
Kim, J. H. et al., Pathol. Oncol Res 19 (2013b): 731-737
Kim, M. et al., Mol Cancer Res 6 (2008): 222-230
Kim, M. S. et al., Histopathology 58 (2011a): 660-668
Kim, Y. et al., Oncotarget. (2016)
Kim, Y. et al., J Biol Chem 288 (2013c): 36502-36518
Kim, Y. et al., J Biol Chem 285 (2010b): 25957-25968
Kim, Y. H. et al., Ann. Surg. Oncol 18 (2011b): 2338-2347
Kiniwa, Y. et al., Cancer Res 61 (2001): 7900-7907
Kirkbride, K. C. et al., Cell Adh. Migr. 5 (2011): 187-198
Kittang, A. O. et al., Curr. Top. Microbiol. Immunol. 341 (2010): 149-172
Kleist, B. et al., J Clin Pathol. (2015)
Knab, L. M. et al., World J Gastroenterol. 20 (2014): 10729-10739
Koga, Y. et al., Rinsho Byori 63 (2015): 361-368
Koike, K., Recent Results Cancer Res 193 (2014): 97-111
Koldehoff, M. et al., Int. J Hematol. 87 (2008): 39-47
Kolla, V. et al., Cancer Res 74 (2014): 652-658
Koo, J. S. et al., Am. J Clin Pathol. 143 (2015): 584-592
Korczak, B. et al., Int. J Cancer 53 (1993): 634-639
Koshikawa, K. et al., Oncogene 21 (2002): 2822-2828
Krieg, A. M., Nat Rev. Drug Discov. 5 (2006): 471-484
Kuang, S. Q. et al., Leukemia 22 (2008): 1529-1538
Kuang, Y. et al., Mol. Imaging Biol 16 (2014): 459-468
Kubo, N. et al., Biochem. Biophys. Res Commun. 430 (2013): 1034-1039
Kubota, H. et al., Cell Stress. Chaperones. 15 (2010): 1003-1011
Kuchma, M. H. et al., Protein J 31 (2012): 195-205
Kunimoto, K. et al., J Cell Physiol 220 (2009): 621-631
Kunzmann, A. T. et al., Cancer Epidemiol. Biomarkers Prev. 22 (2013): 1490-1497
Kuramitsu, Y. et al., Expert. Rev Proteomics. 2 (2005): 589-601
Kurer, M. A., Mol. Biol Rep. 34 (2007): 221-224
Kurisu, S. et al., Cancer Sci. 101 (2010): 2093-2104
Kutty, R. K. et al., J Biol Chem 276 (2001): 2831-2840
Kwiatkowski, D. J. et al., Hum. Mol. Genet. 14 Spec No. 2 (2005): R251-R258
Kwok, H. F. et al., Am. J Cancer Res 5 (2015): 52-71
Laczmanska, I. et al., Acta Biochim. Pol. 58 (2011): 467-470
Lambros, M. B. et al., Hum. Pathol. 38 (2007): 1105-1122
Lane, J. et al., Int. J Mol. Med. 12 (2003): 253-257
Lange, A. et al., Exp. Dermatol. 18 (2009): 527-535
Langnaese, K. et al., Cytogenet. Cell Genet. 94 (2001): 233-240
Lara, P. C. et al., Radiat. Oncol 6 (2011): 148
Lau, L. F., Cell Mol. Life Sci. 68 (2011): 3149-3163
Lawrence, M. S. et al., Nature 505 (2014): 495-501

Le, Tourneau C. et al., Br. J Cancer 99 (2008): 1197-1203
Leal, J. F. et al., Carcinogenesis 29 (2008): 2089-2095
Lebdai, S. et al., Urol. Oncol 33 (2015): 69-8
Lee, A. M. et al., Pharmacogenet. Genomics 26 (2016): 133-137
Lee, C. F. et al., World J Gastroenterol. 14 (2008a): 6072-6077
Lee, C. W. et al., World J Surg. Oncol 11 (2013): 136
Lee, H. J. et al., Nat Cell Biol 9 (2007): 1303-1310
Lee, J. I. et al., Physiol Genomics 33 (2008b): 218-229
Lee, K. Y. et al., J Med. 35 (2004): 141-149
Lei, Y. et al., Oncogene 34 (2015): 485-495
Leng, S. et al., Cancer Res 75 (2015): 3108-3117
Li, H. et al., Biotechnol. Appl. Biochem. (2015a)
Li, J. et al., J Invest Surg. (2013)
Li, J. et al., Tumour. Biol (2015b)
Li, J. F. et al., Zhonghua Wei Chang Wai Ke. Za Zhi. 15 (2012): 388-391
Li, J. P. et al., Drug Des Devel. Ther. 9 (2015c): 1027-1062
Li, M. et al., Int. J Oncol. 24 (2004): 305-312
Li, M. et al., Gene 542 (2014a): 134-140
Li, Q. et al., Mol. Biol Rep. 41 (2014b): 2409-2417
Li, S. R. et al., Biochem. Biophys. Res Commun. 271 (2000): 537-543
Li, Y. et al., J Cell Physiol 212 (2007): 675-681
Li, Z. et al., Biochim. Biophys. Acta 1846 (2014c): 285-296
Liang, J. et al., Med. Oncol 31 (2014a): 899
Liang, J. X. et al., Oncol Rep. 32 (2014b): 2726-2734
Liao, W. et al., Oncotarget. 6 (2015): 24132-24147
Liao, Y. J. et al., PLoS. One. 8 (2013): e77586
Liberati, S. et al., Cells 3 (2014a): 112-128
Liberati, S. et al., Curr. Protein Pept. Sci. 15 (2014b): 732-737
Liddy, N. et al., Nat Med. 18 (2012): 980-987
Lidfeldt, J. et al., PLoS. One. 10 (2015): e0134932
Liggins, A. P. et al., Cancer Immun. 10 (2010): 8
Limm, K. et al., Eur. J Cancer 49 (2013): 1305-1313
Lin, C. Y. et al., Cancer Res 74 (2014a): 5229-5243
Lin, H. S. et al., Arch. Otolaryngol. Head Neck Surg. 130 (2004): 311-316
Lin, J. et al., Leuk. Res 38 (2014b): 601-607
Lin, J. et al., Oncotarget. 6 (2015): 23793-23806
Lin, J. I. et al., Sci. Signal. 6 (2013a): e4
Lin, L. et al., Oncol Lett. 6 (2013b): 740-744
Lin, S. T. et al., J Proteomics. 75 (2012): 5822-5847
Lindahl, A. K. et al., Thromb. Res 64 (1991): 155-168
Lindberg, J. et al., Eur. Urol. 63 (2013): 702-708
Linderoth, J. et al., Br. J Haematol. 141 (2008): 423-432
Liu, G. et al., Cancer Genet. Cytogenet. 197 (2010a): 54-59
Liu, H. et al., Oncol Rep. 34 (2015a): 2267-2272
Liu, M. et al., Mol. Endocrinol. 28 (2014): 1740-1751
Liu, M. et al., Reprod. Sci. 20 (2013a): 605-615
Liu, M. et al., Mol. Biol Rep. 37 (2010b): 3601-3608
Liu, Q. et al., Exp. Ther. Med. 6 (2013): 1277-1282
Liu, R. et al., Clin Cancer Res 21 (2015b): 854-863
Liu, T. Q. et al., Asian Pac. J Cancer Prev. 16 (2015c): 3061-3065
Liu, T. W. et al., Proc. Natl. Acad. Sci. U.S.A. 106 (2009): 14581-14586
Liu, X. et al., Oncogene 32 (2013b): 1266-1273
Liu, Y. et al., Sci. Rep. 5 (2015d): 16954
Liu, Z. et al., Mol. Cancer Res 3 (2005): 21-31
Ljunggren, H. G. et al., J Exp. Med. 162 (1985): 1745-1759
Lo, T. F. et al., PLoS. One. 8 (2013): e75628
Longenecker, B. M. et al., Ann N.Y. Acad. Sci. 690 (1993): 276-291
Lopez-Nieva, P. et al., Carcinogenesis 33 (2012): 452-458
Lorenzen, J. A. et al., Gene Expr. Patterns. 6 (2005): 45-56
Lorenzi, P. L. et al., Mol. Cancer Ther. 7 (2008): 3123-3128
Lorenzi, P. L. et al., Mol. Cancer Ther. 5 (2006): 2613-2623
Lorenzi, P. L. et al., Drug News Perspect. 22 (2009): 61-64
Lossie, A. C. et al., BMC. Genet. 13 (2012): 106
Lu, C. et al., Mol. Cell Biochem. 312 (2008): 71-80
Lu, D. et al., Med. Oncol 32 (2015): 140
Lukas, T. J. et al., Proc. Natl. Acad. Sci. U.S.A. 78 (1981): 2791-2795
Lund, R. R. et al., Mol. Cell Proteomics. 14 (2015): 2988-2999
Lundblad, R. L., Chemical Reagents for Protein Modification 3rd (2004)
Luo, W. et al., Trends Endocrinol. Metab 23 (2012): 560-566
Ma, J. et al., Pathol. Oncol Res 19 (2013): 821-832
Mac, S. M. et al., Mol. Carcinog. 27 (2000): 84-96
Macher-Goeppinger, S. et al., Mod. Pathol. 25 (2012): 308-315
Maekawa, R. et al., J Reprod. Dev. 57 (2011): 604-612
Mah, T. L. et al., BMC. Genomics 15 Suppl 9 (2014): S20
Mak, G. W. et al., Cancer Res 71 (2011): 2949-2958
Mak, G. W. et al., PLoS. One. 7 (2012): e42210
Malta-Vacas, J. et al., Clin Chem Lab Med. 47 (2009): 427-431
Malumbres, M. et al., Curr. Opin. Genet. Dev. 17 (2007): 60-65
Marchetti, A. et al., Int. J Oncol 18 (2001): 175-179
Marimuthu, A. et al., Proteomics. Clin Appl. 7 (2013): 355-366
Marquardt, J. U. et al., Int. J Cancer 128 (2011): 2353-2363
Mascarenhas, Cdo C. et al., Leuk. Lymphoma 55 (2014): 1861-1869
Mason, J. M. et al., Nucleic Acids Res. 43 (2015): 3180-3196
Matnuri, M. et al., Int. J Clin Exp. Pathol. 8 (2015): 13339-13345
Matsuno, A. et al., Br. J Neurosurg. 18 (2004): 343-346
McCarthy, P. L. et al., Br. J Cancer 99 (2008): 639-646
McClung, J. K. et al., Exp. Gerontol. 30 (1995): 99-124
McDonald, S. L. et al., Cancer Biol Ther. 3 (2004): 110-120
McGarvey, T. W. et al., Prostate 54 (2003): 144-155
McGarvey, T. W. et al., Oncogene 20 (2001): 1042-1051
McGarvey, T. W. et al., J Cell Biochem. 95 (2005): 419-428
Medcalf, R. L. et al., FEBS J 272 (2005): 4858-4867
Meierjohann, S., Eur. J Cell Biol 93 (2014): 36-41
Mellor, P. et al., Mol. Cell Biol 33 (2013): 4985-4995
Mesri, E. A. et al., Immunol. Res 57 (2013): 159-165
Meziere, C. et al., J Immunol 159 (1997): 3230-3237
Midorikawa, Y. et al., Jpn. J Cancer Res 93 (2002): 636-643
Mimura, K. et al., J Immunol. 191 (2013): 6261-6272
Mirmalek-Sani, S. H. et al., J Cell Mol. Med. 13 (2009): 3541-3555
Mishra, S. et al., FEBS J 277 (2010): 3937-3946
Mishra, S. et al., Trends Mol. Med. 11 (2005): 192-197
Misra, S. et al., Curr. Drug Targets. 15 (2014): 347-359
Mitchell, S. M. et al., BMC. Cancer 14 (2014): 54
Miyashita, K. et al., Anticancer Agents Med. Chem 9 (2009): 1114-1122
Mizukoshi, E. et al., Hepatology 53 (2011): 1206-1216
Morelli, M. B. et al., Curr. Mol. Pharmacol. 6 (2013): 137-148
Morgan, R. A. et al., Science 314 (2006): 126-129
Mori, M. et al., Transplantation 64 (1997): 1017-1027
Mori, S. et al., PLoS. One. 7 (2012): e39723
Morin, A. et al., FASEB J 26 (2012): 460-467
Mortara, L. et al., Clin Cancer Res. 12 (2006): 3435-3443
Mossink, M. H. et al., Oncogene 22 (2003): 7458-7467

Moussay, E. et al., Autophagy. 7 (2011): 760-770
Mueller, L. N. et al., J Proteome. Res 7 (2008): 51-61
Mueller, L. N. et al., Proteomics. 7 (2007): 3470-3480
Muir, K. et al., Cancer Res 73 (2013): 4722-4731
Mukhopadhyay, T. et al., Anticancer Res 16 (1996): 105-112
Mullapudi, N. et al., PLoS. One. 10 (2015): e0143826
Mumberg, D. et al., Proc. Natl. Acad. Sci. U.S.A. 96 (1999): 8633-8638
Nabissi, M. et al., Carcinogenesis 31 (2010): 794-803
Nagel, S. et al., Genes Chromosomes. Cancer 53 (2014): 917-933
Nakamura, T., Int. J Hematol. 82 (2005): 21-27
Nakao, K. et al., J Gastroenterol. 49 (2014): 589-593
Nalesnik, M. A. et al., Am. J Pathol. 180 (2012): 1495-1508
Navarro, A. et al., Semin. Hematol. 48 (2011): 155-165
Nelson, L. D. et al., Mol. Cancer 11 (2012): 38
Nelson, M. A. et al., Cancer Genet. Cytogenet. 108 (1999): 91-99
Neri, P. et al., Curr. Cancer Drug Targets. 12 (2012): 776-796
Newman, S. et al., PLoS. One. 8 (2013): e64991
Ng, S. K. et al., Clin Experiment. Ophthalmol. 43 (2015): 367-376
Nguyen, H. N. et al., Biochem. Biophys. Res Commun. 357 (2007): 174-180
Nikkuni, O. et al., Pathol. Oncol Res 21 (2015): 1175-1181
Nio, K. et al., J Hepatol. 63 (2015): 1164-1172
Nitta, M. et al., Nucleic Acids Res 28 (2000): 4212-4218
Noorlag, R. et al., Virchows Arch. 466 (2015): 363-373
Nurnberg, A. et al., Nat Rev Cancer 11 (2011): 177-187
O'Shea, C. et al., Int. J Cancer 105 (2003): 754-761
Oeffner, F. et al., Am J Hum. Genet. 84 (2009): 459-467
Ohl, F. et al., J Mol. Med. (Berl) 83 (2005): 1014-1024
Okamoto, Y. et al., Cancer Res 63 (2003): 4167-4173
Olakowski, M. et al., Folia Histochem. Cytobiol. 47 (2009): 249-255
Ono, W. et al., Biochem. Biophys. Res Commun. 434 (2013): 659-663
Osada, S. et al., Oncol Rep. 30 (2013): 1669-1674
Oskarsson, T., Breast 22 Suppl 2 (2013): S66-S72
Otani, S. et al., Br. J Ophthalmol. 90 (2006): 773-777
Ozawa, D. et al., Ann. Surg. Oncol (2014)
Pandi, N. S. et al., Gene 545 (2014): 23-29
Panosyan, E. H. et al., Mol. Cancer Res 12 (2014): 694-702
Papageorgio, C. et al., Int. J Oncol. 31 (2007): 1205-1211
Parihar, J. S. et al., Rev Urol. 16 (2014): 118-121
Park, H. J. et al., J Proteome. Res 7 (2008): 1138-1150
Park, J. H. et al., Cancer Res 65 (2005): 2804-2814
Parker, L. P. et al., Cancer Genomics Proteomics. 6 (2009): 189-194
Paryan, M. et al., Mol. Biol Rep. 40 (2013): 5531-5540
Pavithra, L. et al., Int. J Biochem. Cell Biol 41 (2009): 862-871
Pavlides, S. et al., Cell Cycle 9 (2010): 3485-3505
Pawar, S. A. et al., Proc. Natl. Acad. Sci. U.S.A. 107 (2010): 9210-9215
Peltonen, H. M. et al., PLoS. One. 8 (2013): e79249
Pender-Cudlip, M. C. et al., Cancer Sci. 104 (2013): 760-764
Perez-Escuredo, J. et al., Cell Cycle 15 (2016): 72-83
Perez-Fernandez, J. et al., Nucleic Acids Res 39 (2011): 8105-8121
Perez-Tomas, R., Curr. Med. Chem 13 (2006): 1859-1876
Peters, D. G. et al., Cancer Epidemiol. Biomarkers Prev. 14 (2005): 1717-1723
Phuong, N. T. et al., Oncotarget. (2015)
Pierce, J. M. et al., Proteomics. 9 (2009): 1738-1741
Pinheiro, J. et al., nlme: Linear and Nonlinear Mixed Effects Models (2015)
Plebanski, M. et al., Eur. J Immunol 25 (1995): 1783-1787
Pohler, E. et al., Nat Genet. 44 (2012): 1272-1276
Pollok, S. et al., Biochem. Soc. Trans. 31 (2003): 266-269
Polotskaia, A. et al., Proc. Natl. Acad. Sci. U.S.A. 112 (2015): E1220-E1229
Ponnurangam, S. et al., Oncotarget. (2015)
Porta, C. et al., Virology 202 (1994): 949-955
Pradhan, M. P. et al., BMC. Syst. Biol 7 (2013): 141
Pregizer, S. et al., J Cell Biochem. 102 (2007): 1458-1471
Prieto-Granada, C. et al., Genes Chromosomes. Cancer 54 (2015): 28-38
Przybylo, M. et al., Biochimie 87 (2005): 133-142
Pucci, S. et al., Oncotarget. (2016)
Pylypenko, O. et al., Mol Cell 11 (2003): 483-494
Qin, Q. et al., PLoS. One. 5 (2010): e9999
Rajalingam, K. et al., Cell Cycle 4 (2005): 1503-1505
Rajkumar, T. et al., Indian J Biochem. Biophys. 42 (2005): 271-278
Ramachandran, C., Curr. Pharm. Biotechnol. 8 (2007): 99-104
Rammensee, H. G. et al., Immunogenetics 50 (1999): 213-219
Rana, S. et al., Expert. Rev Anticancer Ther. 8 (2008): 1461-1470
Rao, C. V. et al., Carcinogenesis 30 (2009): 1469-1474
Rappa, G. et al., Mol. Cancer Res 12 (2014): 1840-1850
Raso, E. et al., Magy. Onkol. 57 (2013): 79-83
Rauch, T. A. et al., Tumour. Biol 33 (2012): 287-296
RefSeq, The NCBI handbook [Internet], Chapter 18, (2002), www.ncbi.nlm.nih.gov/books/NBK21091/
Ren, Y. Q. et al., Med. Sci. Monit. 21 (2015): 1297-1303
Resende, C. et al., Helicobacter. 15 Suppl 1 (2010): 34-39
Resende, C. et al., Helicobacter. 16 Suppl 1 (2011): 38-44
Reubi, J. C. et al., J Nucl. Med. 49 (2008): 1735-1738
Rini, B. I. et al., Cancer 107 (2006): 67-74
Roberts, J. D. et al., Cancer Detect. Prev. 22 (1998): 455-462
Rock, K. L. et al., Science 249 (1990): 918-921
Roignot, J. et al., Cell Adh. Migr. 3 (2009): 167-170
Romes, E. M. et al., J Biol Chem 291 (2016): 882-893
Ronkainen, H. et al., Oncol Rep. 25 (2011): 129-133
Rosado, I. V. et al., RNA. 10 (2004): 1073-1083
Rose, M. et al., Epigenetics. 9 (2014): 1626-1640
Rothe, M. et al., Am. J Pathol. 157 (2000): 1597-1604
Rouzer, C. A. et al., J Lipid Res 50 Suppl (2009): S29-S34
Roy, D. et al., Oncol Rep. 23 (2010): 1383-1391
Rozenberg, P. et al., Int. J Cancer 133 (2013): 514-518
Rucki, A. A. et al., World J Gastroenterol. 20 (2014): 2237-2246
Rummel, M. J. et al., Leuk. Lymphoma 45 (2004): 49-54
Ryu, B. et al., PLoS. One. 2 (2007): e594
Ryu, S. J. et al., Expert. Opin. Ther. Targets. 13 (2009): 479-484
S3-Leitlinie Exokrines Pankreaskarzinom, 032-010OL, (2013)
Saiki, R. K. et al., Science 239 (1988): 487-491
Saksena, S. et al., Am. J Physiol Gastrointest. Liver Physiol 298 (2010): G159-G166
Salerno, C. et al., Ric. Clin Lab 20 (1990): 85-93
Salman, B. et al., Oncoimmunology. 2 (2013): e26662
Samuel, A. M. et al., Cell Oncol (Dordr.) 37 (2014): 95-105
Sanchez, G. et al., Cell Cycle 7 (2008): 2299-2305
Sander, B., Semin. Diagn. Pathol. 28 (2011): 245-255
Sandset, P. M. et al., Haemostasis 21 (1991): 219-239
Santos, F. M. et al., Phytomedicine. 18 (2011): 1096-1101
Sasatomi, T. et al., Cancer 94 (2002): 1636-1641
Savitskaya, T. V. et al., Pediatr. Hematol. Oncol 29 (2012): 28-37

Scagliotti, G. V. et al., Ann. Oncol 10 Suppl 5 (1999): S83-S86
Scanlon, C. S. et al., J Dent. Res 92 (2013): 114-121
Scheffer, G. L. et al., Curr. Opin. Oncol 12 (2000): 550-556
Schiffner, S. et al., Carcinogenesis 32 (2011): 1176-1182
Schmid, R. et al., PLoS. One. 8 (2013): e82166
Schramm, A. et al., Nat Genet. 47 (2015): 872-877
Schrier, S. A. et al., Curr. Opin. Ophthalmol. 22 (2011): 325-331
Schroder, W. A. et al., Cancer Med. 3 (2014): 500-513
Schwirzke, M. et al., Anticancer Res 18 (1998): 1409-1421
Seeger, F. H. et al., Immunogenetics 49 (1999): 571-576
Seftor, R. E. et al., Melanoma Res 1 (1991): 43-54
Sehrawat, A. et al., Breast Cancer Res Treat. 146 (2014): 543-555
Sekine, I. et al., Jpn. J Clin Oncol 37 (2007): 329-336
Serra, K. P. et al., Acta Histochem. (2016)
Sesen, J. et al., Int. J Mol. Sci. 15 (2014): 2172-2190
Sethi, M. K. et al., J Proteomics. 126 (2015): 54-67
Setoodeh, R. et al., Int. J Clin Exp. Pathol. 6 (2013): 155-167
Shahmoradgoli, M. et al., Int. J Cancer 132 (2013): 2714-2719
Shaker, M. et al., Pathobiology 78 (2011): 149-161
Shakhova, O., Curr. Opin. Oncol 26 (2014): 215-221
Shao, N. et al., Mol. Biol Rep. 39 (2012): 10997-11004
Sharma, A. et al., Mol. Cancer Res 12 (2014): 1205-1215
Sharpe, L. J. et al., Traffic. 12 (2011): 19-27
Sher, Y. P. et al., PLoS. One. 9 (2014): e94065
Sherman, F. et al., Laboratory Course Manual for Methods in Yeast Genetics (1986)
Shi, B. et al., BMC. Cancer 15 (2015): 380
Shimada, H. et al., Br. J Haematol. 110 (2000): 210-213
Shimizu, S. et al., Oncol Rep. 18 (2007): 1489-1497
Shimozono, N. et al., Cancer Res 75 (2015): 4458-4465
Shintani, Y. et al., Cancer Res 64 (2004): 4190-4196
Shishkin, S. S. et al., Biochemistry (Mosc.) 78 (2013): 1415-1430
Shodeinde, A. et al., J Mol Biochem. 2 (2013): 18-26
Shostak, K. et al., Nat Commun. 5 (2014): 5232
Sierko, E. et al., Semin. Thromb. Hemost. 33 (2007): 653-659
Silveira, S. M. et al., Head Neck 34 (2012): 485-492
Simpson, N. E. et al., Breast Cancer Res Treat. 133 (2012): 959-968
Singh, S. et al., Tumour. Biol. (2014)
Singh, V. et al., OMICS. 19 (2015): 688-699
Singh-Jasuja, H. et al., Cancer Immunol. Immunother. 53 (2004): 187-195
Skawran, B. et al., Mod. Pathol. 21 (2008): 505-516
Skene-Arnold, T. D. et al., Biochem. J 449 (2013): 649-659
Skondra, M. et al., Anticancer Res 34 (2014): 6691-6699
Skrzycki, M. et al., J Recept. Signal. Transduct. Res 33 (2013): 313-318
Slape, C. et al., Leuk. Lymphoma 45 (2004): 1341-1350
Small, E. J. et al., J Clin Oncol. 24 (2006): 3089-3094
Smith, K. A. et al., Proc. Natl. Acad. Sci. U.S.A. 94 (1997): 1816-1821
Smith, K. A. et al., Cell 63 (1990): 1219-1227
Sollini, M. et al., Q. J Nucl. Med. Mol. Imaging 59 (2015): 168-183
Solomon, D. A. et al., Cancer Res 68 (2008): 8657-8660
Song, N. et al., J Zhejiang. Univ Sci. B 14 (2013): 451-459
Song, Z. et al., PLoS. One. 10 (2015): e0128943
Sperlazza, J. et al., Blood 126 (2015): 1462-1472
Steen, H. C. et al., J Interferon Cytokine Res 32 (2012): 103-110
Stefansson, O. A. et al., Breast Cancer Res 16 (2014): 307
Stein, U., Expert. Opin. Ther. Targets. 17 (2013): 1039-1052
Stewart, J. et al., Mod. Pathol. 28 (2015): 428-436
Strekalova, E. et al., Clin. Cancer Res. (2015)
Stremenova, J. et al., Int. J Oncol 36 (2010): 351-358
Stubbs, A. P. et al., Am. J Pathol. 154 (1999): 1335-1343
Sturm, M. et al., BMC. Bioinformatics. 9 (2008): 163
Sugimoto, T. et al., Genes Chromosomes. Cancer 48 (2009): 132-142
Sun, B. C. et al., Zhonghua Yi. Xue. Za Zhi. 86 (2006): 1808-1812
Sun, F. K. et al., J Gastroenterol. Hepatol. 31 (2016a): 484-492
Sun, S. et al., Gene 584 (2016b): 90-96
Sun, S. Y., Cancer Lett. 340 (2013): 1-8
Sun, X. et al., Neoplasia. 14 (2012): 1122-1131
Sundar, R. et al., Cell Cycle 14 (2015): 554-565
Szaflarski, W. et al., Postepy Biochem. 57 (2011): 266-273
Szarvas, T. et al., Int J Cancer 135 (2014): 1596-1604
Szczyrba, J. et al., Int. J Cancer 132 (2013): 775-784
Taintor, A. R. et al., J Am. Acad. Dermatol. 56 (2007): S73-S76
Takahashi, H. et al., Urology 79 (2012): 240-248
Takeda, A. et al., Semin. Cancer Biol 27 (2014): 3-10
Takei, H. et al., Anticancer Res 15 (1995): 1101-1105
Tamada, M. et al., Clin Cancer Res 18 (2012): 5554-5561
Tameda, M. et al., Int. J Oncol 45 (2014): 541-548
Tamura, K. et al., Cancer Res 67 (2007): 5117-5125
Tan, X. et al., Tumour. Biol 35 (2014): 12189-12200
Tang, B. et al., Int. J Oncol 47 (2015): 2208-2216
Tang, W. et al., Genet. Epidemiol. 37 (2013): 512-521
Tano, K. et al., FEBS Lett. 584 (2010): 4575-4580
Tao, H. C. et al., Asian Pac. J Cancer Prev. 14 (2013): 5645-5650
Tavner, F. J. et al., Mol. Cell Biol 18 (1998): 989-1002
Taylor, K. H. et al., Cancer Res 67 (2007): 2617-2625
Tech, K. et al., Cancer Lett. 356 (2015): 268-272
Teufel, R. et al., Cell Mol Life Sci. 62 (2005): 1755-1762
Theiss, A. L. et al., Biochim. Biophys. Acta 1813 (2011): 1137-1143
Thill, M. et al., Eur. J Gynaecol. Oncol 35 (2014): 341-358
Thorsen, K. et al., Mol Cell Proteomics. 7 (2008): 1214-1224
Tian, T. V. et al., Oncogene 33 (2014): 2204-2214
Tietz, O. et al., Curr. Med. Chem 20 (2013): 4350-4369
Timme, S. et al., Oncogene 33 (2014): 3256-3266
Tiwari, R. V. et al., Exp. Biol Med. (Maywood.) 239 (2014): 33-44
To, M. D. et al., Oncogene 25 (2006): 3557-3564
Tomasi, M. L. et al., Oncotarget. 6 (2015): 37706-37723
Tomasi, M. L. et al., Exp. Cell Res 319 (2013): 1902-1911
Tran, E. et al., Science 344 (2014): 641-645
Trotta, C. R. et al., Nature 441 (2006): 375-377
Tsofack, S. P. et al., Mol. Cancer 10 (2011): 145
Tsuchiya, M. et al., Biochem. Biophys. Res Commun. 407 (2011): 378-382
Tucci, M. et al., Curr. Top. Med. Chem 9 (2009): 218-224
Vaillant, A. R. et al., Biochem. Cell Biol 73 (1995): 695-702
Valladares-Ayerbes, M. et al., Cancer Epidemiol. Biomarkers Prev. 19 (2010): 1432-1440
van den Heuvel-Eibrink M M et al., Int. J Clin Pharmacol. Ther. 38 (2000): 94-110
Van Ginkel, P. R. et al., Biochim. Biophys. Acta 1448 (1998): 290-297
van't Veer, M. B. et al., Haematologica 91 (2006): 56-63
Vasseur, S. et al., Mol. Cancer 4 (2005): 4
Vellanki, R. N. et al., PLoS. One. 8 (2013): e54060

Verbeke, H. et al., Biochim. Biophys. Acta 1825 (2012): 117-129
Vilner, B. J. et al., Cancer Res 55 (1995): 408-413
Vinayak, S. et al., Oncology (Williston. Park) 27 (2013): 38-44, 46, 48
Vincent, M. et al., PLoS. One. 5 (2010): e12941
Vincent-Chong, V. K. et al., PLoS. One. 8 (2013): e54705
Vogt, P. K. et al., Curr. Top. Microbiol. Immunol. 347 (2010): 79-104
Voloshanenko, O. et al., Nat Commun. 4 (2013): 2610
von Eyben, F. E., Cancer Genet. Cytogenet. 151 (2004): 93-138
Von Hoff, D. D. et al., N. Engl. J Med. 369 (2013): 1691-1703
Vrabel, D. et al., Klin. Onkol. 27 (2014): 340-346
Wagner, K. W. et al., Oncogene 23 (2004): 6621-6629
Walker, E. J. et al., World J Gastroenterol. 20 (2014): 2224-2236
Walter, S. et al., J Immunol 171 (2003): 4974-4978
Walter, S. et al., Nat Med. 18 (2012): 1254-1261
Wan, Y. Y. et al., Zhonghua Zhong. Liu Za Zhi. 38 (2016): 28-34
Wang, B. S. et al., Cell Stress. Chaperones. 18 (2013a): 359-366
Wang, D. et al., Biochem. Biophys. Res Commun. 458 (2015a): 313-320
Wang, G. et al., Tumour. Biol 36 (2015b): 1055-1065
Wang, H. et al., Tumour. Biol 34 (2013b): 1635-1639
Wang, J. et al., J Clin Invest 112 (2003): 535-543
Wang, J. L. et al., Gene 529 (2013c): 7-15
Wang, L. et al., World J Gastroenterol. 17 (2011): 1434-1441
Wang, L. et al., Xi. Bao. Yu Fen. Zi. Mian. Yi. Xue. Za Zhi. 31 (2015c): 1251-1254
Wang, L. et al., Cancer Cell 25 (2014a): 21-36
Wang, L. J. et al., Oncotarget. 6 (2015d): 5932-5946
Wang, P. et al., Med. Oncol 32 (2015e): 264
Wang, Q. et al., J Pathol. 236 (2015f): 278-289
Wang, S. et al., J Cell Sci. 120 (2007): 567-577
Wang, S. Y. et al., Eur. Rev Med. Pharmacol. Sci. 19 (2015g): 1191-1197
Wang, T. et al., Neurobiol. Aging 36 (2015h): 527-535
Wang, X. et al., BMC. Cancer 14 (2014b): 196
Wang, X. et al., J Biot Chem 290 (2015i): 3925-3935
Wang, X. et al., PLoS. One. 8 (2013d): e72015
Wang, Y. et al., Cancer Lett. 360 (2015j): 171-176
Wang, Y. F. et al., Phytother. Res 29 (2015k): 674-679
Wang, Z. et al., J Cancer Res Clin Oncol 141 (2015l): 1353-1361
Wang, Z. et al., Gastroenterol. Res Pract. 2014 (2014c): 132320
Wang, Z. et al., Oncotarget. 4 (2013e): 2476-2486
Wang, Z. et al., Science 304 (2004): 1164-1166
Wang, Z. et al., J Cell Physiol 224 (2010): 559-565
Wang, Z. et al., Med. Oncol 30 (2013f): 577
Wang, Z. et al., Hum. Pathol. 46 (2015m): 1006-1014
Warner, S. L. et al., Future. Med. Chem 6 (2014): 1167-1178
Wasa, M. et al., Am. J Physiol Cell Physiol 282 (2002): C1246-C1253
Watanabe, M. et al., Proteomics. Clin Appl. 2 (2008): 925-935
Waters, M. G. et al., Nature 349 (1991): 248-251
Watson, P. J. et al., Traffic. 5 (2004): 79-88
Wehner, K. A. et al., Mol. Cell 9 (2002): 329-339
Westin, G. et al., World J Surg. 33 (2009): 2224-2233
Weston, R. et al., Genes Dev. 26 (2012): 1558-1572
Wheler, J. J. et al., BMC. Cancer 15 (2015): 442
Wiese, M. et al., Expert. Opin. Ther. Pat 24 (2014): 723-725
Willcox, B. E. et al., Protein Sci. 8 (1999): 2418-2423
Wilson, C. H. et al., Int. J Oncol 41 (2012): 919-932
Wojtukiewicz, M. Z. et al., Cancer Metastasis Rev 34 (2015): 775-796
Woodburn, K. W. et al., Drug Metab Dispos. 41 (2013): 774-784
World Cancer Report, (2014)
Wu, H. C. et al., Nat Commun. 5 (2014): 3214
Wu, S. et al., Acta Biochim. Biophys. Sin. (Shanghai) 45 (2013): 27-35
Wyatt, L. et al., Cell Cycle 7 (2008): 2290-2295
Wysocki, P. J., Expert. Rev Mol. Diagn. 9 (2009): 231-241
Xiao, H. et al., Biochem. Biophys. Res Commun. 460 (2015): 703-708
Xie, H. et al., PLoS. One. 7 (2012): e46990
Xie, X. et al., Oncol Lett. 7 (2014): 1537-1543
Xing, X. et al., Gene 344 (2005): 161-169
Xu, F. P. et al., Cancer Lett. 245 (2007): 69-74
Xu, L. et al., Nan. Fang Yi. Ke. Da. Xue. Xue. Bao. 26 (2006): 231-233
Xu, Z. et al., Biomed. Res Int 2015 (2015): 459170
Xue, J. et al., J Biol Chem 290 (2015): 18662-18670
Yagel, S. et al., Clin Exp. Metastasis 8 (1990): 305-317
Yan, L. et al., Nan. Fang Yi. Ke. Da. Xue. Xue. Bao. 35 (2015a): 767-71, 776
Yan, L. et al., Am. J Cancer Res 5 (2015b): 1447-1459
Yang, H. et al., Chem Biol Drug Des 84 (2014a): 578-584
Yang, J. et al., Am. J Pathol. 185 (2015): 2194-2205
Yang, J. et al., Cancer 113 (2008): 1532-1543
Yang, J. et al., Neurosurg. Clin N. Am. 23 (2012a): 451-458
Yang, L. et al., Cancer Lett. 336 (2013): 213-221
Yang, S. et al., Gene 576 (2016): 421-428
Yang, Y. et al., PLoS. One. 7 (2012b): e36813
Yang, Y. et al., PLoS. One. 9 (2014b): e97578
Yao, T. W. et al., Mol. Cancer Res 9 (2011): 948-959
Yao, Y. et al., Cell Physiol Biochem. 35 (2015): 983-996
Yasui, W. et al., Gastric. Cancer 8 (2005): 86-94
Yasui, W. et al., Cancer Sci. 95 (2004): 385-392
Yi, C. H. et al., Cancer Lett. 284 (2009): 149-156
Yong, Z. W. et al., Sci. Rep. 4 (2014): 6073
Yoo, K. Y. et al., Breast Cancer 10 (2003): 289-293
Yoon, S. Y. et al., Int. J Oncol 29 (2006): 315-327
Yoshihara, N. et al., J Dermatol. 41 (2014): 311-315
Younes, M. et al., Anticancer Res 20 (2000): 3775-3779
Yu, B. et al., Exp. Cell Res 315 (2009): 3086-3098
Yu, D. M. et al., FEBS J 277 (2010): 1126-1144
Yu, J. et al., Tumour. Biol 36 (2015): 3221-3229
Yu, R. et al., Brain Pathol. 11 (2001): 328-341
Yu, Y. P. et al., Am. J Pathol. 184 (2014): 2840-2849
Yuan, R. H. et al., Ann Surg. Oncol 16 (2009): 1711-1719
Yuan, W. et al., Asian J Androl 7 (2005): 277-288
Yue, C. et al., Int. J Cancer 136 (2015): 117-126
Yun, H. M. et al., Oncogene 33 (2014): 5193-5200
Zajac-Kaye, M., Lung Cancer 34 Suppl 2 (2001): S43-S46
Zanfardino, M. et al., Int. J Oncol 43 (2013): 1763-1770
Zaremba, S. et al., Cancer Res. 57 (1997): 4570-4577
Zekri, A. R. et al., Asian Pac. J Cancer Prev. 16 (2015): 3543-3549
Zhai, L. L. et al., Int. J Clin Exp. Pathol. 8 (2015a): 682-691
Zhai, L. L. et al., Onco. Targets. Ther. 8 (2015b): 2827-2834
Zhai, L. L. et al., Am. J Transl. Res 7 (2015c): 2412-2422
Zhang, B. et al., Br. J Cancer 109 (2013a): 14-23
Zhang, G. et al., FASEB J 27 (2013b): 2893-2901
Zhang, H. et al., Onco. Targets. Ther. 8 (2015a): 2291-2301
Zhang, J. et al., J Cancer Res Clin Oncol 140 (2014a): 1441-1449
Zhang, J. et al., BMC. Dev. Biol 8 (2008): 115

Zhang, J. et al., Zhonghua Bing. Li Xue. Za Zhi. 42 (2013c): 810-814
Zhang, L. et al., Carcinogenesis 34 (2013d): 577-586
Zhang, P. et al., Genome 57 (2014b): 253-257
Zhang, R. et al., Mol. Carcinog 54 (2015b): 1554-1566
Zhang, T. et al., Acta Histochem. 115 (2013e): 48-55
Zhang, Y. et al., J Cancer Res Clin Oncol 137 (2011): 1245-1253
Zhao, G. et al., Biochem. Biophys. Res Commun. 408 (2011): 154-159
Zhao, H. et al., Mol. Biol Cell 15 (2004): 506-519
Zhao, Z. et al., RNA. Biol 12 (2015): 538-554
Zhen, T. et al., Oncotarget. 5 (2014): 3756-3769
Zheng, L. H. et al., Climacteric. 17 (2014): 522-528
Zhou, J. et al., Oncol Rep. 30 (2013): 2229-2237
Zhou, J. et al., Carcinogenesis 36 (2015a): 441-451
Zhou, K. et al., Med. Oncol 31 (2014): 17
Zhou, T. B. et al., J Recept. Signal. Transduct. Res 33 (2013): 28-36
Zhou, W. et al., Mol. Cell Biochem. 398 (2015b): 11-19
Zhu, J. et al., Int. J Clin Exp. Pathol. 8 (2015a): 702-710
Zhu, J. et al., Oncotarget. 6 (2015b): 16757-16765
Zhu, Y. P. et al., Oncotarget. 6 (2015c): 14488-14496
Zhuang, Y. J. et al., Cancer Biol Ther. 16 (2015): 88-96
Zubel, A. et al., Gynecol. Oncol 114 (2009): 332-336

The invention claimed is:

1. A method for producing activated antigen-specific CD8+ cytotoxic T cells that selectively recognize cancer cells that aberrantly present a peptide consisting of the amino acid sequence of VVYDDSTGLIRL (SEQ ID NO:81) in a complex with an HLA-A*02 comprising:
   isolating CD8$^+$ T cells from a HLA-A*02 donor;
   contacting the isolated CD8$^+$ T cells with antigen-presenting cells that display an antigen in a complex with HLA-A*02 for a period of time sufficient to activate the CD8$^+$T cells, wherein said antigen is a peptide consisting of the amino acid sequence of VVYDDSTGLIRL (SEQ ID NO:81).

2. The method of claim 1, wherein the HLA-A*02 donor is a patient with cancer.

3. The method of claim 2, wherein the cancer is lung cancer, CNS tumor, neuroblastoma, prostate cancer, lymphocytic leukemia, Merkel Cell carcinoma (MCC), ovarian cancer or oral cancer.

4. The method of claim 2, wherein the cancer is lung cancer.

5. The method of claim 1, wherein the CD8$^+$ T cells are obtained from tumor infiltrating lymphocytes or peripheral blood mononuclear cells.

6. The method of claim 1, wherein the HLA-A*02 donor is a healthy donor.

7. The method of claim 1, wherein the antigen presenting cells are dendritic cells or macrophages.

8. The method of claim 1, wherein the antigen presenting cells are infected with a recombinant virus expressing the peptide.

9. The method of claim 1, wherein the antigen presenting cells are artificial antigen presenting cells (aAPC).

10. The method of claim 1, further comprising expanding the activated T cells in vitro.

11. The method of claim 10, wherein the expansion is in the presence of an anti-CD28 antibody and IL-12.

* * * * *